US008969336B2

(12) United States Patent
Shimada et al.

(10) Patent No.: US 8,969,336 B2
(45) Date of Patent: Mar. 3, 2015

(54) DIAMINO HETEROCYCLIC CARBOXAMIDE COMPOUND

(75) Inventors: Itsuro Shimada, Tokyo (JP); Kazuo Kurosawa, Tokyo (JP); Takahiro Matsuya, Tokyo (JP); Kazuhiko Iikubo, Tokyo (JP); Yutaka Kondoh, Tokyo (JP); Akio Kamikawa, Tokyo (JP); Hiroshi Tomiyama, Nagano (JP); Yoshinori Iwai, Nagano (JP)

(73) Assignees: Astellas Pharma Inc., Tokyo (JP); Kotobuki Pharmaceutical Co., Ltd., Hanishina-gun (JP)

(*) Notice: Subject to any disclaimer, the term of this patent is extended or adjusted under 35 U.S.C. 154(b) by 266 days.

(21) Appl. No.: 13/266,164

(22) PCT Filed: May 6, 2010

(86) PCT No.: PCT/JP2010/057751
§ 371 (c)(1),
(2), (4) Date: Oct. 25, 2011

(87) PCT Pub. No.: WO2010/128659
PCT Pub. Date: Nov. 11, 2010

(65) Prior Publication Data
US 2012/0040968 A1    Feb. 16, 2012

(30) Foreign Application Priority Data

May 8, 2009   (JP) .................................. 2009-113936

(51) Int. Cl.
| | | |
|---|---|---|
| A61K 31/55 | (2006.01) | |
| A61K 31/497 | (2006.01) | |
| A61K 31/4965 | (2006.01) | |
| A61K 31/505 | (2006.01) | |
| A61K 31/54 | (2006.01) | |
| C07D 243/08 | (2006.01) | |
| C07D 413/14 | (2006.01) | |
| C07D 241/02 | (2006.01) | |
| C07D 237/02 | (2006.01) | |
| C07D 401/12 | (2006.01) | |
| C07D 239/48 | (2006.01) | |
| C07D 241/26 | (2006.01) | |
| C07D 241/28 | (2006.01) | |
| C07D 401/14 | (2006.01) | |
| C07D 403/12 | (2006.01) | |
| C07D 405/12 | (2006.01) | |
| C07D 405/14 | (2006.01) | |
| C07D 409/12 | (2006.01) | |
| C07D 413/12 | (2006.01) | |
| C07D 417/12 | (2006.01) | |
| C07D 471/08 | (2006.01) | |
| C07D 491/113 | (2006.01) | |

(52) U.S. Cl.
CPC ............ *C07D 239/48* (2013.01); *C07D 241/26* (2013.01); *C07D 241/28* (2013.01); *C07D 401/12* (2013.01); *C07D 401/14* (2013.01); *C07D 403/12* (2013.01); *C07D 405/12* (2013.01); *C07D 405/14* (2013.01); *C07D 409/12* (2013.01); *C07D 413/12* (2013.01);
*C07D 417/12* (2013.01); *C07D 471/08* (2013.01); *C07D 491/113* (2013.01)
USPC .............. 514/217.05; 514/235.8; 514/252.11; 514/255.05; 514/218; 514/272; 514/230.5; 514/227.8; 540/575; 544/122; 544/357; 544/230; 544/405; 544/407; 544/105

(58) Field of Classification Search
CPC .. C07D 243/08; C07D 413/14; C07D 241/02; C07D 237/02; C07D 401/02; C07D 409/12; A61K 31/55; A61K 31/535; A61K 31/497; A61K 31/501; A61K 31/54; A61K 31/505
USPC .......... 514/217.05, 252.11, 255.05, 218, 272, 514/230.5, 227.8, 235.38, 235.8; 540/575; 544/122, 357, 230, 405, 407, 105
See application file for complete search history.

(56) References Cited

U.S. PATENT DOCUMENTS 6,797,706 B1 *   9/2004   Hisamichi et al. ............ 514/183

FOREIGN PATENT DOCUMENTS

| CA | 2 692 611 A1 | 1/2009 |
|---|---|---|
| EP | 1 184 376 | 3/2002 |
| EP | 1 914 240 | 4/2008 |
| JP | 2008/013499 | 1/2008 |
| WO | 00/75113 | 12/2000 |
| WO | 00/76980 | 12/2000 |
| WO | 2004/002964 | 1/2004 |
| WO | 2004/080980 | 9/2004 |
| WO | 2008/024974 | 2/2008 |
| WO | 2008/051547 | 5/2008 |

(Continued)

OTHER PUBLICATIONS

Extended European Search Report issued Oct. 25, 2012 in Patent Application No. 10772177.1.

(Continued)

*Primary Examiner* — James O Wilson
*Assistant Examiner* — Ebenezer O Sackey
(74) *Attorney, Agent, or Firm* — Oblon, McClelland, Maier & Neustadt, L.L.P.

(57) ABSTRACT

Provided is a compound useful as an inhibitor against the kinase activity of EML4-ALK fusion protein.

As a result of intensive and extensive studies on compounds having inhibitory activity against the kinase activity of EML4-ALK fusion protein, the present inventors found that the diamino heterocyclic carboxamide compounds of the present invention had inhibitory activity against the kinase activity of EML4-ALK fusion protein. By this finding, the present invention was completed. The compounds of the present invention can be used as a pharmaceutical composition for preventing and/or treating cancer, such as lung cancer, non-small cell lung cancer, and small cell lung cancer.

12 Claims, No Drawings

(56) References Cited

FOREIGN PATENT DOCUMENTS

| | | |
|---|---|---|
| WO | 2008/073687 | 6/2008 |
| WO | 2008/077885 | 7/2008 |
| WO | 2009/008371 | 1/2009 |
| WO | 2009/012421 | 1/2009 |
| WO | 2009/020990 | 2/2009 |
| WO | 2009/032694 | 3/2009 |
| WO | 2009/032703 | 3/2009 |
| WO | 2009/040399 | 4/2009 |
| WO | 2009/089042 | 7/2009 |
| WO | 2009/126514 | 10/2009 |
| WO | 2009/126515 | 10/2009 |
| WO | 2009/136995 | 11/2009 |
| WO | 2009/143389 | 11/2009 |
| WO | 2009/145856 | 12/2009 |

OTHER PUBLICATIONS

International Search Report for PCT/JP2010/057751, mailed Jun. 1, 2010.

Dirks et al., "Expression and Functional Analysis of the Anaplastic Lymphoma Kinase (ALK) Gene in Tumor Cell Lines", Int. J. Cancer, vol. 100, 2002, pp. 49-56.

Soda et al., "Identification of the transforming EML4-ALK fusion gene in non-small-cell lung cancer", Nature, vol. 448, Aug. 2007, pp. 561-566.

Marzec et al., "Inhibition of ALK enzymatic activity in T-cell lymphoma cells induces apoptosis and suppresses proliferation and STAT3 phosphorylation independently of JAk3", Laboratory Investigation, vol. 85, 2005, pp. 1544-1554.

Galkin et al., "Identification of NVP-TAE684, a potent, selective, and efficacious inhibitor of NPM-ALK", PNAS, vol. 104, No. 1, Jan. 2007, pp. 270-275.

Rikova et al., "Global Survey of Phosphotyrosine Signaling Identifies Oncogenic Kinases in Lung Cancer", Cell, vol. 131, Dec. 2007, pp. 1190-1203.

McDermott et al., "Identification of genotype-correlated sensitivity to selective kinase inhibitors by using high-throughput tumor cell line profiling", PNAS, vol. 104, No. 50, Dec. 2007, pp. 19936-19941.

* cited by examiner

DIAMINO HETEROCYCLIC CARBOXAMIDE COMPOUND

This application is the U.S. national phase of International Application No. PCT/JP2010/057751 filed 6 May 2010 which designated the U.S. and claims priority to JP Patent Application No. 2009-113936 filed 8 May 2009, the entire contents of each of which are hereby incorporated by reference.

TECHNICAL FIELD

The present invention relates to diamino heterocyclic carboxamide compounds useful as active ingredients in pharmaceutical compositions, particularly pharmaceutical compositions for cancer therapy.

BACKGROUND ART

Lung cancer is caused by disordered growth of tracheal, bronchial and/or alveolar cells as a result of losing their normal functions. The number of people who die of lung cancer is the largest of the total of cancer deaths (17%), and worldwide about 1.3 million people die of lung cancer each year.

Treatment for lung cancer is divided into three major categories: surgical operation (surgical therapy), anticancer agent (chemotherapy) and radioactive irradiation (radiation therapy), but the effectiveness of treatment will vary depending on the tissue type of lung cancer. For example, although a definite diagnosis of lung cancer is made by a pathologist based on his cytohistopathological diagnosis on a microscope specimen, small cell lung cancer, which constitutes about 20% of lung cancer cases, has often reached an advanced stage at the time of discovery because it generally has a high grade of malignancy and will rapidly grow and spread and will often metastasize to other organs. For this reason, chemotherapy and/or radiation therapy is often used for treatment of this cancer, but the prognosis is poor because small cell lung cancer will often recur although it is relatively sensitive to these therapies. On the other hand, in the case of non-small cell lung cancer, which constitutes the remainder of about 80%, surgical therapy is considered for use until a certain stage, but there is little opportunity to use surgical operation in the subsequent stages where chemotherapy and/or radiation therapy is mainly used for treatment.

Thus, in either type of lung cancer, chemotherapy is an important option for treatment.

ALK (Anaplastic Lymphoma Kinase) is a receptor tyrosine kinase and is a protein having a transmembrane region in the middle part, flanked by a tyrosine kinase region on the carboxyl-terminal side and an extracellular region on the amino-terminal side. It has previously been reported that full-length ALK is expressed in several types of cancer cells of ectodermal origin (e.g., neuroblastoma, glioblastoma, breast cancer, melanoma) (Non-patent Document 1). In some cases of human malignant lymphoma, it has also been reported that the ALK gene is fused with another gene (e.g., NPM gene, CLTCL gene, TFG gene, TPM3 gene, ATIC gene, and TPM4 gene) as a result of chromosomal translocation, and thereby produces an oncogenic fusion tyrosine kinase (Science, vol. 263, p. 1281, 1994; Blood, vol. 86, p. 1954, 1995; Blood, vol. 95, p. 3204, 2000; Blood, vol. 94, p. 3265, 1999; Oncogene, vol. 20, p. 5623, 2001). Also in the case of inflammatory myofibroblastic tumor, it is known that the ALK gene is fused with another gene (e.g., CARS gene, SEC31L1 gene, and RanBP2 gene) as a result of chromosomal translocation, and thereby produces a fusion tyrosine kinase (Laboratory Investigation, a journal of technical methods and pathology, vol. 83, p. 1255, 2003; International Journal of Cancer, vol. 118, p. 1181, 2006; Medicinal Research Reviews, vol. 28, p. 372, 2008). Most of partner molecules to be fused with ALK have a complex-forming domain, and the generated fusion products per se also appear to form complexes. This complex formation would induce uncontrol of ALK tyrosine kinase activity and abnormal activation of intracellular signals, thereby causing canceration (Cellular and Molecular Life Science, vol. 61, p. 2939, 2004; Nature Reviews Cancer, vol. 8, p. 11, 2008).

Moreover, recent reports have indicated the presence of a TPM4-ALK fusion protein in esophageal cancer by proteomics analysis procedures (World Journal of Gastroenterology, vol. 12, p. 7104, 2006; Journal of Molecular Medicine, vol. 85, p. 863, 2007). Further, a fusion gene between EML4 (echinoderm microtubule associated protein like-4) and ALK was confirmed in specimens from lung cancer patients, and it was also reported that this EML4-ALK fusion gene has tumorgenicity and is a causal gene of cancer, and that inhibitors against its kinase activity suppress the growth of various cells where the EML4-ALK fusion protein is expressed (Patent Document 1 and Non-patent Document 2). These documents further show that inhibitors of the EML4-ALK fusion protein are useful as therapeutic agents for lung cancer in EML4-ALK polynucleotide-positive lung cancer patients. Further, in lung cancer, the presence of many variants of EML4-ALK has been proved (Patent Document 1; Annals of surgical oncology, vol. 17, p. 889, 2010; Molecular Cancer Research, vol. 7, p. 1466, 2009; Clinical Cancer Research, vol. 15, p. 3143, 2009; Cancer, vol. 115, p. 1723, 2009; Clinical Cancer Research, vol. 14, p. 6618, 2008; Clinical Cancer Research, vol. 14, p. 4275, 2008), and the presence of TFG-ALK (Cell, vol. 131, p. 1190, 2007) and KIF5B-ALK (Clinical Cancer Research, vol. 15, p. 3143, 2009) has been reported. Furthermore, it is known that there have been cases in which EML4-ALK is expressed in lung cancer patients as well as colon cancer patients and breast cancer patients (Molecular Cancer Research, vol. 7, p. 1466, 2009).

Moreover, Patent Document 1 shows the following compounds A to D (each being known as an ALK inhibitor) as examples of compounds having inhibitory activity against the EML4-ALK fusion protein, and it also discloses the actual values of their inhibitory activity against the EML4-ALK fusion protein. However, there is no specific disclosure about the diamino heterocyclic carboxamide compounds according to the present invention.

[Formula 1]

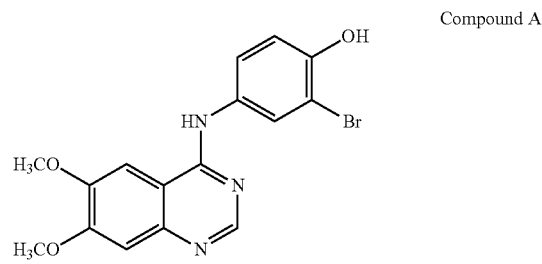

Compound A

-continued

Compound B

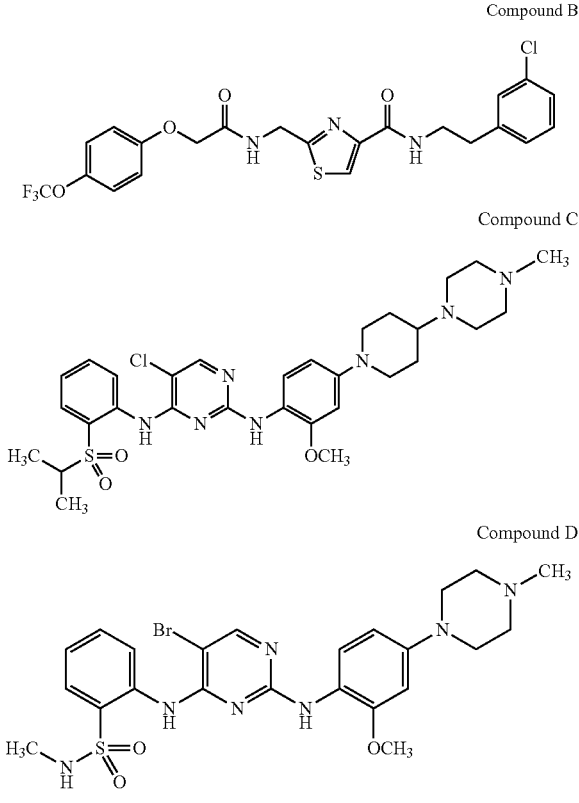

Compound C

Compound D

Their respective chemical names are: 4-[(3'-bromo-4'-hydroxyphenyl)amino]-6,7-dimethoxyquinazoline (also called WHI-P154) for compound A; N-[2-(3-chlorophenyl)ethyl]-2-[({[4-(trifluoromethoxy)phenoxy]acetyl}amino)methyl]-1,3-thiazole-4-carboxamide for compound B; 5-chloro-$N^4$-[2-(isopropylsulfonyl)phenyl]-$N^2$-{2-methoxy-4-[4-(4-methylpiperazin-1-yl)piperidin-1-yl]phenyl}pyrimidine-2,4-diamine (also called TAE684) for compound C; and 2-[(5-bromo-2-{[2-methoxy-4-(4-methylpiperazin-1-yl)phenyl]amino}pyrimidin-4-yl)amino]-N-methylbenzenesulfonamide for compound D.

Moreover, in ALK fusion protein-expressing lymphoma cells, a compound having ALK inhibitory activity, WHI-P154 (compound A shown above), has been reported to inhibit cell growth and induce apoptosis (Non-patent Document 3). However, there is no specific disclosure about the diamino heterocyclic carboxamide compounds according to the present invention.

Likewise, TAE684 (compound C shown above) is known as an inhibitor of a fusion protein from a fusion gene between NPM gene and ALK gene.

TAE684 structurally differs from the compounds of the present invention in that the center ring sandwiched between two —NH groups is a chloro-substituted pyrimidine ring.

Moreover, TAE684 has been reported to inhibit the spread of anaplastic large cell lymphoma (ALCL) by its inhibitory activity against the NPM-ALK fusion protein (Non-patent Document 4). On the other hand, although it is described that compounds including TAE684 have inhibitory activity against focal adhesion kinase (FAK) and are thereby useful for preventing and/or treating non-small cell lung cancer and small cell lung cancer, there is no information about actual therapeutic effects on these lung cancers (Patent Document 2). Furthermore, there is no specific disclosure about the diamino heterocyclic carboxamide compounds according to the present invention.

Further reports were issued showing that ELM4-ALK is expressed in non-small cell lung cancer cells (NCI-H2228), that TFG-ALK is expressed in non-small cell lung cancer patients, and that TAE684 inhibits the growth of non-small cell lung cancer cells (NCI-H2228) (Patent Document 1 and Non-patent Documents 5 and 6).

Further, it is reported that the compound below has Syk inhibitory activity and is useful as an active ingredient in agents for preventing or treating a disease in which Syk is involved, such as allergy, inflammation, immune disease, thrombus, and cancer (Patent Document 3).

[Formula 2]

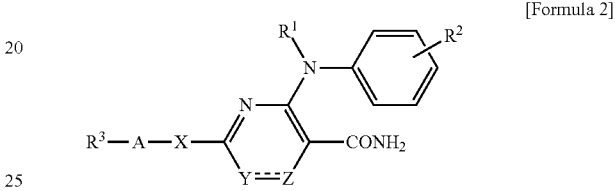

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested, and there is no specific disclosure about therapeutic effects on cancer.

Further, it is reported that the compound below has inhibitory activity against protein kinase C and is useful as an active ingredient in agents for preventing or treating a disease in which protein kinase C is involved, such as diabetic complication, ischemia, inflammation, and cancer (Patent Document 4).

[Formula 3]

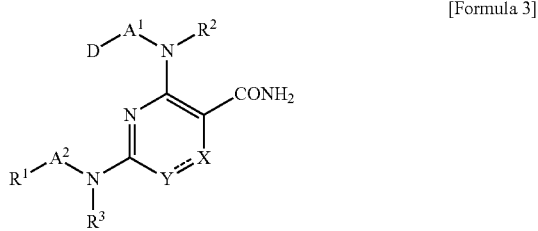

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested, and there is no specific disclosure about therapeutic effects on cancer.

Further, it is reported that the compound below has inhibitory activity against the kinase activity of EML4-ALK fusion protein and mutant EGFR protein and is useful as an active ingredient in therapeutic agents for cancer including lung cancer, etc (Patent Document 5).

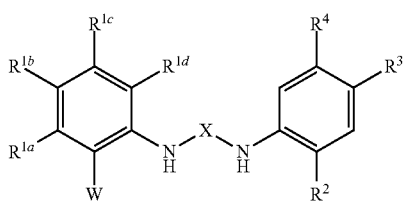

[Formula 4]

(In the formula, —X— is 1,3,5-triazine-2,4-diyl or quinazoline-2,4-diyl which may be substituted. For other symbols in the formula, refer to the publication.)

However, there is no specific disclosure about the diamino heterocyclic carboxamide compounds according to the present invention.

Further, it is reported that the compound below has inhibitory activity against various kinases including ALK and is useful for treating cell proliferative disease (Patent Document 6).

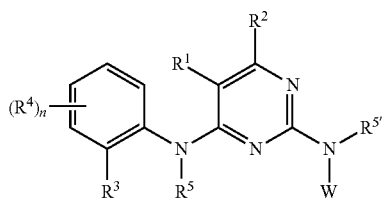

[Formula 5]

(For the symbols in the formula, refer to the publication.)

However, there is no specific disclosure about the diamino heterocyclic carboxamide compounds according to the present invention.

Further, it is reported that the compound below has inhibitory activity against ALK and/or c-Met and is useful for treating proliferative disease (Patent Document 7).

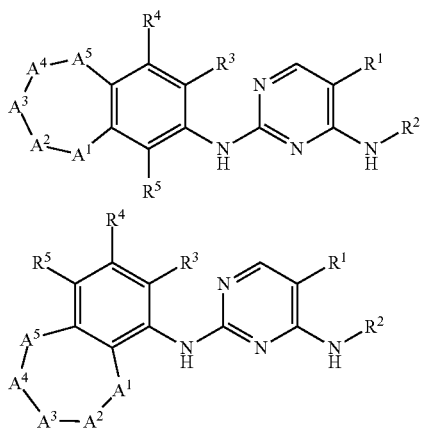

[Formula 6]

(For the symbols in the formula, refer to the publication.)

However, there is no specific disclosure about the diamino heterocyclic carboxamide compounds according to the present invention.

Further, it is reported that the compound below has inhibitory activity against various kinases including ALK and is useful for treating hyperproliferative disease and angiogenic disease (Patent Document 8).

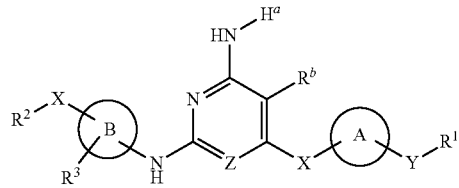

[Formula 7]

(For the symbols in the formula, refer to the publication.)

However, there is no specific disclosure about the diamino heterocyclic carboxamide compounds according to the present invention.

Further, it is reported that the compound below has inhibitory activity against various kinases including IGF-1R and ALK and is useful for treating cancer (Patent Document 9).

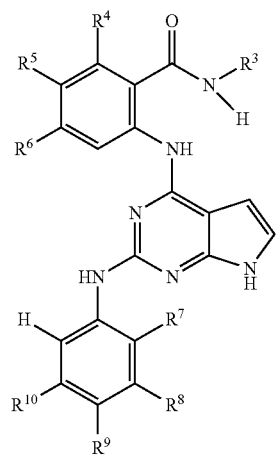

[Formula 8]

(For the symbols in the formula, refer to the publication.)

However, there is no specific disclosure about the diamino heterocyclic carboxamide compounds according to the present invention.

Further, it is reported that the compound below has Syk inhibitory activity and is useful for treating allergy, autoimmune disease, cancer, and abnormal myeloid cell growth (Patent Document 10).

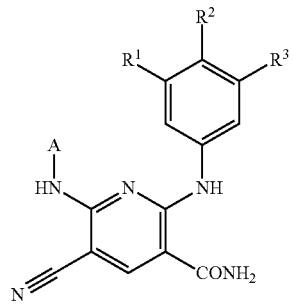

[Formula 9]

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested, and there is no specific disclosure about therapeutic effects on cancer.

Further, it is reported that the compound below has inhibitory activity against Aurora-B kinase and is useful for treating cancer, infectious disease, inflammation, and autoimmune disease (Patent Document 11).

[Formula 10]

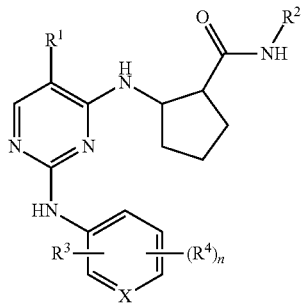

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested.

Further, it is reported that the compound below has STAT6 activation inhibitory activity and Th2 cell differentiation inhibitory activity and is useful for treating respiratory disease, asthma, and chronic obstructive pulmonary disease (Patent Document 12).

[Formula 11]

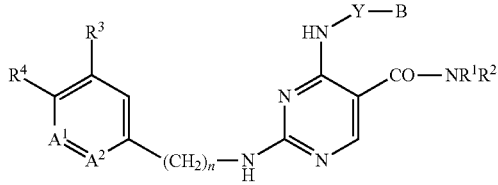

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested, and there is no specific disclosure about therapeutic effects on cancer.

Further, it is reported that the compound below has PKC inhibitory activity and is useful for treating allergy, inflammation, diabetes, cancer and the like (Patent Document 13).

[Formula 12]

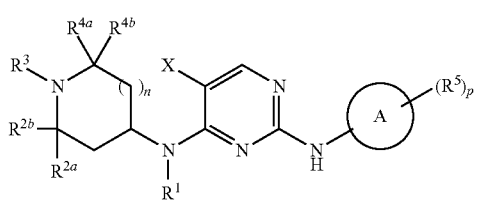

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested, and there is no specific disclosure about therapeutic effects on cancer.

Further, it is reported that the compound below has inhibitory activity against PLK-1 and PLK-3 and is useful for treating cancer, cell proliferative disease, virus infection disease, autoimmune disease, and neurodegenerative disease (Patent Document 14).

[Formula 13]

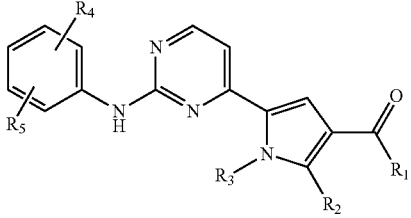

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested.

Further, it is reported that the compound below has HSP-90 inhibitory activity and is useful for treating cell proliferative disease, cancer, inflammation, arthritis, and angiogenic disease (Patent Document 15).

[Formula 14]

(For the symbols in the formula, refer to the publication.)

However, there is no specific disclosure about the diamino heterocyclic carboxamide compounds according to the present invention. Furthermore, the inhibitory activity against the kinase activity of EML44-ALK fusion protein is neither disclosed nor suggested.

Further, it is reported that the compound below has ALK, c-Met and Mps1 kinase inhibitory activity and is useful for treating hyperproliferative disease, cancer, and angiogenic disease (Patent Document 16).

[Formula 15]

(For the symbols in the formula, refer to the publication.)

However, there is no specific disclosure about the diamino heterocyclic carboxamide compounds according to the present invention.

Further, it is reported that the compound below has inhibitory activity against Syk and Jak and is useful for treating heart disease, inflammation, autoimmune disease, and cell proliferative disease (Patent Document 17).

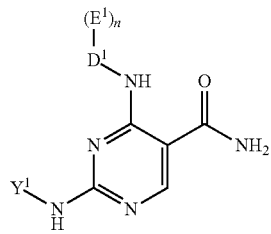

[Formula 16]

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested.

Further, it is reported that the compound below has IKK inhibitory activity and is useful for treating inflammation, immunopathy, cancer, neurodegenerative disease, age-related disease, heart disease, and dysbolism (Patent Document 18).

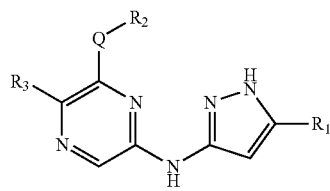

[Formula 17]

(For the symbols in the formula, refer to the publication.)

However, there is no specific disclosure about the diamino heterocyclic carboxamide compounds according to the present invention. Furthermore, the inhibitory activity against the kinase activity of EML4-ALK fusion protein is neither disclosed nor suggested.

Further, it is reported that the compound below has inhibitory activity against various kinases including ALK and is useful for treating cell proliferative disease and cancer (Patent Document 19).

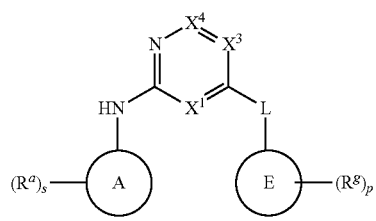

[Formula 18]

(For the symbols in the formula, refer to the publication.)

However, there is no specific disclosure about the diamino heterocyclic carboxamide compounds according to the present invention.

Further, it is reported that the compound below has ALK, ROS, IGF-1R and InsR kinase inhibitory activity and is useful for treating cell proliferative disease (Patent Document 20).

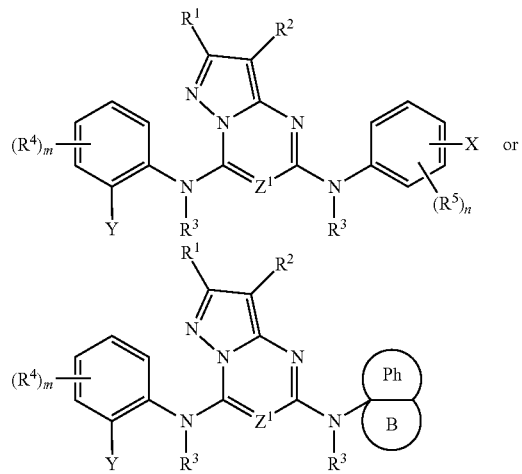

[Formula 19]

(For the symbols in the formula, refer to the publication.)

However, there is no specific disclosure about the diamino heterocyclic carboxamide compounds according to the present invention.

Further, it is reported that the compound below has ALK, ROS, IGF-1R and InsR kinase inhibitory activity and is useful for treating cell proliferative disease (Patent Document 21).

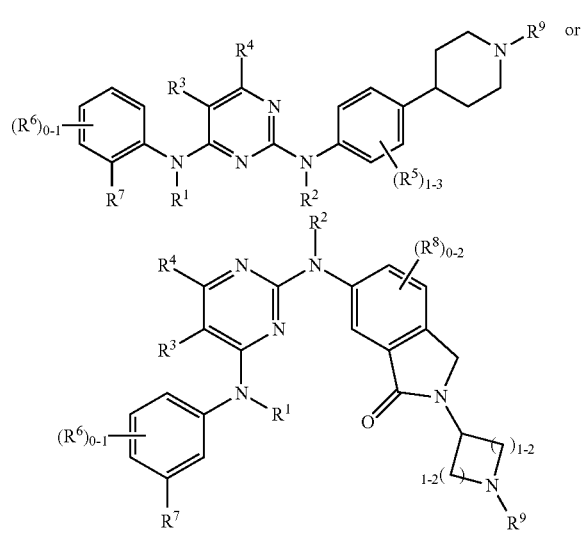

[Formula 20]

(For the symbols in the formula, refer to the publication.)

However, there is no specific disclosure about the diamino heterocyclic carboxamide compounds according to the present invention.

CITATION LIST

Patent Documents

Patent Document 1: European Patent Publication No. EP 1914240
Patent Document 2: International Publication No. WO 2004/080980

Patent Document 3: International Publication No. WO 00/75113
Patent Document 4: International Publication No. WO 00/76980
Patent Document 5: International Publication No. WO 2009/008371
Patent Document 6: International Publication No. WO 2008/073687
Patent Document 7: International Publication No. WO 2008/051547
Patent Document 8: International Publication No. WO 2009/032703
Patent Document 9: International Publication No. WO 2009/020990
Patent Document 10: Japanese Patent Publication No. 2008-13499
Patent Document 11: International Publication No. WO 2008/077885
Patent Document 12: International Publication No. WO 2004/002964
Patent Document 13: International Publication No. WO 2009/012421
Patent Document 14: International Publication No. WO 2009/040399
Patent Document 15: International Publication No. WO 2008/024974
Patent Document 16: International Publication No. WO 2009/032694
Patent Document 17: International Publication No. WO 2009/136995
Patent Document 18: International Publication No. WO 2009/089042
Patent Document 19: International Publication No. WO 2009/143389
Patent Document 20: International Publication No. WO 2009/126514
Patent Document 21: International Publication No. WO 2009/126515

Non-Patent Documents

Non-patent Document 1: International Journal of Cancer, vol. 100, p. 49, 2002
Non-patent Document 2: Nature, vol. 448, no. 2, p. 561, 2007
Non-patent Document 3: Laboratory Investigation, vol. 85, p. 1544, 2005
Non-patent Document 4: Proceedings of the National Academy of Science, vol. 104, no. 1, p. 270, 2007
Non-patent Document 5: Cell, vol. 131, p. 1190, 2007
Non-patent Document 6: Proceedings of the National Academy of Science, vol. 104, no. 50, p. 19936, 2007

SUMMARY OF INVENTION

Technical Problems

The present invention provides a compound which is useful as an active ingredient in pharmaceutical compositions, particularly pharmaceutical compositions for cancer therapy, and which can be used more safely as an active ingredient in pharmaceutical compositions.

Solution to Problems

As a result of extensive and intensive studies on compounds useful as active ingredients in pharmaceutical compositions for cancer therapy, the inventors of the present invention have found that the diamino heterocyclic carboxamide compound of the present invention has excellent inhibitory activity against the kinase activity of EML4-ALK fusion proteins, and is useful as an active ingredient in pharmaceutical compositions for cancer therapy. This finding led to the completion of the present invention.

Namely, the present invention relates to a compound of formula (I) or a salt thereof, as well as a pharmaceutical composition comprising a compound of formula (I) or a salt thereof and an excipient.

[Formula 21]

(wherein the symbols are as defined below:
—X—: a group of formula (II) or (III)

[Formula 22]

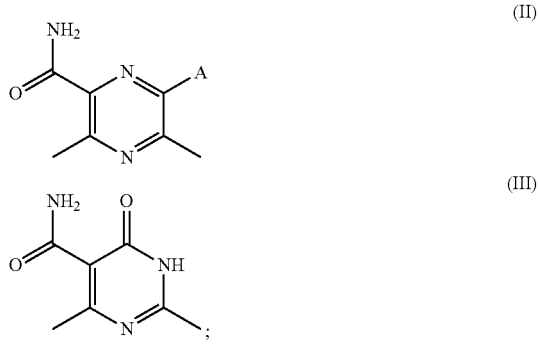

A: —H, halogen, lower alkyl, cycloalkyl, or lower alkenyl;
$R^1$:
(1) phenyl substituted with one or more groups selected from Groups $G_1$ and $G_2$ (provided that if —X— is a group of formula (II) and A is —H, or if —X— is a group of formula (III), $R^1$ is phenyl which is substituted with one or more groups selected from Group $G_2$ and may further be substituted with one or more groups selected from Groups $G_1$ and $G_2$),
(2) an aromatic heterocyclic ring which may be substituted with one or more groups selected from Group $G_3$, or
(3) a bicyclic fused ring which may be substituted with one or more $R^{ZA}$ (provided that naphthyl or benzodioxolyl which may be substituted with one or more $R^{ZA}$ is excluded);
Group $G_1$: halogen, $R^{00}$, —O—$R^{00}$, —NHSO$_2$—$R^{00}$, —SO$_2$NH$_2$, —SO$_2$NH—$R^{00}$, amino, nitro, and cyano;
$R^{00}$: lower alkyl or lower alkenyl, each of which may be substituted with one or more halogens;
Group $G_2$: —SO$_2$—$R^{00}$, —SO$_2$N($R^{00}$)$_2$, —CONH$_2$, —CON($R^{00}$)$_2$, —NHCO—$R^{00}$, —N($R^{00}$)CO—$R^{00}$, —NH—$R^{00}$, —CONH—(CH$_2$)$_n$—O—$R^{00}$, —O—(CH$_2$)$_n$—N($R^{00}$)$_2$, —O—(CH$_2$)$_n$—O—($R^{00}$), —O—(phenyl substituted with an aromatic heterocyclic ring), phenyl, aromatic heterocyclic ring, —W—Y—Z, and a group of formula (IV)

[Formula 23]

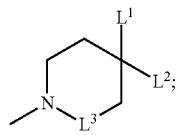

(IV)

n: an integer of 1 to 3.

$L^1$ and $L^2$: $L^1$ and $L^2$, taken together with carbon atoms to which they are respectively attached, form
(1) cycloalkyl which may be fused with phenyl, or
(2) a non-aromatic heterocyclic ring;

$L^3$: a bond or methylene;

—W—: a bond, piperidine-1,4-diyl, or piperazine-1,4-diyl;

—Y—: a bond, —CO—, —SO$_2$—, —O—(CH$_2$)$_m$—, or —N(R$^{00}$)—(CH$_2$)$_m$—;

m: an integer of 0 to 3;

Z:
(1) $R^{Z0}$, or
(2) a non-aromatic heterocyclic ring which may be substituted with one or more groups selected from Group $G_A$;

$R^{Z0}$: cycloalkyl which may be substituted with one or more $R^{00}$;

Group $G_A$: $R^{00}$ which may be substituted with a group selected from the group consisting of OH and $R^{Z0}$, halogen, —SO$_2$—R$^{00}$, —CO—R$^{00}$, —COO—R$^{00}$, —N(R$^{00}$)$_2$, oxo, and —OH;

Group $G_3$: halogen, $R^{00}$, —O—R$^{00}$, phenyl, —O-phenyl, and —W—Z;

$R^{Z4}$: $R^{00}$ or —(CH$_2$)$_n$—Z;

$R^2$:
(1) cycloalkyl which may be substituted with one or more groups selected from Group $G_4$ (it is to be noted that the cycloalkyl may be fused with phenyl or pyrazole, each of which may be substituted with one or more —O-lower alkyl),
(2) a non-aromatic heterocyclic ring which may be substituted with one or more groups selected from Group $G_4$,
(3) phenyl which may be substituted with one or more groups selected from Group $G_4$ excluding oxo,
(4) pyridyl which may be substituted with one or more groups selected from Group $G_4$ excluding oxo, or
(5) lower alkyl which may be substituted with one or more groups selected from Group $G_5$ (provided that 2-(dimethylamino)ethyl, 2-(dimethylamino)propyl, and 2-(dimethylamino)butyl are excluded);

Group $G_4$: lower alkyl which may be substituted with a group selected from Group $G_B$, amino, —N(lower alkyl)$_2$, —NH-lower alkyl, —NHCO-lower alkyl, —NHCOO-lower alkyl, —CONH$_2$, —CONH—R$^{ZB}$, —O-lower alkyl, —CO-lower alkyl, —COO-lower alkyl, —OH, —COOH, oxo, —SO$_2$-lower alkyl, $R^{ZB}$, —CO—R$^{ZB}$, cycloalkyl, and —W—Z;

Group $G_B$: amino, —OH, cycloalkyl, and $R^{ZB}$;

$R^{ZB}$: phenyl which may be substituted with a group selected from the group consisting of halogen and —O-lower alkyl;

Group $G_5$:
(1) a group of Group $G_4$,
(2) cycloalkyl which may be substituted with one or more groups selected from Group $G_4$,
(3) a non-aromatic heterocyclic ring which may be substituted with one or more groups selected from Group $G_4$,
(4) phenyl which may be substituted with one or more groups selected from Group $G_4$ excluding oxo, and
(5) pyridyl which may be substituted with one or more groups selected from Group $G_4$ excluding oxo;

$R^3$: —H or lower alkyl, or $R^2$ and $R^3$ taken together with nitrogen atoms to which they are attached may form cyclic amino which may be substituted with a group selected from Group $G_4$.)

It is to be noted that in —SO$_2$N(R$^{00}$)$_2$, —CON(R$^{00}$)$_2$, —N(R$^{00}$)CO—R$^{00}$, —O—(CH$_2$)$_n$—N(R$^{00}$)$_2$, and —N(R$^{00}$)$_2$, two $R^{00}$ contained in each of these groups may be the same or different. Further, in —N(lower alkyl)$_2$, two lower alkyl may be the same or different.

Unless otherwise specified, when symbols used in one chemical formula are also used in another chemical formula, the same symbols have the same meanings.

The present invention also relates to an inhibitor against the kinase activity of EML4-ALK fusion protein, which comprises a compound of formula (I) or a salt thereof.

Moreover, the present invention also relates to a pharmaceutical composition for cancer therapy, which comprises a compound of formula (I) or a salt thereof. It is to be noted that the pharmaceutical composition includes a therapeutic agent for cancer, which comprises a compound of formula (I) or a salt thereof.

Moreover, the present invention also relates to the use of a compound of formula (I) or a salt thereof for the manufacture of a pharmaceutical composition for cancer therapy, the use of a compound of formula (I) or a salt thereof for cancer therapy, as well as a method for cancer therapy, which comprises administering an effective amount of a compound of formula (I) or a salt thereof to a patient.

Advantageous Effect of Invention

The compound of formula (I) or a salt thereof has inhibitory activity against the kinase activity of EML4-ALK fusion protein, as well as growth inhibitory activity against EML4-ALK fusion protein-dependent cells, and can be used as an active ingredient in pharmaceutical compositions for preventing and/or treating cancer, such as lung cancer in one embodiment, non-small cell lung cancer or small cell lung cancer in another embodiment, ALK fusion polynucleotide-positive cancer in yet another embodiment, ALK fusion polynucleotide-positive lung cancer in yet another embodiment, ALK fusion polynucleotide-positive non-small cell lung cancer in yet another embodiment, ALK fusion protein-positive cancer in yet another embodiment, ALK fusion protein-positive lung cancer in yet another embodiment, ALK fusion protein-positive non-small cell lung cancer in yet another embodiment, EML4-ALK fusion polynucleotide-positive cancer in yet another embodiment, EML4-ALK fusion polynucleotide-positive lung cancer in yet another embodiment, EML4-ALK fusion polynucleotide-positive non-small cell lung cancer in yet another embodiment, EML4-ALK fusion protein-positive cancer in yet another embodiment, EML4-ALK fusion protein-positive lung cancer in yet another embodiment, or EML4-ALK fusion protein-positive non-small cell lung cancer in yet another embodiment.

DESCRIPTION OF EMBODIMENTS

The present invention will now be described in more detail below.

As used herein, the term "halogen" means F, Cl, Br or I.

The term "lower alkyl" refers to linear or branched alkyl containing 1 to 6 carbon atoms (hereinafter abbreviated as "$C_{1-6}$"). Examples include methyl, ethyl, n-propyl, isopropyl, n-butyl, isobutyl, sec-butyl, tert-butyl, n-pentyl, n-hexyl, and the like. Another embodiment is $C_{1-4}$ alkyl, and yet another embodiment is methyl, ethyl or isopropyl.

The term "lower alkenyl" refers to a monovalent group of a $C_{2-6}$ linear or branched hydrocarbon chain having at least one double bond. Examples include vinyl, propenyl, isopropenyl, butenyl, pentenyl, 1-methylvinyl, 1-methyl-2-propenyl, 1,3-butadienyl, 1,3-pentadienyl, etc. Another embodiment is isopropenyl.

The term "cycloalkyl" refers to an optionally bridged $C_{3-10}$ saturated cyclic hydrocarbon group, including cyclopropyl, cyclobutyl, cyclopentyl, cyclohexyl, cycloheptyl, cyclooctyl, bicyclo[2.2.1]heptyl, bicyclo[3.1.1]heptyl, adamantyl, etc. Other examples include those partially unsaturated, such as cyclopentenyl, cyclohexenyl, cyclooctadienyl, bicyclo[3.1.1]heptenyl, etc.

The term "cyclic amino" refers to a monovalent group of a 3- to 8-membered monocyclic non-aromatic cyclic amine which has at least one nitrogen atom and may further have the same or different one or more heteroatoms selected from the group consisting of nitrogen, oxygen and sulfur, wherein at least one nitrogen atom has a binding hand. Specific examples include aziridinyl, azetidinyl, pyrrolidinyl, piperidinyl, azepanyl, azocanyl, piperazinyl, homopiperazinyl, morpholinyl, oxazepanyl, thiomorpholinyl, thiazepanyl, and the like. Alternatively, another embodiment is a monovalent group of a 5- or 6-membered monocyclic non-aromatic cyclic amine. Yet another embodiment is pyrrolidinyl, piperidinyl, piperazinyl or morpholinyl. It should be noted that such a ring may be bridged, as exemplified by 2,5-diazabicyclo[2.2.1]heptyl, 9-azabicyclo[3.3.1]nonyl and the like, or may have an unsaturated bond in part of the ring, as exemplified by dihydropyrrolyl, dihydropyridyl, tetrahydropyridyl, tetrahydropyrazyl, or the like.

The term "non-aromatic heterocyclic ring" refers to a monovalent group of a 3- to 10-membered monocyclic non-aromatic heterocyclic ring which has 1 to 4 heteroatoms selected from the group consisting of nitrogen, oxygen and sulfur. Examples include aziridinyl, azetidinyl, pyrrolidinyl, piperidinyl, azepanyl, diazepanyl, azocanyl, piperazinyl, homopiperazinyl, morpholinyl, oxazepanyl, thiomorpholinyl, thiazepanyl, tetrahydropyranyl, tetrahydrofuryl, dioxanyl, dioxolanyl, tetrahydrothienyl, tetrahydrothiopyranyl, and the like. Another embodiment is a monovalent group of a 5- or 6-membered monocyclic non-aromatic heterocyclic ring. It should be noted that such a ring may be bridged, as exemplified by 2,5-diazabicyclo[2.2.1]heptyl, 9-azabicyclo[3.3.1]nonyl or the like, or may have an unsaturated bond in part of the ring, as exemplified by dihydropyrrolyl, dihydropyridyl, tetrahydropyridyl, tetrahydropyrazyl or the like.

The term "aromatic heterocyclic ring" refers to a monovalent group of a 5- to 10-membered monocyclic aromatic heterocyclic ring which has 1 to 4 heteroatoms selected from the group consisting of nitrogen, oxygen and sulfur. Examples include pyridyl, pyrrolyl, pyrazinyl, pyrimidinyl, pyridazinyl, imidazolyl, pyrazolyl, thiazolyl, oxazolyl, thienyl, furyl, 1,2,4-oxadiazolyl and the like. Another embodiment is pyridyl, imidazolyl, or pyrazolyl. Yet another embodiment is pyridyl.

The term "bicyclic fused ring" refers to (a) a monovalent group of a 9- to 11-membered bicyclic fused ring in which one of the two rings of the 9- to 11-membered bicyclic fused ring is a 5- to 7-membered monocyclic heterocyclic ring having 1 to 3 heteroatoms selected from the group consisting of nitrogen, oxygen and sulfur, and the other one of the two rings is a benzene ring (provided that benzodioxolyl is excluded), (b) a monovalent group of a 9- to 11-membered bicyclic fused ring in which one of the two rings of the 9- to 11-membered bicyclic fused ring is $C_{5-7}$ cycloalkyl, and the other one of the two rings is a benzene ring, or (c) azulenyl. Another embodiment is a monovalent group of a 9- to 11-membered bicyclic fused ring in which one of the two rings of the 9- to 11-membered bicyclic fused ring is a 5- to 7-membered monocyclic heterocyclic ring having 1 to 3 heteroatoms selected from the group consisting of nitrogen, oxygen and sulfur, and the other one of the two rings is a benzene ring (provided that benzodioxolyl is excluded), and examples include quinolyl, benzothiazolyl, benzoimidazolyl, indolyl, indazolyl, benzothienyl, benzofuryl, tetrahydroisoquinolyl, 2,3-dihydro-1,4-benzodioxynyl, 1,2,3-benzothiadiazolyl, 2,1,3-benzothiadiazolyl, 3,4-dihydro-1,4-benzoxadinyl, etc. Yet another embodiment is azulenyl. It is to be noted that when one of the rings is a monocyclic heterocyclic ring having a saturated carbon atom, these rings may be substituted with oxo, as exemplified by 3-oxo-3,4-dihydro-1,4-benzoxadinyl and 1-oxo-1,2,3,4-tetrahydroisoquinolyl.

The term "ALK fusion polynucleotide" refers to a fusion polynucleotide in which the ALK gene is fused with another gene and thereby expresses an oncogenic fusion tyrosine kinase. Examples include EML4-ALK fusion polynucleotide, TFG-ALK fusion polynucleotide, KIF5-ALK fusion polynucleotide, NPM-ALK fusion polynucleotide, CLTCL-ALK fusion polynucleotide, TPM3-ALK fusion polynucleotide, TPM4-ALK fusion polynucleotide, ATIC-ALK fusion polynucleotide, CARS-ALK fusion polynucleotide, SEC31L1-ALK fusion polynucleotide, RanBP2-ALK fusion polynucleotide and the like.

The term "ALK fusion protein" refers to a fusion tyrosine kinase produced by expression of ALK fusion polynucleotide.

The term "EML4-ALK fusion polynucleotide" refers to a fusion polynucleotide in which the ALK gene is fused with the EML4 gene and thereby expresses an oncogenic ALK fusion protein, including variants thereof, such as EML4-ALK fusion polynucleotide v1 (polynucleotide of SEQ ID NO: 1 of Patent Document 1), EML4-ALK fusion polynucleotide v2 (polynucleotide of SEQ ID NO: 6 of Patent Document 1) and EML4-ALK fusion polynucleotide v3 (polynucleotide of SEQ ID NO: 129 of Patent Document 1), as well as various variants (Annals of surgical oncology, vol. 17, p. 889, 2010, Molecular Cancer Research, vol. 7, p. 1466, 2009, Clinical Cancer Research, vo. 15, p. 3143, 2009, Cancer, vol. 115, p. 1723, 2009, Clinical Cancer Research, vol. 14, p. 6618, 2008, Clinical Cancer Research, vol. 14, p. 4275, 2008, etc.).

The term "EML4-ALK fusion protein" refers to a fusion tyrosine kinase created by expression of EML4-ALK fusion polynucleotide.

A compound of formula (I) or a salt thereof wherein —X— in formula (I) represents a group of formula (II) means a compound of formula (V) or a salt thereof.

[Formula 24]

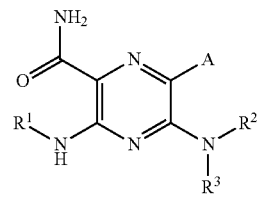

(V)

A compound of formula (I) or a salt thereof wherein —X— in formula (I) represents a group of formula (III) means a compound of formula (VI) or a salt thereof.

[Formula 25]

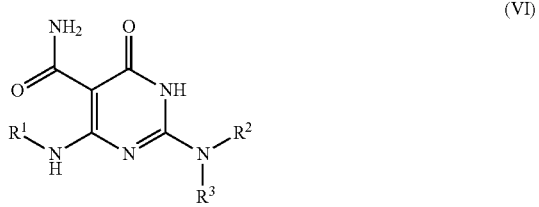

(VI)

The phrase "may be substituted" is intended to mean "unsubstituted" or "having 1 to 5 substituents." When substituted with a plurality of groups, these groups may be the same or different from each other.

The phrase "is (are) substituted" or "substituted" is intended to mean "having 1 to 5 substituents." When substituted with a plurality of groups, these groups may be the same or different from each other.

The phrase "lower alkyl which may be substituted with one or more halogens" refers to, for example, lower alkyl which may be substituted with the same or different 1 to 7 halogens. Another embodiment is lower alkyl which may be substituted with 1 to 5 halogens. Yet another embodiment is lower alkyl which may be substituted with 1 to 3 halogens.

The phrase "lower alkenyl which may be substituted with one or more halogens" refers to, for example, lower alkenyl which may be substituted with 1 to 3 halogens.

Some embodiments of the compounds of formula (I) or a salt thereof are given below.

(1) Compounds of formula (I) or a salt thereof, wherein
(1-1) —X— is a group of formula (II), and A is halogen or lower alkyl,
(1-2) —X— is a group of formula (II), and A is a halogen,
(1-3) —X— is a group of formula (II), and A is lower alkyl,
(1-4) —X— is a group of formula (II), and A is chloro, ethyl or isopropyl,
(1-5) —X— is a group of formula (II), and A is chloro,
(1-6) —X— is a group of formula (II), and A is ethyl or isopropyl,
(1-7) —X— is a group of formula (II), and A is ethyl, or
(1-8) —X— is a group of formula (II), and A is isopropyl.

(2) Compounds of formula (I) or a salt thereof, wherein
(2-1) $R^1$ is phenyl which is substituted with —W—Y—Z and may further be substituted with a group selected from the group consisting of halogen, $R^{oo}$, —O—$R^{oo}$, —NHSO$_2$—$R^{oo}$, —SO$_2$NH—$R^{oo}$, cyano, —SO$_2$—$R^{oo}$, —SO$_2$N($R^{oo}$)$_2$, —CONH—$R^{oo}$, —CON($R^{oo}$)$_2$, —NHCO—$R^{oo}$, —N($R^{oo}$)CO—$R^{oo}$, —O—(CH$_2$)$_n$—O—$R^{oo}$, and cycloalkyl, $R^{oo}$ is lower alkyl which may be substituted with one or more halogens, —Y— is a bond, and Z is a non-aromatic heterocyclic ring which may be substituted with one or more groups selected from Group $G_A$, (2-2) $R^1$ is phenyl in which the carbon at the 4-position is substituted with —W—Y—Z and the carbon at the 3-position may be substituted with a group selected from the group consisting of halogen, $R^{oo}$, and —O—$R^{oo}$, $R^{oo}$ is lower alkyl which may be substituted with one or more halogens, —Y— is a bond, and Z is a non-aromatic heterocyclic ring which may be substituted with one or more $R^{oo}$, (2-3) $R^1$ is phenyl in which the carbon at the 4-position is substituted with a group selected from the group consisting of 4-(4-methylpiperazin-1-yl)piperidin-1-yl, 4-(1-methylpiperidin-4-yl)piperazin-1-yl, 4-methylpiperazin-1-yl and 4-isopropylpiperazin-1-yl and the carbon at the 3-position may be substituted with a group selected from the group consisting of fluoro, methyl, trifluoromethyl and methoxy, (2-4) $R^1$ is phenyl in which the carbon at the 4-position is substituted with 4-(4-methylpiperazin-1-yl)piperidin-1-yl and the carbon at the 3-position may be substituted with a group selected from the group consisting of methyl, trifluoromethyl and methoxy, (2-5) $R^1$ is phenyl in which the carbon at the 4-position is substituted with 4-methylpiperazin-1-yl and the carbon at the 3-position may be substituted with a group selected from the group consisting of fluoro and methoxy, (2-6) $R^1$ is 4-{4-(4-methylpiperazin-1-yl)piperidin-1-yl}phenyl, (2-7) $R^1$ is 3-methyl-4-{4-(4-methylpiperazin-1-yl)piperidin-1-yl}phenyl, (2-8) $R^1$ is 4-{4-(4-methylpiperazin-1-yl)piperidin-1-yl}-3-(trifluoromethyl)phenyl, (2-9) $R^1$ is 3-methoxy-4-{4-(4-methylpiperazin-1-yl)piperidin-1-yl}phenyl, (2-10) $R^1$ is 4-(4-methylpiperazin-1-yl)phenyl, (2-11) $R^1$ is 3-fluoro-4-(4-methylpiperazin-1-yl)phenyl, (2-12) $R^1$ is 3-methoxy-4-(4-methylpiperazin-1-yl)phenyl, (2-13) $R^1$ is 3-methyl-4-{4-(1-methylpiperidin-4-yl)piperazin-1-yl}phenyl, or (2-14) $R^1$ is 4-(4-isopropylpiperazin-1-yl)-3-methylphenyl.

(3) Compounds of formula (I) or a salt thereof, wherein
(3-1) $R^2$ is
(i) cycloalkyl which may be substituted with one or more groups selected from the group consisting of —N(lower alkyl)$_2$, lower alkyl, —COO-lower alkyl, —OH, —COOH, —CONH—$R^{ZB}$, and morpholinyl, or
(ii) a non-aromatic heterocyclic ring which may be substituted with one or more groups selected from the group consisting of lower alkyl, —CO-lower alkyl, oxo, —CO—$R^{ZB}$, and benzyl, (3-2) $R^2$ is cycloalkyl which may be substituted with one or more groups selected from the group consisting of —N(lower alkyl)$_2$, lower alkyl, —COO-lower alkyl, —OH, —COOH, —CONH—$R^{ZB}$, and morpholinyl, (3-3) $R^2$ is a non-aromatic heterocyclic ring which may be substituted with one or more groups selected from the group consisting of lower alkyl, —CO-lower alkyl, oxo, —CO—$R^{ZB}$, and benzyl, (3-4) $R^2$ is
(i) cyclohexyl which may be substituted with one or more groups selected from the group consisting of —N(lower alkyl)$_2$, lower alkyl, —COO-lower alkyl, —OH, —COOH, —CONH—$R^{ZB}$, and morpholinyl,
(ii) piperidinyl which may be substituted with one or more groups selected from the group consisting of lower alkyl, —CO-lower alkyl, oxo, —CO—$R^{ZB}$, and benzyl, or
(iii) tetrahydropyranyl, (3-5) $R^2$ is cyclohexyl which may be substituted with one or more groups selected from the group consisting of —N(lower alkyl)$_2$, lower alkyl, —COO-lower alkyl, —OH, —COOH, —CONH—$R^{ZB}$, and morpholinyl, (3-6) $R^2$ is piperidinyl which may be substituted with one or more groups selected from the group consisting of lower alkyl, —CO-lower alkyl, oxo, —CO—$R^{ZB}$, and benzyl, (3-7) R² is tetrahydropyranyl,
(3-8) R² is 4-hydroxycyclohexyl, 4-hydroxy-4-methylcyclohexyl, or tetrahydropyran-4-yl,
(3-9) R² is 4-hydroxycyclohexyl,
(3-10) R² is 4-hydroxy-4-methylcyclohexyl, or
(3-11) R² is tetrahydropyran-4-yl.
(4) Compounds of formula (I) or a salt thereof, wherein R³ is —H.
(5) Compounds, in which any combination of two or more of (1) to (4) shown above is applied. Examples of embodiments of the combination include:
 (5-1) Compounds or a salt thereof, in which (1) and (4) shown above are applied,
 (5-2) Compounds or a salt thereof, in which (1), (2), and (4) shown above are applied,
 (5-3) Compounds or a salt thereof, in which (1), (2), (3), and (4) shown above are applied,
 (5-4) Compounds or a salt thereof, in which (1-1), (2-1), (3-1), and (4) shown above are applied,
 (5-5) Compounds or a salt thereof, in which (1-4), (2-1), (3-1), and (4) shown above are applied,
 (5-6) Compounds or a salt thereof, in which (1-4), (2-2), (3-1), and (4) shown above are applied,
 (5-7) Compounds or a salt thereof, in which (1-4), (2-3), (3-1), and (4) shown above are applied,
 (5-8) Compounds or a salt thereof, in which (1-4), (2-3), (3-8), and (4) shown above are applied, and
 (5-9) Compounds or a salt thereof, in which any consistent combination of two or more selected from the group consisting of (1-5), (1-7), (1-8), (2-6), (2-7), (2-8), (2-9), (2-10), (2-11), (2-12), (2-13), (2-14), (3-9), (3-10), (3-11) and (4) shown above is applied.
Other embodiments of the compound of formula (I) or a salt thereof are given below.
(6) Compounds of formula (I) or a salt thereof, wherein
 (6-1) —X— is a group of formula (II), and A is lower alkyl,
 (6-2) —X— is a group of formula (II), and A is ethyl or isopropyl,
 (6-3) —X— is a group of formula (II), and A is ethyl, or
 (6-4) —X— is a group of formula (II), and A is isopropyl.
(7) Compounds of formula (I) or a salt thereof, wherein
 (7-1) R¹ is phenyl in which the carbon at the 4-position is substituted with —W—Y—Z and, as another substituent, the carbon at the 2- or 3-position may be substituted with R⁰⁰ or —O—R⁰⁰, and —Y— is a bond,
 (7-2) R¹ is phenyl in which the carbon at the 4-position is substituted with —W—Y—Z and, as another substituent, the carbon at the carbon at the 3-position may be substituted with R⁰⁰ or —O—R⁰⁰, —W— is piperidine-1,4-diyl (attached via the nitrogen atom to phenyl to which —W— is attached) or a bond, —Y— is a bond, and —Z is piperazin-1-yl in which the nitrogen atom at the 4-position may be substituted with lower alkyl,
 (7-3) R¹ is phenyl in which the carbon at the 4-position is substituted with 4-(4-methylpiperazin-1-yl)piperidin-1-yl and, as another substituent, the carbon at the 3-position may be substituted with methyl, trifluoromethyl, methoxy, or ethoxy,
 (7-4) R¹ is 3-methyl-4-{4-(4-methylpiperazin-1-yl)piperidin-1-yl}phenyl,
 (7-5) R¹ is 4-{4-(4-methylpiperazin-1-yl)piperidin-1-yl}-3-(trifluoromethyl)phenyl,
 (7-6) R¹ is 3-methoxy-4-{4-(4-methylpiperazin-1-yl)piperidin-1-yl}phenyl,
 (7-7) R¹ is 3-ethoxy-4-{4-(4-methylpiperazin-1-yl)piperidin-1-yl}phenyl,
 (7-8) R¹ is 4-{4-(4-methylpiperazin-1-yl)piperidin-1-yl}phenyl,
 (7-9) R¹ is phenyl in which the carbon at the 4-position is substituted with 4-methylpiperazin-1-yl or 4-isopropylpiperazin-1-yl and, as another substituent, the carbon at the 3-position may be substituted with methyl, trifluoromethyl, or methoxy,
 (7-10) R¹ is 3-methyl-4-(4-methylpiperazin-1-yl)phenyl,
 (7-11) R¹ is 4-(4-methylpiperazin-1-yl)-3-(trifluoromethyl)phenyl,
 (7-12) R¹ is 3-methoxy-4-(4-methylpiperazin-1-yl)phenyl,
 (7-13) R¹ is 4-(4-methylpiperazin-1-yl)phenyl,
 (7-14) R¹ is 4-(4-isopropylpiperazin-1-yl)-3-methylphenyl,
 (7-15) R¹ is phenyl in which the carbon at the 3-position is substituted with —SO₂—R⁰⁰,
 (7-16) R¹ is 3-(methylsulfonyl)phenyl,
 (7-17) R¹ is phenyl in which the carbon at the 3-position is substituted with —W—Y—Z and, as another substituent, the carbon at the 4-position may be substituted with —O—R⁰⁰, —W— is a bond, and —Y— is a bond,
 (7-18) R¹ is phenyl in which the carbon at the 3-position is substituted with 4-methylpiperazin-1-yl and, as another substituent, the carbon at the 4-position may be substituted with methoxy,
 (7-19) R¹ is 4-methoxy-3-(4-methylpiperazin-1-yl)phenyl,
 (7-20) R¹ is 3-(4-methylpiperazin-1-yl)phenyl,
 (7-21) R¹ is 2-methoxy-4-{4-(4-methylpiperazin-1-yl)piperidin-1-yl}phenyl,
 (7-22) R¹ is 1-methylindazol-6-yl,
 (7-23) R¹ is 4-morpholin-4-ylphenyl,
 (7-24) R¹ is 4-(1-methylpiperidin-4-yl)phenyl,
 (7-25) R¹ is 4-{4-(cyclopropylmethyl)piperazin-1-yl}-3-(trifluoromethyl)phenyl, or
 (7-26) R¹ is 4-{3-(dimethylamino)pyrrolidin-1-yl}-3-(trifluoromethyl)phenyl.
(8) Compounds of formula (I) or a salt thereof, wherein
 (8-1) R² is cycloalkyl substituted with —OH and lower alkyl,
 (8-2) R² is cyclohexyl substituted with —OH and lower alkyl,
 (8-3) R² is cyclohexyl in which the carbon at the 4-position is substituted with —OH and lower alkyl,
 (8-4) R² is cyclohexyl in which the carbon at the 4-position is substituted with —OH and methyl,
 (8-5) R² is cycloalkyl substituted with —OH,
 (8-6) R² is cyclohexyl substituted with —OH,
 (8-7) R² is 4-hydroxycyclohexyl,
 (8-8) R² is a non-aromatic heterocyclic ring which may be substituted with lower alkyl,
 (8-9) R² is tetrahydropyranyl which may be substituted with lower alkyl, or piperidinyl which may be substituted with lower alkyl,
 (8-10) R² is tetrahydropyran-4-yl,
 (8-11) R² is piperidin-4-yl in which the nitrogen atom at the 1-position may be substituted with lower alkyl,
 (8-12) R² is 1-methylpiperidin-4-yl, or
 (8-13) R² is piperidin-4-yl.
(9) Compounds of formula (I) or a salt thereof, wherein R³ is —H.
(10) Compounds of (6-3) shown above or a salt thereof.
(11) Compounds of (7-4), (7-5), (7-6), (7-7), (7-8), (7-10), (7-13), or (7-14) shown above or a salt thereof.
(12) Compounds of (8-4), (8-7), (8-10), or (8-13) shown above or a salt thereof.

(13) Compounds, in which
(13-1) any combination of two or more of (6) to (9) shown above is applied, or a salt thereof, or
(13-2) any combination of two or more of (9) to (12) shown above is applied, or a salt thereof.

Examples of specific compounds falling within the present invention include the following compounds.

6-ethyl-5-[(trans-4-hydroxycyclohexyl)amino]-3-{[4-(4-methylpiperazin-1-yl)phenyl]amino}pyrazine-2-carboxamide, 6-ethyl-5-[(trans-4-hydroxycyclohexyl)amino]-3-({4-[4-(4-methylpiperazin-1-yl)piperidin-1-yl]phenyl}amino)pyrazine-2-carboxamide, 5-[(trans-4-hydroxycyclohexyl)amino]-6-isopropyl-3-{[4-(4-methylpiperazin-1-yl)phenyl]amino}pyrazine-2-carboxamide, 6-ethyl-5-[(trans-4-hydroxycyclohexyl)amino]-3-({4-[4-(4-methylpiperazin-1-yl)piperidin-1-yl]-3-(trifluoromethyl)phenyl}amino)pyrazine-2-carboxamide, 6-ethyl-5-[(trans-4-hydroxycyclohexyl)amino]-3-({3-methyl-4-[4-(4-methylpiperazin-1-yl)piperidin-1-yl]phenyl}amino)pyrazine-2-carboxamide, 5-[(trans-4-hydroxycyclohexyl)amino]-6-isopropyl-3-({4-[4-(4-methylpiperazin-1-yl)piperidin-1-yl]-3-(trifluoromethyl)phenyl}amino)pyrazine-2-carboxamide, 6-ethyl-5-[(cis-4-hydroxy-4-methylcyclohexyl)amino]-3-({3-methyl-4-[4-(4-methylpiperazin-1-yl)piperidin-1-yl]phenyl}amino)pyrazine-2-carboxamide, 6-ethyl-5-[(trans-4-hydroxycyclohexyl)amino]-3-{[4-(4-isopropylpiperazin-1-yl)-3-methylphenyl]amino}pyrazine-2-carboxamide, 6-ethyl-5-[(trans-4-hydroxy-4-methylcyclohexyl)amino]-3-({3-methyl-4-[4-(4-methylpiperazin-1-yl)piperidin-1-yl]phenyl}amino)pyrazine-2-carboxamide, 6-ethyl-3-({3-methyl-4-[4-(4-methylpiperazin-1-yl)piperidin-1-yl]phenyl}amino)-5-(tetrahydro-2H-pyran-4-ylamino)pyrazine-2-carboxamide, 6-chloro-5-[(trans-4-hydroxycyclohexyl)amino]-3-({3-methyl-4-[4-(4-methylpiperazin-1-yl)piperidin-1-yl]phenyl}amino)pyrazine-2-carboxamide, 6-ethyl-3-({4-[4-(4-methylpiperazin-1-yl)piperidin-1-yl]phenyl}amino)-5-(tetrahydro-2H-pyran-4-ylamino)pyrazine-2-carboxamide, 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide, 6-isopropyl-3-({4-[4-(4-methylpiperazin-1-yl)piperidin-1-yl]phenyl}amino)-5-(tetrahydro-2H-pyran-4-ylamino)pyrazine-2-carboxamide, 6-ethyl-3-{[3-fluoro-4-(4-methylpiperazin-1-yl)phenyl]amino}-5-(tetrahydro-2H-pyran-4-ylamino)pyrazine-2-carboxamide, 6-isopropyl-3-{[3-methoxy-4-(4-methylpiperazin-1-yl)phenyl]amino}-5-(tetrahydro-2H-pyran-4-ylamino)pyrazine-2-carboxamide, 6-isopropyl-3-{[4-(4-methylpiperazin-1-yl)phenyl]amino}-5-(tetrahydro-2H-pyran-4-ylamino)pyrazine-2-carboxamide, or 6-ethyl-3-({3-methyl-4-[4-(1-methylpiperidin-4-yl)piperazin-1-yl]phenyl}amino)-5-(tetrahydro-2H-pyran-4-ylamino)pyrazine-2-carboxamide, or a salt thereof.

Examples of specific compounds falling within the present invention include those selected from Compound groups P and Q shown below.

Compound group P:
a group consisting of 6-ethyl-5-[(trans-4-hydroxycyclohexyl)amino]-3-({4-[4-(4-methylpiperazin-1-yl)piperidin-1-yl]phenyl}amino)pyrazine-2-carboxamide, 6-ethyl-5-[(trans-4-hydroxycyclohexyl)amino]-3-{[4-(4-methylpiperazin-1-yl)-3-(trifluoromethyl)phenyl]amino}pyrazine-2-carboxamide, 6-ethyl-5-[(trans-4-hydroxycyclohexyl)amino]-3-({4-[4-(4-methylpiperazin-1-yl)piperidin-1-yl]-3-(trifluoromethyl)phenyl}amino)pyrazine-2-carboxamide, 6-ethyl-5-[(trans-4-hydroxycyclohexyl)amino]-3-{[3-methyl-4-(4-methylpiperazin-1-yl)phenyl]amino}pyrazine-2-carboxamide, 6-ethyl-5-[(trans-4-hydroxycyclohexyl)amino]-3-({3-methyl-4-[4-(4-methylpiperazin-1-yl)piperidin-1-yl]phenyl}amino)pyrazine-2-carboxamide, 6-ethyl-5-[(cis-4-hydroxy-4-methylcyclohexyl)amino]-3-({3-methyl-4-[4-(4-methylpiperazin-1-yl)piperidin-1-yl]phenyl}amino)pyrazine-2-carboxamide, 6-ethyl-5-[(trans-4-hydroxycyclohexyl)amino]-3-{[4-(4-isopropylpiperazin-1-yl)-3-methylphenyl]amino}pyrazine-2-carboxamide, 3-({3-ethoxy-4-[4-(4-methylpiperazin-1-yl)piperidin-1-yl]phenyl}amino)-6-ethyl-5-[(trans-4-hydroxycyclohexyl)amino]pyrazine-2-carboxamide, 6-ethyl-5-[(trans-4-hydroxy-4-methylcyclohexyl)amino]-3-({3-methyl-4-[4-(4-methylpiperazin-1-yl)piperidin-1-yl]phenyl}amino)pyrazine-2-carboxamide, 6-ethyl-3-({3-methyl-4-[4-(4-methylpiperazin-1-yl)piperidin-1-yl]phenyl}amino)-5-(tetrahydro-2H-pyran-4-ylamino)pyrazine-2-carboxamide, 6-ethyl-3-({3-methyl-4-[4-(4-methylpiperazin-1-yl)piperidin-1-yl]phenyl}amino)-5-(piperidin-4-ylamino)pyrazine-2-carboxamide, 6-ethyl-3-{[4-(4-methylpiperazin-1-yl)phenyl]amino}-5-(tetrahydro-2H-pyran-4-ylamino)pyrazine-2-carboxamide, 6-ethyl-3-({4-[4-(4-methylpiperazin-1-yl)piperidin-1-yl]phenyl}amino)-5-(tetrahydro-2H-pyran-4-ylamino)pyrazine-2-carboxamide, and 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide, as well as salts of these compounds.

Compound group Q:
a group consisting of 6-ethyl-5-[(trans-4-hydroxycyclohexyl)amino]-3-{[3-(methylsulfonyl)phenyl]amino}pyrazine-2-carboxamide, 6-ethyl-5-[(trans-4-hydroxy-4-methylcyclohexyl)amino]-3-{[3-(methylsulfonyl)phenyl]amino}pyrazine-2-carboxamide, 6-ethyl-5-[(trans-4-hydroxycyclohexyl)amino]-3-({2-methoxy-4-[4-(4-methylpiperazin-1-yl)piperidin-1-yl]phenyl}amino)pyrazine-2-carboxamide, 6-ethyl-5-[(trans-4-hydroxycyclohexyl)amino]-3-{[4-(4-methylpiperazin-1-yl)phenyl]amino}pyrazine-2-carboxamide, 6-ethyl-5-[(trans-4-hydroxycyclohexyl)amino]-3-[(1-methyl-1H-indazol-6-yl)amino]pyrazine-2-carboxamide, 6-ethyl-5-[(trans-4-hydroxycyclohexyl)amino]-3-({3-methoxy-4-[4-(4-methylpiperazin-1-yl)piperidin-1-yl]phenyl}amino)pyrazine-2-carboxamide, 5-[(trans-4-hydroxycyclohexyl)amino]-6-isopropyl-3-{[4-(4-methylpiperazin-1-yl)phenyl]amino}pyrazine-2-carboxamide, 6-ethyl-5-[(trans-4-hydroxycyclohexyl)amino]-3-{[3-(4-methylpiperazin-1-yl)phenyl]amino}pyrazine-2-carboxamide, 6-ethyl-5-[(trans-4-hydroxycyclohexyl)amino]-3-{[3-methoxy-4-(4-methylpiperazin-1-yl)phenyl]amino}pyrazine-2-carboxamide,
6-ethyl-5-[(trans-4-hydroxycyclohexyl)amino]-3-[(4-morpholin-4-ylphenyl)amino]pyrazine-2-carboxamide,
6-ethyl-5-[(trans-4-hydroxycyclohexyl)amino]-3-{[4-methoxy-3-(4-methylpiperazin-1-yl)phenyl]amino}pyrazine-2-carboxamide,
6-ethyl-5-[(trans-4-hydroxycyclohexyl)amino]-3-{[4-(1-methylpiperidin-4-yl)phenyl]amino}pyrazine-2-carboxamide,
5-[(trans-4-hydroxycyclohexyl)amino]-6-isopropyl-3-({4-[4-(4-methylpiperazin-1-yl)piperidin-1-yl]-3-(trifluoromethyl)phenyl}amino)pyrazine-2-carboxamide,
6-ethyl-5-[(cis-4-hydroxy-4-methylcyclohexyl)amino]-3-{[3-methyl-4-(4-methylpiperazin-1-yl)phenyl]amino}pyrazine-2-carboxamide,
3-({4-[4-(cyclopropylmethyl)piperazin-1-yl]-3-(trifluoromethyl)phenyl}amino)-6-ethyl-5-[(trans-4-hydroxycyclohexyl)amino]pyrazine-2-carboxamide,
3-({4-[3-(dimethylamino)pyrrolidin-1-yl]-3-(trifluoromethyl)phenyl}amino)-6-ethyl-5-[(trans-4-hydroxycyclohexyl)amino]pyrazine-2-carboxamide,
6-ethyl-5-[(cis-4-ethyl-4-hydroxycyclohexyl)amino]-3-({3-methyl-4-[4-(4-methylpiperazin-1-yl)piperidin-1-yl]phenyl}amino)pyrazine-2-carboxamide,
6-ethyl-5-[(trans-4-ethyl-4-hydroxycyclohexyl)amino]-3-({3-methyl-4-[4-(4-methylpiperazin-1-yl)piperidin-1-yl]phenyl}amino)pyrazine-2-carboxamide,
6-ethyl-5-[(cis-4-hydroxy-4-isopropylcyclohexyl)amino]-3-({3-methyl-4-[4-(4-methylpiperazin-1-yl)piperidin-1-yl]phenyl}amino)pyrazine-2-carboxamide,
6-ethyl-5-[(trans-4-hydroxy-4-isopropylcyclohexyl)amino]-3-({3-methyl-4-[4-(4-methylpiperazin-1-yl)piperidin-1-yl]phenyl}amino)pyrazine-2-carboxamide, and
6-ethyl-3-({3-methyl-4-[4-(4-methylpiperazin-1-yl)piperidin-1-yl]phenyl}amino)-5-[(1-methylpiperidin-4-yl)amino]pyrazine-2-carboxamide, as well as salts of these compounds.

The compounds of formula (I) may have tautomers and/or geometrical isomers (including cis-trans isomers of compounds having a saturated ring group such as a cycloalkyl group), depending on the type of their substituents. Even when the compounds of formula (I) appear herein only in one isomer form, the present invention encompasses the other isomers, and also encompasses separated isomers or mixtures thereof.

Further, since some compounds of formula (I) have an asymmetric carbon atom or axial asymmetry, optical isomers based on this asymmetry may also exist. The present invention also encompasses separated optical isomers of the compounds of formula (I) or mixtures thereof.

Furthermore, the present invention encompasses pharmaceutically acceptable prodrugs of the compounds represented by formula (I). The term "pharmaceutically acceptable prodrug" refers to a compound having a group which can be converted into an amino group, a hydroxyl group, a carboxyl group or the like by solvolysis or under physiological conditions. Examples of a prodrug-forming group include those described in Prog. Med., 5, 2157-2161 (1985) or those described in "Development of Pharmaceuticals" (Hirokawa Publishing, 1990) vol. 7, Molecular Design 163-198.

Likewise, salts of the compounds of formula (I) are pharmaceutically acceptable salts of the compounds of formula (I). The compounds of formula (I) may form acid or base addition salts, depending on the type of their substituents. Specific examples include acid addition salts with inorganic acids (e.g., hydrochloric acid, hydrobromic acid, hydroiodic acid, sulfuric acid, nitric acid, phosphoric acid, and the like) or with organic acids (e.g., formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like), salts with inorganic bases (e.g., sodium, potassium, magnesium, calcium, aluminum, and the like) or with organic bases (e.g., methylamine, ethylamine, ethanolamine, lysine, ornithine, and the like), salts with various amino acids and amino acid derivatives (e.g., acetylleucine, and the like), as well as ammonium salt, etc.

Moreover, the present invention also encompasses the compounds of formula (I) and salts thereof in the form of various hydrates, solvates, and crystalline polymorphic substances. The present invention also encompasses the compounds labeled with various radioactive or non-radioactive isotopes.

The compounds of formula (I) and pharmaceutically acceptable salts thereof can be prepared by applying various known synthesis methods on the basis of characteristics derived from their skeletal structure or the type of their substituents. In some cases, depending on the type of functional group, it is technically effective to replace such a functional group with an appropriate protecting group (a group which can be easily converted into the original functional group) at the starting material stage or at the intermediate stage. Examples of such a protecting group include those described in Greene and Wuts, "Greene's Protective Groups in Organic Synthesis (fourth edition, 2007)" and so on, which may be selected and used as appropriate, depending on reaction conditions. In such a method, after introduction of the protecting group and subsequent reaction, the protecting group may be removed if necessary to obtain a desired compound.

Likewise, a prodrug of the compound of formula (I) can be prepared by introducing a specific group at the starting material stage or at the intermediate stage, as in the case of the above protecting group, or by subjecting the obtained compound of formula (I) to further reaction. The reaction may be accomplished by applying conventional esterification, amidation, dehydration or other techniques known to those skilled in the art.

Explanation will be given below of typical processes for preparing the compounds of formula (I). Each process may also be accomplished by reference to the documents cited in this explanation. It should be noted that the processes of the present invention are not limited to the examples illustrated below.

(Preparation Process 1)

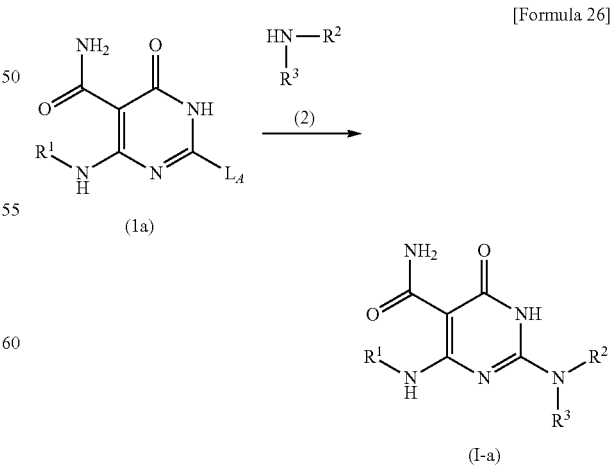

[Formula 26]

(In the formula, -L$_A$ represents a leaving group, and examples include lower alkylsulfanyl.)

This process is intended to prepare the compound of the present invention (I-a) by reacting compound (1a) with compound (2).

In this reaction, compounds (1a) and (2) are used in equal amounts or one of them is used in an excessive amount. A mixture of these compounds is stirred in a solvent inert to the reaction or in the absence of a solvent under cooling to reflux conditions, preferably at 0° C. to 200° C., generally for 0.1 hours to 5 days. The reaction may be performed using a microwave reaction system, because it is advantageous for smooth reaction in some cases. A solvent used for this purpose is not particularly limited, as long as it is inert to the reaction, and examples include aromatic hydrocarbons (e.g., benzene, toluene, xylene), ethers (e.g., diethyl ether, tetrahydrofuran (THF), dioxane, dimethoxyethane), halogenated hydrocarbons (e.g., 1,2-dichloroethane, chloroform), alcohols (e.g., methanol, ethanol, 2-propanol), 1-methyl-2-pyrrolidinone (NMP), N,N-dimethylformamide (DMF), N,N-dimethylacetamide (DMA), 1,3-dimethyl-2-imidazolidinone (DMI), dimethyl sulfoxide (DMSO), acetonitrile, and mixtures thereof. The reaction may be performed in the presence of an organic base (e.g., triethylamine, N,N-diisopropylethylamine, N-methylmorpholine, or the like) or an inorganic base (e.g., potassium carbonate, sodium carbonate, potassium hydroxide, or the like), because it is advantageous for smooth reaction in some cases.

When the reaction is performed in the presence of such a base as shown above, depending on the properties or the like of starting compounds, the desired reaction is impossible or difficult to proceed, for example, due to decomposition or the like of the starting compounds. In this case, the reaction may be performed in the presence of a mineral acid (e.g., hydrochloric acid, hydrobromic acid, and the like), an organic acid (e.g., acetic acid, propionic acid, and the like) or a sulfonic acid (e.g., methanesulfonic acid, p-toluenesulfonic acid, and the like), because it is advantageous for smooth reaction in some cases. Further, when $-L_A$ is lower alkylsulfanyl, the S atom may be oxidized with various oxidizing agents such as Oxone®, m-chloroperbenzoic acid (mCPBA) and peracetic acid to convert the lower alkylsulfanyl into lower alkylsulfinyl or lower alkylsulfonyl and then the lower alkylsulfinyl or lower alkylsulfonyl may be reacted with compound (2), because it is advantageous for smooth reaction in some cases.

Documents

S. R. Sandler and W. Karo, "Organic Functional Group Preparations," second edition, vol. 1, Academic Press Inc., 1991

The Chemical Society of Japan, "Fifth Series of Experimental Chemistry," vol. 14 (2005) (MARUZEN Co., Ltd., Japan)

(Preparation Process 2)

[Formula 27]

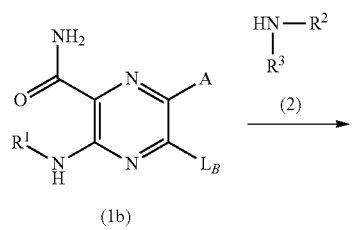

(1b)

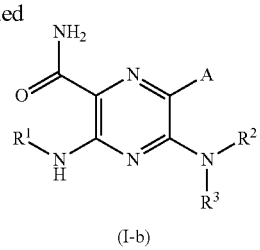

(I-b)

(In the formula, $-L_B$ represents a leaving group, and examples include a halogen (e.g., F, Cl), a sulfonyloxy group (e.g., methanesulfonyloxy, p-toluenesulfonyloxy, trifluoromethanesulfonyloxy), lower alkylsulfanyl, and lower alkylsulfonyl.)

This process is intended to prepare the compound of the present invention (I-b) by reacting compound (1b) with compound (2).

In this reaction, the procedure of Preparation Process 1 may be applied.

(Starting Material Synthesis 1)

[Formula 28]

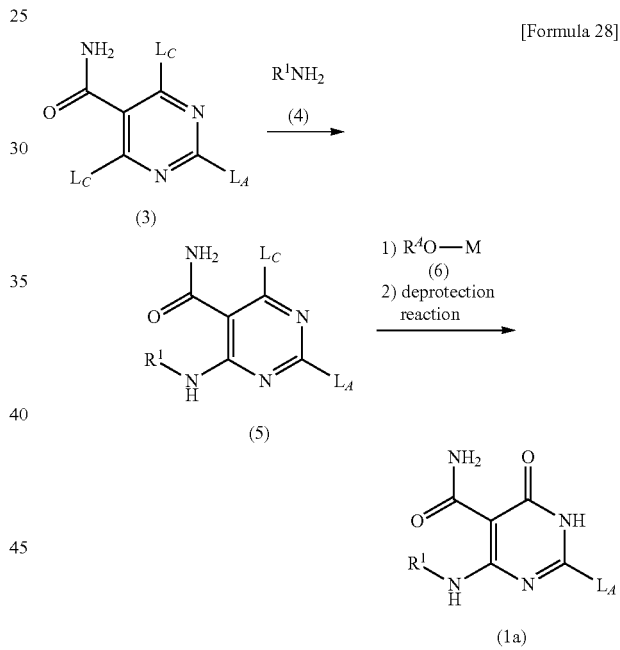

(In the formula, $-L_C$ represents a leaving group, and examples include a halogen (e.g., F, Cl) and a sulfonyloxy group (e.g., methanesulfonyloxy, p-toluenesulfonyloxy, trifluoromethanesulfonyloxy); $R^4$ represents acyl, benzyl, lower alkyl, or —H; and M represents an alkali metal.)

This process is intended to prepare compound (1a) by reacting compound (5), which is obtained by reacting compound (3) with compound (4), with compound (6) and thereafter subjecting to deprotection reaction to remove $R^4$.

In the reaction which gives compound (5), the procedure of Preparation Process 1 may be applied. In the reaction which gives compound (1a), the procedure of Preparation Process 1 may be applied and the reaction may be performed using compound (6) or a reagent which produces compound (6) in the system, and thereafter deprotection reaction may be conducted under reaction conditions which are selected as appropriate from, for example, reaction conditions described in Greene and Wuts, "Greene's Protective Groups in Organic Synthesis (fourth edition, 2007)." Examples of compound (6) include sodium acetate and sodium methoxide. It is to be noted that compound (1a) can also be prepared by performing the reaction using a hydrogen peroxide solution in place of compound (6) and thereafter performing acid treatment with hydrochloric acid or the like.

(Starting Material Synthesis 2)

[Formula 29]

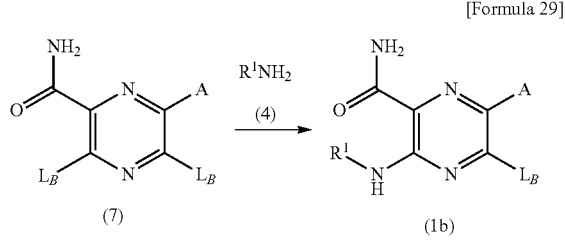

This process is intended to prepare compound (1b) by reacting compound (7) with compound (4).

In this reaction, the procedure of Preparation Process 1 may be applied.

The compound of formula (I) is isolated and purified as a free compound or as a pharmaceutically acceptable salt, hydrate, solvate or crystalline polymorphic substance thereof. A pharmaceutically acceptable salt of the compound of formula (I) may also be prepared by being subjected to conventional salt-forming reaction.

Isolation and purification may be accomplished by applying conventional chemical operations such as extraction, fractional crystallization, various types of fractionation chromatography, etc.

Various isomers can be prepared by selecting appropriate starting compounds or can be separated on the basis of differences in the physical and chemical properties of isomers. For example, optical isomers can be derived into optically pure isomers by conventional optical resolution techniques (e.g., fractional crystallization resulting in a diastereomer salt with an optically active base or acid, chromatography on a chiral column or the like, and the like). They can also be prepared from appropriate optically active starting compounds.

The compounds of formula (I) were confirmed for their pharmacological activity in the following tests. Unless otherwise specified, the test examples shown below may be accomplished by a method described in EP 1914240 or any publicly-known method and, when using commercially available reagents, kits, or the like, may be accomplished in accordance with the instructions attached to these commercially available products. It is to be noted that the term "EML4-ALK fusion protein v1" refers to a polypeptide of the amino acid sequence represented by SEQ ID NO: 2 of Patent Document 1, and the term "EML4-ALK fusion protein v3" refers to a polypeptide of the amino acid sequence represented by SEQ ID NO: 130 of Patent Document 1.

Test Example 1

Evaluation of Inhibitory Activity Against the Kinase Activity of EML4-ALK Fusion Protein A recombinant retrovirus was created from expression plasmid FLAG-EML4-ALKv1/pMX-iresCD8 in which cDNA for EML4-ALK fusion protein v1 was integrated, and injected into mouse lymphoid cell line BA/F3 cells. Using a magnetic bead reagent for cell separation and a purification column (anti-CD8 monoclonal antibody immobilized on magnetic beads and a MiniMACS purification column; both are products of Miltenyi Biotec Inc.), cell surface CD8-expressing cells were purified to establish EML4-ALK fusion protein v1-expressing BA/F3 cells. From the cells, EML4-ALK fusion protein v1 was purified and subjected to kinase activity evaluation. EML4-ALK fusion protein v1 was investigated for its phosphorylation activity toward a peptide substrate by using a kinase activity detection kit (HTRF KinEASE-TK; Cisbio Inc.). Test compounds were each added to a reaction solution containing the enzyme protein to give 8 final concentrations from 1000 nM to 0.3 nM, followed by addition of ATP and reaction for 1 hour. The ATP concentration used was 100 μM. Another reaction solution was prepared to contain the enzyme protein but no test compound (in which the solvent DMSO alone was added at 0.4% in place of the test compound), followed by reaction in the same manner with or without ATP addition. In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, some compounds of the present invention were found to have inhibitory activity against the kinase activity of EML4-ALK fusion protein v1. Table 1 shows the $IC_{50}$ values obtained for some compounds of the present invention. Ex denotes Example No. In the table below, Compound X denotes a racemic form of the compound of Example 174 shown in International Publication No. WO 2009/136995 (rac-2-{[(1R,2S)-2-aminocyclohexyl]amino}-4-{[4'-(morpholin-4-yl)biphenyl-4-yl]amino}pyrimidine-5-carboxamide), and Compound Y denotes the compound of Examples 26-22 shown in International Publication No. WO 00/76980 (5-{[2-(dimethylamino)ethyl]amino}-6-ethyl-3-[(3-methylphenyl)amino]pyrazine-2-carboxamide).

TABLE 1

| Ex | $IC_{50}$(nM) |
|---|---|
| 86 | 17 |
| 110 | 0.99 |
| 284 | 8.9 |
| 325 | 5.3 |
| 328 | 76 |
| 340 | 0.37 |
| 341 | 2.8 |
| 343 | 2.1 |
| 347 | 1.7 |
| 354 | 0.77 |
| 355 | 0.33 |
| 357 | 17 |
| 370 | 0.65 |
| 377 | 0.24 |
| 378 | 0.26 |
| 383 | 0.23 |
| 387 | 0.26 |
| 388 | 0.17 |
| 391 | 0.22 |
| 392 | 0.21 |
| 399 | 0.94 |
| 406 | 0.34 |
| 426 | 0.49 |
| 459 | 0.26 |
| 466 | 0.93 |
| 490 | 3.1 |
| 491 | 2.8 |
| 493 | 2.6 |
| 494 | 4.1 |

TABLE 1-continued

| Ex | IC$_{50}$(nM) |
|---|---|
| 512 | 1.5 |
| 534 | 1.0 |
| 538 | 2.3 |
| 544 | 1.9 |
| 545 | 11 |
| 546 | 7.8 |
| 547 | 1.5 |
| 549 | 2.1 |
| 550 | 11 |
| 553 | 1.4 |
| 554 | 4.5 |
| 558 | 2.2 |
| Compound X | 220 |
| Compound Y | >1000 |

Test Example 2

Evaluation of Growth Inhibitory Activity Against EML4-ALK Fusion Protein-Dependent Cells EML4-ALK fusion protein v1-expressing BA/F3 cells can grow in the absence of IL-3. In other words, they are cells that EML4-ALK fusion protein v1-dependently grow.

In a 96-well plate (Iwaki), BA/F3 cells expressing EML4-ALK fusion protein v1 were seeded at 500 cells per well in RPMI1640 medium (Invitrogen) containing 10% fetal bovine serum, followed by addition of a test compound (final concentration: 10 μM to 0.1 nM). As a negative control, DMSO used as a solvent of the test compound was added. Then, the cells were cultured under 5% $CO_2$ at 37° C. for 2 days. A cell counting reagent (AlmarBlue; Biosource) was added, and the cells were cultured for 150 minutes, followed by measurement of fluorescence intensity with a luminometer (Safire; Tecan) in accordance with instructions attached to the reagent. Assuming that the value measured for the medium alone and the value measured for the negative control were 100% inhibition and 0% inhibition, respectively, the inhibition rate was calculated for each compound to thereby determine the concentration causing 50% inhibition (IC$_{50}$ value) by the logistic regression method.

As a result, some compounds of the present invention showed growth inhibitory activity against BA/F3 cells expressing EML4-ALK fusion protein v1. Table 2 shows the IC$_{50}$ values obtained for some compounds of the present invention. Ex denotes Example No. In the table below, Compound X and Compound Y respectively denote the compounds described in Test Example 1.

TABLE 2

| Ex | IC$_{50}$(nM) |
|---|---|
| 86 | 68 |
| 110 | 64 |
| 284 | 85 |
| 325 | 20 |
| 328 | 76 |
| 340 | 9.5 |
| 341 | 11 |
| 343 | 11 |
| 347 | 17 |
| 354 | 8.6 |
| 355 | 9.2 |
| 357 | 60 |
| 370 | 4.9 |
| 377 | 6.9 |
| 378 | 6.1 |

TABLE 2-continued

| Ex | IC$_{50}$(nM) |
|---|---|
| 383 | 5.9 |
| 387 | 10 |
| 388 | 4.1 |
| 391 | 6.5 |
| 392 | 6.3 |
| 399 | 11 |
| 406 | 9.8 |
| 426 | 11 |
| 459 | 8.1 |
| 466 | 9.3 |
| 490 | 18 |
| 491 | 16 |
| 493 | 19 |
| 494 | 42 |
| 512 | 19 |
| 534 | 24 |
| 538 | 7.7 |
| 544 | 27 |
| 545 | 25 |
| 546 | 23 |
| 547 | 5.7 |
| 549 | 14 |
| 550 | 39 |
| 553 | 4.7 |
| 554 | 14 |
| 558 | 16 |
| Compound X | 821 |
| Compound Y | >1000 |

From the results of Test Examples 1 and 2 shown above, it was confirmed that the compounds of the present invention had inhibitory activity against the kinase activity of EML4-ALK fusion protein v1 and growth inhibitory activity against EML4-ALK fusion protein v1-expressing BA/F3 cells. On the other hand, Compounds X and Y described in Test Example 1 were confirmed to have extremely weak inhibitory activity against the kinase activity of EML4-ALK fusion protein v1 and growth inhibitory activity against EML4-ALK fusion protein v1-expressing BA/F3 cells, compared with the compounds of the present invention.

Test Example 3

Antitumor Test (In Vivo) on EML4-ALK Fusion Protein-Dependent Cells

Expression plasmid EML4-ALKv1/pMXS in which cDNA for EML4-ALK fusion protein v1 was integrated was trasfected into 3T3 fibroblast cells by the phosphate calcium method to thereby establish EML4-ALK fusion protein v1 expressing 3T3 cells. $3 \times 10^6$ cells of EML4-ALK fusion protein v1 expressing 3T3 cells suspended in PBS were inoculated subcutaneously by injection to the back of 5 weeks old male Balb/c nude mice (Charles River Japan, Inc.). After 7 days of the inoculation, the administration of test compound was initiated. The test was conducted in the solvent group and the compound group, 4 animals per group. The test compound was suspended in a solvent composed of 0.5% methylcellulose and administered orally at a dose of 10 mg/kg. Administrations were performed once a day for 5 days, and body weight and tumor size were measured every other day. Tumor volume was calculated using the following formula.

[Tumor volume(mm$^3$)]=[Tumor major axis(mm)]×[tumor minor axis(mm)]$^2$×0.5

Assuming that the tumor volume of the solvent group on the day of starting and the day of finishing administration of the test compound was 100% inhibition and 0% inhibition, respectively, the inhibition rate of the test compound was calculated. When regression of tumor volume is induced from the day of starting administration, the tumor volume on the day of starting administration and the state in which the tumor disappeared were assumed to be 0% regression and 100% regression, respectively, and the rate of regression of the test compound was calculated.

As a result, it was confirmed that among the compounds of the present invention, there were compounds that inhibited growth of tumor of EML4-ALK fusion protein v1 expressing 3T3 cells and compounds that induced regression of tumor of EML4-ALK fusion protein v1 expressing 3T3 cells. Table 3 shows the inhibition rate of some compounds of the present invention. It is to be noted that in the table below, the numerical values specified with "(regression)" each indicate a rate of regression. Ex denotes Example No.

TABLE 3

| Ex | (%) |
|---|---|
| 370 | 81 |
| 378 | 92 |
| 392 | 28 (regression) |
| 426 | 81 |
| 466 | 54 (regression) |
| 546 | 79 |
| 549 | 67 (regression) |
| 553 | 63 |
| 558 | 37 (regression) |

Thus, when orally administered, the compounds of the present invention inhibited tumor growth in mice inoculated with EML4-ALK fusion protein v1 expressing 3T3 cells or induced regression of tumor, thereby confirming that the compounds of the present invention had oral activity.

Test Example 4

Antitumor Test (In Vivo) on EML4-ALK Fusion Protein-Dependent Cells

The antitumor effects on EML4-ALK fusion protein-dependent cells can also be confirmed by use of human non-small cell lung cancers cell line NCI-H2228 cells (cells derived from EML4-ALK fusion polynucleotide-positive lung cancer patients (EML4-ALK fusion protein v3-dependent cells)) in place of the EML4-ALK fusion protein v1 expressing 3T3 cells of Test Example 3, as shown below.

$3 \times 10^6$ cells of NCI-H2228 cells suspended in 50% Matrigel (Invitrogen) were inoculated subcutaneously by injection to the back of 5 weeks old male NOD/SCID mice (Charles River Japan, Inc.). After 3 weeks of the inoculation, the administration of test compounds was initiated. The test was conducted in the solvent group and test compound groups, 6 animals per group. The test compounds were each dissolved in a solvent composed of 10% 1-methyl-2-pyrrolidinone (SIGMA-ALDRICH Inc.)/90% polyethylene glycol 300 (Fluka Inc.) and administered orally at a dose of 1 mg/kg. Administrations were performed once a day for 14 days, and body weight and tumor size were measured every other day. Tumor volume was calculated using the following formula.

[Tumor volume(mm$^3$)]=[Tumor major axis(mm)]× [tumor minor axis(mm)]$^2$×0.5

Assuming that the tumor volume of the solvent group on the day of starting and the day of finishing administration was 100% inhibition and 0% inhibition, respectively, the inhibition rate was calculated for each compound.

As a result, it was confirmed that among the compounds of the present invention, there were compounds that inhibited growth of tumor of NCI-H2228 cells. For example, the compound of Example 549 inhibited growth of tumor of NCI-H2228 cells by 69%.

Thus, when orally administered, the compounds of the present invention inhibited tumor growth in mice inoculated with human non-small cell lung cancer cell line NCI-H2228 cells, thereby confirming that the compounds of the present invention had oral activity.

On the other hand, when Compounds X and Y described in Test Example 1 were administered, no significant growth inhibition against NCI-H2228 cells (tumor) was shown, compared with the solvent group. The significance test was conducted by Student's t-test.

In view of the foregoing, in Test Examples 1 and 2, the compounds of the present invention were confirmed to have inhibitory activity against the kinase activity of EML4-ALK fusion protein, as well as growth inhibitory activity against EML4-ALK fusion protein-dependent cells. Further, in Test Examples 3 and 4, the compounds of the present invention were also confirmed to have an antitumor effect on EML4-ALK fusion protein-dependent cells (tumor) based on the above actions. These indicate that the compounds of the present invention are useful as active ingredients in pharmaceutical compositions for preventing and/or treating cancer, such as lung cancer in one embodiment, non-small cell lung cancer or small cell lung cancer in another embodiment, ALK fusion polynucleotide-positive cancer in yet another embodiment, ALK fusion polynucleotide-positive lung cancer in yet another embodiment, ALK fusion polynucleotide-positive non-small cell lung cancer in yet another embodiment, ALK fusion protein-positive cancer in yet another embodiment, ALK fusion protein-positive lung cancer in yet another embodiment, ALK fusion protein-positive non-small cell lung cancer in yet another embodiment, EML4-ALK fusion polynucleotide-positive cancer in yet another embodiment, EML4-ALK fusion polynucleotide-positive lung cancer in yet another embodiment, EML4-ALK fusion polynucleotide-positive non-small cell lung cancer in yet another embodiment, EML4-ALK fusion protein-positive cancer in yet another embodiment, EML4-ALK fusion protein-positive lung cancer in yet another embodiment, or EML4-ALK fusion protein-positive non-small cell lung cancer in yet another embodiment.

So far, as to the ALK gene, the presence of various types of active point mutation and overexpression associated with gene amplification have been confirmed in cells derived from neuroblastoma patients (Nature, vol. 455, p. 971, 2008; Cancer Research, vol. 68, p. 3389, 2008). Further, it is known that a compound having inhibitory activity against the kinase activity of ALK protein shows an antitumor effect on cells derived from mutant ALK polynucleotide-positive cancer patients and cells derived from cancer patients with overexpression of ALK polynucleotide (Cancer Research, vol. 68, p. 3389, 2008). These indicate that the compounds of the present invention are useful as active ingredients in pharmaceutical compositions for preventing and/or treating neuroblastoma, such as mutant ALK polynucleotide-positive cancer in one embodiment, cancer with overexpression of ALK polynucleotide in another embodiment, mutant ALK polynucleotide-positive neuroblastoma in yet another embodiment, or neuroblastoma with overexpression of ALK polynucleotide in yet another embodiment.

The compounds of formula (I) were also confirmed for their pharmacological activity in the following tests. Unless otherwise specified, the test examples shown below may be accomplished in a known manner and, when using commercially available reagents and/or kits, may be accomplished in accordance with the instructions attached to these commercially available products.

Test Example 5

Evaluation of Inhibitory Activity Against the Kinase Activity of RET Protein

A partial protein of only a kinase domain of RET protein was purchased from Carna Biosciences Inc., Japan. The phosphorylation activity toward a peptide substrate was investigated using an EZ reader (Caliper). Test compounds were each mixed with a protein solution to give 8 final concentrations from 100 nM to 0.03 nM, followed by addition of a mixed liquid of ATP and substrate peptide (Caliper) and reaction for 30 minutes. The ATP concentration used was 100 µM. A reaction liquid which contained protein but no test compound (in which the solvent DMSO alone was added at 0.8% in place of the test compound) was prepared, followed by reaction in the same manner with or without ATP addition. In the absence of the test compound, the phosphorylation peptide peak without ATP addition and with ATP addition was assumed to be 100% inhibition and 0% inhibition, respectively. The test compound concentration causing 50% inhibition ($IC_{50}$ value) was calculated by the logistic regression method.

As a result, some compounds of the present invention showed inhibitory activity against the kinase activity of RET protein. Table 4 shows the $IC_{50}$ values obtained for some compounds of the present invention. Ex denotes Example No.

TABLE 4

| Ex | $IC_{50}$(nM) |
| --- | --- |
| 565 | 1.1 |
| 566 | 0.95 |
| 567 | 1.7 |
| 568 | 1.5 |
| 569 | 1.0 |
| 570 | 2.3 |
| 571 | 1.1 |
| 572 | 1.3 |
| 573 | 1.0 |
| 574 | 1.0 |
| 575 | 1.3 |
| 576 | 1.3 |
| 577 | 3.4 |
| 578 | 1.5 |
| 579 | 1.1 |
| 580 | 3.6 |
| 581 | 2.9 |
| 582 | 1.1 |

RET (Rearranged during transfection) is a receptor tyrosine kinase and is a protein having a transmembrane region in the middle part, flanked by a tyrosine kinase region on the carboxyl-terminal side and an extracellular region on the amino-terminal side.

From the results of Test Example 5, it was confirmed that the compounds of the present invention had inhibitory activity against the kinase activity of RET protein. So far, as to the RET gene, active point mutation has been confirmed in cells or cancer tissue specimens derived from non-small cell lung cancers, small cell lung cancer, thyroid cancer, adrenal pheochromocytoma, colon cancer, and pancreatic cancer, and fusion with H4, H4L, PRKAR1A, NCOA4, GOLGA5, HTIF1, TIF1G, TKTN1, RFG9, ELKS, PCM1, RFP, and HOOK3 genes has been confirmed in cells or cancer tissue specimens derived from thyroid cancer, ovarian cancer, and mesothelioma (point mutation in non-small cell lung cancer: Nature Genetics, 2007, 39, 347-351; point mutation in small cell lung cancer: Japanese Journal of Cancer Research, 1995, 86, 1127-1130; fusion and point mutation in thyroid cancer: Endocrine Reviews, 2006, 27, 535-560; point mutation in adrenal tumor: Journal of Clinical Endocrinology and Metabolism, 1996, 81, 2041-2046; point mutation in colon cancer: Science, 2006, 314, 268-274; point mutation in pancreatic cancer: Cancer Research, 2005, 65, 11536-11544; fusion in ovarian cancer: International Journal of Surgical Pathology, 2009, 17, 107-110; fusion in mesothelioma: Cancer letters, 2008, 265, 55-66). Further, it is known that a compound having inhibitory activity against the kinase activity of RET protein shows an antitumor effect on cells derived from mutant RET polynucleotide-positive cancer patients and cells derived from fusion RET polynucleotide-positive cancer patients (Endocrine Reviews, 2006, 27, 535-560). These indicate that the compounds of the present invention are useful as active ingredients in pharmaceutical compositions for preventing and/or treating thyroid cancer, such as adrenal pheochromocytoma in one embodiment, colon cancer in another embodiment, pancreatic cancer in yet another embodiment, ovarian cancer in yet another embodiment, mesothelioma in yet another embodiment, mutant RET polynucleotide-positive cancer in yet another embodiment, mutant RET polynucleotide-positive lung cancer in yet another embodiment, mutant RET polynucleotide-positive non-small cell lung cancer in yet another embodiment, mutant RET polynucleotide-positive small cell lung cancer in yet another embodiment, mutant RET polynucleotide-positive thyroid cancer in yet another embodiment, mutant RET polynucleotide-positive adrenal pheochromocytoma in yet another embodiment, mutant RET polynucleotide-positive colon cancer in yet another embodiment, mutant RET polynucleotide-positive pancreatic cancer in yet another embodiment, RET fusion polynucleotide-positive cancer in yet another embodiment, RET fusion polynucleotide-positive thyroid cancer in yet another embodiment, RET fusion polynucleotide-positive ovarian cancer in yet another embodiment, or RET fusion polynucleotide-positive mesothelioma in yet another embodiment.

Test Example 6

Evaluation of Inhibitory Activity Against the Kinase Activity of ROS Protein

A partial protein of only a kinase domain of ROS protein was purchased from Carna Biosciences Inc., Japan, and tests were conducted as in Test Example 5, except that the ATP concentration in the mixed solution of ATP and substrate peptide (Caliper) was 50 uM.

As a result, some compounds of the present invention showed inhibitory activity against the kinase activity of ROS protein. Table 5 shows the $IC_{50}$ values obtained for some compounds of the present invention. Ex denotes Example No.

TABLE 5

| Ex | $IC_{50}$(nM) |
| --- | --- |
| 565 | 0.40 |
| 566 | 0.86 |
| 567 | 0.23 |
| 568 | 1.0 |

TABLE 5-continued

| Ex | IC$_{50}$(nM) |
|---|---|
| 569 | 0.65 |
| 570 | 0.51 |
| 571 | 0.86 |
| 572 | 0.37 |
| 573 | 0.78 |
| 574 | 1.3 |
| 575 | 1.6 |
| 576 | 1.9 |
| 577 | 1.9 |
| 578 | 0.51 |
| 579 | 0.58 |
| 580 | 0.29 |
| 581 | 0.41 |
| 582 | 1.2 |

ROS (v-Ros avian UR2 sarcoma virus oncogene homolog 1) is a receptor tyrosine kinase and is a protein having a transmembrane region in the middle part, flanked by a tyrosine kinase region on the carboxyl-terminal side and an extracellular region on the amino-terminal side.

From the results of Test Example 6, it was confirmed that the compounds of the present invention had inhibitory activity against the kinase activity of ROS protein. So far, as to the ROS gene, fusion with the FIG gene, the SLC34A2 gene, and the CD74 gene has been confirmed in cells or cancer tissue specimens derived from non-small cell lung cancers and glioblastoma (Biochimica et Biophysica Acta (BBA) Reviews on Cancer, 2009, 1795, 37-52). Further, since it is known that siRNA which inhibits molecule expression of cell lines derived from SLC34A2-ROS fusion polynucleotide-positive cancer patients shows an antitumor effect on the cell lines (Cell, 2007, 131, 1190-1203), it can be expected that a compound having inhibitory activity against the kinase activity of ROS protein shows an antitumor effect on ROS fusion polynucleotide-positive cancer. These indicate that the compounds of the present invention are useful as active ingredients in pharmaceutical compositions for preventing and/or treating glioblastoma, such as ROS fusion polynucleotide-positive cancer in one embodiment, ROS fusion polynucleotide-positive lung cancer in another embodiment, ROS fusion polynucleotide-positive non-small cell lung cancer in yet another embodiment, or ROS fusion polynucleotide-positive glioblastoma in yet another embodiment.

Test Example 7

Evaluation of Inhibitory Activity Against the Kinase Activity of FLT3 Protein

A partial protein of only a kinase domain of FLT3 protein was purchased from Carna Biosciences Inc., Japan, and tests were conducted as in Test Example 5.

As a result, some compounds of the present invention showed inhibitory activity against the kinase activity of FLT3 protein. Table 6 shows the IC$_{50}$ values obtained for some compounds of the present invention. Ex denotes Example No.

TABLE 6

| Ex | IC$_{50}$(nM) |
|---|---|
| 565 | 0.44 |
| 566 | 0.51 |
| 567 | 0.46 |
| 568 | 0.50 |
| 569 | 0.35 |

TABLE 6-continued

| Ex | IC$_{50}$(nM) |
|---|---|
| 570 | 0.66 |
| 571 | 0.39 |
| 572 | 0.34 |
| 573 | 0.37 |
| 574 | 0.36 |
| 575 | 0.72 |
| 576 | 0.51 |
| 577 | 0.41 |
| 578 | 0.56 |
| 579 | 0.36 |
| 580 | 0.49 |
| 581 | 0.52 |
| 582 | 0.37 |

FLT3 (Fms-like tyrosine kinase 3) is a receptor tyrosine kinase and is a protein having a transmembrane region in the middle part, flanked by a tyrosine kinase region on the carboxyl-terminal side and an extracellular region on the amino-terminal side.

From the results of Test Example 7, it was confirmed that the compounds of the present invention had inhibitory activity against the kinase activity of FLT3 protein. So far, as to the FLT3 gene, active point mutation and internal tandem duplication mutation in the juxtamembrane region (FLT3-ITD) have been confirmed in cells derived from acute myelocytic leukemia patients, and fusion with the SPTBN1 gene has been confirmed in cells derived from atypical chronic myelocytic leukemia patients (active point mutation and internal tandem duplication in the juxtamembrane region in acute myelocytic leukemia: Current Pharmaceutical Design, 2005, 11, 3449-3457; fusion in atypical chronic myelocytic leukemia: Experimental Hematology, 2007, 35, 1723-1727). Further, it is known that a compound having inhibitory activity against the kinase activity of FLT3 protein shows an antitumor effect on cells derived from mutant FLT3 polynucleotide-positive cancer patients and cells derived from SPTBN1-FLT3 fusion polynucleotide-positive cancer patients (Current Pharmaceutical Design, 2005, 11, 3449-3457; Experimental Hematology, 2007, 35, 1723-1727). These indicate that the compounds of the present invention are useful as active ingredients in pharmaceutical compositions for preventing and/or treating acute myelocytic leukemia, such as atypical chronic myelocytic leukemia patients in one embodiment, mutant FLT3 polynucleotide-positive cancer in another embodiment, mutant FLT3 polynucleotide-positive acute myelocytic leukemia in yet another embodiment, FLT3 fusion polynucleotide-positive cancer in yet another embodiment, or FLT3 fusion polynucleotide-positive atypical chronic myelocytic leukemia in yet another embodiment.

Test Example 8

Kinase Inhibition Profiling

The inhibition rates against 78 types of tyrosine kinases (ABL, ARG, BTK, BMX, ITK, TEC, TXK, FRK, BLK, LCK, HCK, LYN, FGR, FYN, SRC, YES, BRK, SRM, CSK, CTK, FER, FES, ACK, TNK1, HER4, EGFR, HER2, JAK1, TYK2, JAK2, JAK3, ROS, ALK, LTK, IRR, INSR, IGF1R, DDR1, DDR2, MUSK, TRKA, TRKB, TRKC, TYRO3, AXL, MER, MET, RON, RET, FGFR4, FGFR1, FGFR2, FGFR3, FLT4, KDR, FLT1, FLT3, FMS, KIT, PDGFRa, PDGFRb, TIE2, EphA1, EphA2, EphA8, EphA7, EphA6, EphA4, EphA3, EphA5, EphB4, EphB3, EphB1, EphB2, FAK, PYK2, SYK, ZAP70) were calculated for each test compound at 5 nM. Activity measurement was made by Carna Biosciences Inc., Japan, and the data were analyzed as follows: assuming that the average signal of control wells containing all reaction components was 0% inhibition and the average signal in the absence of the enzyme was 100% inhibition, the inhibition rate was calculated for each test substance from the average signal of two test wells.

As a result, at a concentration of 5 nM, some compounds of the present invention showed 50% or more inhibitory activity against 7 types of kinases including ALK, RET, ROS and FLT3 and, hence, appear to be highly selective for specific kinases and to have fewer fears about safety, which fears are induced by inhibition of non-target kinases responsible for side effects.

A pharmaceutical composition which comprises one or more compounds of formula (I) or pharmaceutically acceptable salts thereof as an active ingredient can be prepared in a conventional manner by using a pharmaceutical excipient, a pharmaceutical carrier or other additives commonly used in the art.

Any mode of administration may be used, either oral administration in the dosage form of tablets, pills, capsules, granules, powders, solutions or the like, or parenteral administration in the dosage form of injections (e.g., intraarticular, intravenous, intramuscular, and the like), suppositories, eye drops, eye ointments, percutaneous solutions, ointments, percutaneous patches, transmucosal solutions, transmucosal patches, inhalants or the like.

Solid compositions used for oral administration include tablets, powders, granules, and the like. In these solid compositions, one or more active ingredients are mixed with at least one inert excipient, for example, lactose, mannitol, glucose, hydroxypropylcellulose, microcrystalline cellulose, starch, polyvinylpyrrolidone, and/or magnesium aluminometasilicate, or the like. The compositions may also comprise inert additives, for example, lubricants (e.g., magnesium stearate and the like), disintegrating agents (e.g., carboxymethyl starch sodium and the like), stabilizers, and/or solubilizers, as in the usual cases. Tablets or pills may be coated with sugar coating or a gastric or enteric film, if necessary.

Liquid compositions for oral administration include pharmaceutically acceptable emulsions, solutions, suspensions, syrups, elixirs, or the like, and comprise commonly-used inert diluents such as purified water or ethanol. These liquid compositions may comprise, in addition to inert diluents, auxiliaries (e.g., solubilizers, wetting agents, suspending agents, and the like), sweeteners, flavors, aromatics, and/or antiseptics.

Injections for parenteral administration include sterile aqueous or non-aqueous solutions, suspensions or emulsions. Examples of aqueous solvents include injectable distilled water or physiological saline. Examples of non-aqueous solvents include propylene glycol, polyethylene glycol or vegetable oils (e.g., olive oil and the like), as well as alcohols (e.g., ethanol and the like) or Polysorbate 80 (pharmacopoeia name), and the like. These compositions may further comprise isotonizing agents, antiseptics, wetting agents, emulsifiers, dispersants, stabilizers or solubilizers. They are sterilized, for example, by filtration through a bacteria-retaining filter, by incorporation with disinfectants or by irradiation. Alternatively, they may be formulated into a sterile solid composition and reconstituted for use by being dissolved or suspended in sterile water or a sterile injectable solvent before use.

Formulations for external use include ointments, plasters, creams, jellies, cataplasms, sprays, lotions, eye drops, eye ointments, and the like. They comprise commonly-used ointment bases, lotion bases, aqueous or non-aqueous solutions, suspensions, emulsions or the like. Examples of ointment or lotion bases include polyethylene glycol, propylene glycol, white petrolatum, white beeswax, polyoxyethylene hydrogenated castor oil, glycerine monostearate, stearyl alcohol, cetyl alcohol, Lauromacrogol, sorbitan sesquioleate, and the like.

Transmucosal formulations such as inhalants or transnasal formulations are used in solid, liquid or semi-solid form and can be prepared in a conventionally known manner. For example, such formulations may be supplemented as appropriate with known excipients and further with pH adjustors, antiseptics, surfactants, lubricants, stabilizers, thickeners and so on. For their administration, an appropriate device for inhalation or insufflation may be used. For example, using a known device (e.g., a metered-dose inhalation device and the like) or a nebulizer, the compound(s) may be administered alone or as a powder of a formulated mixture or as a solution or suspension in combination with a pharmaceutically acceptable carrier. Dry powder inhalators or the like may be for single or multiple administration use, and dry powders or powder-containing capsules may be used in such devices. Alternatively, they may be in the form of pressurized aerosol sprays or the like which use an appropriate propellant, for example, a preferred gas such as chlorofluoroalkane, hydrofluoroalkane, carbon dioxide, or the like.

In general, for oral administration, the daily dosage is desirably about 0.001 to 100 mg/kg, preferably 0.005 to 30 mg/kg, and more preferably 0.01 to 10 mg/kg body weight, given as a single dose or in 2 to 4 divided doses. For intravenous administration, the daily dosage is desirably about 0.0001 to 10 mg/kg body weight, given in one or several doses per day. Likewise, for transmucosal formulations, the daily dosage is about 0.001 to 100 mg/kg body weight, given in one or several doses per day. The dosage may be determined as appropriate for each case in consideration of symptom, age, sex and so on.

The compounds of formula (I) can be used in combination with various therapeutic or prophylactic agents for diseases against which the compounds of formula (I) would be effective. In general, when an antitumor agent is administered alone during chemotherapy for tumor, particularly malignant tumor, the antitumor agent has a limit in its effect in terms of side effects and the like, and thus often fails to produce a sufficient antitumor effect. For this reason, in clinical cases, multidrug therapy is used in which two or more drugs with different mechanisms of action are combined. By combining antitumor agents with different mechanisms of action, this combination therapy aims to reduce side effects and/or enhance the desired antitumor effect, for example, 1) to reduce the number of non-sensitive cell population, 2) to prevent or delay the development of drug resistance, 3) to disperse toxicity by combination of drugs with different toxicity levels, and the like. In such combination therapy, drugs may be administered simultaneously or separately in succession or at desired time intervals. Formulations for simultaneous administration may be in either mixed or separate form.

Drugs which can be combined include chemotherapeutics (e.g., alkylating agent, antimetabolite, and the like), immunotherapeutic agents, hormonal therapeutic agents, and cell growth factor inhibitors, more specifically drugs such as cisplatin, carboplatin, paclitaxel, docetaxel, gemcitabine, irinotecan, vinorelbine, bevacizumab, pemetrexed and the like.

EXAMPLES

How to prepare the compounds of formula (I) will be further explained in more detail by way of the following examples. It should be noted that the present invention is not limited to the compounds shown in the following examples. In addition, how to prepare the starting compounds is shown in preparation examples. Processes for preparing the compounds of formula (I) are not limited only to those actually shown in the following examples, and the compounds of formula (I) may also be prepared by any combination of these processes or by any process obvious to those skilled in the art.

In the examples, preparation examples and tables shown below, the following abbreviations are used as needed.
Rex: Preparation Example No., Ex: Example No., Structure: chemical structural formula, Data: physical and chemical data (FAB+: FAB-MS[M+H]$^+$, ESI+: ESI-MS[M+H]$^+$, APCI/ESI+: APCI/ESI-MS[M+H]+(APCI/ESI means simultaneous measurement of APCI and ESI), FAB−: FAB-MS [M−H]$^-$, ESI−: ESI-MS[M−H]$^-$, APCI−: APCI-MS[M−H]$^-$, $^1$H-NMR (CDCl$_3$): δ(ppm) of $^1$H-NMR peaks in chloroform-d, $^1$H-NMR (CD3OD): δ (ppm) of $^1$H-NMR peaks in methanol-d, $^1$H-NMR (CDCl3+CD3OD): δ (ppm) of $^1$H-NMR peaks in a mixed solution of chloroform-d and methanol-d, $^1$H-NMR (DMSO-d$_6$): δ (ppm) of $^1$H-NMR peaks in DMSO-d$_6$, XRD: diffraction angle) 2θ(°) of main peak in powder X ray diffraction measurement, HCl: which means that the intended product was obtained as hydrochloride, 2HCl: which means that the intended product was obtained as a dihydrochloride, TsOH: which means that the intended product was obtained as a p-toluene sulfonic acid salt, HFM: which means that the intended product was obtained as a hemifumaric acid salt, FM: which means that the intended product was obtained as a fumaric acid salt, Me: methyl, Et: ethyl, nPr: normalpropyl, iPr: isopropyl, cPr: cyclopropyl, cHex: cyclohexyl, Ph: phenyl, Bn: benzyl, Boc: tert-butyloxycarbonyl, Ac: acetyl. Syn: preparation process (indicating that the intended compound was prepared from corresponding starting materials as in the indicated Preparation Example or Example). In the Tables Shown in Preparation Examples or Examples, there are cis-trans isomers and their configurations are undecided, but as to compounds that show a single configuration of one of cis and trans, no indication of configuration is made in their chemical structural formulas and, instead, the symbol "*" is given to their preparation example Nos. or example Nos. Compounds that are give the same number following the symbol "*" indicate that one of the compounds is a cis form and the other is a trans form.

The measurement of powder X ray diffraction was performed using RINT-TTR II under the following conditions; tube: Cu, tube current: 300 mA, tube voltage: 50 kV, sampling width: 0.020°, scan rate: 4°/min, wavelength: 1.54056 Å, range of diffraction angle measured (2θ): 2.5 to 40°. It is to be noted that the powder X ray diffraction should not strictly be understood, because, due to the nature of powder X ray diffraction data, crystal lattice space and overall pattern are important in determination of crystal identity, and the relative intensity may vary in some degree depending on the direction of crystal growth, particle size, and measurement conditions.

Preparation Example 4

A mixture of 4-methyl-3-nitrobenzoic acid (1.97 g) and thionyl chloride (6 mL) was heated under reflux for 18 hours. The reaction liquid was concentrated under reduced pressure, followed by an azeotropic process with toluene to give a red-brown oil. To a mixture of the red-brown oil and THF (25 mL), diethylamine (2.6 mL) was added under ice cooling and stirred at room temperature for 5 hours. The reaction liquid was poured into water and extracted with ethyl acetate. The organic layer was washed with saturated aqueous sodium chloride and then dried over anhydrous sodium sulfate, and the solvent was distilled off under reduced pressure to give N,N-diethyl-4-methyl-3-nitrobenzamide (2.61 g) as a brown oil.

Preparation Example 41

To a mixture of 2-methoxy-4-nitrobenzenesulfonylchloride (600 mg) and THF (5 mL), a mixture of piperidine (406 mg) and THF (1 mL) was added and stirred at room temperature for 12 hours. After addition of 10% hydrochloric acid, the reaction liquid was extracted with ethyl acetate. The organic layer was washed with saturated aqueous sodium chloride and then dried over anhydrous sodium sulfate, and the solvent was distilled off under reduced pressure to give 1-[(2-methoxy-4-nitrophenyl)sulfonyl]piperidine (714 mg) as a yellow solid.

Preparation Example 48

A mixture of 2-fluoro-5-nitrobenzoic acid (600 mg) and thionyl chloride (2 mL) was heated under reflux for 15 hours. The reaction liquid was concentrated under reduced pressure, followed by an azeotropic process with toluene to give a yellow crystal. To a mixture of the yellow crystal and THF (11 mL), triethylamine (0.47 mL) and isopropylamine (0.29 mL) were added under ice cooling and stirred at room temperature for 5 hours. The reaction liquid was poured into water and extracted with ethyl acetate. The organic layer was washed with saturated aqueous sodium chloride and then dried over anhydrous sodium sulfate, and the solvent was distilled off under reduced pressure to give a yellow crystal. To a mixture of the yellow crystal (723 mg) and methanol (8 mL) and water (3 mL), ammonium chloride (2.05 g) and zinc powder (2.09 g) were added, and the mixture was heated under reflux for 3 hours. After filtration of the reaction suspension through celite, the filtrate was concentrated under reduced pressure. The residue was poured into saturated aqueous sodium hydrogen carbonate and extracted with ethyl acetate. The organic layer was washed with saturated aqueous sodium chloride and then dried over anhydrous sodium sulfate, and the solvent was distilled off under reduced pressure. The residue was purified by silica gel column chromatography (eluent; chloroform:methanol) to give 5-amino-2-fluoro-N-isopropylbenzamide (527 mg) as a light brown crystal.

Preparation Example 160

To a mixture of 3,5-dichloro-6-ethylpyrazine-2-carboxamide (1.0 g) and DMF (15 mL), thionyl chloride (1 mL) was added at room temperature and stirred for 20 minutes. The reaction liquid was poured into ice-cold water and extracted with ethyl acetate. The organic layer was washed with saturated aqueous sodium chloride and then dried over anhydrous sodium sulfate, and the solvent was distilled off under reduced pressure. The residue was purified by silica gel column chromatography (eluent; ethyl acetate:n-hexane) to give 3,5-dichloro-6-ethylpyrazine-2-carbonitrile (608 mg) as a slightly yellow oil.

Preparation Example 194

To a solution of a mixture of methyl 5-chloro-3-{[4-(4-methylpiperazin-1-yl)phenyl]amino}pyrazine-2-carboxylate (Preparation Example 193) (20 mg) and THF (2 mL), O-methylhydroxylamine hydrochloride (14 mg) was added. To the reaction liquid, lithium hexamethyldisilazide (0.39 mL, 1M THF solution) was added under ice cooling and stirred for 20 minutes. The reaction liquid was poured into saturated aqueous sodium hydrogen carbonate and extracted with ethyl acetate, and then the organic layer was washed with saturated aqueous sodium chloride. After drying over anhydrous sodium sulfate, the solvent was distilled off under reduced pressure to give 5-chloro-N-methoxy-3-{[4-(4-methylpiperazin-1-yl)phenyl]amino}pyrazine-2-carboxamide (21 mg) as a yellow powder.

Preparation Example 240

To a mixture of 1-(2-iodo-4-nitrophenyl)-4-methylpiperazine (Preparation Example 241) (406 mg), toluene (3 mL) and water (3 mL), sodium carbonate (496 mg), phenylboronic acid (157 mg) and tetrakis(triphenylphosphine)palladium (68 mg) were added in an argon atmosphere and stirred overnight at 110° C. The reaction liquid was poured into water and extracted with ethyl acetate. The organic layer was washed with saturated aqueous sodium chloride and then dried over anhydrous sodium sulfate, and the solvent was distilled off under reduced pressure. The residue was purified by silica gel column chromatography (eluent; chloroform/methanol) to give 1-methyl-4-(5-nitrobiphenyl-2-yl)piperazine (348 mg) as a yellow brown oil.

Preparation Example 244

To a mixture of N-[2-(4-methylpiperazin-1-yl)-5-nitrophenyl]acetamide (433 mg) and DMF (5 mL), 63% sodium hydride in oil (66 mg) was added under ice cooling and stirred at room temperature for 1 hour. The reaction liquid was ice cooled again, and methyl iodide (0.11 mL) was added and stirred at room temperature for 4 hours. The reaction liquid was poured into saturated aqueous ammonium chloride and extracted with ethyl acetate. The organic layer was washed with saturated aqueous sodium chloride and then dried over anhydrous sodium sulfate, and the solvent was distilled off under reduced pressure. The residue was purified by silica gel column chromatography (eluent; chloroform:methanol) to give N-methyl-N-[2-(4-methylpiperazin-1-yl)-5-nitrophenyl]acetamide (200 mg) as an orange solid.

Preparation Example 246

To a mixture of tert-butyl (4-oxocyclohexyl)carbamate (3.04 g) and THF (100 mL), ethyllithium (0.5 M benzene-cyclohexane solution) (56.8 mL) was added at −78° C. and stirred over 4 hours until it reached −50° C. After addition of water (150 mL), the reaction liquid was heated to room temperature and extracted with ethyl acetate. The organic layer was washed with saturated aqueous sodium chloride and then dried over sodium sulfate, and the solvent was distilled off. The resulting residue was purified by silica gel column chromatography (eluent; chloroform:methanol=30:1) and further purified (eluent; n-hexane:ethyl acetate=2:1 to 1:1) to give tert-butyl (4-ethyl-4-hydroxycyclohexyl)carbamate (Preparation Example 246) (0.202 g), which was a low-polarity product, as a white solid and tert-butyl (4-ethyl-4-hydroxycyclohexyl)carbamate (Preparation Example 248), which was a high-polarity product, as a colorless syrup.

Preparation Example 247

To a mixture of tert-butyl (4-ethyl-4-hydroxycyclohexyl)carbamate (Preparation Example 246) (0.202 g) and dioxane (2 mL), 26% hydrogen chloride-dioxane (1.1 mL) was added under ice cooling and stirred at room temperature for 12 hours. The solvent was distilled off to give 4-amino-1-ethylcyclohexanol hydrochloride (0.140 g) as a white viscous solid.

Preparation Example 249

To a mixture of tert-butyl (4-ethyl-4-hydroxycyclohexyl)carbamate (Preparation Example 248) (0.256 g) and dioxane (2 mL), 26% hydrogen chloride-dioxane (1.4 mL) was added under ice cooling and stirred at room temperature for 17 hours. The precipitated solid was collected by filtration to give 4-amino-1-ethylcyclohexanol hydrochloride (0.152 g) as a white solid.

Preparation Example 250

To a mixture of tert-butyl (4-oxocyclohexyl)carbamate (3.04 g) and THF (100 mL), isopropyllithium (0.7 M pentane solution) (40.3 mL) was added at −78° C. and stirred over 4 hours until it reached −50° C. After addition of water (150 mL), the reaction liquid was heated to room temperature and extracted with ethyl acetate. The organic layer was washed with saturated aqueous sodium chloride and then dried over sodium sulfate, and the solvent was distilled off. The resulting residue was purified by silica gel column chromatography (eluent; n-hexane:ethyl acetate=3:1) and further purified (eluent; chloroform:methanol=30:1) to give tert-butyl (4-isopropyl-4-hydroxycyclohexyl)carbamate (Preparation Example 250) (0.854 g), which was a low-polarity product, as a white solid and tert-butyl (4-isopropyl-4-hydroxycyclohexyl)carbamate (Preparation Example 252) (0.179 g), which was a high-polarity product, as a yellow oil.

Preparation Example 251

To a mixture of tert-butyl (4-isopropyl-4-hydroxycyclohexyl)carbamate (Preparation Example 250) (0.392 g) and dioxane (3 mL), 26% hydrogen chloride-dioxane (2.0 mL) was added under ice cooling and stirred at room temperature for 18 hours. The precipitated solid was collected by filtration to give 4-amino-1-isopropylcyclohexanol hydrochloride (0.190 g) as a white solid.

Preparation Example 253

To a mixture of tert-butyl (4-isopropyl-4-hydroxycyclohexyl)carbamate (Preparation Example 252) (0.179 g) and dioxane (1.5 mL), 26% hydrogen chloride-dioxane (0.9 mL) was added under ice cooling and stirred at room temperature for 18 hours. The precipitated solid was collected by filtration to give 4-amino-1-isopropylcyclohexanol hydrochloride (0.086 g) as a white solid.

Preparation Example 287

To a mixture of propane-2-thiol (3.30 mL), potassium carbonate (6.60 g) and DMF (40 mL), 1-fluoro-4-methyl-2-nitrobenzene (4.85 g) was added and stirred at room temperature for 5 hours. After addition of water, the reaction liquid was extracted with ethyl acetate, and the extract was washed with water and saturated aqueous sodium chloride. After drying over anhydrous sodium sulfate, the solvent was distilled off under reduced pressure to give 1-(isopropylsulfanyl)-4-methyl-2-nitrobenzene (6.60 g) as a yellow oil.

Preparation Example 291

To a mixture of 1-(isopropylsulfanyl)-4-methyl-2-nitrobenzene (Preparation Example 287) (6.60 g) and chloroform (150 mL), m-chloroperbenzoic acid (18.0 g) was added and stirred at 50° C. for 12 hours. After the reaction liquid was cooled, saturated aqueous sodium hydrogen carbonate and 5% aqueous sodium sulfite were added, and the reaction liquid was extracted with chloroform. After the organic layer was dried over anhydrous sodium sulfate, the solvent was distilled off under reduced pressure to give 2-(isopropylsulfonyl)-4-methyl-1-nitrobenzene (7.41 g) as a yellow solid.

Preparation Example 292

To a mixture of 2-(isopropylsulfonyl)-4-methyl-1-nitrobenzene (Preparation Example 291) (7.41 g) and acetic acid (70 mL), iron powder (5.43 g) was added and stirred at 80° C. for 3 hours. Thereafter, insoluble materials in the reaction liquid were removed, and the solvent was distilled off under reduced pressure. After addition of ethyl acetate (150 mL) and removal of insoluble materials, the residue was washed with water and saturated aqueous sodium chloride. After drying over anhydrous sodium sulfate, the solvent was distilled off under reduced pressure. The residue was washed with ethyl acetate-diisopropyl ether to give 2-(isopropylsulfonyl)-4-methylaniline (3.86 g) as a light yellow solid.

Preparation Example 298

To a mixture of 55% sodium hydride in oil (733 mg) and DMF (20 mL), a mixture of 3-(methylsulfonyl)aniline (1.44 g) and THF (20 mL) were added under ice cooling and stirred for 30 minutes under ice cooling. After dropwise addition of a mixture of 4,6-dichloro-2-(methylsulfanyl)pyrimidine-5-carboxamide (2.0 g) and DMF (30 mL) over 15 minutes, the reaction liquid was further stirred under ice cooling for 15 minutes. After addition of 10% aqueous citric acid (300 mL) and extraction with ethyl acetate, the organic layer was washed with saturated aqueous sodium chloride. After drying over anhydrous magnesium sulfate, the solvent was concentrated, and the precipitated solid was collected by filtration and dried to give 4-chloro-2-(methylsulfanyl)-6-{[3-(methylsulfonyl)phenyl]amino}pyrimidine-5-carboxamide (1.95 g) as a light yellow solid.

Preparation Example 299

To a mixture of 4-chloro-2-(methylsulfanyl)-6-{[3-(methylsulfonyl)phenyl]amino}pyrimidine-5-carboxamide (Preparation Example 298) (1.95 g) and DMSO (30 mL), potassium carbonate (1.81 g) and 30% hydrogen peroxide solution (2.65 mL) were added and stirred at 50° C. for 1.5 hours. The reaction liquid was ice-cooled, and 1M hydrochloric acid (25 mL) and thereafter water (150 mL) were added and stirred for 30 minutes. The precipitated solid was collected by filtration and washed with water to give 2-(methylsulfanyl)-4-{[3-(methylsulfonyl)phenyl]amino}-6-oxo-1,6-dihydropyrimidine-5-carboxamide (1.40 g) as a light yellow solid.

Preparation Example 304

To a mixture of 4-chloro-6-[(6-methylpyridin-3-yl)amino]-2-(methylsulfanyl)pyrimidine-5-carboxamide (Preparation Example 303) (51 mg) and methanol (1 mL), sodium methoxide (11 mg) was added under ice cooling and stirred overnight at room temperature. Water was added to the reaction liquid, and the solid was collected by filtration to give 4-methoxy-6-[(6-methylpyridin-3-yl)amino]-2-(methylsulfanyl)pyrimidine-5-carboxamide (41 mg).

Preparation Example 311

To a mixture of 4-{[3-(methylcarbamoyl)phenyl]amino}-2-(methylsulfanyl)-6-oxo-1,6-dihydropyrimidine-5-carboxamide (Preparation Example 306) (500 mg), dichloromethane (40 mL) and methanol (40 mL), a mixture of Oxone® (922 mg) and water (10 mL) was added and stirred at room temperature for 18 hours. To the reaction liquid, chloroform and water were added, and the precipitated solid was collected by filtration and washed with water to give 4-{[3-(methylcarbamoyl)phenyl]amino}-2-(methylsulfinyl)-6-oxo-1,6-dihydropyrimidine-5-carboxamide (234 mg) as a light yellow solid.

Preparation Example 339

To a mixture of 4-methoxy-6-[(6-methoxy-pyridin-3-yl)amino]-2-(methylsulfanyl)pyrimidine-5-carboxamide (Preparation Example 337) (0.35 g) and water (2.2 mL), concentrated hydrochloric acid (2.2 mL) was added and stirred at 80° C. for 1.5 hours. After the reaction liquid was cooled, 1M aqueous sodium hydroxide was added so that the reaction liquid became almost neutral, and then the resulting solid was collected by filtration to give 4-[(6-methoxy-pyridin-3-yl)amino]-2-(methylsulfanyl)-6-oxo-1,6-dihydropyrimidine-5-carboxamide (0.34 g).

Preparation Example 342

To a mixture of 4,6-dichloro-2-(methylsulfanyl)pyrimidine-5-carboxylic acid (1.50 g) and dichloromethane (15 mL), oxalyl chloride (1.20 mL) and DMF (0.015 mL) were added under ice cooling and stirred 30 minutes under ice cooling and 2 hours at room temperature. The solvent was distilled off under reduced pressure, followed by an azeotropic process with toluene. The resulting residue was dissolved in THF, followed by dropwise addition of 40% aqueous methylamine at −10° C. After the dropwise addition was completed, the reaction liquid was concentrated, and water was added. The resulting solid was collected by filtration and washed with water to give a white solid. The solid was dissolved in ethyl acetate, washed with saturated aqueous sodium chloride, and then dried over anhydrous magnesium sulfate. The solvent was distilled off. To a mixture of the resulting residue and dioxane (20 mL), 3-(methylsulfonyl)aniline hydrochloride (432 mg) and N,N-diisopropylethylamine (0.73 mL) were added and stirred at 100° C. for 4 hours. After cooling, the reaction liquid was diluted with ethyl acetate and washed with saturated aqueous sodium chloride. After drying over anhydrous magnesium sulfate, the solvent was distilled off, and the residue was purified by silica gel column chromatography (eluent; chloroform:methanol=100:0 to 30:1) to give 4-chloro-N-methyl-2-(methylsulfanyl)-6-{[3-(methylsulfonyl)phenyl]amino}pyrimidine-5-carboxamide (445 mg) as a white solid.

Preparation Example 346

To a mixture of 4-chloro-2-(methylsulfanyl)-6-(quinolin-3-ylamino)pyrimidine-5-carboxamide (Preparation Example 344) (0.68 g) and sodium acetate (0.80 g), DMF (7 mL) was added and stirred at 100° C. for 6 hours. After the reaction liquid was returned to room temperature, water was added, and the resulting solid was collected by filtration to give 5-carbamoyl-2-(methylsulfanyl)-6-(quinolin-3-ylamino)pyrimidin-4-yl acetate (0.71 g).

Preparation Example 349

To 5-carbamoyl-2-(methylsulfanyl)-6-(quinolin-3-ylamino)pyrimidin-4-yl acetate (Preparation Example 346) (0.71 g), ethanol (14 mL) and THF (14 mL) were added, and 1M aqueous sodium hydroxide (6 mL) was added and stirred at room temperature for 1 hour. Then, 1M hydrochloric acid (6 mL) was added, and the precipitated solid was collected by filtration and dried to give 2-(methylsulfanyl)-6-oxo-4-(quinolin-3-ylamino)-1,6-dihydropyrimidine-5-carboxamide (0.63 g).

Preparation Example 353

A mixture of 3,5-dichloro-6-ethylpyrazine-2-carboxamide (600 mg), 3-(methylsulfonyl)aniline (467 mg), N,N-diisopropylethylamine (0.48 mL) and dioxane (18 mL) was stirred in a sealed tube at 170° C. for 17 hours. After cooling, the mixture was partitioned using ethyl acetate and water, and the organic layer was washed with saturated aqueous sodium chloride and then dried over anhydrous magnesium sulfate. After the solvent was distilled off, the residue was washed with chloroform, and the solid was collected by filtration and dried to give 5-chloro-6-ethyl-3-{[3-(methylsulfonyl)phenyl]amino}pyrazine-2-carboxamide (412 mg) as a yellow solid.

Preparation Example 364

To a mixture of 4-chloro-6-[(5-methylpyridin-3-yl)amino]-2-(methylsulfanyl)pyrimidine-5-carboxamide (Preparation Example 359) (194 mg) and DMF (5 mL), sodium acetate (257 mg) was added and stirred at 100° C. for 5 hours. After the reaction liquid was cooled, ethyl acetate and water were added, and the precipitated powder was collected by filtration and dried to give a light yellow solid. To a mixture of the solid, ethanol (5 mL), methanol (20 mL) and THF (5 mL), 1M aqueous sodium hydroxide (3 mL) was added and stirred at room temperature for 1 hour, at 60° C. for 1 hour, and at 80° C. for 1 hour. After the reaction liquid was cooled, 1M hydrochloric acid (3 mL) was added, and the reaction liquid was extracted with chloroform-isopropanol. Silica gel was added to the organic layer, and the solvent was distilled off, followed by purification by silica gel column chromatography (eluent; chloroform:methanol=100:0 to 20:1) to give a crude product. This crude product was washed with a small amount of methanol to give 4-[(5-methylpyridin-3-yl)amino]-2-(methylsulfanyl)-6-oxo-1,6-dihydropyrimidine-5-carboxamide (27 mg) as a yellow solid.

Preparation Example 397

To a mixture of 5-chloro-6-ethyl-3-{[4-(methylsulfanyl)phenyl]amino}pyrazine-2-carboxamide (Preparation Example 394) (92 mg) and acetic acid (2.5 mL), sodium tungstate dihydrate (29 mg) and 30% hydrogen peroxide solution (0.15 mL) were added and stirred at room temperature for 30 minutes. After water and ethyl acetate were added to the reaction liquid, 1M aqueous sodium hydroxide was added and stirred for 30 minutes, and the reaction liquid was partitioned. After drying over anhydrous sodium sulfate, the organic layer was filtered and concentrated. The resulting residue was washed with ethyl acetate to give 5-chloro-6-ethyl-3-{[4-(methylsulfonyl)phenyl]amino}pyrazine-2-carboxamide (103 mg).

Preparation Example 398

To a mixture of 3,5-dichloro-6-(1-hydroxy-1-methylethyl)pyrazine-2-carboxamide (2.64 g) and pyridine (30 mL), mesyl chloride (2.45 mL) was added under ice cooling. After stirring at room temperature for 5 hours, pyridine was distilled off under reduced pressure, and the resulting residue was partitioned using ethyl acetate and water. The resulting organic layer was washed with 10% aqueous citric acid, saturated aqueous sodium hydrogen carbonate and saturated aqueous sodium chloride, and dried over anhydrous magnesium sulfate, and the solvent was distilled off to give a light brown syrup. To the light brown syrup, ethanol (60 mL) and THF (30 mL) were added, and then 10% palladium on carbon (0.7 g) was added and stirred at room temperature for 14 hours under 3 atmospheric pressure of hydrogen. After filtration through celite, the filtrate was distilled off under reduced pressure, and the residue was diluted with ethyl acetate and then washed with saturated aqueous sodium hydrogen carbonate and saturated aqueous sodium chloride. After the solvent was distilled off, the residue was purified by silica gel column chromatography (eluent; chloroform:methanol=100:0 to 40:1). The resulting crude product was washed with diisopropyl ether to give 3,5-di-chloro-6-isopropylpyrazine-2-carboxamide (632 mg) as a white solid.

Preparation Example 399

To a mixture of tert-butyl (1-methyl-4-oxocyclohexyl)carbamate (4.00 g) and methanol (50 mL), ammonium formate (10.2 g) and water (5 mL) were added and stirred for 1 hour until they were completely dissolved. Then, 10% palladium on carbon (2.0 g) was added and stirred at room temperature for 65 hours. After insoluble materials were separated by filtration through celite, the solvent was distilled off, and chloroform was added to the resulting residue, followed by drying over anhydrous magnesium sulfate. The solvent was distilled off to give tert-butyl (4-amino-1-methylcyclohexyl)carbamate (3.73 g) as a colorless syrup.

Preparation Example 400

To a mixture of tert-butyl (4-amino-1-methylcyclohexyl)carbamate (Preparation Example 399) (3.73 g) and ethanol (30 mL), 4M hydrogen chloride in ethyl acetate (30 mL) was added under ice cooling and stirred at room temperature for 20 hours. The precipitated solid was collected by filtration and washed with ethyl acetate to give 1-methylcyclohexane-1,4-diamine dihydrochloride (2.10 g) as a white solid.

Preparation Example 412

To a mixture of tert-butyl 4-(4,4,5,5-tetramethyl-1,3,2-dioxaborolan-2-yl)-3,6-dihydropyridine-1(2H)-carboxylate (3.16 g), 4-bromo-3-methoxy-1-nitrobenzene (2.63 g) and DMF (31.6 mL), [1,1'-bis(diphenylphosphino)ferrocene]dichloropalladium(II), dichloromethane adduct (0.50 g) and potassium carbonate (4.24 g) were added and stirred at 80° C. for 4 hours. After this mixture was concentrated under reduced pressure, water and ethyl acetate were added, and insoluble materials were filtered through celite. The organic layer was washed with saturated aqueous sodium chloride. After drying over anhydrous magnesium sulfate, the solvent was distilled off, and the residue was purified by silica gel column chromatography (eluent; n-hexane:ethyl acetate=1:0 to 2:1) to give tert-butyl 4-(2-methoxy-4-nitrophenyl)-3,6-dihydropyridine-1(2H)-carboxylate (2.21 g) as a yellow solid.

Preparation Example 413

To a mixture of tert-butyl 4-(2-methoxy-4-nitrophenyl)-3,6-dihydropyridine-1(2H)-carboxylate (Preparation Example 412) (2.21 g), ethanol (40 mL) and THF (20 mL), 10% palladium on carbon (1.0 g) was added and stirred at room temperature for 3 hours under a hydrogen atmosphere at normal pressure. After filtration through celite, the filtrate was distilled off under reduced pressure to give tert-butyl 4-(4-amino-2-methoxy-phenyl)piperidine-1-carboxylate (1.97 g) as a gray solid.

Preparation Example 417

A mixture of 5-chloro-6-(1-hydroxy-1-methylethyl)-3-{[4-(4-methylpyrazin-1-yl)phenyl]amino}pyrazine-2-carboxamide (Preparation Example 416) (430 mg) and acetic acid (10 mL) was stirred at 120° C. for 5 hours. After the reaction liquid was cooled, the solvent was distilled off, and water and saturated aqueous sodium hydrogen carbonate were added to neutralize. After extraction with ethyl acetate, the extract was washed with saturated aqueous sodium hydrogen carbonate and saturated aqueous sodium chloride and dried over anhydrous magnesium sulfate. The solvent was distilled off, and the residue was washed with diisopropyl ether to give 5-chloro-6-isopropenyl-3-{[4-(4-methylpiperazin-1-yl)phenyl]amino}pyrazine-2-carboxamide (265 mg) as an orange solid.

Preparation Example 430

To a mixture of 7-nitro-2H-1,4-benzoxazine-3(4H)-one (2.0 g), benzyltriethylammonium chloride (470 mg), potassium carbonate (4.27 g) and acetonitrile (60 mL), 1-bromo-2-chloroethane (1.28 mL) was added and stirred at 75° C. for 3 hours. After the reaction liquid was cooled, saturated aqueous sodium hydrogen carbonate was added, and the reaction liquid was extracted with ethyl acetate and the extract was washed with saturated aqueous sodium chloride. After drying over anhydrous magnesium sulfate, the solvent was distilled off under reduced pressure, and the residue was purified by silica gel column chromatography (eluent: chloroform) to give 4-(2-chloroethyl)-7-nitro-2H-1,4-benzoxazine-3(4H)-one (1.92 g) as a yellow powder.

Preparation Example 432

To a mixture of 4-(2-chloroethyl)-7-nitro-2H-1,4-benzoxazine-3(4H)-one (Preparation Example 430) (1.08 g), potassium carbonate (0.87 g) and acetonitrile (10.8 mL), 1-methylpiperazine (1.39 mL) was added and stirred at 80° C. for 48 hours. After the reaction liquid was cooled, saturated aqueous sodium hydrogen carbonate was added, and the reaction liquid was extracted with ethyl acetate and the extract was washed with saturated aqueous sodium chloride. After drying over anhydrous magnesium sulfate, the solvent was distilled off under reduced pressure, and the residue was purified by silica gel column chromatography (eluent; chloroform:methanol=100:0 to 20:1) to give 4-[2-(4-methylpiperazin-1-yl)ethyl]-7-nitro-2H-1,4-benzoxazine-3(4H)-one (690 mg) as a yellow liquid.

Preparation Example 440

A mixture of 3,5-dichloro-6-(1-hydroxy-1-methylethyl)pyrazine-2-carboxamide (1.10 g), 4-[4-(4-methylpiperazin-1-yl)piperidin-1-yl]-3-(trifluoromethyl)aniline (Preparation Example 436) (1.58 g), N,N-diisopropylethylamine (0.80 mL) and dioxane (31 mL) was stirred at 100° C. for 135 hours. After cooling, water was added, followed by extraction with ethyl acetate. Further, insoluble materials were separated by filtration, and the insoluble materials were dissolved in methanol and thereafter mixed with the organic layer. The solvent was distilled off under reduced pressure, followed by drying to give a brown solid. A mixture of the brown solid and acetic acid (30 mL) was stirred at 120° C. for 5 hours. After the solvent was distilled off, saturated aqueous sodium hydrogen carbonate was added, and the precipitated solid was collected by filtration and washed with water. The resulting solid was purified by basic silica gel column chromatography (eluent: chloroform) to give 5-chloro-6-isopropenyl-3-({4-[4-(4-methylpiperazin-1-yl)piperidin-1-yl]-3-(trifluoromethyl)phenyl}amino)pyrazine-2-carboxamide (0.99 g) as a yellow solid.

Preparation Example 444

After a mixture of palladium acetate (188 mg), 1,1'-binaphthalene-2,2'-diylbis(diphenylphosphine) (781 mg), cesium carbonate (4.09 g) and THF (20 mL) was stirred for 30 minutes, a mixture of 1-bromo-3-methoxy-5-nitrobenzene (1.94 g), 1-methylpiperazine (2.76 mL) and THF (20 mL) was added and heated under reflux for 14 hours. After cooling, the reaction liquid was diluted with ethyl acetate, and insoluble materials were separated by filtration. After extraction with 2M hydrochloric acid from the filtrate, the resulting aqueous layer was basified with 50% aqueous potassium hydroxide and then extracted with chloroform. After the organic layer was dried over anhydrous magnesium sulfate, the solvent was distilled off, and the residue was purified by silica gel column chromatography (eluent; chloroform:methanol=100:0 to 20:1) to give 1-(3-methoxy-5-nitrophenyl)-4-methylpiperazine (1.01 g) as an orange syrup.

Preparation Example 454

To a mixture of tert-butyl 4-(4-amino-2-methoxy-phenyl)piperidine-1-carboxylate (Preparation Example 413) (4.25 g) and THF (100 mL), sodium hydrogen carbonate (1.28 g) and water (30 mL) were added, followed by dropwise addition of benzyl chloroformate (1.98 mL) under ice cooling and stirring overnight. After addition of water and extraction with ethyl acetate, the extract was washed with saturated aqueous sodium chloride. After drying over anhydrous magnesium sulfate, the solvent was distilled off, and the residue was purified by silica gel column chromatography (eluent: n-hexane:ethyl acetate=2:1) to give tert-butyl 4-(4-{[(benzyloxy)carbonyl]amino}-2-methoxyphenyl)piperidine-1-carboxylate (4.92 g) as a colorless amorphous.

Preparation Example 455

A mixture of tert-butyl 4-(4-{[(benzyloxy)carbonyl]amino}-2-methoxyphenyl)piperidine-1-carboxylate (Preparation Example 454) (4.92 g), trifluoroacetic acid (10 mL) and 1,2-dichloroethane (50 mL) was stirred at room temperature for 1 hour. The reaction solvent was concentrated under reduced pressure, and after addition of saturated aqueous sodium hydrogen carbonate, the residue was extracted with chloroform. After drying over anhydrous magnesium sulfate, the solvent was distilled off, and the residue was solidified by addition of diethyl ether to give benzyl (3-methoxy-4-piperidin-4-ylphenyl)carbamate (3.24 g) as a white solid.

Preparation Example 464

To a mixture of benzyl (3-methoxy-4-piperidin-4-ylphenyl)carbamate (Preparation Example 455) (1.52 g) and 1,2-dichloroethane (70 mL), formalin (3.62 mL) and sodium triacetoxyborohydride (1.42 g) were added and stirred overnight at room temperature. After addition of water and saturated aqueous sodium hydrogen carbonate, the reaction liquid was extracted with chloroform, and the organic layer was dried over anhydrous magnesium sulfate. After the solvent was distilled off under reduced pressure, the residue was purified by silica gel column chromatography (eluent; chloroform:methanol:saturated aqueous ammonia=100:0:0 to 10:1:0.1) to give benzyl [3-methoxy-4-(1-methylpiperidin-4-yl)phenyl]carbamate (1.26 g) as a white solid.

Preparation Example 467

To a mixture of 7-amino-4-[3-(4-methylpiperazin-1-yl)propyl]-2H-1,4-benzoxazine-3(4H)-one (Preparation Example 435) (300 mg) and THF (9 mL), gradual dropwise addition of borane-tetrahydrofuran complex (3.0 mL, 1M THF solution) was conducted under ice cooling under an argon atmosphere. After the dropwise addition was completed, the mixture was stirred at room temperature for 1 hour and further stirred at 70° C. for 3 hours. After methanol (10 mL) was gradually added to the reaction liquid under ice cooling, 1M hydrochloric acid (5 mL) and thereafter 1M aqueous sodium hydroxide (10 mL) were added and stirred at room temperature for 1 hour. After dilution with water, the reaction liquid was extracted with ethyl acetate. After the solvent was distilled off, the residue was purified by silica gel column chromatography (eluent; chloroform:methanol=100:0 to 20:1) to give 4-[3-(4-methylpiperazin-1-yl)propyl]-3,4-dihydro-2H-1,4-benzoxazine-7-amine (120 mg).

Preparation Example 468

To a mixture of benzyl [3-methoxy-4-(1-methylpiperidin-4-yl)phenyl]carbamate (Preparation Example 464) (1.26 g), ethanol (20 mL) and THF (10 mL), 5% palladium on carbon (0.38 g) was added and stirred overnight at room temperature under a hydrogen atmosphere at normal pressure. After filtration through celite, the filtrate was distilled off under reduced pressure to give 3-methoxy-4-(1-methylpiperidin-4-yl)aniline (0.80 g) as a light pink solid.

Preparation Example 472

To a mixture of 2-[methyl(3-nitrophenyl)amino]ethanol (780 mg) and dichloromethane (20 mL), triethylamine (0.66 mL) and mesyl chloride (0.37 mL) were added sequentially under ice cooling and stirred for 3 hours. Water was added to the reaction liquid, and the organic layer was separated and washed with saturated aqueous sodium chloride. After drying over anhydrous magnesium sulfate, the solvent was distilled off to give 2-[methyl(3-nitrophenyl)amino]ethyl methanesulfonate (1.0 g) as a yellow solid.

Preparation Example 473

A mixture of 2-[methyl(3-nitrophenyl)amino]ethyl methanesulfonate (Preparation Example 472) (1.0 g), 1-methylpiperazine (1.61 mL) and NMP (5 mL) was reacted at 130° C. for 30 minutes using a microwave reaction system. The reaction liquid was diluted with water, extracted with a mixed solvent of chloroform and methanol (10:1), and then washed with saturated aqueous sodium chloride. After drying over anhydrous magnesium sulfate, the solvent was distilled off, and the residue was purified by silica gel column chromatography (eluent; chloroform:methanol:saturated aqueous ammonia=10:1:0.1) to give N-methyl-N-[2-(4-methylpiperazin-1-yl)ethyl]-3-nitroaniline (890 mg) as a yellow oil.

Preparation Example 502

To a mixture of 8-(2-methoxy-5-nitrophenyl)-1,4-dioxa-8-azaspiro[4.5]decane (Preparation Example 495) (795 mg) and dioxane (16 mL), 4M hydrochloric acid (6.8 mL) was added and stirred overnight at 80° C. The reaction liquid was concentrated under reduced pressure, and saturated aqueous sodium hydrogen carbonate was added to the concentrate. The concentrate was extracted with chloroform and then washed with saturated aqueous sodium chloride. After drying over anhydrous sodium sulfate, the solvent was distilled off under reduced pressure, and the residue was purified by silica gel column chromatography (eluent; ethyl acetate:n-hexane) to give 1-(2-methoxy-5-nitrophenyl)piperidin-4-one (296 mg).

Preparation Example 503

To a mixture of 1-(2-methoxy-5-nitrophenyl)piperidin-4-one (Preparation Example 502) (296 mg), 1-methylpiperazine (0.20 mL) and 1,2-dichloroethane (11 mL), sodium triacetoxyborohydride (385 mg) was added and stirred overnight at room temperature. After addition of water and saturated aqueous sodium hydrogen carbonate, the reaction liquid was extracted with chloroform, and the organic layer was dried over anhydrous sodium sulfate. The solvent was distilled off under reduced pressure, and the residue was purified by silica gel column chromatography (eluent: chloroform:methanol=100:0 to 10:1) to give 1-[1-(2-methoxy-5-nitrophenyl)piperidin-4-yl]-4-methylpiperazine (0.40 g) as a brown oil.

Preparation Example 516

To a mixture of 1-fluoro-2-methyl-4-nitrobenzene (3.0 g), potassium carbonate (5.35 g) and DMF (30 mL), 1,4-dioxa-8-azaspiro[4.5]decane (4.15 g) was added and stirred at 80° C. for 20 hours. After cooling, the reaction liquid was diluted with ethyl acetate and washed with water and saturated aqueous sodium chloride. After drying over anhydrous magnesium sulfate, the solvent was distilled off, and the residue was purified by silica gel column chromatography (eluent; chloroform:methanol=100:0 to 100:1) to give 8-(2-methyl-4-nitrophenyl)-1,4-dioxa-8-azaspiro[4.5]decane (5.13 g) as a yellow solid.

Preparation Example 545

To a mixture of 5-chloro-6-(2-hydroxypropan-2-yl)-3-{[3-methoxy-4-(4-methylpiperazin-1-yl)phenyl]amino}pyrazine-2-carboxamide (Preparation Example 544) (300 mg) and trifluoroacetic acid (3 mL), triethylsilane (0.55 mL) was added under ice cooling and stirred under ice cooling for 10 minutes and at room temperature for 22 hours. After the reaction liquid was concentrated, the residue was diluted with chloroform and washed with saturated aqueous sodium hydrogen carbonate. After drying over anhydrous magnesium sulfate, the solvent was distilled off, and the residue was purified by silica gel column chromatography (eluent; chloroform:methanol:saturated aqueous ammonia=100:0:0 to 20:1:0.1) to give a crude product. The crude product was washed with diisopropyl ether to give 5-chloro-6-isopropyl-3-{[3-methoxy-4-(4-methylpiperazin-1-yl)phenyl] amino}pyrazine-2-carboxamide (219 mg) as an orange solid.

Tables 7 to 47 show the chemical structures of the compounds prepared in the above preparation examples, and the chemical structures of the compounds of preparation examples prepared by the same manner as shown in the above preparation examples using corresponding starting materials. Tables 48 to 84 show the preparation processes and physical and chemical data of these preparation examples compounds.

Example 4

A mixture of 4-{[2-(isopropylsulfonyl)phenyl]amino}-2-(methylsulfanyl)-6-oxo-1,6-dihydropyrimidine-5-carboxamide (Preparation Example 294) (200 mg), 1-(aminomethyl)-N,N-dimethylcyclohexylamine (409 mg) and NMP (1 mL) was heated at 180° C. for 10 minutes using a microwave reaction system. After cooling, the reaction liquid was diluted with ethyl acetate, and the precipitated crystal was collected by filtration and washed with ethyl acetate to give a white solid. To the white solid, a mixed solvent of ethanol and water was added, heated and then cooled, and the precipitated solid was collected by filtration to give 2-({[1-(dimethylamino) cyclohexyl]methyl}amino)-4-{[2-(isopropylsulfonyl)phenyl]amino}-6-oxo-1,6-dihydropyrimidine-5-carboxamide (136 mg) as a white solid.

Example 19

A mixture of 4-{[2-(isopropylsulfonyl)phenyl]amino}-2-(methylsulfanyl)-6-oxo-1,6-dihydropyrimidine-5-carboxamide (Preparation Example 294) (200 mg), tert-butyl 2-(aminomethyl)piperidine-1-carboxylate (1.12 g) and NMP (1 mL) was heated at 180° C. for 10 minutes using a microwave reaction system. After cooling, the reaction liquid was diluted with ethyl acetate and washed with water and saturated aqueous sodium chloride. After drying over anhydrous magnesium sulfate, the solvent was distilled off, and the residue was purified by silica gel column chromatography (chloroform:methanol=100:0 to 20:1) to give a white amorphous. To a mixture of the white amorphous, ethyl acetate (10 mL) and ethanol (5 mL), 4M hydrogen chloride in ethyl acetate (5 mL) was added under ice cooling and stirred at room temperature for 4 hours. The precipitated solid was collected by filtration and dried to give 4-{[2-(isopropylsulfonyl)phenyl]amino}-6-oxo-2-[(piperidin-2-ylmethyl)amino]-1,6-dihydropyrimidine-5-carboxamide hydrochloride (126 mg) as a white solid.

Example 29

To a mixture of tert-butyl 3-[(5-carbamoyl-4-{[2-(isopropylsulfonyl)phenyl]amino}-6-oxo-1,6-dihydropyrimidine-2-yl)amino]piperidine-1-carboxylate (Example 28) (299 mg) and ethyl acetate (3 mL), 4M hydrogen chloride in ethyl acetate (2.7 mL) was added under ice cooling and stirred at room temperature for 1 hour. The precipitated solid was collected by filtration and dried to give 4-{[2-(isopropylsulfonyl)phenyl]amino}-6-oxo-2-(piperidin-3-ylamino)-1,6-dihydropyrimidine-5-carboxamide dihydrochloride (194 mg) as a white solid.

Example 31

To a mixture of 4-{[2-(isopropylsulfonyl)phenyl]amino}-6-oxo-2-(piperidin-3-ylamino)-1,6-dihydropyrimidine-5-carboxamide dihydrochloride (Example 29) (67 mg) and pyridine (1.3 mL), mesyl chloride (0.10 mL) was added under ice cooling and stirred for 1 hour. After ethanol was added to the reaction system, the reaction system was concentrated. The resulting residue was partitioned using chloroform and saturated aqueous sodium hydrogen carbonate, and the organic layer was dried. The organic layer was concentrated, followed by an azeotropic process with toluene. The resulting residue was solidified with ethyl acetate-hexane. The resulting solid was recrystallized from ethanol to give 4-{[2-(isopropylsulfonyl)phenyl]amino}-2-{[1-(methylsulfonyl)piperidin-3-yl]amino}-6-oxo-1,6-dihydropyrimidine-5-carboxamide (43 mg).

Example 37

A mixture of 4-{[3-(methylcarbamoyl)phenyl]amino}-2-(methylsulfinyl)-6-oxo-1,6-dihydropyrimidine-5-carboxamide (Preparation Example 311) (234 mg), 1-(aminomethyl) cyclohexaneamine (172 mg) and NMP (2 mL) was stirred at 80° C. for 30 minutes. After cooling, the reaction liquid was diluted with ethyl acetate, and the precipitated solid was collected by filtration. This solid was heated with ethanol-water and washed to give 2-{[(1-aminocyclohexyl)methyl] amino}-4-{[3-(methylcarbamoyl)phenyl]amino}-6-oxo-1, 6-dihydropyrimidine-5-carboxamide (215 mg) as a white solid.

Example 84

A mixture of 5-chloro-6-ethyl-3-{[3-(methylsulfonyl)phenyl]amino}pyrazine-2-carboxamide (Preparation Example 353) (150 mg), 1-(aminomethyl)cyclohexaneamine (163 mg) and NMP (1 mL) was heated at 180° C. for 20 minutes using a microwave reaction system. The reaction liquid was cooled, and ethyl acetate and water were added and stirred for 30 minutes. Thereafter, the precipitated powder was collected by filtration. This powder was heated with ethanol-water (1:1) and washed to give 5-{[(1-aminocyclohexyl)methyl]amino}-6-ethyl-3-{[3-(methylsulfonyl)phenyl]amino}pyrazine-2-carboxamide (112 mg) as a white solid.

Example 146

A mixture of 3,5-dichloro-6-ethylpyrazine-2-carboxamide (200 mg), 3-chloro-4-methylsulfonylaniline (374 mg) and NMP (1 mL) was stirred at 230° C. for 1 hour using a microwave reaction system. Thereafter, trans-4-aminocyclohexanol (524 mg) was added to the reaction liquid and stirred at 190° C. for 30 minutes using a microwave reaction system. After cooling, the reaction liquid was partitioned using ethyl acetate and water, and the organic layer was washed with saturated aqueous sodium hydrogen carbonate and saturated aqueous sodium chloride. After drying over anhydrous magnesium sulfate, the solvent was distilled off, and the residue was purified by silica gel column chromatography (eluent; chloroform:methanol=10:0 to 30:1) to give a crude product. This product was heated with ethanol and washed to give a light yellow solid. To the light yellow solid, ethyl acetate was added and heated, and insoluble materials were separated by filtration and the filtrate was concentrated. After the filtrate was concentrated, the residue was heated and washed with ethanol to give 3-{[3-chloro-4-(methylsulfonyl)phenyl]

amino}-6-ethyl-5-[(trans-4-hydroxycyclohexyl)amino]pyrazine-2-carboxamide (39 mg) as a light yellow solid.

Example 159

To a mixture of 5-[(trans-4-hydroxycyclohexyl)amino]-3-{[3-(methylsulfonyl)phenyl]amino}pyrazine-2-carboxamide (Example 111) (298 mg), chloroform (40 mL) and acetonitrile (10 mL), N-chlorosuccinimide (108 mg) was added and stirred at 70° C. for 8 hours. After the reaction liquid was cooled, silica gel was added, and the solvent was distilled off, followed by purification by silica gel column chromatography (eluent; chloroform:methanol=10:0 to 10:1). The resulting crude product was solidified from chloroform and collected by filtration. The resulting solid was heated with ethyl acetate and washed with ethyl acetate to give 6-chloro-5-[(trans-4-hydroxycyclohexyl)amino]-3-{[3-(methylsulfonyl)phenyl]amino}pyrazine-2-carboxamide (189 mg) as a white solid.

Example 181

To a mixture of 5-[(trans-4-hydroxycyclohexyl)amino]-3-{[3-(methylsulfonyl)phenyl]amino}pyrazine-2-carboxamide (Example 111) (150 mg), chloroform (40 mL) and acetonitrile (20 mL), N-bromosuccinimide (69 mg) was added and stirred at room temperature for 2 hours. To the reaction liquid, silica gel was added, and the solvent was distilled off, followed by purification by silica gel column chromatography (eluent; chloroform:methanol=10:0:0 to 10:1). The resulting crude product was solidified with ethyl acetate and washed with ethyl acetate to give 6-bromo-5-[(trans-4-hydroxycyclohexyl)amino]-3-{[3-(methylsulfonyl)phenyl]amino}pyrazine-2-carboxamide (130 mg) as a light yellow solid.

Example 190

To a mixture of 5-[(trans-4-hydroxycyclohexyl)amino]-3-{[3-(methylsulfonyl)phenyl]amino}pyrazine-2-carboxamide (Example 111) (150 mg), chloroform (40 mL) and acetonitrile (20 mL), N-iodosuccinimide (87 mg) was added and stirred at room temperature for 2 hours. To the reaction liquid, silica gel was added, and the solvent was distilled off, followed by purification by silica gel column chromatography (eluent; chloroform:methanol=10:0 to 10:1). The resulting crude product was solidified with ethyl acetate and washed with ethyl acetate to give 5-[(trans-4-hydroxycyclohexyl)amino]-6-iodo-3-{[3-(methylsulfonyl)phenyl]amino}pyrazine-2-carboxamide (153 mg) as a light yellow solid.

Example 196

A mixture of 5-chloro-6-ethyl-3-{[3-(methylsulfonyl)phenyl]amino}pyrazine-2-carboxamide (Preparation Example 353) (8.8 mg), 1-methyl-piperidin-3-ylamine (8.0 mg) and NMP (0.5 mL) was heated at 190° C. for 30 minutes using a microwave reaction system. After the reaction liquid was cooled, the organic layer was distilled off under reduced pressure, and the residue was separated and purified by HPLC (column: SunFire® C18, 5 µm, 19 mm×100 mm, solvent: MeOH/0.1% HCOOH—H$_2$O=10/90 (0 min)-10/90 (1 min)-95/5 (9 min)-95/5 (12 min), flow rate: 25 mL/min) to give (6-ethyl-5-[(1-methylpiperidin-3-yl)amino]-3-{[3-(methylsulfonyl)phenyl]amino}pyrazine-2-carboxamide (2.4 mg).

Example 302

To a mixture of 5-[(4-amino-4-methylcyclohexyl)amino]-3-{[3-(methylsulfonyl)phenyl]amino}-6-propylpyrazine-2-carboxamide (Example 301) (89 mg) and dichloromethane (5 mL), formalin (0.30 mL) and sodium triacetoxyborohydride (82 mg) were added and stirred at room temperature for 1.5 hours. After the reaction liquid was diluted with chloroform, it was washed with saturated aqueous sodium hydrogen carbonate and dried over anhydrous magnesium sulfate. After the drying agent was separated by filtration, silica gel was added, and the solvent was distilled off, followed by purification of the residue by silica gel column chromatography (eluent; chloroform:methanol:saturated aqueous ammonia=10:0:0 to 10:1:0.1). The resulting residue was washed with ethyl acetate to give 5-{[4-(dimethylamino)-4-methylcyclohexyl]amino}-3-{[3-(methylsulfonyl)phenyl]amino}-6-propylpyrazine-2-carboxamide (31 mg) as a light yellow solid.

Example 309

To a mixture of 6-ethyl-5-[(cis-4-hydroxy-4-methylcyclohexyl)amino]-3-[(4-methyl-3-nitrophenyl)amino]pyrazine-2-carboxamide (Example 308) (242 mg) and methanol (10 mL), 5% palladium on carbon (25 mg) was added and stirred under a hydrogen atmosphere at room temperature for 4 hours. After filtration of the reaction liquid, the filtrate was concentrated under reduced pressure to give 3-[(3-amino-4-methylphenyl)amino]-6-ethyl-5-[(cis-4-hydroxy-4-methylcyclohexyl)amino]pyrazine-2-carboxamide (162 mg) as a green solid.

Example 310

To a mixture of 3-[(3-amino-4-methylphenyl)amino]-6-ethyl-5-[(cis-4-hydroxy-4-methylcyclohexyl)amino]pyrazine-2-carboxamide (Example 309) (150 mg), THF (2 mL) and DMF (2 mL), N,N-diisopropylethylamine (49 mg) and acrylic acid chloride (34 mg) were added under ice cooling and stirred for 30 minutes. The reaction liquid was poured into water and extracted with ethyl acetate. The organic layer was washed with water and saturated aqueous sodium chloride sequentially and then dried over anhydrous sodium sulfate, and the solvent was distilled off under reduced pressure. The residue was purified by silica gel column chromatography (eluent; chloroform:methanol) to give 3-{[3-(acryloylamino)-4-methylphenyl]amino}-6-ethyl-5-[(cis-4-hydroxy-4-methylcyclohexyl)amino]pyrazine-2-carboxamide (48 mg) as a light yellow powder.

Example 343

To a mixture of 5-[(trans-4-hydroxycyclohexyl)amino]-6-isopropenyl-3-{[4-(4-methylpiperazin-1-yl)phenyl]amino}pyrazine-2-carboxamide (Example 342) (205 mg), ethanol (20 mL) and THF (10 mL), 10% palladium on carbon (100 mg) was added under a hydrogen atmosphere and stirred at room temperature for 18 hours. After the catalyst was separated by filtration, the solvent was distilled off, and the residue was purified by basic silica gel column chromatography (eluent: chloroform). The resulting yellow solid was washed with ethyl acetate to give 5-[(trans-4-hydroxycyclohexyl)amino]-6-isopropyl-3-{[4-(4-methylpiperazin-1-yl)phenyl]amino}pyrazine-2-carboxamide (136 mg) as a yellow solid.

Example 381

To a mixture of tert-butyl 4-[4-({3-carbamoyl-5-ethyl-6-[(trans-4-hydroxycyclohexyl)amino]pyrazin-2-yl}amino)-2-methoxyphenyl]piperidine-1-carboxylate (Example 382) (270 mg) and ethyl acetate (10 mL), 4M hydrogen chloride in ethyl acetate (4 mL) was added under ice cooling and stirred at room temperature for 1 hour. The reaction liquid was concentrated under reduced pressure, and saturated aqueous sodium hydrogen carbonate and chloroform were added to the residue. The precipitated solid was collected by filtration and dried to give 6-ethyl-5-[(trans-4-hydroxycyclohexyl)amino]-3-[(3-methoxy-4-piperidin-4-ylphenyl)amino]pyrazine-2-carboxamide (85 mg) as a light yellow solid.

Example 405

To a mixture of 6-ethyl-5-[(trans-4-hydroxycyclohexyl)amino]-3-[(4-piperidin-4-ylphenyl)amino]pyrazine-2-carboxamide (Example 358) (43 mg) and dichloroethane (1 mL), pyridine (0.01 mL) and acetic anhydride (0.01 mL) were added under ice cooling and stirred at room temperature for 20 minutes. After addition of saturated aqueous sodium hydrogen carbonate, the reaction liquid was partitioned using chloroform and saturated aqueous sodium hydrogen carbonate. After drying over anhydrous sodium sulfate, the organic layer was concentrated, and the resulting residue was solidified with ethyl acetate-hexane to give 3-{[4-(1-acetylpiperidin-4-yl)phenyl]amino}-6-ethyl-5-[(trans-4-hydroxycyclohexyl)amino]pyrazine-2-carboxamide (26 mg) as a white solid.

Example 436

To a mixture of methyl 4-[(5-carbamoyl-3-ethyl-6-{[4-(4-methylpiperazin-1-yl)-3-(trifluoromethyl)phenyl]amino}pyrazin-2-yl)amino]cyclohexanecarboxylate (Example 435) (126 mg), THF (2 mL) and methanol (2 mL), 10% aqueous sodium hydroxide (1 mL) was added and heated under reflux for 2 hours. To the reaction liquid, 10% hydrochloric acid was added to give a pH of about 7, and the resulting solid was collected by filtration. This solid was purified by silica gel column chromatography (eluent; chloroform:methanol) to give 4-[(5-carbamoyl-3-ethyl-6-{[4-(4-methylpiperazin-1-yl)-3-(trifluoromethyl)phenyl]amino}pyrazin-2-yl)amino]cyclohexanecarboxylic acid (Example 436) (47 mg), which was a low-polarity product, as a light yellow white powder and 4-[(5-carbamoyl-3-ethyl-6-{[4-(4-methylpiperazin-1-yl)-3-(trifluoromethyl)phenyl]amino}pyrazin-2-yl)amino]cyclohexanecarboxylic acid (Example 437) (59 mg), which was a high-polarity product, as a light yellow powder.

Example 438

To a mixture of 4-[(5-carbamoyl-3-ethyl-6-{[4-(4-methylpiperazin-1-yl)-3-(trifluoromethyl)phenyl]amino}pyrazin-2-yl)amino]cyclohexanecarboxylic acid (Example 436) (62 mg), o-anisidine (42 mg) and DMF (2 mL), 1-hydroxy-1H-benzotriazole monohydrate (46 mg) and 1-ethyl-3-(3-dimethylaminopropyl)carbodiimide hydrochloride (65 mg) were added and stirred at room temperature for 7 hours. The reaction liquid was poured into saturated aqueous sodium hydrogen carbonate and extracted with ethyl acetate. The organic layer was washed with water and saturated aqueous sodium chloride sequentially and then dried over anhydrous sodium sulfate, and the solvent was distilled off under reduced pressure. The residue was purified by silica gel column chromatography (eluent; chloroform:methanol) to give 6-ethyl-5-({4-[(2-methoxy-phenyl)carbamoyl]cyclohexyl}amino)-3-{[4-(4-methylpiperazin-1-yl)-3-(trifluoromethyl)phenyl]amino}pyrazine-2-carboxamide (33 mg) as a yellow powder.

Example 495

A mixture of 6-chloro-3-{[3-(1,4-dioxa-8-azaspiro[4.5]deca-8-yl)-4-methoxyphenyl]amino}-5-[(trans-4-hydroxycyclohexyl)amino]pyrazine-2-carboxamide (Example 482) (0.80 g), acetic acid (4 mL) and water (4 mL) was stirred at 80° C. for 3 hours. To the reaction liquid, concentrated hydrochloric acid (1 mL) was added and stirred at 80° C. for 2 hours. The reaction liquid was cooled and concentrated under reduced pressure, and then chloroform was added, followed by washing with saturated aqueous sodium hydrogen carbonate. After the organic layer was dried over anhydrous magnesium sulfate, the solvent was distilled off, followed by purification by silica gel column chromatography (eluent; chloroform:methanol=10:1 to 30:1) to give 6-chloro-5-[(trans-4-hydroxycyclohexyl)amino]-3-{[4-methoxy-3-(4-oxopiperidin-1-yl)phenyl]amino}pyrazine-2-carboxamide (0.74 g) as a yellow amorphous.

Example 499

To a mixture of 6-chloro-5-[(trans-4-hydroxycyclohexyl)amino]-3-{[4-methoxy-3-(4-oxopiperidin-1-yl)phenyl]amino}pyrazine-2-carboxamide (Example 495) (0.346 mg), N-methylpiperazine (0.12 mL) and 1,2-dichloroethane (10 mL), sodium triacetoxyborohydride (225 mg) was added and stirred at room temperature for 5 hours. After addition of saturated aqueous sodium hydrogen carbonate, the reaction liquid was extracted with chloroform, and the organic layer was washed with saturated aqueous sodium chloride. After drying over anhydrous sodium sulfate, the solvent was distilled off under reduced pressure, and the residue was purified by silica gel column chromatography (eluent; chloroform:methanol:saturated aqueous ammonia=100:0:0 to 20:1:0.1) to give a crude product. The crude product was solidified with ethyl acetate-diisopropyl ether and then washed with ethyl acetate to give 6-chloro-5-[(trans-4-hydroxycyclohexyl)amino]-3-({4-methoxy-3-[4-(4-methylpiperazin-1-yl)piperidin-1-yl]phenyl}amino)pyrazine-2-carboxamide (39 mg) as a light yellow solid.

Example 508

A mixture of 6-bromo-5-[(trans-4-hydroxycyclohexyl)amino]-3-{[3-(methylsulfonyl)phenyl]amino}pyrazine-2-carboxamide (Example 181) (50 mg), cyclopropylboronic acid (18 mg), tetrakistriphenylphosphine palladium (24 mg), potassium carbonate (71 mg), dioxane (2.5 mL) and water (0.5 mL) was stirred at 115° C. overnight. After cooling, the reaction liquid was partitioned using chloroform, saturated aqueous sodium hydrogen carbonate and saturated aqueous sodium chloride. After drying, the organic layer was concentrated, and the resulting residue was purified by silica gel column chromatography (eluent; chloroform:methanol:saturated aqueous ammonia=100:0:0 to 10:1:0.1). The resulting residue was solidified with ethyl acetate-hexane to give 6-cyclopropyl-5-[(trans-4-hydroxycyclohexyl)amino]-3-{[3-(methylsulfonyl)phenyl]amino}pyrazine-2-carboxamide (10 mg) as a yellow solid.

Example 534

To a mixture of 5-[(1-benzylpiperidin-4-yl)amino]-6-ethyl-3-({3-methyl-4-[4-(4-methylpiperazin-1-yl)piperidin-1-yl]phenyl}amino)pyrazine-2-carboxamide (Example 507) (1.31 g), ethanol (26 mL) and acetic acid (13 mL), palladium hydroxide (0.65 g) was added and stirred under a hydrogen atmosphere at room temperature for 3 days. After the catalyst was separated by filtration, the solvent was concentrated and partitioned using chloroform and saturated aqueous sodium hydrogen carbonate. The organic layer was concentrated to give 6-ethyl-3-({3-methyl-4-[4-(4-methylpiperazin-1-yl)piperidin-1-yl]phenyl}amino)-5-(piperidin-4-ylamino)pyrazine-2-carboxamide (0.73 g) as a light yellow solid.

Tables 85 to 164 show the chemical structures of the compounds prepared in the above examples, and the chemical structures of the examples compounds prepared by the same manner as shown in the above examples using corresponding starting materials. Tables 165 to 183 show the preparation processes and physical and chemical data of these examples compounds.

TABLE 7-continued

| Rex | Structure |
|---|---|
| 12 | (iPr-NH-C(O)-phenyl-Me, NO2) |
| 13 | (iPr-NH-C(O)-phenyl(Me)-NH-pyrimidine(C(O)NH2)(=O)(NH)(SMe)) |
| 14 | (iPr-NH-C(O)-phenyl(Me)-NH-pyrimidine(C(O)NH2)(Cl)(N)(SMe)) |

TABLE 8

| Rex | Structure |
|---|---|
| 15 | (Me-NH-C(O)-phenyl(Me)-NH-pyrimidine(C(O)NH2)(=O)(NH)(SMe)) |
| 16 | (Me-NH-C(O)-phenyl(Me)-NH-pyrimidine(C(O)NH2)(Cl)(N)(SMe)) |
| 17 | (NEt2-SO2-phenyl-NH-pyrimidine(C(O)NH2)(=O)(NH)(SMe)) |

TABLE 8-continued

| Rex | Structure |
|---|---|
| 18 | (NEt2-SO2-phenyl(Me)-NH-pyrimidine(C(O)NH2)(Cl)(N)(SMe)) |
| 19 | (piperidinyl-SO2-phenyl(Me)-NH-pyrimidine(C(O)NH2)(=O)(NH)(SMe)) |
| 20 | (piperidinyl-SO2-phenyl(Me)-NH-pyrimidine(C(O)NH2)(Cl)(N)(SMe)) |
| 21 | (Me-NH-C(O)-phenyl(Cl)-NH2) |
| 22 | (Me-NH-C(O)-phenyl(Cl)-NO2) |
| 23 | (Me-NH-C(O)-phenyl(Cl)-NH-pyrimidine(C(O)NH2)(=O)(NH)(SMe)) |
| 24 | (Me-NH-C(O)-phenyl(Cl)-NH-pyrimidine(C(O)NH2)(Cl)(N)(SMe)) |

TABLE 8-continued

| Rex | Structure |
|---|---|
| 25 | 4-amino-2-chloro-N,N-diethylbenzamide |
| 26 | 2-chloro-N,N-diethyl-4-nitrobenzamide |
| 27 | 4-[[6-carbamoyl-2-(methylthio)-5-oxo-1H-pyrimidin-4-yl]amino]-2-chloro-N,N-diethylbenzamide |
| 28 | 4-[[5-carbamoyl-6-chloro-2-(methylthio)pyrimidin-4-yl]amino]-2-chloro-N,N-diethylbenzamide |

TABLE 9

| Rex | Structure |
|---|---|
| 29 | 3-amino-4-methyl-N-isopropylbenzenesulfonamide |
| 30 | 3-[[6-carbamoyl-2-(methylthio)-5-oxo-1H-pyrimidin-4-yl]amino]-N-isopropyl-4-methylbenzenesulfonamide |
| 31 | 3-[[5-carbamoyl-6-chloro-2-(methylthio)pyrimidin-4-yl]amino]-N-isopropyl-4-methylbenzenesulfonamide |
| 32 | 3-[[6-carbamoyl-2-(methylthio)-5-oxo-1H-pyrimidin-4-yl]amino]-4-methyl-N-methylbenzenesulfonamide |
| 33 | 3-[[5-carbamoyl-6-chloro-2-(methylthio)pyrimidin-4-yl]amino]-4-methyl-N-methylbenzenesulfonamide |
| 34 | 4-[[6-carbamoyl-2-(methylthio)-5-oxo-1H-pyrimidin-4-yl]amino]-2-chloro-phenyl piperidin-1-yl ketone |
| 35 | 4-[[5-carbamoyl-6-chloro-2-(methylthio)pyrimidin-4-yl]amino]-2-chloro-phenyl piperidin-1-yl ketone |
| 36 | 4-amino-2-chloro-N-isopropylbenzamide |
| 37 | 2-chloro-N-isopropyl-4-nitrobenzamide |
| 38 | 4-[[6-carbamoyl-2-(methylthio)-5-oxo-1H-pyrimidin-4-yl]amino]-2-chloro-N-isopropylbenzamide |
| 39 | 4-[[5-carbamoyl-6-chloro-2-(methylthio)pyrimidin-4-yl]amino]-2-chloro-N-isopropylbenzamide |

TABLE 9-continued

| Rex | Structure |
|---|---|
| 40 | (piperidine-SO2-phenyl(OMe)-NH2) |
| 41 | (piperidine-SO2-phenyl(OMe)-NO2) |
| 42 | (piperidine-SO2-phenyl(OMe)-NH-pyrimidine(SMe)(C(O)NH2)(=O)) |

TABLE 10

| Rex | Structure |
|---|---|
| 43 | (piperidine-SO2-phenyl(OMe)-NH-pyrimidine(SMe)(C(O)NH2)(Cl)) |
| 44 | (Et2N-SO2-phenyl(OMe)-NH2) |
| 45 | (Et2N-SO2-phenyl(OMe)-NO2) |
| 46 | (Et2N-SO2-phenyl(OMe)-NH-pyrimidine(SMe)(C(O)NH2)(=O)) |
| 47 | (Et2N-SO2-phenyl(OMe)-NH-pyrimidine(SMe)(C(O)NH2)(Cl)) |

TABLE 10-continued

| Rex | Structure |
|---|---|
| 48 | (iPr-NH-C(O)-phenyl(F)-NH2) |
| 49 | (iPr-NH-C(O)-phenyl(F)-NH-pyrimidine(SMe)(C(O)NH2)(=O)) |
| 50 | (iPr-NH-C(O)-phenyl(F)-NH-pyrimidine(SMe)(C(O)NH2)(Cl)) |
| 51 | (piperidine-C(O)-phenyl(F)-NH2) |
| 52 | (piperidine-C(O)-phenyl(F)-NH-pyrimidine(SMe)(C(O)NH2)(=O)) |
| 53 | (piperidine-C(O)-phenyl(F)-NH-pyrimidine(SMe)(C(O)NH2)(Cl)) |
| 54 | (morpholine-C(O)-phenyl(F)-NH-pyrimidine(SMe)(C(O)NH2)(=O)) |

TABLE 10-continued
| Rex | Structure |
|---|---|
| 55 | 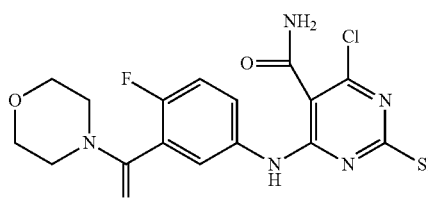 |
| 56 | 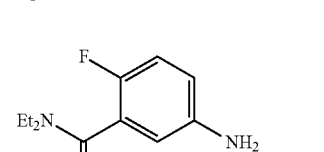 |

TABLE 11-continued
| Rex | Structure |
|---|---|
| 69 | 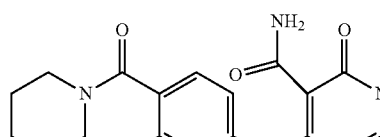 |
| 70 | 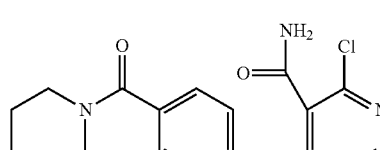 |
TABLE 12
| Rex | Structure |
|---|---|
| 71 | 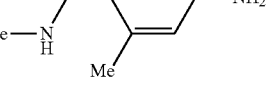 |
| 72 | 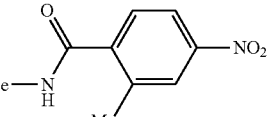 |
| 73 | 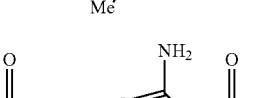 |
| 74 | 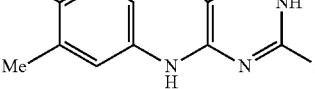 |
| 75 | 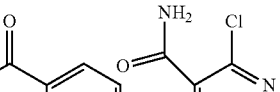 |
| 76 | 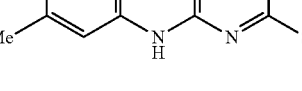 |
TABLE 12-continued
| Rex | Structure |
|---|---|
| 77 | 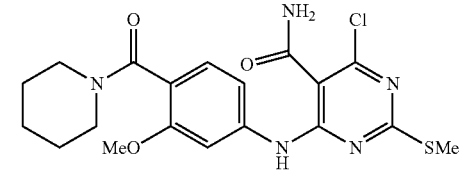 [SMILES: COc1cc(Nc2nc(SC)nc(Cl)c2C(N)=O)ccc1C(=O)N1CCCCC1] |
| 78 | 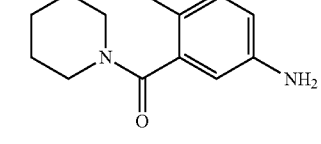 |
| 79 | 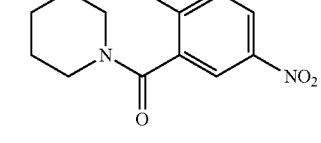 |
| 80 | 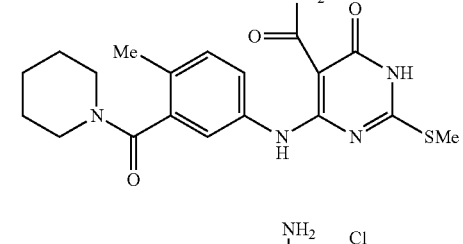 |
| 81 | 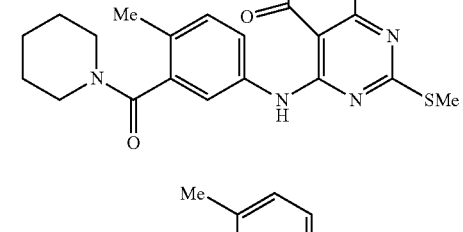 |
| 82 | 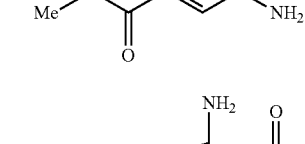 |
| 83 | 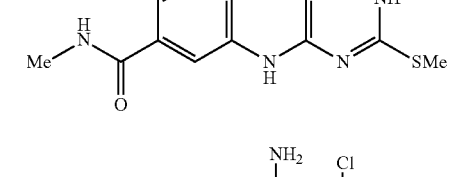 |
| 84 | 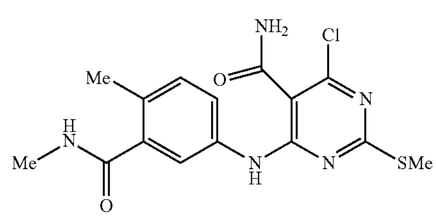 [SMILES: CNC(=O)c1cc(Nc2nc(SC)nc(Cl)c2C(N)=O)ccc1C] |

TABLE 13

| Rex | Structure |
|---|---|
| 85 | 4-amino-N-methyl-2-(trifluoromethyl)benzamide |
| 86 | 4-[[5-carbamoyl-2-(methylthio)-6-oxo-1,6-dihydropyrimidin-4-yl]amino]-N-methyl-2-(trifluoromethyl)benzamide |
| 87 | 4-[[5-carbamoyl-6-chloro-2-(methylthio)pyrimidin-4-yl]amino]-N-methyl-2-(trifluoromethyl)benzamide |
| 88 | 5-amino-2-fluoro-N-methylbenzamide |
| 89 | 5-[[5-carbamoyl-2-(methylthio)-6-oxo-1,6-dihydropyrimidin-4-yl]amino]-2-fluoro-N-methylbenzamide |
| 90 | 5-[[5-carbamoyl-6-chloro-2-(methylthio)pyrimidin-4-yl]amino]-2-fluoro-N-methylbenzamide |
| 91 | 4-amino-2-methoxy-N-methylbenzenesulfonamide |
| 92 | 2-methoxy-N-methyl-4-nitrobenzenesulfonamide |

TABLE 13-continued

| Rex | Structure |
|---|---|
| 93 | 4-[[5-carbamoyl-2-(methylthio)-6-oxo-1,6-dihydropyrimidin-4-yl]amino]-2-methoxy-N-methylbenzenesulfonamide |
| 94 | 4-[[5-carbamoyl-6-chloro-2-(methylthio)pyrimidin-4-yl]amino]-2-methoxy-N-methylbenzenesulfonamide |
| 95 | 4-amino-2-methoxy-N-methylbenzamide |
| 96 | 2-methoxy-N-methyl-4-nitrobenzamide |
| 97 | 4-[[5-carbamoyl-2-(methylthio)-6-oxo-1,6-dihydropyrimidin-4-yl]amino]-2-methoxy-N-methylbenzamide |
| 98 | 4-[[5-carbamoyl-6-chloro-2-(methylthio)pyrimidin-4-yl]amino]-2-methoxy-N-methylbenzamide |

TABLE 14

| Rex | Structure |
|---|---|
| 99 | (4-amino-2-(trifluoromethyl)phenyl)(piperidin-1-yl)methanone |
| 100 | 4-[[5-carbamoyl-2-(methylthio)-6-oxo-1,6-dihydropyrimidin-4-yl]amino]-2-(trifluoromethyl)phenyl](piperidin-1-yl)methanone |

TABLE 14-continued

| Rex | Structure |
|---|---|
| 101 | (structure) |
| 102 | (structure) |
| 103 | (structure) |
| 104 | (structure) |
| 105 | (structure) |
| 106 | (structure) |
| 107 | (structure) |
| 108 | (structure) |
| 109 | (structure) |
| 110 | (structure) |
| 111 | (structure) |
| 112 | (structure) |

TABLE 15

| Rex | Structure |
|---|---|
| 113 | (structure) |
| 114 | (structure) |

TABLE 15-continued
| Rex | Structure |
|---|---|
| 115 | 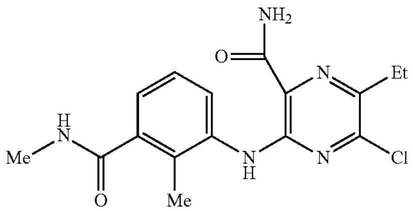 [SMILES: CCc1nc(C(N)=O)c(Nc2cccc(C(=O)NC)c2C)nc1Cl] |
| 116 | 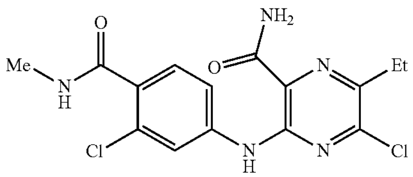 [SMILES: CCc1nc(C(N)=O)c(Nc2ccc(C(=O)NC)c(Cl)c2)nc1Cl] |
| 117 | 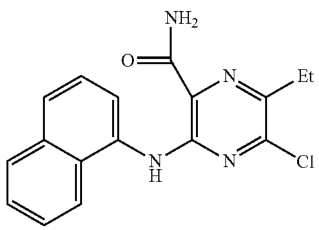 [SMILES: CCc1nc(C(N)=O)c(Nc2cccc3ccccc23)nc1Cl] |
| 118 | 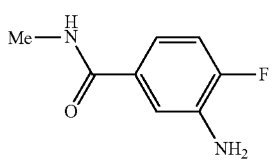 [SMILES: CNC(=O)c1ccc(F)c(N)c1] |
| 119 | 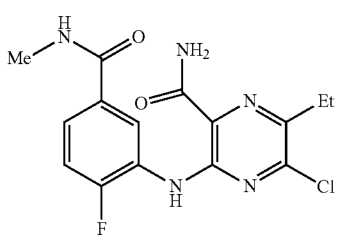 [SMILES: CCc1nc(C(N)=O)c(Nc2cc(C(=O)NC)ccc2F)nc1Cl] |
| 120 | 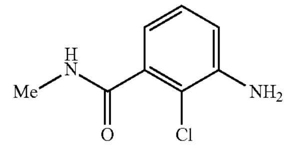 |
| 121 | 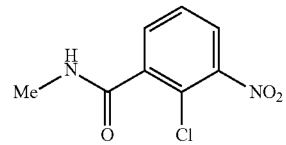 [SMILES: CNC(=O)c1cccc(N)c1Cl] |
| 122 | 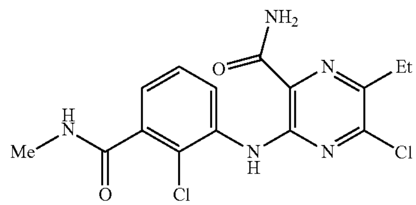 [SMILES: CCc1nc(C(N)=O)c(Nc2cccc(C(=O)NC)c2Cl)nc1Cl] |
| 123 | 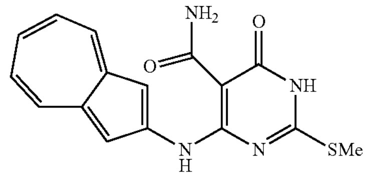 [SMILES: CSc1nc(Nc2cc3cccccc-3c2)c(C(N)=O)c(=O)[nH]1] |
| 124 | 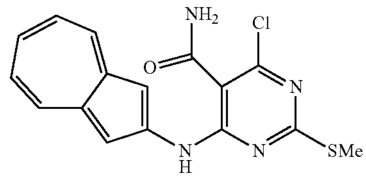 [SMILES: CSc1nc(Cl)c(C(N)=O)c(Nc2cc3cccccc-3c2)n1] |
| 125 | 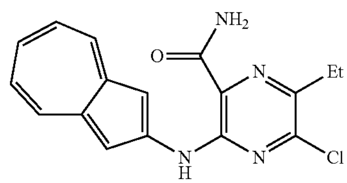 [SMILES: CCc1nc(C(N)=O)c(Nc2cc3cccccc-3c2)nc1Cl] |
| 126 | 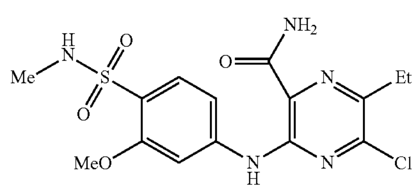 [SMILES: CCc1nc(C(N)=O)c(Nc2ccc(S(=O)(=O)NC)c(OC)c2)nc1Cl] |
TABLE 16
| Rex | Structure |
|---|---|
| 127 | 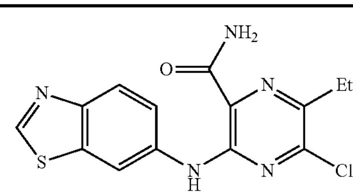 |
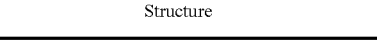

TABLE 16-continued

| Rex | Structure |
|---|---|
| 128 | (structure) |
| 129 | (structure) |
| 130 | (structure) |
| 131 | (structure) |
| 132 | (structure) |
| 133 | (structure) |
| 134 | (structure) |
| 135 | (structure) |

TABLE 16-continued
| Rex | Structure |
|---|---|
| 136 | 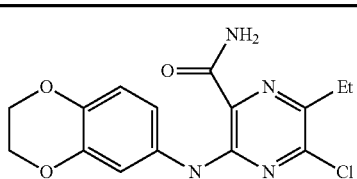 |
| 137 | 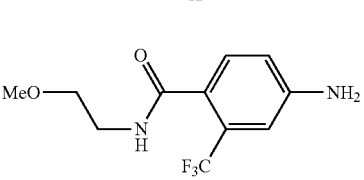 |
| 138 | 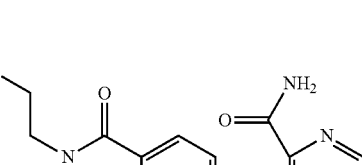 |
| 139 | 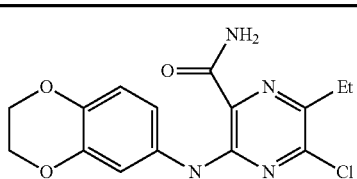 |
| 140 | 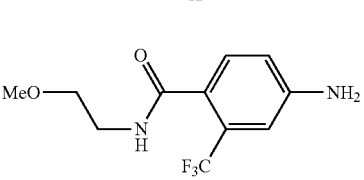 |
TABLE 17
| Rex | Structure | Rex | Structure |
|---|---|---|---|
| 141 | 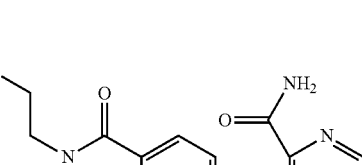 | 144 | |
| 142 | | 145 | |
| 143 | | 146 | |

TABLE 17-continued

| Rex | Structure |
|---|---|
| 147 | (piperidinyl-sulfonyl-methoxyphenyl)amino-chloro-ethyl-pyrazinecarboxamide |
| 148 | (4-methyl-2-nitrophenyl)amino-chloro-ethyl-pyrazinecarboxamide |
| 149 | (2-methylbenzothiazol-6-yl)amino-chloro-ethyl-pyrazinecarboxamide |
| 150 | (2-ethylbenzothiazol-6-yl)amino-chloro-ethyl-pyrazinecarboxamide |
| 151 | (benzo[1,2,5]thiadiazol-5-yl)amino-chloro-ethyl-pyrazinecarboxamide |
| 152 | (1-methylindazol-6-yl)amino-chloro-ethyl-pyrazinecarboxamide |
| 153 | (benzo[1,2,3]thiadiazol-6-yl)amino-chloro-ethyl-pyrazinecarboxamide |
| 154 | (1-methylindol-6-yl)amino-chloro-ethyl-pyrazinecarboxamide |

TABLE 18

| Rex | Structure |
|---|---|
| 155 | N-methyl-2-(trifluoromethyl)benzene-1,4-diamine |
| 156 | [4-(methylamino)-3-(trifluoromethyl)phenyl]amino-chloro-ethyl-pyrazinecarboxamide |
| 157 | (3R,4S)-1-{1-[4-amino-3-methoxyphenyl]piperidin-4-yl}pyrrolidine-3,4-diol |
| 158 | (3R,4S)-1-{1-[3-methoxy-4-nitrophenyl]piperidin-4-yl}pyrrolidine-3,4-diol |

TABLE 18-continued

| Rex | Structure |
|---|---|
| 159 | 3,4-dihydroxypyrrolidin-1-yl-piperidinyl attached to phenyl (with OMe) linked via NH to pyrazine bearing CONH₂, Et, and Cl substituents |
| 160 | 2-cyano-3-ethyl-5,6-dichloropyrazine |
| 161 | 4-methylpiperazinyl-pyridinyl-NH-pyrazine(CONH₂, Et, Cl) |
| 162 | 4-methylpiperazinyl-piperidinyl-pyridinyl-NH₂ |
| 163 | 4-methylpiperazinyl-piperidinyl-pyridinyl-NO₂ |
| 164 | 4-methylpiperazinyl-piperidinyl-pyridinyl-NH-pyrazine(CONH₂, Et, Cl) |
| 165 | 4-methylpiperazinyl-pyridinyl-NH-pyrazine(CONH₂, Et, Cl) |
| 166 | morpholinyl-pyridinyl-NH-pyrazine(CONH₂, Et, Cl) |
| 167 | 4-methylpiperazinyl-piperidinyl-pyridinyl-NH₂ |

TABLE 18-continued

| Rex | Structure |
|---|---|
| 168 | Me-N(piperazine)-N(piperidine)-N-(pyridin-2-yl with 5-NO₂) |

TABLE 19

| Rex | Structure |
|---|---|
| 169 | 4-methylpiperazinyl–piperidinyl–pyridin-2-ylamino linked to 3-carboxamide-5-ethyl-6-chloropyrazine |
| 170 | Methylsulfonyl-piperazinyl–piperidinyl-(2-methoxyphenyl)amino linked to 3-carboxamide-5-ethyl-6-chloropyrazine |
| 171 | Morpholino-phenylamino linked to 3-carboxamide-5-ethyl-6-chloropyrazine |
| 172 | 4-methylpiperazinyl-(3-methylphenyl)amino linked to 3-carboxamide-5-ethyl-6-chloropyrazine |
| 173 | 4-methylpiperazinyl-piperidinyl-(2-methylphenyl)amino linked to 3-carboxamide-5-ethyl-6-chloropyrazine |

TABLE 19-continued

| Rex | Structure |
|---|---|
| 174 | 4-methylpiperazinyl-chloro-phenyl linked via NH to pyrazine carboxamide with Et and Cl substituents |
| 175 | Boc-piperazinyl-phenyl linked via NH to pyrazine carboxamide with Et and Cl substituents |
| 176 | 4,4-difluoropiperidinyl-(2-trifluoromethyl)-4-aminophenyl |
| 177 | 4,4-difluoropiperidinyl-(2-trifluoromethyl)-4-nitrophenyl |
| 178 | 4,4-difluoropiperidinyl-(3-trifluoromethyl)phenyl linked via NH to pyrazine carboxamide with Et and Cl substituents |
| 179 | 4-methylpiperazinyl-(cyano)phenyl linked via NH to pyrazine carboxamide with Et and Cl substituents |
| 180 | 4-(cyclopropylmethyl)piperazinyl-(2-trifluoromethyl)-4-aminophenyl |
| 181 | 4-(cyclopropylmethyl)piperazinyl-(2-trifluoromethyl)-4-nitrophenyl |
| 182 | 4-(cyclopropylmethyl)piperazinyl-(3-trifluoromethyl)phenyl linked via NH to pyrazine carboxamide with Et and Cl substituents |

TABLE 20

| Rex | Structure |
|---|---|
| 183 | (3-dimethylamino-pyrrolidin-1-yl)-4-amino-2-trifluoromethylbenzene |
| 184 | (3-dimethylamino-pyrrolidin-1-yl)-4-nitro-2-trifluoromethylbenzene |
| 185 | pyrazine-2-carboxamide, 5-chloro-6-ethyl-3-[[4-(3-dimethylaminopyrrolidin-1-yl)-3-trifluoromethylphenyl]amino]- |
| 186 | pyrazine-2-carboxamide, 5-chloro-6-ethyl-3-[[4-(4-ethylpiperazin-1-yl)-3-trifluoromethylphenyl]amino]- |
| 187 | 1-(3,5-dimethylpiperazin-1-yl)-4-amino-2-trifluoromethylbenzene |
| 188 | 1-(3,5-dimethylpiperazin-1-yl)-4-nitro-2-trifluoromethylbenzene |
| 189 | pyrazine-2-carboxamide, 5-chloro-6-ethyl-3-[[4-(3,5-dimethylpiperazin-1-yl)-3-trifluoromethylphenyl]amino]- |
| 190 | 1-(3,4,5-trimethylpiperazin-1-yl)-4-amino-2-trifluoromethylbenzene |

TABLE 20-continued

| Rex | Structure |
|---|---|
| 191 | 1-(3,4,5-trimethylpiperazin-1-yl)-4-nitro-2-trifluoromethylbenzene |
| 192 | pyrazine-2-carboxamide, 5-chloro-6-ethyl-3-[[4-(3,4,5-trimethylpiperazin-1-yl)-3-trifluoromethylphenyl]amino]- |
| 193 | pyrazine-2-carboxylic acid methyl ester, 5-chloro-3-[[4-(4-methylpiperazin-1-yl)phenyl]amino]- |
| 194 | pyrazine-2-carboxamide, N-methoxy-5-chloro-3-[[4-(4-methylpiperazin-1-yl)phenyl]amino]- |
| 195 | pyrazine-2-carboxamide, 5-chloro-6-ethyl-3-[[4-[(4-methylpiperazin-1-yl)methyl]phenyl]amino]- |
| 196 | pyrazine-2-carboxamide, 5-chloro-6-ethyl-3-[[4-[2-(4-methylpiperazin-1-yl)ethyl]phenyl]amino]- |

TABLE 21

| Rex | Structure |
|---|---|
| 197 | pyrazine-2-carboxamide, 5-chloro-6-ethyl-3-[[4-(4-Boc-piperazin-1-yl)-3-trifluoromethylphenyl]amino]- |

TABLE 21-continued

| Rex | Structure |
|---|---|
| 198 | (Boc-piperazinyl)(Me)phenyl-NH-pyrazine(CONH2)(Et)(Cl) |
| 199 | 3,3-dimethylpiperidinyl-(CF3)phenyl-NH2 |
| 200 | (4-Me-piperazinyl)phenyl-NH-pyrazine with cPr-CH2-O-NH-C(O)- and Cl |
| 201 | (4-Me-piperazinyl)phenyl-NH-pyrazine with morpholino-ethyl-O-NH-C(O)- and Cl |
| 202 | pyrrolidinyl-piperidinyl-(CF3)phenyl-NH2 |
| 203 | pyrrolidinyl-piperidinyl-(CF3)phenyl-NO2 |
| 204 | pyrrolidinyl-piperidinyl-(CF3)phenyl-NH-pyrazine(CONH2)(Et)(Cl) |
| 205 | (4-Me-piperazinyl-SO2)phenyl-NH-pyrazine(CONH2)(Et)(Cl) |
| 206 | (Boc-piperidinyl)(Me)phenyl-NH-pyrazine(CONH2)(Et)(Cl) |
| 207 | (2S,5R)-1,2,5-trimethylpiperazinyl-(CF3)phenyl-NH2 |
| 208 | (2S,5R)-1,2,5-trimethylpiperazinyl-(CF3)phenyl-NO2 |
| 209 | (2S,5R)-1,2,5-trimethylpiperazinyl-(CF3)phenyl-NH-pyrazine(CONH2)(Et)(Cl) |
| 210 | (4-Me-piperazinyl)(2,5-diMe)phenyl-NH2 |

TABLE 22
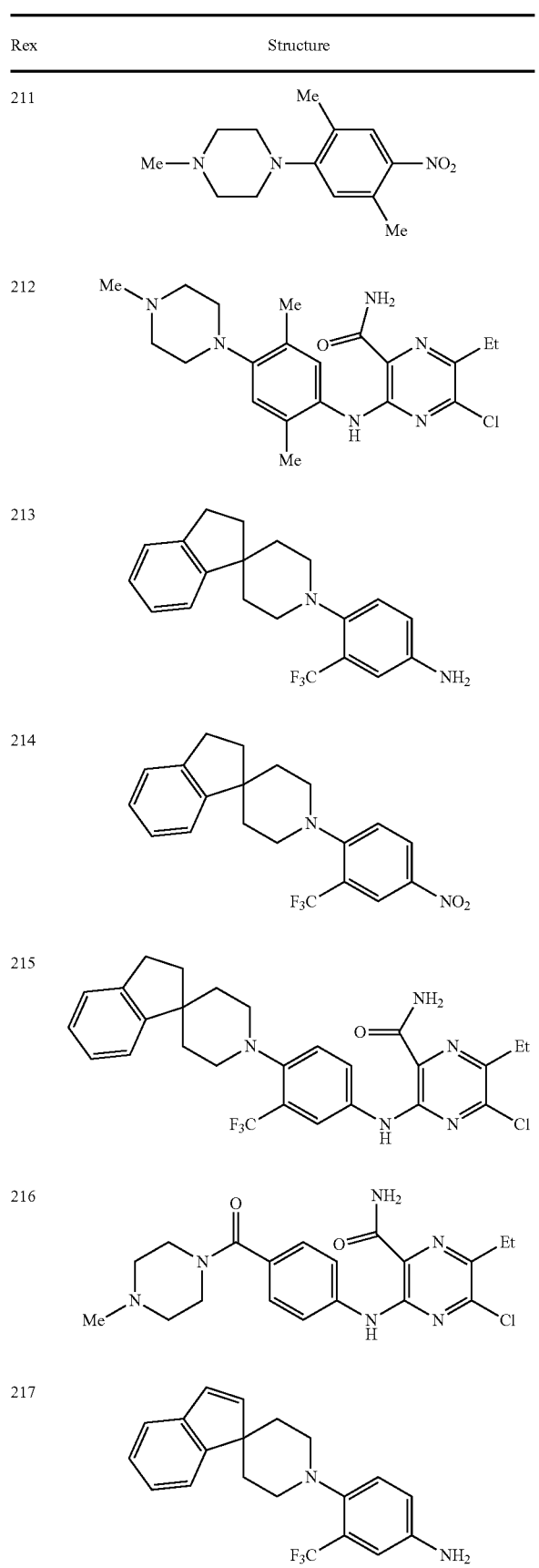
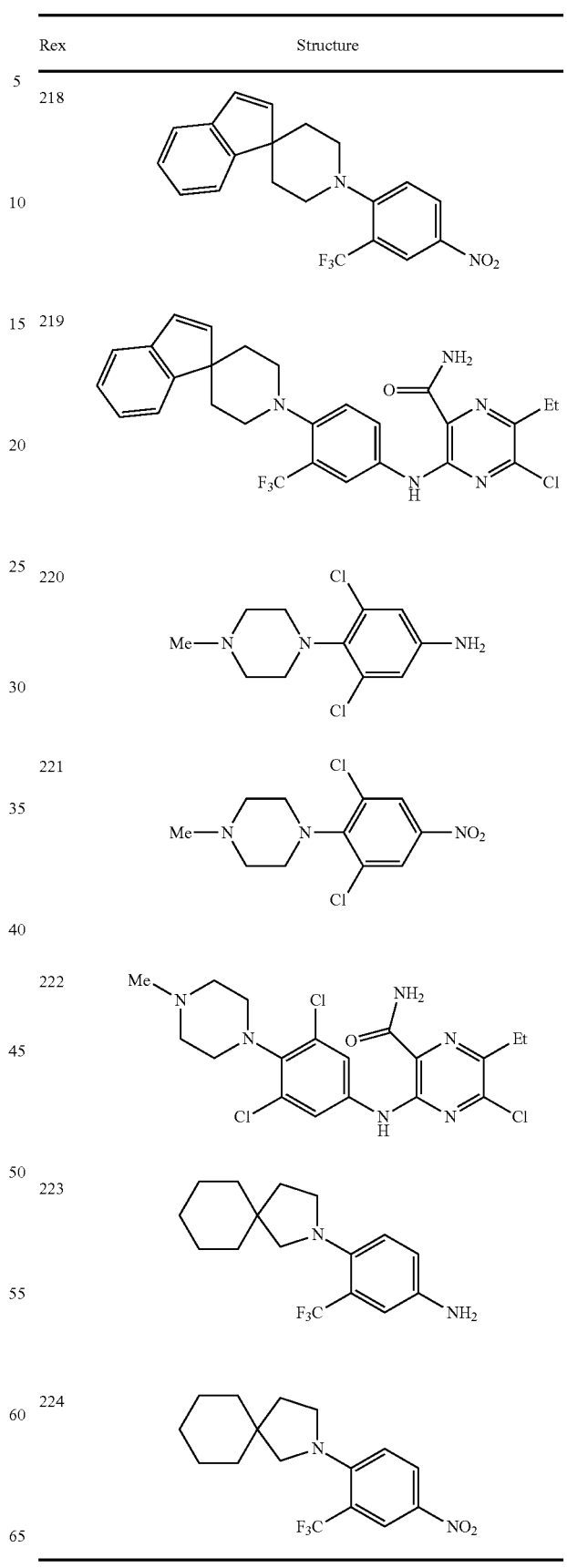

TABLE 23

| Rex | Structure |
|---|---|
| 225 | (spiro cyclohexane-pyrrolidine)-N-phenyl(CF3)-NH-pyrazine(CONH2)(Et)(Cl) |
| 226 | Boc-piperazine-phenyl(OMe)-NH-pyrazine(CONH2)(Et)(Cl) |
| 227 | 2-oxopyridin-1-yl-phenyl-NH-pyrazine(CONH2)(Et)(Cl) |
| 228 | Boc-piperidine-phenyl(CF3)-NH2 |
| 229 | Boc-tetrahydropyridine-phenyl(CF3)-NO2 |
| 230 | Boc-piperidine-phenyl(CF3)-NH-pyrazine(CONH2)(Et)(Cl) |
| 231 | (4-Me-piperazinyl)methyl-phenyl(Me)-NH-pyrazine(CONH2)(Et)(Cl) |
| 232 | Et2N-CH2CH2-O-phenyl-NH-pyrazine(CONH2)(Et)(Cl) |

TABLE 23-continued

| Rex | Structure |
|---|---|
| 233 | (1-Me-piperidin-4-yl)-O-phenyl-NH-pyrazine(CONH2)(Et)(Cl) |
| 234 | (4-Me-piperazinyl)-phenyl(NHAc)-NH2 |
| 235 | (4-Me-piperazinyl)-phenyl(NHAc)-NH-pyrazine(CONH2)(Et)(Cl) |
| 236 | (4-Me-piperazinyl)-phenyl(NHSO2Me)-NH2 |
| 237 | (4-Me-piperazinyl)-phenyl(NHSO2Me)-NO2 |
| 238 | (4-Me-piperazinyl)-phenyl(NHSO2Me)-NH-pyrazine(CONH2)(Et)(Cl) |

TABLE 24

| Rex | Structure |
|---|---|
| 239 | (4-Me-piperazinyl)-phenyl(Ph)-NH2 |

TABLE 24-continued

| Rex | Structure |
|---|---|
| 240 | Me-N(piperazine)-N-(phenyl with NO2 and Ph) |
| 241 | Me-N(piperazine)-N-(phenyl with NO2 and I) |
| 242 | Me-N(piperazine)-phenyl(Ph)-NH-pyrazine(CONH2, Et, Cl) |
| 243 | Me-N(piperazine)-phenyl-NH2 with Me-N(Ac) |
| 244 | Me-N(piperazine)-phenyl-NO2 with Me-N(Ac) |
| 245 | Me-N(piperazine)-phenyl(Me-N-Ac)-NH-pyrazine(CONH2, Et, Cl) |
| 246*[1] | Boc-NH-cyclohexyl(OH)(Et) |
| 247*[2] | H2N-cyclohexyl(OH)(Et)·HCl |
| 248*[1] | Boc-NH-cyclohexyl(OH)(Et) |
| 249*[2] | H2N-cyclohexyl(OH)(Et)·HCl |
| 250*[3] | Boc-NH-cyclohexyl(OH)(iPr) |

TABLE 24-continued

| Rex | Structure |
|---|---|
| 251*[4] | H2N-cyclohexyl(OH)(iPr)·HCl |
| 252*[3] | Boc-NH-cyclohexyl(OH)(iPr) |

TABLE 25

| Rex | Structure |
|---|---|
| 253*[3] | H2N-cyclohexyl(OH)(iPr)·HCl |
| 254 | Me-N(piperazine)-phenyl(SO2Me)-NH-pyrazine(CONH2, Et, Cl) |
| 255 | Boc-N(diazepane)-N-phenyl(Me)-NH2 |
| 256 | Boc-N(diazepane)-N-phenyl(Me)-NH-pyrazine(CONH2, Et, Cl) |
| 257 | Boc-N(diazepane)-piperidine-N-phenyl(Me)-NH2 |
| 258 | Boc-N(diazepane)-piperidine-N-phenyl(Me)-NO2 |
| 259 | O=piperidinone-N-phenyl(Me)-NO2 |

TABLE 25-continued

| Rex | Structure |
|---|---|
| 260 | (structure) |
| 261 | (structure) |
| 262 | (structure) |
| 263 | (structure) |
| 264 | (structure) |
| 265 | (structure) |
| 266 | (structure) |

TABLE 26

| Rex | Structure |
|---|---|
| 267 | (structure) |
| 268 | (structure) |
| 269 | (structure) |
| 270 | (structure) |
| 271 | (structure) |
| 272 | (structure) |
| 273 | (structure) |
| 274 | (structure) |

TABLE 26-continued

| Rex | Structure |
|---|---|
| 275 | 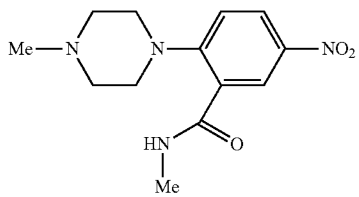 [SMILES: CNC(=O)c1cc([N+](=O)[O-])ccc1N1CCN(C)CC1] |
| 276 | 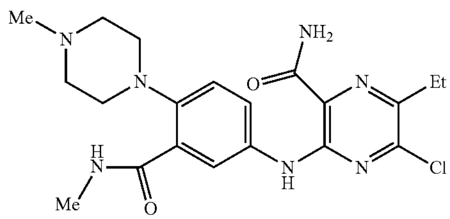 [SMILES: CCc1nc(C(N)=O)c(Nc2ccc(N3CCN(C)CC3)c(C(=O)NC)c2)nc1Cl] |
| 277 | 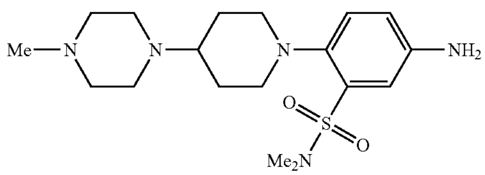 [SMILES: CN1CCN(C2CCN(c3ccc([N+](=O)[O-])cc3S(=O)(=O)N(C)C)CC2)CC1] |
| 278 | 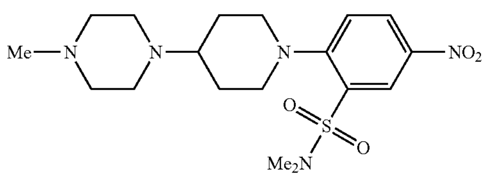 |
| 279 | 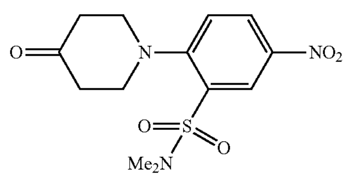 [SMILES: CN(C)S(=O)(=O)c1cc([N+](=O)[O-])ccc1N1CCC(=O)CC1] |
| 280 | 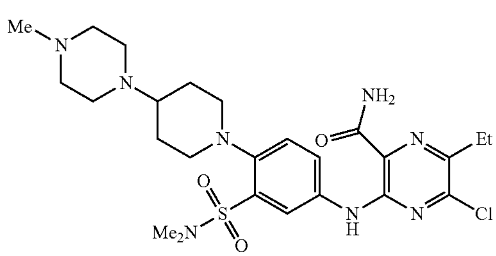 [SMILES: CCc1nc(C(N)=O)c(Nc2ccc(N3CCC(N4CCN(C)CC4)CC3)c(S(=O)(=O)N(C)C)c2)nc1Cl] |

TABLE 27

| Rex | Structure |
|---|---|
| 281 | |
| 282 | 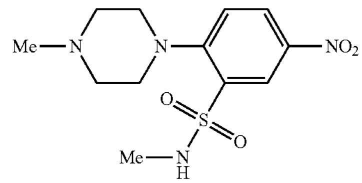 [SMILES: CNS(=O)(=O)c1cc([N+](=O)[O-])ccc1N1CCN(C)CC1] |
| 283 | 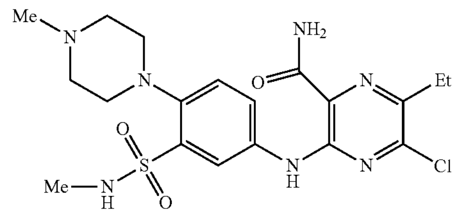 [SMILES: CCc1nc(C(N)=O)c(Nc2ccc(N3CCN(C)CC3)c(S(=O)(=O)NC)c2)nc1Cl] |
| 284 | 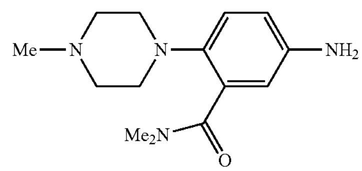 [SMILES: CN1CCN(c2ccc(N)cc2C(=O)N(C)C)CC1] |
| 285 | 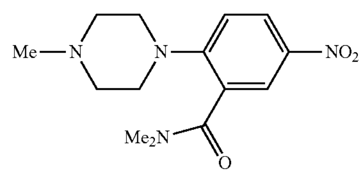 [SMILES: CN1CCN(c2ccc([N+](=O)[O-])cc2C(=O)N(C)C)CC1] |
| 286 | 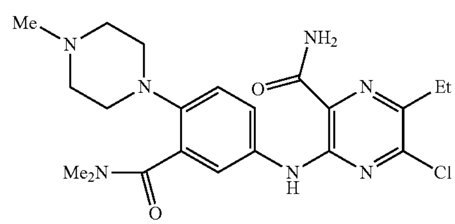 [SMILES: CCc1nc(C(N)=O)c(Nc2ccc(N3CCN(C)CC3)c(C(=O)N(C)C)c2)nc1Cl] |
| 287 | 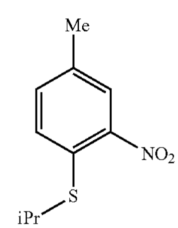 [SMILES: Cc1ccc(SC(C)C)c([N+](=O)[O-])c1] |
| 288 | 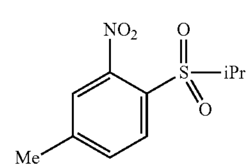 [SMILES: Cc1ccc(S(=O)(=O)C(C)C)c([N+](=O)[O-])c1] |
| 289 | 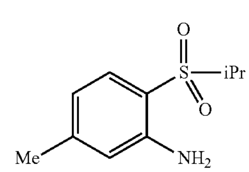 |

TABLE 27-continued

| Rex | Structure |
|---|---|
| 290 | 4-Me, 2-NO₂, 1-S-iPr benzene |
| 291 | 2-NO₂, 5-Me, 1-SO₂-iPr benzene |
| 292 | 5-Me, 2-NH₂, 1-SO₂-iPr benzene |
| 293 | 4-amino-6-((2-(isopropylsulfonyl)phenyl)amino)-2-(methylthio)pyrimidine-5-carboxamide |
| 294 | 4-((2-(isopropylsulfonyl)phenyl)amino)-6-oxo-2-(methylthio)-1,6-dihydropyrimidine-5-carboxamide |

TABLE 28

| Rex | Structure |
|---|---|
| 295 | 4-amino-6-((4-methyl-2-(isopropylsulfonyl)phenyl)amino)-2-(methylthio)pyrimidine-5-carboxamide (Me at top) |
| 296 | 4-amino-6-((4-methyl-2-(isopropylsulfonyl)phenyl)amino)-2-(methylthio)pyrimidine-5-carboxamide |
| 297 | 4-((4-methyl-2-(isopropylsulfonyl)phenyl)amino)-6-oxo-2-(methylthio)-1,6-dihydropyrimidine-5-carboxamide |
| 298 | 4-amino-6-((3-(methylsulfonyl)phenyl)amino)-2-(methylthio)pyrimidine-5-carboxamide-Cl |
| 299 | 4-((3-(methylsulfonyl)phenyl)amino)-6-oxo-2-(methylthio)-1,6-dihydropyrimidine-5-carboxamide |
| 300 | 4-amino-6-((4-(methylsulfonyl)phenyl)amino)-2-(methylthio)pyrimidine-5-carboxamide-Cl |
| 301 | 4-((4-(methylsulfonyl)phenyl)amino)-6-oxo-2-(methylthio)-1,6-dihydropyrimidine-5-carboxamide |
| 302 | 4-((4-methyl-2-(isopropylsulfonyl)phenyl)amino)-6-oxo-2-(methylthio)-1,6-dihydropyrimidine-5-carboxamide |

TABLE 28-continued
| Rex | Structure |
|---|---|
| 303 | 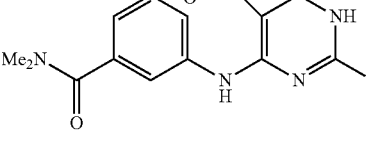 |
| 304 | 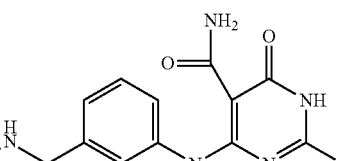 |
| 305 | 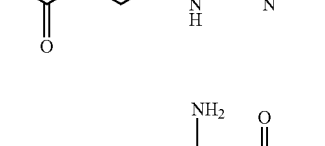 |
| 306 | 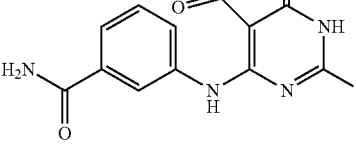 |
| 307 | 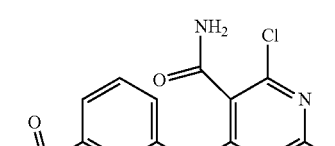 |
| 308 | 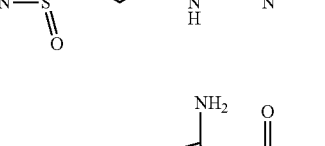 |
TABLE 29
| Rex | Structure |
|---|---|
| 309 | 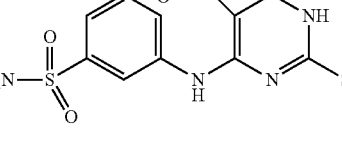 |
| 310 | 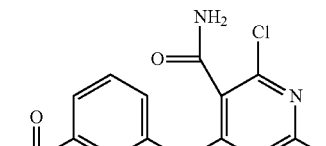 |
| 311 | 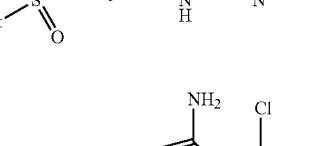 |
| 312 | 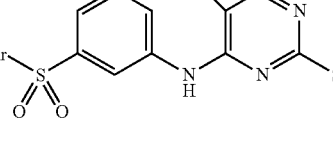 |
| 313 | 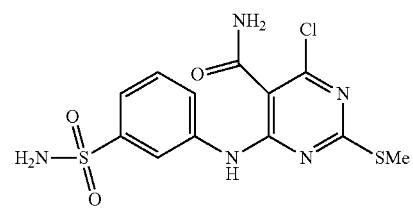 [SMILES: CSc1nc(Cl)c(C(N)=O)c(Nc2cccc(S(N)(=O)=O)c2)n1] |
| 314 | 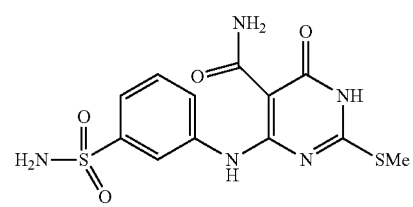 [SMILES: CSc1nc(Nc2cccc(S(N)(=O)=O)c2)c(C(N)=O)c(=O)[nH]1] |
| 315 | 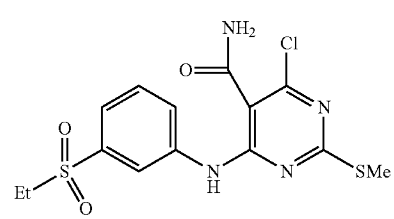 [SMILES: CCS(=O)(=O)c1cccc(Nc2nc(SC)nc(Cl)c2C(N)=O)c1] |
| 316 | 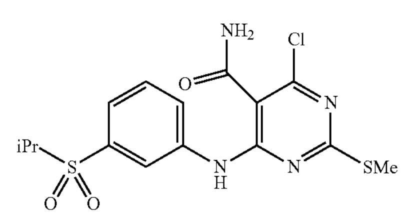 [SMILES: CSc1nc(Cl)c(C(N)=O)c(Nc2cccc(S(=O)(=O)C(C)C)c2)n1] |

TABLE 29-continued

| Rex | Structure |
|---|---|
| 317 | 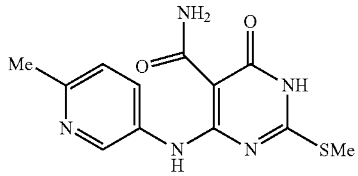 [SMILES: CSc1nc(Nc2ccc(C)nc2)c(C(N)=O)c(=O)[nH]1] |
| 318 | 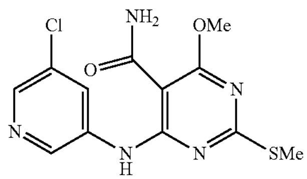 [SMILES: COc1nc(SC)nc(Nc2cncc(Cl)c2)c1C(N)=O] |
| 319 | 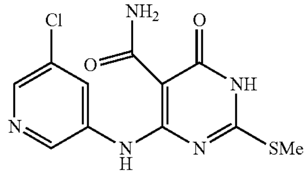 [SMILES: CSc1nc(Nc2cncc(Cl)c2)c(C(N)=O)c(=O)[nH]1] |
| 320 | 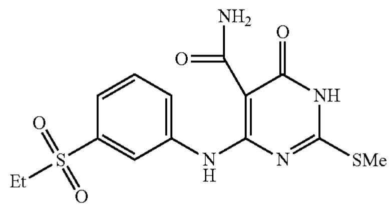 [SMILES: CCS(=O)(=O)c1cccc(Nc2nc(SC)[nH]c(=O)c2C(N)=O)c1] |
| 321 | 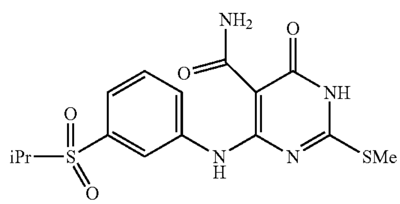 [SMILES: CSc1nc(Nc2cccc(S(=O)(=O)C(C)C)c2)c(C(N)=O)c(=O)[nH]1] |
| 322 | 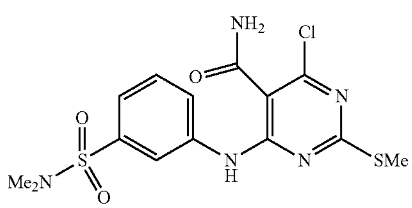 [SMILES: CSc1nc(Cl)c(C(N)=O)c(Nc2cccc(S(=O)(=O)N(C)C)c2)n1] |
| 323 | 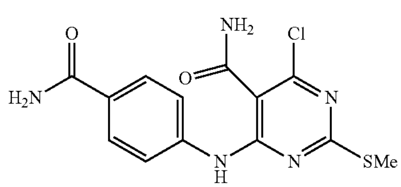 [SMILES: CSc1nc(Cl)c(C(N)=O)c(Nc2ccc(C(N)=O)cc2)n1] |
| 324 | 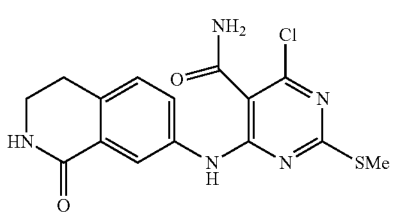 [SMILES: CSc1nc(Cl)c(C(N)=O)c(Nc2ccc3c(c2)C(=O)NCC3)n1] |

TABLE 30

| Rex | Structure |
|---|---|
| 325 | 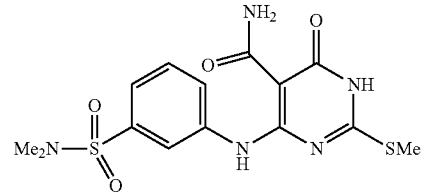 [SMILES: CSc1nc(Nc2cccc(S(=O)(=O)N(C)C)c2)c(C(N)=O)c(=O)[nH]1] |
| 326 | 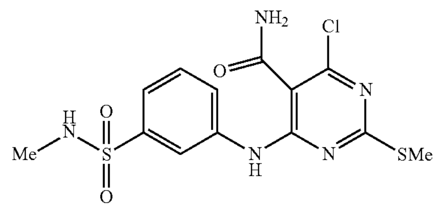 [SMILES: CNS(=O)(=O)c1cccc(Nc2nc(SC)nc(Cl)c2C(N)=O)c1] |
| 327 | 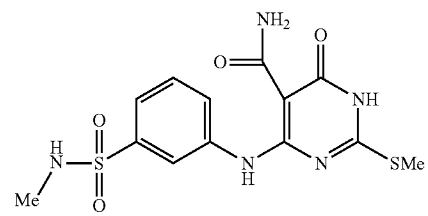 [SMILES: CNS(=O)(=O)c1cccc(Nc2nc(SC)[nH]c(=O)c2C(N)=O)c1] |
| 328 | 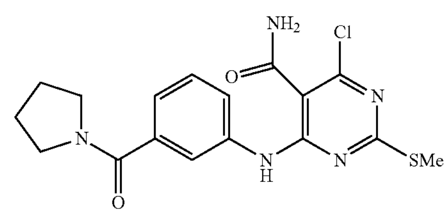 [SMILES: CSc1nc(Cl)c(C(N)=O)c(Nc2cccc(C(=O)N3CCCC3)c2)n1] |
| 329 | 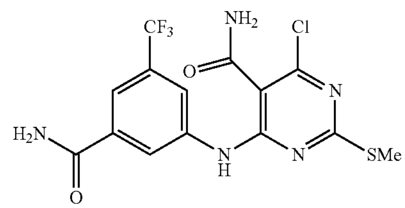 [SMILES: CSc1nc(Cl)c(C(N)=O)c(Nc2cc(C(N)=O)cc(C(F)(F)F)c2)n1] |
| 330 | 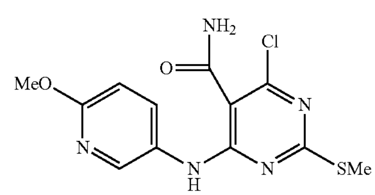 [SMILES: COc1ccc(Nc2nc(SC)nc(Cl)c2C(N)=O)cn1] |
| 331 | 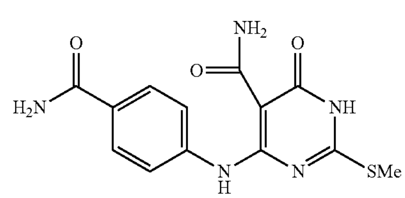 [SMILES: CSc1nc(Nc2ccc(C(N)=O)cc2)c(C(N)=O)c(=O)[nH]1] |

TABLE 30-continued
| Rex | Structure |
|---|---|
| 332 | 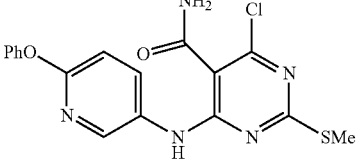 |
| 333 | 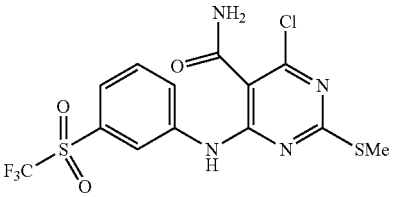 [SMILES: CSc1nc(Cl)c(C(N)=O)c(Nc2cccc(S(=O)(=O)C(F)(F)F)c2)n1] |
| 334 | 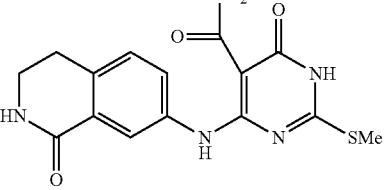 |
| 335 | 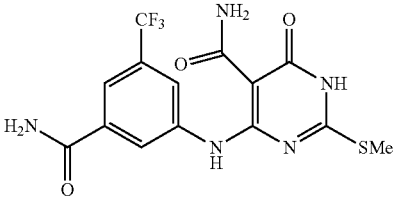 [SMILES: CSc1nc(Nc2cc(C(N)=O)cc(C(F)(F)F)c2)c(C(N)=O)c(=O)[nH]1] |
| 336 | 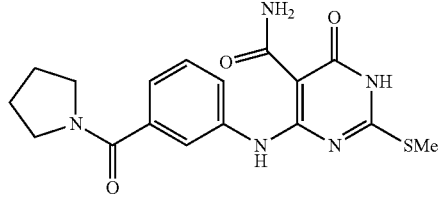 [SMILES: CSc1nc(Nc2cccc(C(=O)N3CCCC3)c2)c(C(N)=O)c(=O)[nH]1] |
| 337 | 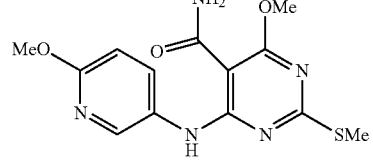 |
| 338 | 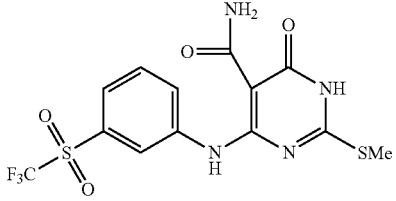 [SMILES: CSc1nc(Nc2cccc(S(=O)(=O)C(F)(F)F)c2)c(C(N)=O)c(=O)[nH]1] |
| 339 | 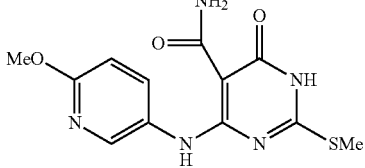 |
| 340 | 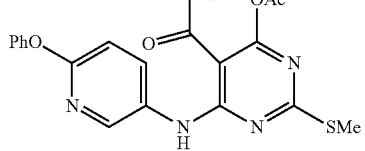 |
TABLE 31
| Rex | Structure |
|---|---|
| 341 | 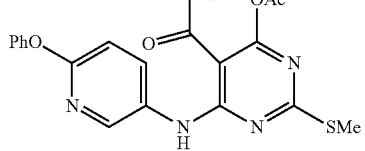 |
| 342 | 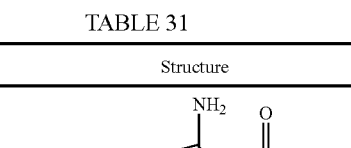 |
| 343 | 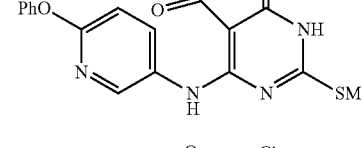 |
| 344 | 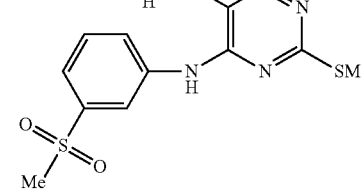 |
| 345 | 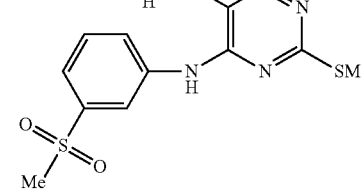 |

TABLE 31-continued

| Rex | Structure |
|---|---|
| 346 | (quinolin-3-ylamino pyrimidine with CONH2, OAc, SMe) |
| 347 | (6-phenylpyridin-3-ylamino pyrimidine with CONH2, OAc, SMe) |
| 348 | (6-phenylpyridin-3-ylamino pyrimidine with CONH2, oxo, NH, SMe) |
| 349 | (quinolin-3-ylamino pyrimidine with CONH2, oxo, NH, SMe) |
| 350 | (2-phenylpyridin-3-ylamino pyrimidine with CONH2, Cl, SMe) |
| 351 | (methylsulfonyl-chloro-phenylamino pyrimidine with CONH2, Cl, SMe) |
| 352 | (6-chloropyridin-3-ylamino pyrimidine with CONH2, Cl, SMe) |
| 353 | (3-methylsulfonylphenylamino pyrazine with CONH2, Et, Cl) |

TABLE 31-continued

| Rex | Structure |
|---|---|
| 354 | (methylsulfonyl-chloro-phenylamino pyrimidine with CONH2, oxo, NH, SMe) |

TABLE 32

| Rex | Structure |
|---|---|
| 355 | (2-phenylpyridin-3-ylamino pyrimidine with CONH2, OAc, SMe) |
| 356 | (2-chloropyridin-3-ylamino pyrimidine with CONH2, Cl, SMe) |
| 357 | (6-chloropyridin-3-ylamino pyrimidine with CONH2, OAc, SMe) |
| 358 | (2-phenylpyridin-3-ylamino pyrimidine with CONH2, oxo, NH, SMe) |
| 359 | (5-methylpyridin-3-ylamino pyrimidine with CONH2, Cl, SMe) |
| 360 | (6-methoxypyridin-3-ylamino pyrazine with CONH2, Et, Cl) |

TABLE 32-continued

| Rex | Structure |
|---|---|
| 361 | (pyridine with Cl, NH linker, pyrimidine with CONH2, OAc, SMe) |
| 362 | (6-Cl-pyridin-3-yl, NH linker, pyrimidine with CONH2, =O, NH, SMe) |
| 363 | (2-Cl-pyridin-3-yl, NH linker, pyrimidine with CONH2, =O, NH, SMe) |
| 364 | (Me-pyridinyl, NH linker, pyrimidine with CONH2, =O, NH, SMe) |
| 365 | (6-CF3-pyridin-3-yl, NH linker, pyrimidine with CONH2, Cl, SMe) |
| 366 | (6-CF3-pyridin-3-yl, NH linker, pyrimidine with CONH2, OAc, SMe) |
| 367 | (2,5-diCl-pyridin-3-yl, NH linker, pyrimidine with CONH2, Cl, SMe) |
| 368 | (2,5-diCl-pyridin-3-yl, NH linker, pyrimidine with CONH2, OAc, SMe) |
| 369 | (2,5-diCl-pyridin-3-yl, NH linker, pyrimidine with CONH2, =O, NH, SMe) |
| 370 | (6-CF3-pyridin-3-yl, NH linker, pyrimidine with CONH2, =O, NH, SMe) |

TABLE 33

| Rex | Structure |
|---|---|
| 371 | (4-Ph-pyridin-3-yl, NH linker, pyrimidine with CONH2, Cl, SMe) |
| 372 | (4-Ph-pyridin-3-yl, NH linker, pyrimidine with CONH2, OAc, SMe) |
| 373 | (4-Ph-pyridin-3-yl, NH linker, pyrimidine with CONH2, =O, NH, SMe) |
| 374 | (pyridin-3-yl, NH linker, pyrimidine with CONH2, Cl, SMe) |
| 375 | (5-Br-pyridin-3-yl, NH linker, pyrimidine with CONH2, Cl, SMe) |

TABLE 33-continued

| Rex | Structure |
|---|---|
| 376 | (structure) |
| 377 | (structure) |
| 378 | (structure) |
| 379 | (structure) |
| 380 | (structure) |
| 381 | (structure) |
| 382 | (structure) |
| 383 | (structure) |

TABLE 33-continued

| Rex | Structure |
|---|---|
| 384 | (structure) |
| 385 | (structure) |
| 386 | (structure) |

TABLE 34

| Rex | Structure |
|---|---|
| 387 | (structure) |
| 388 | (structure) |
| 389 | (structure) |
| 390 | (structure) |

TABLE 34-continued
| Rex | Structure |
|---|---|
| 391 | 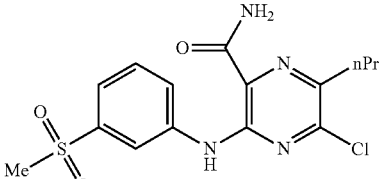 |
| 392 | 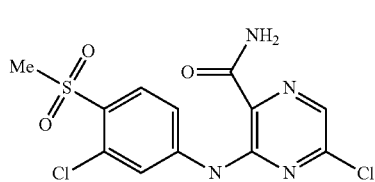 |
| 393 | 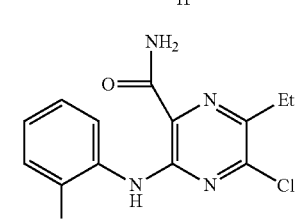 |
| 394 | 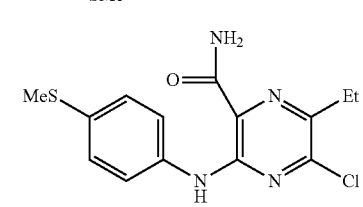 |
| 395 | 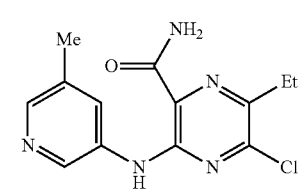 [SMILES: CCc1nc(C(N)=O)c(Nc2cncc(C)c2)nc1Cl] |
| 396 | 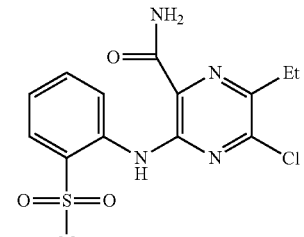 |
| 397 | 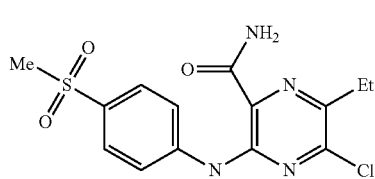 |
| 398 | 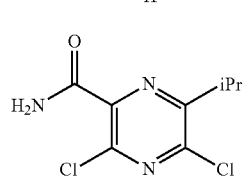 |
| 399 | 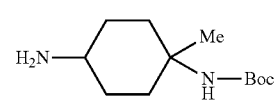 [SMILES: CC1(NC(=O)OC(C)(C)C)CCC(N)CC1] |
| 400 | 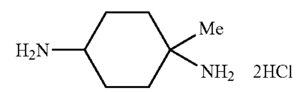 |
| 401 | 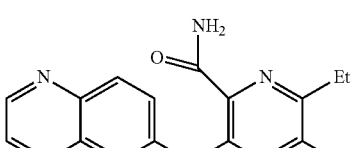 |
| 402 | 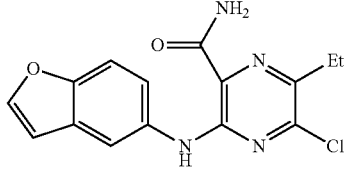 [SMILES: CCc1nc(C(N)=O)c(Nc2ccc3occc3c2)nc1Cl] |
TABLE 35
| Rex | Structure |
|---|---|
| 403 | 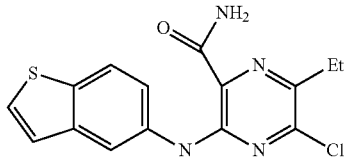 |
| 404 | 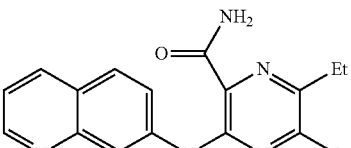 |
| 405 | 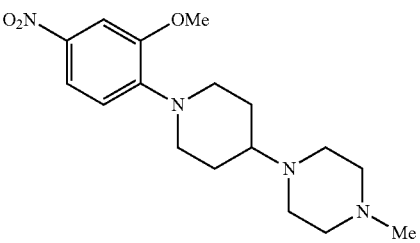 |
| 406 | 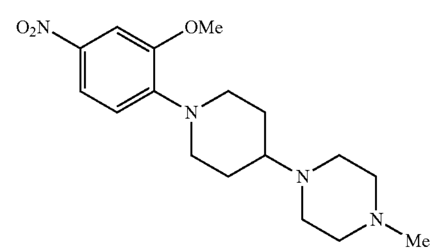 [SMILES: COc1cc([N+](=O)[O-])ccc1N1CCC(N2CCN(C)CC2)CC1] |

TABLE 35-continued
| Rex | Structure |
|---|---|
| 407 | 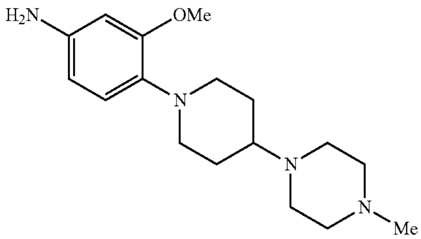 |
| 408 | 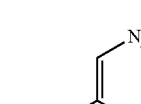 |
| 409 | 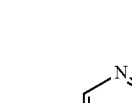 |
| 410 | 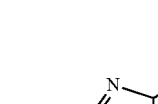 |
| 411 | 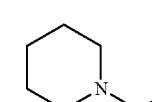 |
| 412 | 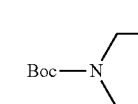 |
| 413 | 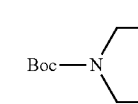 |
| 414 | 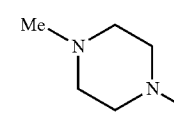 |
| 415 | 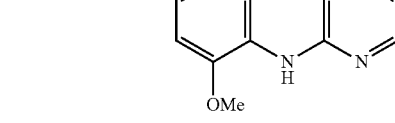 |
| 416 | 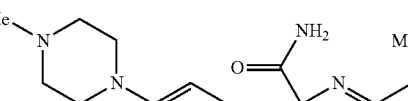 |
| 417 | 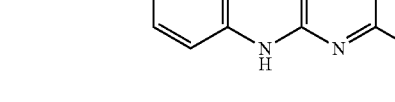 |
| 418 | 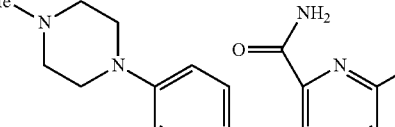 |
TABLE 36
| Rex | Structure |
|---|---|
| 419 | 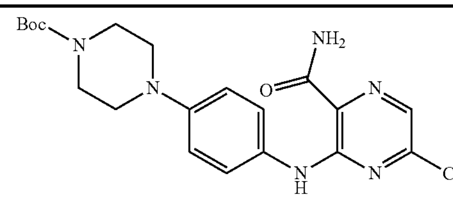 |
| 420 | 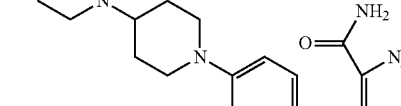 |
| 421 | 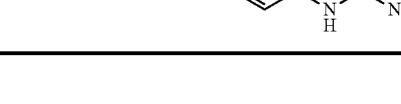 |

TABLE 36-continued
| Rex | Structure |
|---|---|
| 422 | 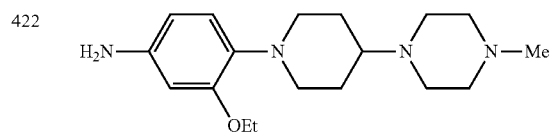 |
| 423 | 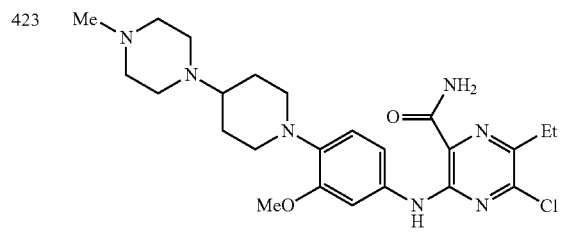 |
| 424 | 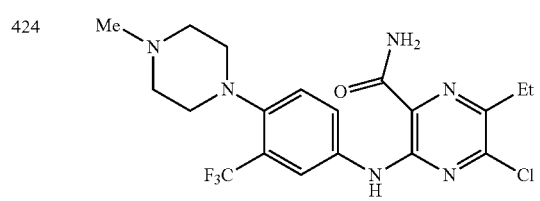 |
| 425 | 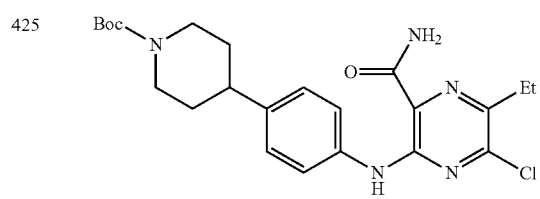 |
| 426 | 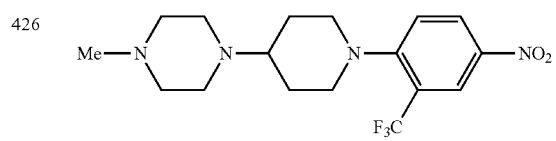 |
| 427 | 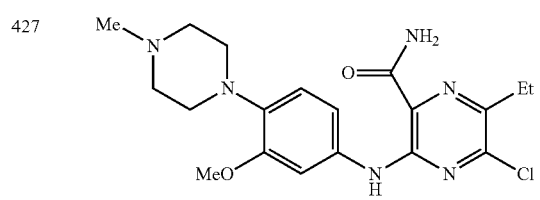 |
| 428 | 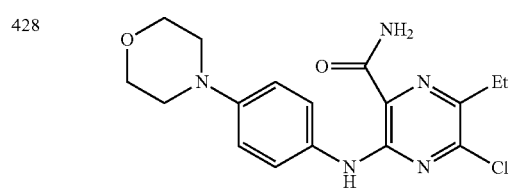 |
| 429 | 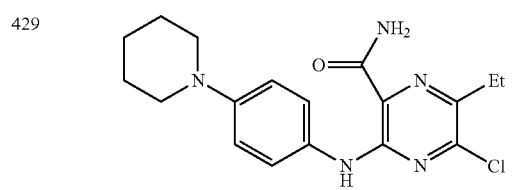 |
TABLE 36-continued
| Rex | Structure |
|---|---|
| 430 | 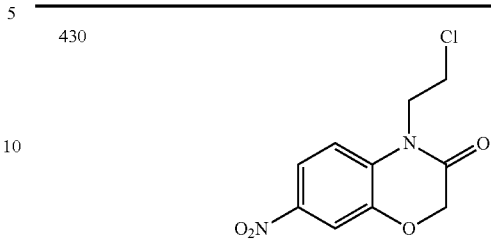 |
| 431 | 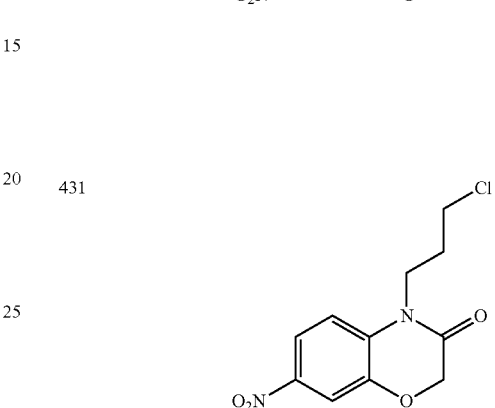 |
| 432 | 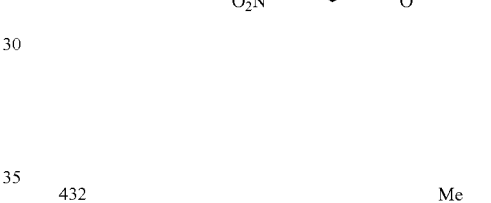 |
TABLE 37
| Rex | Structure |
|---|---|
| 433 | 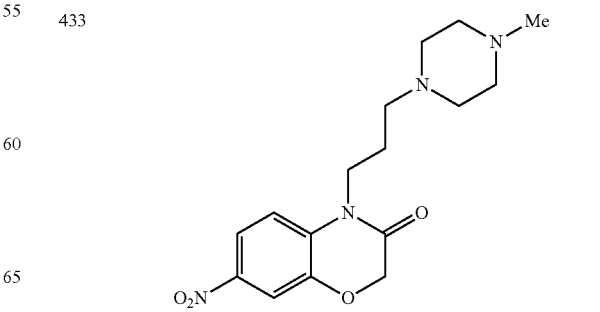 |

TABLE 37-continued
| Rex | Structure |
|---|---|
| 434 | 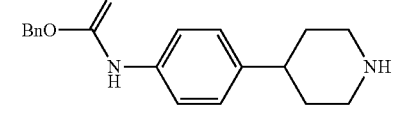 |
| 435 | 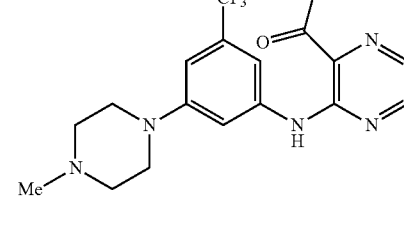 |
| 436 | 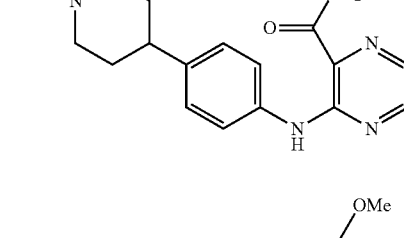 |
| 437 | 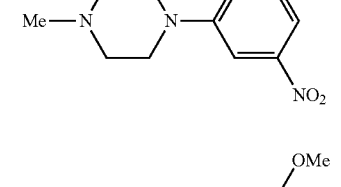 |
| 438 | 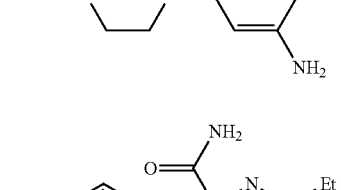 |
| 439 | 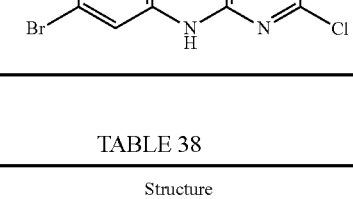 |
| 440 | 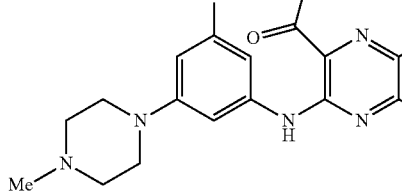 |
| 441 | 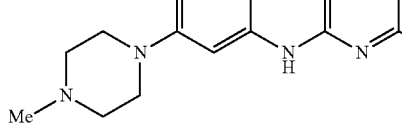 |
| 442 | 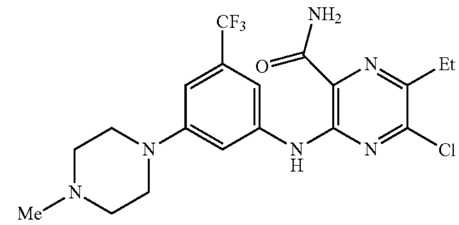 |
| 443 | 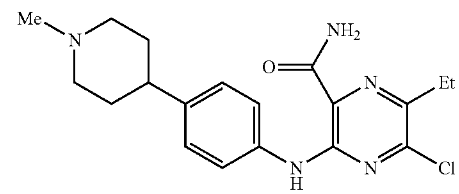 [SMILES: CCc1nc(C(N)=O)c(Nc2ccc(N3CCN(C)CC3)cc2)nc1Cl] |
| 444 | 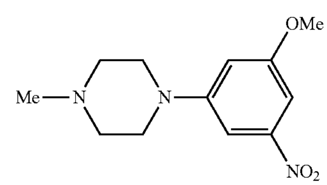 [SMILES: COc1cc(N2CCN(C)CC2)cc([N+](=O)[O-])c1] |
| 445 | 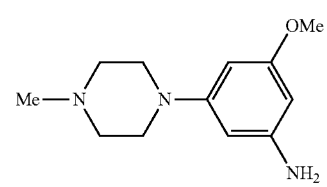 [SMILES: COc1cc(N)cc(N2CCN(C)CC2)c1] |
| 446 | 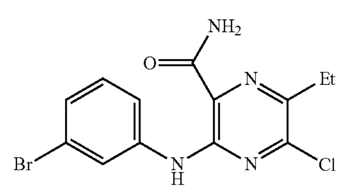 [SMILES: CCc1nc(C(N)=O)c(Nc2cccc(Br)c2)nc1Cl] |
TABLE 38
| Rex | Structure |
|---|---|
| 447 | 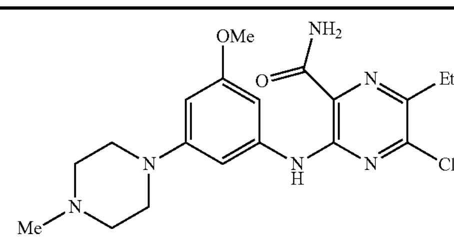 |

TABLE 38-continued

| Rex | Structure |
|---|---|
| 448 | BnO-C(=O)-NH-[4-phenyl]-[piperidin-4-yl]-N-[1-methylpiperidin-4-yl] |
| 449 | H2N-[4-phenyl]-[piperidin-4-yl]-N-[1-methylpiperidin-4-yl] |
| 450 | 1-Me-piperidin-4-yl–N–piperidin-4-yl–[4-phenyl]–NH–[3-carbamoyl-5-ethyl-6-chloropyrazin-2-yl] |
| 451 | 3-nitrophenyl–N–piperidin-4-yl–N-methylpiperazine |
| 452 | 3-aminophenyl–N–piperidin-4-yl–N-methylpiperazine |
| 453 | [4-methylpiperazin-1-yl]-piperidin-4-yl–[3-phenyl]–NH–[3-carbamoyl-5-ethyl-6-chloropyrazin-2-yl] |
| 454 | Boc-piperidin-4-yl–[2-methoxy-4-(OBn-carbamate)phenyl] |
| 455 | HN-piperidin-4-yl–[2-methoxy-4-(OBn-carbamate)phenyl] |
| 456 | 2-CF3-4-nitrophenyl–N–(4-methylpiperazin-1-yl) |

TABLE 38-continued

| Rex | Structure |
|---|---|
| 457 | 2-CF3-5-aminophenyl–N–(4-methylpiperazin-1-yl) |
| 458 | [4-CF3-2-(4-methylpiperazin-1-yl)phenyl]–NH–[3-carbamoyl-5-ethyl-6-chloropyrazin-2-yl] |
| 459 | [4-nitro-2-(2-methoxyethoxy)phenyl]–N–piperidin-4-yl–N-methylpiperazine |
| 460 | [4-amino-2-(2-methoxyethoxy)phenyl]–N–piperidin-4-yl–N-methylpiperazine |

TABLE 39

| Rex | Structure |
|---|---|
| 461 | [5-(4-methylpiperazin-1-yl)-2-methoxyphenyl]–NH–[3-carbamoyl-5-ethyl-6-chloropyrazin-2-yl] |
| 462 | Boc-piperidin-4-yl–[2-methoxy-5-(OBn-carbamate)phenyl] |

TABLE 39-continued

| Rex | Structure |
|-----|-----------|
| 463 | 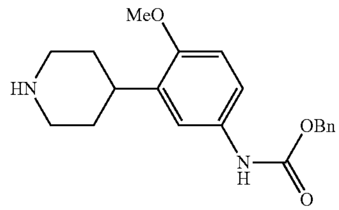 [SMILES: COc1ccc(NC(=O)OCc2ccccc2)cc1C1CCNCC1] |
| 464 | 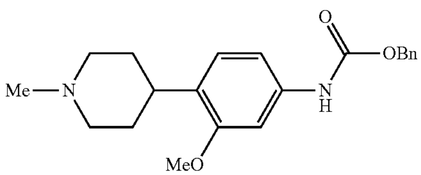 [SMILES: COc1cc(NC(=O)OCc2ccccc2)ccc1C1CCN(C)CC1] |
| 465 | 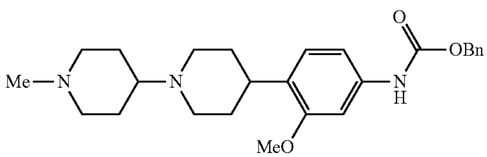 [SMILES: COc1cc(NC(=O)OCc2ccccc2)ccc1C1CCN(C2CCN(C)CC2)CC1] |
| 466 | 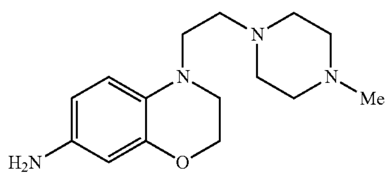 [SMILES: CN1CCN(CCN2CCOc3cc(N)ccc32)CC1] |
| 467 | 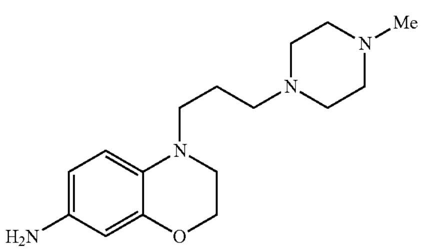 [SMILES: CN1CCN(CCCN2CCOc3cc(N)ccc32)CC1] |
| 468 | 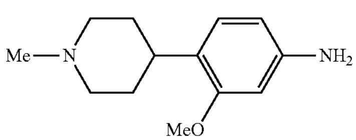 [SMILES: COc1cc(N)ccc1C1CCN(C)CC1] |
| 469 | 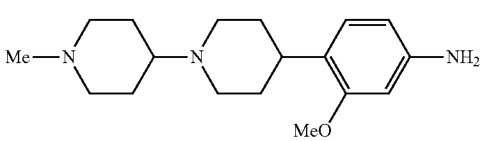 [SMILES: COc1cc(N)ccc1C1CCN(C2CCN(C)CC2)CC1] |
| 470 | 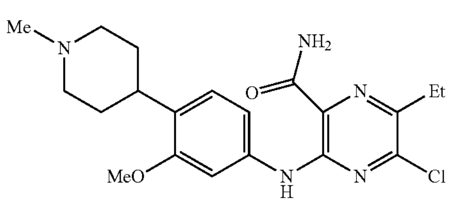 [SMILES: CCc1nc(C(N)=O)c(Nc2ccc(C3CCN(C)CC3)c(OC)c2)nc1Cl] |

TABLE 39-continued

| Rex | Structure |
|-----|-----------|
| 471 | 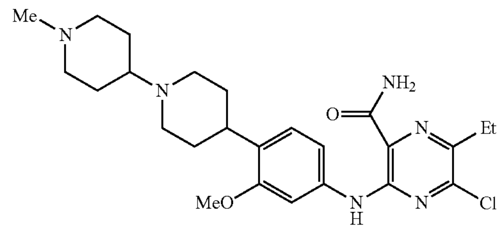 [SMILES: CCc1nc(C(N)=O)c(Nc2ccc(C3CCN(C4CCN(C)CC4)CC3)c(OC)c2)nc1Cl] |
| 472 | 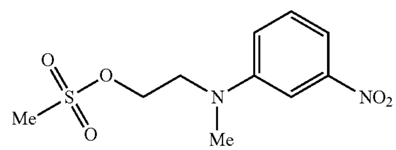 [SMILES: CN(CCOS(C)(=O)=O)c1cccc([N+](=O)[O-])c1] |
| 473 | 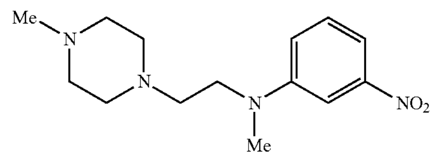 [SMILES: CN1CCN(CCN(C)c2cccc([N+](=O)[O-])c2)CC1] |
| 474 | 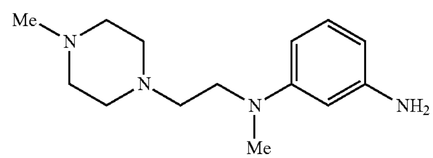 |

TABLE 40

| Rex | Structure |
|-----|-----------|
| 475 | 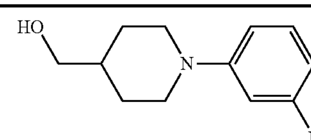 |
| 476 | 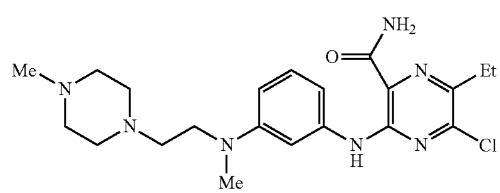 [SMILES: CCc1nc(C(N)=O)c(Nc2cccc(N(C)CCN3CCN(C)CC3)c2)nc1Cl] |
| 477 | 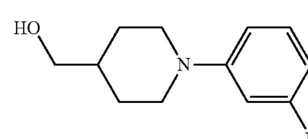 |
| 478 | 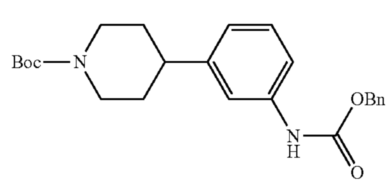 [SMILES: CC(C)(C)OC(=O)N1CCC(c2cccc(NC(=O)OCc3ccccc3)c2)CC1] |

TABLE 40-continued

| Rex | Structure |
|-----|-----------|
| 479 | 3-(piperidin-4-yl)phenyl benzyl carbamate |
| 480 | 3-(1-methylpiperidin-4-yl)phenyl benzyl carbamate |
| 481 | 3-(1-methylpiperidin-4-yl)aniline |
| 482 | 3-(1'-methyl-[1,4'-bipiperidin]-4-yl)phenyl benzyl carbamate |
| 483 | 3-(1'-methyl-[1,4'-bipiperidin]-4-yl)-4-methoxyphenyl benzyl carbamate |
| 484 | 3-(1'-methyl-[1,4'-bipiperidin]-4-yl)aniline |
| 485 | 3-chloro-5-(4-methylpiperazin-1-yl)phenyl pyrazinecarboxamide (Cl, Et) |
| 486 | 2-methoxy-5-amino-(1'-methyl-[1,4'-bipiperidin]-4-yl)benzene |

TABLE 40-continued

| Rex | Structure |
|-----|-----------|
| 487 | MeO/methylpiperidinyl pyrazinecarboxamide (Cl, Et) |
| 488 | 1-methylpiperidin-4-yl phenyl pyrazinecarboxamide (Cl, Et) |

TABLE 41

| Rex | Structure |
|-----|-----------|
| 489 | MeO/1'-methyl-[1,4'-bipiperidin]-4-yl pyrazinecarboxamide (Cl, Et) |
| 490 | 1'-methyl-[1,4'-bipiperidin]-4-yl phenyl pyrazinecarboxamide (Cl, Et) |
| 491 | 4-(hydroxymethyl)piperidin-1-yl phenyl pyrazinecarboxamide (Cl, Et) |
| 492 | 1-(3-nitrophenyl)piperidin-4-one |

TABLE 41-continued

| Rex | Structure |
|---|---|
| 493 | (structure) |
| 494 | (structure) |
| 495 | (structure) |
| 496 | (structure) |
| 497 | (structure) |
| 498 | (structure) |
| 499 | (structure) |
| 500 | (structure) |
| 501 | (structure) |
| 502 | (structure) |

TABLE 42

| Rex | Structure |
|---|---|
| 503 | (structure) |
| 504 | (structure) |
| 505 | (structure) |

TABLE 42-continued
| Rex | Structure |
|---|---|
| 506 | 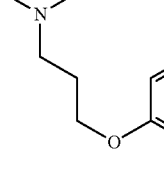 |
| 507 | 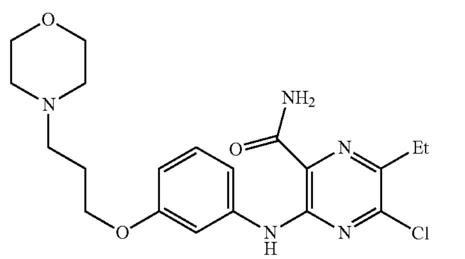 [SMILES: CCc1nc(C(N)=O)c(Nc2cccc(OCCCN3CCOCC3)c2)nc1Cl] |
| 508 | 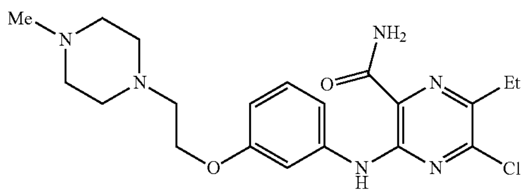 [SMILES: CCc1nc(C(N)=O)c(Nc2cccc(OCCN3CCN(C)CC3)c2)nc1Cl] |
| 509 | 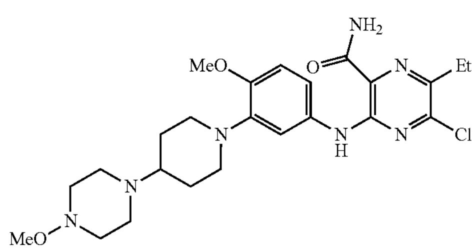 [SMILES: CCc1nc(C(N)=O)c(Nc2ccc(OC)c(N3CCC(N4CCN(OC)CC4)CC3)c2)nc1Cl] |
| 510 | 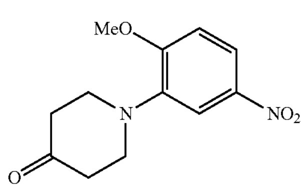 [SMILES: COc1ccc([N+](=O)[O-])cc1N1CCC(=O)CC1] |
| 511 | 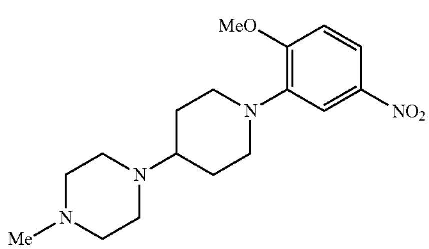 [SMILES: COc1ccc([N+](=O)[O-])cc1N1CCC(N2CCN(C)CC2)CC1] |
| 512 | 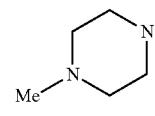 |
| 513 | 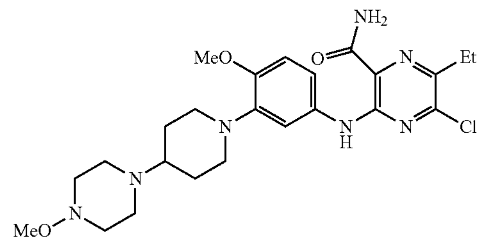 [SMILES: CCc1nc(C(N)=O)c(Nc2ccc(OC)c(N3CCC(N4CCN(OC)CC4)CC3)c2)nc1Cl] |
| 514 | 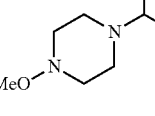 |
TABLE 43
| Rex | Structure |
|---|---|
| 515 | 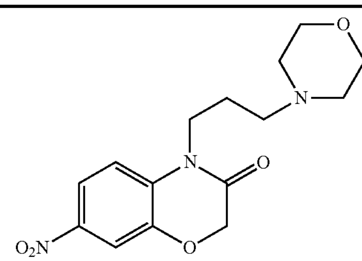 |
| 516 | 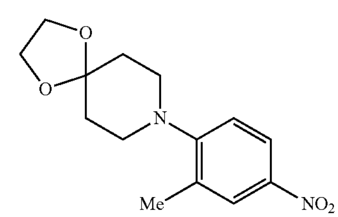 |
| 517 | 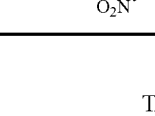 |

TABLE 43-continued

| Rex | Structure |
|---|---|
| 518 | 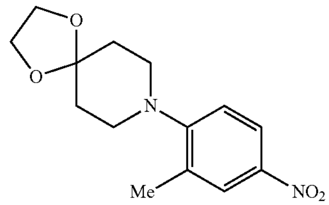 [SMILES: Cc1cc([N+](=O)[O-])ccc1N1CCC2(CC1)OCCO2] |
| 519 | 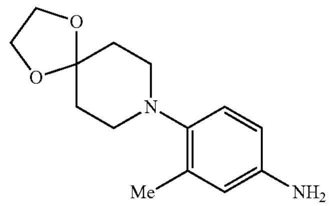 [SMILES: Cc1cc([N+](=O)[O-])ccc1N1CCC2(CC1)OCCO2] |
| 520 | 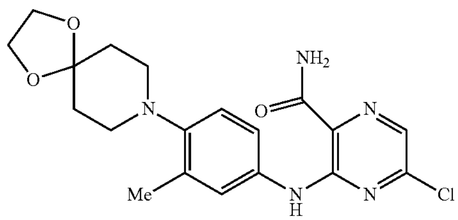 [SMILES: Cc1cc(Nc2nc(Cl)cnc2C(N)=O)ccc1N1CCC2(CC1)OCCO2] |
| 521 | 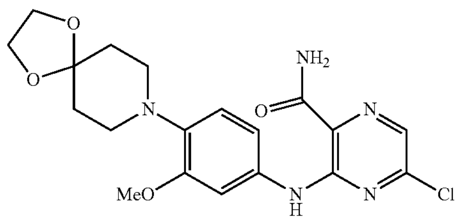 [SMILES: COc1cc(Nc2nc(Cl)cnc2C(N)=O)ccc1N1CCC2(CC1)OCCO2] |
| 522 | 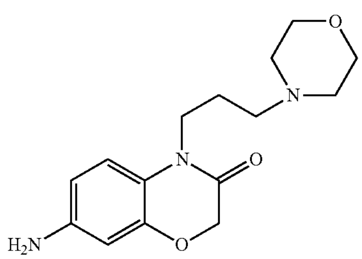 |
| 523 | 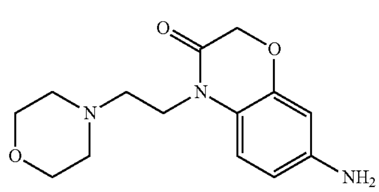 [SMILES: Nc1ccc2c(c1)OCC(=O)N2CCN1CCOCC1] |
| 524 | 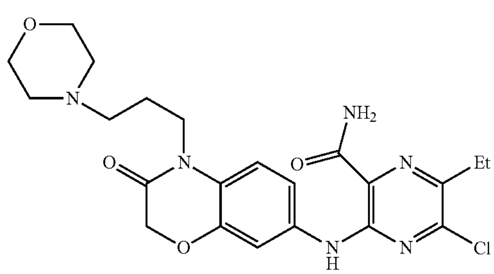 [SMILES: CCc1nc(C(N)=O)c(Nc2ccc3c(c2)OCC(=O)N3CCCN2CCOCC2)nc1Cl] |

TABLE 43-continued

| Rex | Structure |
|---|---|
| 525 | |
| 526 | |

TABLE 44

| Rex | Structure |
|---|---|
| 527 | 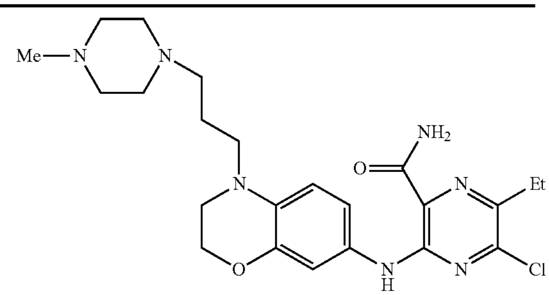 |
| 528 | 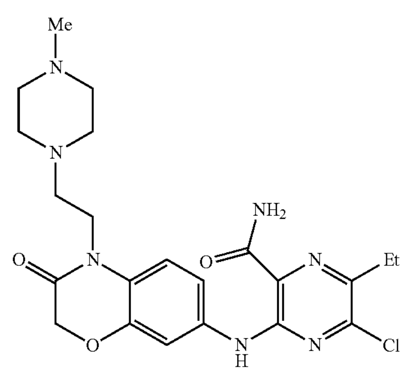 [SMILES: CCc1nc(C(N)=O)c(Nc2ccc3c(c2)OCC(=O)N3CCN2CCN(C)CC2)nc1Cl] |
| 529 | 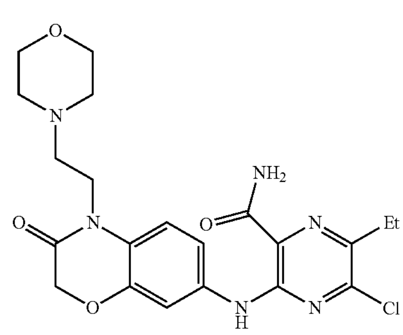 [SMILES: CCc1nc(C(N)=O)c(Nc2ccc3c(c2)OCC(=O)N3CCN2CCOCC2)nc1Cl] |

TABLE 44-continued

| Rex | Structure |
|---|---|
| 530 | (structure) |
| 531 | (structure) |
| 532 | (structure) |
| 533 | (structure) |
| 534 | (structure) |
| 535 | (structure) |
| 536 | (structure) |

TABLE 45

| Rex | Structure |
|---|---|
| 537 | (structure) |
| 538 | (structure) |

TABLE 45-continued

| Rex | Structure |
|---|---|
| 539 | (structure) |
| 540 | (structure) |
| 541 | (structure) |
| 542 | (structure) |
| 543 | (structure) |
| 544 | (structure) |
| 545 | (structure) |
| 546 | (structure) |

TABLE 46

| Rex | Structure |
|---|---|
| 547 | (structure) |
| 548 | (structure) |
| 549 | (structure) |
| 550 | (structure) |
| 551 | (structure) |

TABLE 46-continued

| Rex | Structure |
|---|---|
| 552 | (structure) |
| 553 | (structure) |
| 554 | (structure) |
| 555 | (structure) |
| 556 | (structure) |

TABLE 47

| Rex | Structure |
|---|---|
| 557 | (structure) |
| 558 | (structure) |
| 559 | (structure) |
| 560 | (structure) |
| 561 | (structure) |
| 562 | (structure) |

TABLE 48

| Rex | Syn | Data |
|---|---|---|
| 1 | Rex299 | ESI-: 402 |
| 2 | Rex298 | ESI-: 420 |
| 3 | Rex292 | $^1$H-NMR (CDCl3): 1.11 (3H, br-s), 1.21 (3H, br-s), 2.17 (3H, s), 3.28 (2H, br-s), 3.51 (2H, br-s), 3.66 (2H, br-s), 6.66-6.68 (2H, m), 7.03 (1H, dd, J = 0.8 Hz, 8.0 Hz). |
| 4 | Rex4 | EI: 236 |
| 5 | Rex299 | ESI-: 388 |
| 6 | Rex298 | ESI-: 406 |
| 7 | Rex292 | $^1$H-NMR (CDCl3): 1.50-1.65 (6H, m), 2.16 (3H, s), 3.36 (2H, br-s), 3.71 (4H, m), 6.66-6.69 (2H, m), 7.02 (1H, d, J = 7.6 Hz). |
| 8 | Rex4 | EI: 248 |
| 9 | Rex299 | $^1$H-NMR (DMSO-d6): 1.48-1.59 (6H, m), 2.30 (3H, s), 2.41 (3H, s), 3.33 (2H, br-s), 3.54 (2H, br-s), 7.02 (1H, dd, J = 1.2 Hz, 8.0 Hz), 7.28 (1H, d, J = 8.0 Hz), 7.47 (1H, d, J = 4.0 Hz), 7.99 (1H, d, J = 1.2 Hz), 9.16 (1H, d, J = 4.4 Hz), 12.68 (1H, s), 12.84 (1H, s). |
| 10 | Rex298 | ESI-: 418 |

TABLE 48-continued

| Rex | Syn | Data |
|---|---|---|
| 11 | Rex292 | $^1$H-NMR (CDCl3): 1.24 (6H, d, J = 6.8 Hz), 2.19 (3H, s), 3.70 (2H, br-s), 4.23-4.29 (1H, m), 5.85 (1H, br-s), 6.97 (1H, dd, J = 1.6 Hz, 7.6 Hz), 7.06 (1H, d, J = 7.6 Hz), 7.13 (1H, d, J = 1.6 Hz). |
| 12 | Rex4 | $^1$H-NMR (CDCl3): 1.29 (6H, d, J = 6.4 Hz), 2.65 (3H, s), 4.25-4.34 (1H, m), 5.99 (1H, br-s), 7.42 (1H, d, J = 8.0 Hz), 7.94 (1H, dd, d = 2.0 Hz, 8.0 Hz), 8.30 (1H, d, J = 1.6 Hz). |

TABLE 49

| Rex | Syn | Data |
|---|---|---|
| 13 | Rex299 | $^1$H-NMR (DMSO-d6): 1.14 (6H, d, J = 6.4 Hz), 2.31 (3H, s), 2.43 (3H, s), 4.06-4.11 (1H, m), 7.31 (1H, d, J = 8.0 Hz), 7.47 (1H, d, J = 4.4 Hz), 7.54 (1H, dd, J = 1.6 Hz, 8.0 Hz), 8.14 (1H, d, J = 7.6 Hz), 8.47 (1H, d, J = 1.6 Hz), 9.17 (1H, d, J = 4.4 Hz), 12.69 (1H, s), 12.84 (1H, s). |
| 14 | Rex298 | ESI-: 392 |
| 15 | Rex299 | $^1$H-NMR (DMSO-d6): 2.31 (3H, s), 2.44 (3H, s), 2.76 (3H, d, J = 4.4 Hz), 7.31 (1H, d, J = 8.0 Hz), 7.47 (1H, d, J = 4.4 Hz), 7.52 (1H, dd, J = 1.6 Hz, 8.0 Hz), 8.36 (1H, d, J = 4.8 Hz), 8.49 (1H, d, J = 1.6 Hz), 9.19 (1H, d, J = 4.4 Hz), 12.70 (1H, s), 12.85 (1H, s). |
| 16 | Rex298 | ESI-: 364 |
| 17 | Rex299 | ESI-: 424 |
| 18 | Rex298 | ESI-: 442 |
| 19 | Rex299 | ESI-: 436 |
| 20 | Rex298 | ESI-: 454 |
| 21 | Rex292 | $^1$H-NMR (CDCl3): 3.00 (3H, d, J = 4.9 Hz), 3.94 (2H, m), 6.44 (1H, m), 6.58 (1H, dd, J = 2.4 Hz, 8.5 Hz), 6.64 (1H, d, J = 2.4 Hz), 7.67 (1H, d, J = 8.5 Hz). |
| 22 | Rex4 | $^1$H-NMR (CDCl3): 3.07 (3H, d, J = 4.9 Hz), 6.15 (1H, m), 7.82 (1H, d, J = 8.3 Hz), 8.17 (1H, dd, J = 2.2 Hz, 8.3 Hz), 8.29 (1H, d, J = 2.2 Hz). |
| 23 | Rex299 | ESI-: 366 |
| 24 | Rex298 | ESI-: 384 |
| 25 | Rex292 | $^1$H-NMR (CDCl3): 1.05 (3H, t, J = 7.1 Hz), 1.24 (3H, t, J = 7.1 Hz), 3.18 (2H, q, J = 7.1 Hz), 3.35 (1H, m), 3.83 (3H, m), 6.56 (1H, dd, J = 2.2 Hz, 8.1 Hz), 6.67 (1H, d, J = 2.2 Hz), 7.03 (1H, d, J = 8.1 Hz). |

TABLE 50

| Rex | Syn | Data |
|---|---|---|
| 26 | Rex4 | $^1$H-NMR (CDCl3): 1.09 (3H, t, J = 7.1 Hz), 1.29 (3H, t, J = 7.1 Hz), 3.06-3.21 (2H, m), 3.35-3.44 (1H, m), 3.76-3.85 (1H, m), 7.74 (1H, d, J = 8.3 Hz), 8.18 (1H, dd, J = 2.2 Hz, 8.3 Hz), 8.29 (1H, d, J = 2.2 Hz). |
| 27 | Rex299 | ESI-: 408 |
| 28 | Rex298 | ESI-: 426 |
| 29 | Rex292 | $^1$H-NMR (CDCl3): 1.08 (6H, d, J = 6.4 Hz), 2.21 (1H, s), 3.40-3.47 (1H, m), 4.21 (1H, d, J = 6.8 Hz), 7.14-7.18 (1H, m). |
| 30 | Rex299 | $^1$H-NMR (DMSO-d$_6$): 0.86-0.96 (6H, m), 2.43 (1H, s), 3.15-3.20 (1H, m), 3.35 (3H, s), 7.43-7.70 (4H, m), 8.23 (1H, s), 9.18 (1H, s), 12.79 (1H, s), 13.06 (1H, s). |
| 31 | Rex298 | ESI-: 428 |
| 32 | Rex299 | $^1$H-NMR (DMSO-d6): 2.32-2.54 (9H, m), 7.33-7.70 (4H, m), 8.52 (1H, s), 9.18 (1H, s), 12.81 (1H, s), 13.09 (1H, s). |
| 33 | Rex298 | ESI-: 400 |

TABLE 50-continued

| Rex | Syn | Data |
|---|---|---|
| 34 | Rex299 | $^1$H-NMR (DMSO-d6): 1.45-1.59 (6H, m), 2.54 (3H, s), 3.12 (2H, m), 3.56-3.63 (2H, m), 7.28-7.30 (1H, m), 7.38-7.41 (1H, m), 7.58-7.59 (1H, m), 7.99-7.99 (1H, m), 9.16-9.17 (1H, m), 12.85 (1H, br-s), 13.13 (1H, br-s). |
| 35 | Rex298 | ESI-: 438 |
| 36 | Rex292 | $^1$H-NMR (CDCl3): 1.25 (6H, d, J = 6.6 Hz), 3.94 (2H, m), 4.20-4.32 (1H, m), 6.22 (1H, m), 6.55-6.58 (1H, m), 6.63 (1H, d, J = 2.2 Hz), 7.61 (1H, dd, J = 1.2 Hz, 8.3 Hz). |

TABLE 51

| Rex | Syn | Data |
|---|---|---|
| 37 | Rex4 | $^1$H-NMR (CDCl3): 1.30 (6H, d, J = 6.6 Hz), 4.28-4.36 (1H, m), 5.90 (1H, m), 7.78 (1H, d, J = 8.5 Hz), 8.16 (1H, dd, J = 2.2 Hz, 8.3 Hz), 8.28 (1H, d, J = 2.2 Hz). |
| 38 | Rex299 | $^1$H-NMR (DMSO-d6): 1.14 (6H, d, J = 6.6 Hz), 2.56 (3H, s), 4.01-4.02 (1H, m), 7.36-7.37 (2H, m), 7.58-7.59 (1H, m), 7.94-7.95 (1H, m), 8.24-8.26 (1H, m), 9.17 (1H, m), 12.85 (1H, br-s), 13.14 (1H, br-s). |
| 39 | Rex298 | ESI-: 412 |
| 40 | Rex292 | $^1$H-NMR (CDCl3): 1.43-1.50 (2H, m), 1.57-1.63 (4H, m), 3.11-3.13 (4H, m), 3.84 (1H, s), 6.16-6.25 (2H, m), 7.62-7.66 (1H, m). |
| 41 | Rex41 | $^1$H-NMR (CDCl3): 1.54-1.63 (6H, m), 3.25 (4H, t, J = 5.6 Hz), 4.04 (1H, s), 7.83 (1H, d, J = 0.2 Hz), 7.88 (1H, dd, J = 0.2 Hz, 8.8 Hz), 8.07 (1H, d, J = 8.8 Hz). |
| 42 | Rex299 | ESI-: 452 |
| 43 | Rex298 | $^1$H-NMR (DMSO-d6): 1.44-1.50 (6H, m), 3.30-3.04 (4H, m), 3.10 (1H, s), 3.85 (1H, s), 7.46-7.48 (1H, m), 7.55-7.56 (1H, m), 7.64-7.66 (1H, m), 7.93 (1H, br-s), 9.53 (1H, br-s). |
| 44 | Rex292 | $^1$H-NMR (CDCl3): 1.09 (6H, t, J = 7.2 Hz), 2.28 (4H, q, J = 7.2 Hz), 3.84 (1H, s), 6.17-6.23 (2H, m), 7.67-7.71 (1H, m). |
| 45 | Rex41 | $^1$H-NMR (CDCl3): 1.13 (6H, t, J = 7.2 Hz), 3.37 (4H, q, J = 7.2 Hz), 4.04 (3H, s), 7.82 (1H, d, J = 2.8 Hz), 7.87 (1H, dd, J = 2.8 Hz, 8.8 Hz), 8.12 (1H, d, J = 8.8 Hz). |
| 46 | Rex299 | ESI-: 440 |
| 47 | Rex298 | ESI-: 458 |

TABLE 52

| Rex | Syn | Data |
|---|---|---|
| 48 | Rex48 | $^1$H-NMR (CDCl3): 1.26 (6H, d, J = 6.4 Hz), 3.66 (2H, br-s), 4.25-4.31 (1H, m), 6.57 (1H, br-s), 6.69-6.73 (1H, m), 6.89 (1H, dd, J = 8.4 Hz, 11.6 Hz), 7.35 (1H, dd, J = 3.2 Hz, 6.8 Hz). |
| 49 | Rex299 | $^1$H-NMR (DMSO-d6): 1.14 (6H, d, J = 6.4 Hz), 2.39 (3H, s), 4.01-4.06 (1H, m), 7.24 (1H, t, J = 9.2 Hz), 7.49-7.53 (2H, m), 7.88 (1H, dd, J = 2.8 Hz, 6.4 Hz), 8.18 (1H, d, J = 8.0 Hz), 9.16 (1H, d, J = 4.4 Hz), 12.74 (1H, s), 12.96 (1H, s). |
| 50 | Rex298 | $^1$H-NMR (DMSO-d6): 1.14 (6H, d, J = 6.8 Hz), 2.41 (3H, s), 4.01-4.07 (1H, m), 7.24 (1H, t, J = 9.2 Hz), 7.62-7.66 (2H, m), 7.82-7.84 (1H, m), 7.87 (1H, s), 8.14 (1H, s), 8.15 (1H, m), 9.38 (1H, s). |
| 51 | Rex48 | $^1$H-NMR (CDCl3): 1.50-1.65 (6H, m), 3.28 (2H, br-s), 3.63 (2H, br-s), 3.71 (2H, br-s), 6.61-6.65 (2H, m), 6.86 (1H, t, J = 7.6 Hz). |
| 52 | Rex299 | $^1$H-NMR (DMSO-d6): 1.44-1.61 (6H, m), 2.45 (3H, s), 3.21 (2H, br-s), 3.59 (2H, br-s), 7.26 (1H, t, J = 8.8 Hz), 7.49-7.53 (2H, m), 7.63 (1H, dd, J = 2.4 Hz, 6.4 Hz), 9.14 (1H, d, J = 4.4 Hz), 12.72 (1H, s), 12.89 (1H, s). |

TABLE 52-continued

| Rex | Syn | Data |
| --- | --- | --- |
| 53 | Rex298 | $^1$H-NMR (DMSO-d6): 1.45-1.62 (6H, m), 2.33 (3H, s), 3.22 (2H, m), 3.59 (2H, br-s), 7.26 (1H, t, J = 8.8 Hz), 7.57-7.62 (2H, m), 7.86 (1H, s), 8.13 (1H, s), 9.35 (1H, s). |
| 54 | Rex299 | $^1$H-NMR (DMSO-d6): 2.45 (3H, s), 3.26 (2H, br-s), 3.53 (2H, t, J = 4.8 Hz), 3.63 (4H, br-s), 7.28 (1H, t, J = 8.8 Hz), 7.51-7.57 (2H, m), 7.65 (1H, dd, J = 2.8 Hz, 6.0 Hz), 9.14 (1H, d, J = 4.4 Hz), 12.73 (1H, s), 12.89 (1H, s). |

TABLE 53

| Rex | Syn | Data |
| --- | --- | --- |
| 55 | Rex298 | $^1$H-NMR (DMSO-d6): 2.41 (3H, s), 3.27 (2H, m), 3.54 (2H, t, J = 4.8 Hz), 3.64 (4H, br-s), 7.28 (1H, t, J = 8.8 Hz), 7.61-7.64 (2H, m), 7.88 (1H, br-s), 8.14 (1H, br-s), 9.38 (1H, s). |
| 56 | Rex292 | $^1$H-NMR (CDC3): 1.08 (3H, t, J = 7.2 Hz), 1.23 (3H, t, J = 7.2 Hz), 3.24 (2H, q, J = 7.2 Hz), 3.55 (2H, m), 3.70 (2H, br-s), 6.56 (1H, dd, J = 3.2 Hz, 5.6 Hz), 6.62 (1H, m), 6.85 (1H, t, J = 8.8 Hz). |
| 57 | Rex299 | $^1$H-NMR (DMSO-d6): 1.01 (3H, t, J = 7.2 Hz), 1.13 (3H, t, J = 7.2 Hz), 2.45 (3H, s), 3.17 (2H, q, J = 7.2 Hz), 3.44 (2H, m), 7.26 (1H, t, J = 8.8 Hz), 7.46 (1H, m), 7.52 (1H, d, J = 4.4 Hz), 7.67 (1H, dd, J = 2.8 Hz, 6.0 Hz), 9.15 (1H, d, J = 4.4 Hz), 12.73 (1H, s), 12.94 (1H, s). |
| 58 | Rex298 | $^1$H-NMR (DMSO-d6): 1.02 (3H, t, J = 7.2 Hz), 1.13 (3H, t, J = 7.2 Hz), 2.40 (3H, s), 3.18 (2H, q, J = 7.2 Hz), 3.45 (2H, q, J = 7.2 Hz), 7.27 (1H, t, J = 9.2 Hz), 7.58-7.61 (2H, m), 7.87 (1H, br-s), 8.14 (1H, br-s), 9.35 (1H, s). |
| 59 | Rex292 | $^1$H-NMR (CDCl3): 1.05 (6H, d, J = 6.4 Hz), 3.27-3.49 (1H, m), 3.90 (1H, s), 4.55 (1H, d, J = 6.4 Hz), 6.62-6.28 (2H, m), 7.65-7.69 (1H, m). |
| 60 | Rex41 | $^1$H-NMR (CDCl3): 1.08 (6H, t, J = 6.8 Hz), 3.48 (1H, q, J = 7.6 Hz), 4.11 (1H, s), 4.75 (1H, d, J = 7.6 Hz), 7.88 (1H, d, J = 2.0 Hz), 7.94 (1H, dd, J = 2.0 Hz, 8.4 Hz), 8.12 (1H, d, J = 8.4 Hz). |
| 61 | Rex299 | $^1$H-NMR (DMSO-d6): 0.94-0.99 (6H, m), 3.18-3.24 (1H, m), 2.49 (1H, m), 3.92 (1H, s), 7.06-7.08 (1H, m), 7.20-7.23 (1H, m), 7.39-7.40 (1H, m), 7.61-7.69 (2H, m), 9.20 (1H, br-s), 12.88 (1H, br-s), 13.28 (1H, br-s). |

TABLE 54

| Rex | Syn | Data |
| --- | --- | --- |
| 62 | Rex298 | ESI-: 444 |
| 63 | Rex292 | $^1$H-NMR (CDCl3): 1.40-1.46 (2H, m), 1.62-1.67 (4H, m), 2.96-2.99 (4H, m), 3.97 (1H, br-s), 7.06-7.10 (2H, m), 7.15-7.18 (1H, m). |
| 64 | Rex41 | $^1$H-NMR (CDCl3): 1.45-1.71 (7H, m), 3.06 (4H, t, J = 5.6 Hz), 7.46-7.52 (1H, m), 8.00-8.04 (1H, m), 8.43-8.46 (1H, m). |
| 65 | Rex299 | ESI-: 440 |
| 66 | Rex298 | $^1$H-NMR (DMSO-d6): 1.31-1.38 (4H, m), 1.51-1.55 (7H, m), 2.44 (1H, s), 2.83-2.92 (7H, m), 7.56-7.58 (2H, m), 8.14-8.26 (3H, m), 9.77 (1H, br-s). |
| 67 | Rex292 | $^1$H-NMR (CDCl3): 1.43-1.45 (2H, m), 1.64 (4H, m), 2.22 (1H, s), 3.21 (2H, m), 3.66-3.76 (4H, m), 6.48-6.51 (2H, m), 6.94 (1H, d, J = 8.0 Hz). |
| 68 | Rex4 | $^1$H-NMR (CDCl3): 1.43-1.87 (6H, m), 2.42 (3H, s), 3.13-3.15 (2H, m), 3.69-3.83 (2H, m), 7.32 (1H, d, J = 8.4 Hz), 8.07-8.11 (2H, m). |
| 69 | Rex299 | ESI-: 400 |
| 70 | Rex298 | ESI-: 418 |
| 71 | Rex292 | $^1$H-NMR (CD3OD): 2.23 (3H, s), 2.84 (3H, s), 6.50-6.55 (2H, m), 7.14 (1H, d, J = 8.4 Hz). |

TABLE 54-continued

| Rex | Syn | Data |
| --- | --- | --- |
| 72 | Rex4 | $^1$H-NMR (CDCl3): 2.54 (3H, s), 3.04 (3H, d, J = 4.8 Hz), 5.80 (1H, br-s), 7.49 (1H, d, J = 8.4 Hz), 8.04-8.12 (1H, m). |
| 73 | Rex299 | ESI-: 346 |
| 74 | Rex298 | ESI-: 364 |
| 75 | Rex292 | $^1$H-NMR (CDCl3): 1.54-1.62 (6H, m), 3.20-3.23 (2H, m), 3.62-3.64 (1H, m), 3.77 (5H, m), 6.20 (1H, d, J = 2.0 Hz), 6.27 (1H, dd, J = 2.0 Hz, 8.1 Hz), 7.02 (1H, d, J = 8.1 Hz). |
| 76 | Rex299 | ESI-: 416 |

TABLE 55

| Rex | Syn | Data |
| --- | --- | --- |
| 77 | Rex298 | ESI-: 434 |
| 78 | Rex292 | $^1$H-NMR (CDCl3): 1.45-1.47 (2H, m), 1.65 (4H, m), 2.17 (3H, s), 3.18-3.21 (2H, m), 3.59-3.66 (3H, m), 3.78-3.82 (1H, m), 6.49 (1H, d, J = 2.7 Hz), 6.60 (1H, dd, J = 2.7 Hz, 8.3 Hz), 6.97 (1H, d, J = 8.3 Hz). |
| 79 | Rex4 | $^1$H-NMR (CDCl3): 1.48-1.54 (2H, m), 1.70 (4H, m), 2.42 (3H, s), 3.16-3.20 (2H, m), 3.73-3.80 (2H, m), 7.39 (1H, d, J = 8.5 Hz), 8.05 (1H, d, J = 2.2 Hz), 8.12 (1H, dd, J = 2.2 Hz, 8.5 Hz). |
| 80 | Rex299 | ESI-: 400 |
| 81 | Rex298 | ESI-: 418 |
| 82 | Rex292 | $^1$H-NMR (CDCl3): 2.31 (3H, s), 2.98 (3H, d, J = 4.9 Hz), 3.60 (2H, m), 5.69 (1H, m), 6.64 (1H, dd, J = 2.7 Hz, 8.1 Hz), 6.70 (1H, d, J = 2.7 Hz), 6.98 (1H, d, J = 8.1 Hz). |
| 83 | Rex299 | ESI-: 346 |
| 84 | Rex298 | ESI-: 364 |
| 85 | Rex48 | $^1$H-NMR (CDCl3): 2.97 (3H, d, J = 4.8 Hz), 4.03 (2H, br-s), 5.76 (1H, br-s), 6.77 (1H, dd, J = 2.4 Hz, 8.0 Hz), 6.90 (1H, d, J = 2.4 Hz), 7.33 (1H, d, J = 8.0 Hz). |
| 86 | Rex299 | $^1$H-NMR (DMSO-d6): 2.51 (3H, s), 2.73 (3H, d, J = 4.4 Hz), 7.48 (1H, d, J = 8.4 Hz), 7.63-7.65 (2H, m), 8.22 (1H, d, J = 1.6 Hz), 8.38 (1H, d, J = 4.8 Hz), 9.18 (1H, d, J = 4.4 Hz), 12.89 (1H, s), 13.27 (1H, s). |
| 87 | Rex298 | $^1$H-NMR (DMSO-d6): 2.45 (3H, s), 2.73 (3H, d, J = 4.8 Hz), 7.48 (1H, d, J = 8.4 Hz), 7.88 (1H, d, J = 8.8 Hz), 7.89 (1H, s), 8.12 (1H, d, J = 2.0 Hz), 8.17 (1H, s), 8.38 (1H, m), 9.62 (1H, s). |

TABLE 56

| Rex | Syn | Data |
| --- | --- | --- |
| 88 | Rex48 | $^1$H-NMR (CDCl3): 3.01 (3H, dd, J = 1.2 Hz, 5.2 Hz), 3.69 (2H, br-s), 6.70-6.74 (1H, m), 6.77 (1H, br-s), 6.90 (1H, dd, J = 8.4 Hz, 11.6 Hz), 7.38 (1H, dd, J = 3.2 Hz, 6.4 Hz). |
| 89 | Rex299 | $^1$H-NMR (DMSO-d6): 2.49 (3H, s), 2.77 (3H, d, J = 4.4 Hz), 7.26 (1H, t, J = 8.8 Hz), 7.53-7.58 (2H, m), 7.95 (1H, dd, J = 2.8 Hz, 6.4 Hz), 8.24 (1H, br-s), 9.16 (1H, d, J = 4.4 Hz), 12.75 (1H, s), 12.96 (1H, s). |
| 90 | Rex298 | $^1$H-NMR (DMSO-d6): 2.40 (3H, s), 2.77 (3H, d, J = 4.8 Hz), 7.26 (1H, t, J = 10.0 Hz), 7.64-7.68 (1H, m), 7.87 (1H, s), 7.92 (1H, dd, J = 2.4 Hz, 6.4 Hz), 8.14 (1H, br-s), 8.21 (1H, br-s), 9.39 (1H, br-s). |
| 91 | Rex292 | $^1$H-NMR (CDCl3): 2.55 (3H, s), 3.91 (3H, s), 6.22-6.30 (2H, m), 7.65-7.69 (1H, m). |
| 92 | Rex41 | $^1$H-NMR (CDCl3): 2.66 (3H, d, J = 5.2 Hz), 4.11 (3H, s), 4.84 (1H, d, J = 5.2 Hz), 7.89 (1H, d, J = 2.0 Hz), 7.94 (1H, dd, J = 2.0 Hz, 8.8 Hz), 8.12 (1H, d, J = 8.8 Hz). |
| 93 | Rex299 | ESI-: 398 |
| 94 | Rex298 | ESI-: 416 |

TABLE 56-continued

| Rex | Syn | Data |
|---|---|---|
| 95 | Rex292 | $^1$H-NMR (CDCl3): 2.97 (3H, d, J = 4.6 Hz), 3.90 (3H, s), 3.96 (2H, m), 6.20 (1H, d, J = 2.2 Hz), 6.34 (1H, dd, J = 2.2 Hz, 8.5 Hz), 7.66 (1H, m), 8.04 (1H, d, J = 8.5 Hz). |
| 96 | Rex4 | $^1$H-NMR (CDCl3): 3.04 (3H, d, J = 4.9 Hz), 4.09 (3H, s), 7.74 (1H, m), 7.84 (1H, d, J = 2.2 Hz), 7.93 (1H, dd, J = 2.2 Hz, 8.5 Hz), 8.39 (1H, d, J = 8.5 Hz). |
| 97 | Rex299 | ESI−: 362 |

TABLE 57

| Rex | Syn | Data |
|---|---|---|
| 98 | Rex298 | ESI−: 380 |
| 99 | Rex48 | $^1$H-NMR (CDCl3): 0.83-0.88 (1H, m), 1.42-1.65 (5H, m), 3.15 (2H, dd, J = 9.2 Hz, 15.2 Hz), 3.64-3.76 (2H, m), 4.01 (1H, br-s), 6.78 (1H, dd, J = 2.4 Hz, 8.4 Hz), 6.90 (1H, d, J = 2.8 Hz), 7.05 (1H, d, J = 8.4 Hz). |
| 100 | Rex299 | $^1$H-NMR (DMSO-d6): 1.37-1.59 (6H, m), 2.54 (3H, s), 3.06-3.11 (2H, m), 3.51-3.62 (2H, m), 7.40 (1H, d, J = 8.4 Hz), 7.61-7.66 (2H, m), 8.27 (1H, d, J = 2.0 Hz), 9.18 (1H, d, J = 4.0 Hz), 12.89 (1H, s), 13.28 (1H, s). |
| 101 | Rex298 | $^1$H-NMR (DMSO-d6): 1.37-1.59 (6H, m), 2.45 (3H, s), 3.06-3.11 (2H, m), 3.52-3.62 (2H, m), 7.40 (1H, d, J = 8.0 Hz), 7.90 (1H, br-s), 7.92 (1H, m), 8.16 (1H, br-s), 8.19 (1H, d, J = 2.0 Hz), 9.62 (1H, s). |
| 102 | Rex353 | ESI−: 346 |
| 103 | Rex353 | ESI−: 454 |
| 104 | Rex353 | ESI−: 346 |
| 105 | Rex353 | ESI−: 346 |
| 106 | Rex299 | $^1$H-NMR (DMSO-d6): 2.53 (3H, s), 2.72 (3H, d, J = 4.4 Hz), 7.41 (1H, d, J = 8.8 Hz), 7.48-7.56 (2H, m), 8.36 (1H, d, J = 4.6 Hz), 9.16 (1H, d, J = 3.7 Hz), 12.80 (1H, s), 13.10 (1H, s). |
| 107 | Rex298 | $^1$H-NMR (DMSO-d6): 2.43 (3H, s), 2.73 (3H, d, J = 4.6 Hz), 7.41 (1H, d, J = 8.5 Hz), 7.65 (1H, dd, J = 2.7 Hz, 8.8 Hz), 7.77 (1H, d, J = 2.4 Hz), 7.88 (1H, s), 8.14 (1H, s), 8.35 (1H, d, J = 4.6 Hz), 9.43 (1H, s). |

TABLE 58

| Rex | Syn | Data |
|---|---|---|
| 108 | Rex353 | $^1$H-NMR (CDCl3): 1.29 (3H, t, J = 7.6 Hz), 2.87 (2H, q, J = 7.3 Hz), 3.04 (3H, d, J = 4.9 Hz), 5.56 (1H, br-s), 6.25 (1H, br-s), 7.34 (1H, d, J = 8.8 Hz), 7.74 (1H, br-s), 7.81 (1H, dd, J = 2.9 Hz, 8.8 Hz), 7.93 (1H, d, J = 2.7 Hz), 10.95 (1H, br-s). |
| 109 | Rex353 | $^1$H-NMR (CDCl3): 1.31 (3H, t, J = 7.6 Hz), 2.89 (2H, q, J = 7.3 Hz), 3.03 (3H, d, J = 4.9 Hz), 4.04 (3H, s), 5.53 (1H, br-s), 6.12 (1H, br-s), 7.28 (1H, m), 7.49 (1H, s), 7.74 (1H, br-s), 8.58 (1H, d, J = 8.3 Hz), 11.43 (1H, br-s). |
| 110 | Rex292 | $^1$H-NMR (CDCl3): 2.18 (3H, s), 2.98 (3H, d, J = 4.9 Hz), 3.88 (2H, m), 5.97 (1H, m), 6.64 (1H, d, J = 8.1 Hz), 7.44 (1H, dd, J = 2.0 Hz, 8.3 Hz), 7.51 (1H, m). |
| 111 | Rex4 | $^1$H-NMR (CDCl3): 2.64 (3H, s), 3.05 (3H, d, J = 4.9 Hz), 6.17 (1H, m), 7.67 (1H, dd, J = 2.0 Hz, 8.3 Hz), 7.76 (1H, d, J = 2.0 Hz), 8.00 (1H, d, J = 8.3 Hz). |
| 112 | Rex353 | ESI−: 346 |
| 113 | Rex353 | ESI−: 400 |
| 114 | Rex292 | $^1$H-NMR (CDCl3): 2.21 (3H, s), 2.99 (3H, d, J = 4.9 Hz), 3.70 (2H, m), 5.72 (1H, m), 6.71-6.77 (2H, m), 7.00-7.04 (1H, m). |

TABLE 58-continued

| Rex | Syn | Data |
|---|---|---|
| 115 | Rex353 | $^1$H-NMR (CDCl3): 1.30 (3H, t, J = 7.3 Hz), 2.42 (3H, s), 2.87 (2H, q, J = 7.3 Hz), 3.02 (3H, d, J = 4.9 Hz), 5.50 (1H, m), 5.75 (1H, m), 7.09-7.11 (1H, m), 7.75 (1H, m), 8.16-8.18 (1H, m), 10.74 (1H, m). |
| 116 | Rex353 | ESI−: 366 |
| 117 | Rex353 | ESI−: 325 |

TABLE 59

| Rex | Syn | Data |
|---|---|---|
| 118 | Rex292 | $^1$H-NMR (CDCl3): 2.98 (3H, d, J = 4.9 Hz), 3.85 (2H, br-s), 6.06 (1H, br-s), 6.98-7.01 (2H, m), 7.25-7.29 (1H, m). |
| 119 | Rex353 | $^1$H-NMR (CDCl3): 1.31 (3H, t, J = 7.6 Hz), 2.92 (2H, q, J = 7.3 Hz), 3.05 (3H, d, J = 4.9 Hz), 5.57 (1H, br-s), 6.13 (1H, br-s), 7.18 (1H, m), 7.52 (1H, m), 7.73 (1H, m), 8.87 (1H, d, J = 8.5 Hz), 11.15 (1H, br-s). |
| 120 | Rex292 | $^1$H-NMR (CDCl3): 3.00 (3H, d, J = 4.9 Hz), 4.19 (2H, br-s), 5.92 (1H, br-s), 6.80 (1H, dd, J = 1.7 Hz, 7.6 Hz), 6.87 (1H, dd, J = 1.7 Hz, 7.6 Hz), 7.08 (1H, m, J = 7.6 Hz). |
| 121 | Rex4 | $^1$H-NMR (CDCl3): 3.06 (3H, s), 5.57 (1H, br-s), 6.04 (1H, br-s), 7.42 (1H, d, J = 8.1 Hz), 7.74 (1H, dd, J = 1.5 Hz, 7.6 Hz), 7.83 (1H, dd, J = 2.0 Hz, 8.1 Hz). |
| 122 | Rex353 | $^1$H-NMR (CDCl3): 1.31 (3H, t, J = 7.6 Hz), 2.91 (2H, q, J = 7.3 Hz), 3.04 (3H, d, J = 4.9 Hz), 5.56 (1H, br-s), 5.95 (1H, br-s), 7.21 (1H, m), 7.34 (1H, m), 7.74 (1H, br-s), 8.56 (1H, m), 11.40 (1H, br-s). |
| 123 | Rex299 | $^1$H-NMR (DMSO-d6): 2.84 (3H, s), 7.21 (2H, t, J = 9.6 Hz), 7.52 (1H, t, J = 9.6 Hz), 7.53 (2H, s), 7.64 (1H, d, J = 4.0 Hz), 8.22 (2H, d, J = 9.2 Hz), 9.24 (1H, d, J = 4.0 Hz), 12.92 (1H, br-s), 13.73 (1H, s). |
| 124 | Rex298 | ESI−: 343 |
| 125 | Rex353 | ESI−: 325 |
| 126 | Rex353 | ESI−: 398 |
| 127 | Rex353 | ESI+: 334 |

TABLE 60

| Rex | Syn | Data |
|---|---|---|
| 128 | Rex353 | $^1$H-NMR (DMSO-d6): 1.24 (3H, t, J = 7.6 Hz), 2.89 (2H, q, J = 7.3 Hz), 4.53 (2H, s), 6.92 (1H, d, J = 8.5 Hz), 7.11-7.16 (2H, m), 8.02 (1H, br-s), 8.25 (1H, br-s), 10.78 (1H, br-s), 11.06 (1H, br-s). |
| 129 | Rex353 | ESI−: 265 |
| 130 | Rex353 | ESI−: 350 |
| 131 | Rex353 | ESI−: 289 |
| 132 | Rex353 | ESI+: 488 |
| 133 | Rex353 | $^1$H-NMR (CDCl3): 1.31 (3H, t, J = 7.2 Hz), 2.64 (6H, s), 2.91 (2H, q, J = 7.2 Hz), 4.30 (1H, br-s), 5.60 (1H, br-s), 7.56 (1H, br-s), 7.77 (1H, m), 7.95 (1H, d, J = 8.0 Hz), 11.12 (1H, br-s). |
| 134 | Rex353 | $^1$H-NMR (CDCl3): 1.30 (3H, t, J = 7.2 Hz), 2.89 (2H, q, J = 7.6 Hz), 2.99 (3H, d, J = 4.9 Hz), 5.59 (1H, br-s), 6.60 (1H, br-s), 7.53 (1H, dd, J = 2.4 Hz, 9.2 Hz), 7.60 (1H, d, J = 8.8 Hz), 7.75 (1H, br-s), 7 96 (1H, d, J = 2.4 Hz), 10.95 (1H, s). |
| 135 | Rex353 | ESI+: 368 |
| 136 | Rex353 | ESI+: 364 |
| 137 | Rex292 | $^1$H-NMR (CDCl3): 2.44 (3H, s), 2.50 (3H, s), 6.79 (1H, dd, J = 2.4 Hz, 8.4 Hz), 7.06 (1H, d, J = 8.4 Hz), 7.25 (1H, d, J = 2.4 Hz). |
| 138 | Rex353 | ESI−: 382 |
| 139 | Rex292 | $^1$H-NMR (CDCl3): 3.15-3.17 (4H, m), 3.70-3.72 (4H, m), 3.85 (3H, s), 4.13 (2H, br-s), 6.19 (1H, d, J = 2.0 Hz), 6.23 (1H, dd, J = 2.0 Hz, 8.4 Hz), 7.01 (1H, d, J = 8.4 Hz). |

TABLE 60-continued

| Rex | Syn | Data |
|---|---|---|
| 140 | Rex41 | ¹H-NMR (CDCl3): 3.28-3.30 (4H, m), 3.72-3.74 (4H, m), 4.06 (3H, s), 7.86 (1H, d, J = 2.0 Hz), 7.89 (1H, dd, J = 2.0 Hz, 8.4 Hz), 8.80 (1H, d, J = 8.4 Hz,). |

TABLE 61

| Rex | Syn | Data |
|---|---|---|
| 141 | Rex353 | ESI−: 454 |
| 142 | Rex353 | ¹H-NMR (DMSO-d6): 1.24 (3H, t, J = 7.6 Hz), 2.79 (2H, q, J = 7.3 Hz), 4.56 (2H, s), 6.84 (1H, d, J = 8.5 Hz), 6.98 (1H, dd, J = 2.4 Hz, 8.5 Hz), 7.46 (1H, d, J = 2.2 Hz), 8.01 (1H, br-s), 8.24 (1H, br-s), 10.65 (1H, br-s), 11.11 (1H, br-s). |
| 143 | Rex353 | ESI+: 317 |
| 144 | Rex353 | ¹H-NMR (DMSO-d6): 1.24 (3H, t, J = 7.6 Hz), 2.78 (2H, q, J = 7.3 Hz), 4.20-4.24 (4H, m), 6.81-6.89 (2H, m), 7.29 (1H, d, J = 2.4 Hz), 7.98 (1H, br-s), 8.21 (1H, br-s), 10.98 (1H, br-s). |
| 145 | Rex48 | ¹H-NMR (CDCl3): 3.36 (3H, s), 3.53 (2H, t, J = 5.1 Hz), 3.61 (2H, m), 4.01 (2H, br-s), 6.14 (1H, br-s), 6.76 (1H, dd, J = 2.0 Hz, 8.3 Hz), 6.91 (1H, d, J = 2.2 Hz), 7.33 (1H, d, J = 8.3 Hz). |
| 146 | Rex353 | ¹H-NMR (CDCl3): 1.31 (3H, t, J = 7.6 Hz), 2.90 (2H, q, J = 7.3 Hz), 3.39 (3H, s), 3.58 (2H, m), 3.64 (2H, m), 5.79 (1H, br-s), 6.38 (1H, br-s), 7.52 (1H, d, J = 3.7 Hz), 7.75 (1H, br-s), 7.87 (1H, dd, J = 2.0 Hz, 8.3 Hz), 11.05 (1H, br-s). |
| 147 | Rex353 | ¹H-NMR (CDCl3): 1.24-1.59 (9H, m), 2.90 (2H, q, J = 7.6 Hz), 3.10-3.17 (4H, m), 3.95 (3H, s), 5.59 (1H, br-s), 7.13 (1H, d, J = 8.8 Hz), 7.63 (1H, d, J = 8.4 Hz), 7.75-7.81 (3H, m), 11.16 (1H, br-s). |
| 148 | Rex353 | ¹H-NMR (CDCl3): 1.25 (3H, t, J = 7.6 Hz), 2.60 (3H, s), 2.92 (2H, q, J = 7.6 Hz), 5.59 (1H, br-s), 7.28 (1H, br-s), 7.73 (1H, br-s), 7.75 (1H, m), 8.44 (1H, d, J = 2.0 Hz), 10.99 (1H, br-s). |
| 149 | Rex353 | ¹H-NMR (CDCl3): 1.21-1.34 (3H, m), 2.82-2.92 (5H, m), 5.61 (1H, br-s), 7.51 (1H, d, J = 6.8 Hz), 7.72-7.75 (1H, m), 7.87 (1H, d, J = 6.8 Hz), 8.42 (1H, d, J = 2.8 Hz), 10.99 (1H, br-s). |

TABLE 62

| Rex | Syn | Data |
|---|---|---|
| 150 | Rex353 | ESI+: 364 |
| 151 | Rex353 | ¹H-NMR (CDCl3): 1.25 (3H, t, J = 7.6 Hz), 2.92 (3H, q, J = 7.6 Hz), 5.63 (1H, br-s), 7.53 (1H, dd, J = 3.6 Hz, 6.9 Hz), 7.76 (1H, br-s), 7.90 (1H, d, J = 6.0 Hz), 8.78 (1H, d, J = 3.6 Hz), 11.27 (1H, br-s). |
| 152 | Rex353 | ESI+: 329 |
| 153 | Rex353 | ¹H-NMR (CDCl3): 1.34 (3H, t, J = 7.6 Hz), 2.95 (2H, q, J = 7.6 Hz), 5.65 (1H, br-s), 7.74 (1H, dd, J = 2.0 Hz, 9.2 Hz), 7.79 (1H, br-s), 8.02 (1H, d, J = 9.2 Hz), 9.28 (1H, d, J = 2.0 Hz), 11.25 (1H, br-s). |
| 154 | Rex353 | ¹H-NMR (CDCl3): 1.30 (3H, t, J = 7.6 Hz), 2.86 (2H, q, J = 7.6 Hz), 3.79 (3H, s), 5.49 (1H, m), 6.44 (1H, d, J = 3.2 Hz), 7.01 (1H, d, J = 3.2 Hz), 7.15 (1H, dd, J = 0.2 Hz, 8.4 Hz), 7.54 (1H, d, J = 8.4 Hz), 7.74 (1H, m), 7.98 (1H, s), 10.84 (1H, m). |
| 155 | Rex292 | ¹H-NMR (CDC3): 2.84 (3H, s), 3.37 (2H, br-s), 3.99 (1H, br-s), 6.62 (1H, d, J = 8.4 Hz), 6.82 (1H, dd, J = 2.8 Hz, 8.4 Hz), 6.86 (1H, d, J = 2.8 Hz). |
| 156 | Rex353 | ¹H-NMR (CDCl3): 1.28 (3H, t, J = 7.6 Hz), 2.85 (2H, q, J = 7.6 Hz), 2.91 (3H, q, J = 4.8 Hz), 4.32 (1H, br-s), 5.51 (1H, br-s), 6.73 (1H, d, J = 8.4 Hz), 7.66-7.70 (3H, m), 10.50 (1H, br-s). |
| 157 | Rex292 | ¹H-NMR (DMSO-d6): 1.67-1.78 (2H, m), 2.07 (2H, m), 3.03-3.27 (8H, m), 3.73 (3H, s), 3.90-4.16 (3H, m), 5.79 (2H, br-s), 6.29 (1H, d, J = 8.5 Hz), 6.50-6.54 (2H, m). |

TABLE 62-continued

| Rex | Syn | Data |
|---|---|---|
| 158 | Rex503 | ESI+: 338 |
| 159 | Rex353 | ESI+: 491 |
| 160 | Rex160 | ¹H-NMR (CDCl3): 1.35 (3H, t, J = 7.6 Hz), 3.02 (2H, q, J = 7.6 Hz). |
| 161 | Rex353 | ESI+: 375 |

TABLE 63

| Rex | Syn | Data |
|---|---|---|
| 162 | Rex292 | ESI+: 276 |
| 163 | Rex444 | ESI+: 306 |
| 164 | Rex353 | ESI+: 459 |
| 165 | Rex353 | ESI+: 376 |
| 166 | Rex353 | ¹H-NMR (CDCl3): 1.28 (3H, t, J = 7.6 Hz), 2.84 (2H, q, J = 7.6 Hz), 3.46-3.48 (4H, m), 3.83-3.85 (4H, m), 5.55 (1H, br-s), 6.67 (1H, d, J = 8.8 Hz), 8.43 (1H, d, J = 2.4 Hz), 10.45 (1H, br-s). |
| 167 | Rex292 | ESI+: 276 |
| 168 | Rex444 | ESI+: 306 |
| 169 | Rex353 | ESI+: 459 |
| 170 | Rex353 | ESI+: 552 |
| 171 | Rex353 | ¹H-NMR (CDCl3): 1.28 (3H, t, J = 7.2 Hz), 2.84 (2H, q, J = 7.2 Hz), 3.12-3.14 (4H, m), 3.86-3.88 (4H, m), 5.51 (1H, br-s), 6.91 (1H, dd, J = 2.4 Hz, 7.2 Hz), 7.55 (1H, dd, J = 2.4 Hz, 7.2 Hz), 7.71 (1H, br-s), 10.58 (1H, br-s). |
| 172 | Rex353 | ¹H-NMR (CDCl3): 1.28 (3H, t, J = 7.6 Hz), 2.31 (3H, s), 2.36 (3H, s), 2.84 (2H, q, J = 7.6 Hz), 2.92-2.94 (4H, m), 5.48 (1H, br-s), 7.02 (1H, d, J = 8.8 Hz), 7.34 (1H, d, J = 2.4 Hz), 7.55 (1H, dd, J = 2.7 Hz, 8.5 Hz), 7.71 (1H, br-s), 10.60 (1H, br-s). |
| 173 | Rex353 | ¹H-NMR (CDCl3): 1.28 (3H, t, J = 7.6 Hz), 1.68-1.74 (6H, m), 1.92-1.95 (2H, m), 2.29-2.36 (7H, m), 2.50-2.65 (8H, m), 2.84 (2H, q, J = 7.6 Hz), 3.13-3.16 (2H, m), 5.54 (1H, br-s), 6.98 (1H, d, J = 6.5 Hz), 7.33 (1H, d, J = 2.6 Hz), 7.51 (1H, d, J = 2.7 Hz), 7.71 (1H, br-s), 10.58 (1H, br-s). |

TABLE 64

| Rex | Syn | Data |
|---|---|---|
| 174 | Rex353 | ¹H-NMR (CDCl3): 1.29 (3H, t, J = 7.3 Hz), 2.37 (3H, s), 2.62 (4H, m), 2.85 (2H, q, J = 7.3 Hz), 3.03 (4H, m), 5.53 (1H, br-s), 7.05 (1H, d, J = 8.8 Hz), 7.51 (1H, dd, J = 2.7 Hz, 8.8 Hz), 7.72 (1H, d, J = 2.4 Hz), 10.70 (1H, br-s). |
| 175 | Rex353 | ¹H-NMR (CDCl3): 1.28 (t, J = 7.2 Hz, 3H), 1.49 (s, 9H), 2.84 (q, J = 7.2 Hz, 2H), 3.09 (m, 4H), 3.58 (m, 4H), 5.62 (br-s, 1H), 6.92 (d, J = 9.2 Hz, 2H), 7.54 (d, J = 9.2 Hz, 2H), 7.71 (br-s, 1H), 10.60 (s, 1H). |
| 176 | Rex292 | ¹H-NMR (CDCl3): 1.60 (2H, br-s), 2.04-2.17 (4H, m), 2.91-2.94 (4H, m), 6.80 (1H, dd, J = 2.8 Hz, 8.4 Hz), 6.91 (1H, d, J = 2.8 Hz), 7.17 (1H, d, J = 8.4 Hz). |
| 177 | Rex516 | ¹H-NMR (CDCl3): 2.13-2.22 (4H, m), 3.18-3.20 (4H, m), 7.36 (1H, d, J = 8.8 Hz), 8.35 (1H, dd, J = 2.4 Hz, 9.2 Hz), 8.53 (1H, d, J = 2.4 Hz). |
| 178 | Rex353 | ESI−: 462 |
| 179 | Rex353 | ESI+: 400 |
| 180 | Rex292 | ¹H-NMR (CDCl3): 0.16-0.20 (2H, m), 0.55-0.59 (2H, m), 0.97 (1H, m), 2.40 (2H, d, J = 6.4 Hz), 2.75 (2H, m), 2.96 (4H, m), 3.72 (2H, m), 6.79 (1H, dd, J = 2.8 Hz, 8.4 Hz), 6.89 (1H, d, J = 2.8 Hz), 7.24 (1H, d, J = 8.4 Hz). |
| 181 | Rex516 | EI: 329 |
| 182 | Rex353 | ESI+: 483 |

TABLE 64-continued

| Rex | Syn | Data |
|---|---|---|
| 183 | Rex292 | $^1$H-NMR (CDCl3): 1.80-1.88 (1H, m), 2.06-2.14 (1H, m), 2.24 (6H, s), 2.85-3.20 (5H, m), 3.65 (2H, br-s), 6.78 (1H, dd, J = 2.9 Hz, 8.5 Hz), 6.90 (1H, d, J = 2.7 Hz), 7.14 (1H, d, J = 8.5 Hz). |

TABLE 65

| Rex | Syn | Data |
|---|---|---|
| 184 | Rex516 | $^1$H-NMR (CDCl3): 1.90-1.97 (1H, m), 2.21-2.29 (1H, m), 2.32 (3H, s), 2.77-2.82 (1H, m), 3.43-3.53 (1H, m), 3.62-3.67 (3H, m), 6.79 (1H, d, J = 9.5 Hz), 8.16 (1H, dd, J = 2.7 Hz, 9.5 Hz), 8.53 (1H, d, J = 2.7 Hz). |
| 185 | Rex353 | $^1$H-NMR (CDCl3): 1.29 (3H, t, J = 7.3 Hz), 1.84-1.89 (1H, m), 2.12-2.16 (1H, m), 2.26 (6H, s), 2.83-2.89 (3H, m), 3.20-3.41 (4H, m), 5.57 (1H, br-s), 7.09 (1H, d, J = 8.8 Hz), 7.71-7.82 (3H, m), 10.68 (1H, br-s). |
| 186 | Rex353 | $^1$H-NMR (CDCl3): 1.10-1.15 (3H, m), 1.30 (3H, t, J = 7.3 Hz), 2.45-2.52 (2H, m), 2.85-2.97 (10H, m), 5.57 (1H, br-s), 7.37-7.39 (1H, m), 7.73 (1H, br-s), 7.87-7.88 (2H, m), 10.86 (1H, br-s). |
| 187 | Rex292 | $^1$H-NMR (CDCl3): 1.04 (6H, d, J = 6.3 Hz), 2.28-2.33 (2H, m), 2.81 (2H, dd, J = 2.0 Hz, 9.0 Hz), 3.02-3.07 (2H, m), 3.69 (2H, br-s), 6.78 (1H, dd, J = 2.7 Hz, 8.5 Hz), 6.89 (1H, d, J = 2.9 Hz), 7.15 (1H, d, J = 8.5 Hz). |
| 188 | Rex516 | $^1$H-NMR (CDCl3): 1.10 (3H, s), 1.11 (3H, s), 2.48-2.53 (2H, m), 3.08-3.13 (2H, m), 3.22 (2H, d, J = 10.7 Hz), 7.22 (1H, d, J = 9.0 Hz), 8.29 (1H, dd, J = 2.7 Hz, 9.0 Hz), 8.50 (1H, d, J = 2.7 Hz). |
| 189 | Rex353 | $^1$H-NMR (CDCl3): 1.05-1.09 (6H, m), 1.22-1.46 (3H, m), 2.34-2.40 (2H, m), 2.71-3.76 (6H, m), 5.57 (1H, br-s), 7.32 (1H, d, J = 8.5 Hz), 7.74 (1H, br-s), 7.85-7.88 (2H, m), 10.85 (1H, br-s). |

TABLE 66

| Rex | Syn | Data |
|---|---|---|
| 190 | Rex292 | $^1$H-NMR (CDCl3): 1.41 (3H, s), 1.42 (3H, s), 2.68 (3H, s), 2.87-2.90 (2H, m), 2.81 (2H, dd, J = 2.0 Hz, 9.0 Hz, 2H), 3.00 (m, 2H), 3.23 (m, 2H), 3.81 (br-s), 6.80 (1H, dd, J = 2.9 Hz, 8.5 Hz), 6.88 (1H, d, J = 2.9 Hz), 7.24 (1H, d, J = 7.8 Hz). |
| 191 | Rex516 | $^1$H-NMR (CDCl3): 1.15 (3H, s), 1.16 (3H, s), 2.36 (3H, s), 2.46-2.50 (2H, m), 2.79-2.85 (2H, m), 3.19 (2H, dd, J = 2.7 Hz, 9.0 Hz), 7.22-7.24 (1H, m), 8.30 (1H, dd, J = 2.7 Hz, 9.0 Hz), 8.50 (1H, d, J = 2.7 Hz). |
| 192 | Rex353 | $^1$H-NMR (CDCl3): 1.11 (6H, m), 1.30 (3H, t, J = 7.3 Hz), 2.33-2.44 (5H, m), 2.67-2.79 (2H, m), 2.85-2.91 (4H, m), 5.54 (1H, br-s), 7.33 (1H, d, J = 8.3 Hz), 7.73 (1H, br-s), 7.85-7.87 (2H, m), 10.85 (1H, br-s). |
| 193 | Rex353 | ESI+: 362 |
| 194 | Rex194 | ESI+: 377 |
| 195 | Rex353 | ESI+: 389 |
| 196 | Rex353 | ESI+: 403 |
| 197 | Rex353 | $^1$H-NMR (CDCl3): 1.30 (3H, t, J = 7.6 Hz), 1.48 (9H, s), 2.76-2.91 (6H, m), 3.55 (4H, m), 5.57 (1H, br-s), 7.31 (1H, d, J = 8.8 Hz), 7.74 (1H, br-s), 7.86-7.90 (2H, m), 10.89 (1H, br-s). |
| 198 | Rex353 | $^1$H-NMR (CDCl3): 1.28 (3H, t, J = 7.6 Hz), 1.48 (9H, s), 2.32 (3H, s), 2.82-2.88 (6H, m), 3.56 (4H, t, J = 4.9 Hz), 5.52 (1H, br-s), 6.98 (1H, d, J = 8.5 Hz), 7.36 (1H, d, J = 2.7 Hz), 7.55 (1H, dd, J = 2.7 Hz, 8.5 Hz), 7.72 (1H, br-s), 10.62 (1H, br-s). |

TABLE 67

| Rex | Syn | Data |
|---|---|---|
| 199 | Rex516 | 1H-NMR (CDCl3): 0.99 (s, 6H), 1.29 (t, J = 5.6 Hz, 2H), 1.59-1.67 (m, 2H), 2.46 (s, 2H), 2.67 (m, 2H), 3.67 (br-s, 2H), 6.77 (dd, J = 2.9 Hz, 8.5 Hz, 1H), 6.89 (d, J = 2.7 Hz, 1H), 7.16 (d, J = 6.5 Hz, 1H). |
| 200 | Rex194 | ESI+: 417 |
| 201 | Rex194 | ESI+: 476 |
| 202 | Rex292 | $^1$H-NMR (CDCl3): 1.81-1.85 (2H, m), 1.99-2.03 (2H, m), 2.18-2.21 (4H, m), 2.79-2.84 (2H, m), 3.01-3.04 (2H, m), 3.12-3.34 (4H, m), 3.66-3.69 (2H, m), 9.92 (1H, dd, J = 2.4 Hz, 8.0 Hz), 6.98 (1H, d, J = 2.4 Hz), 7.24 (1H, d, J = 8.0 Hz). |
| 203 | Rex516 | EI: 343 |
| 204 | Rex353 | ESI+: 497 |
| 205 | Rex353 | ESI−: 437 |
| 206 | Rex353 | ESI−: 472 |
| 207 | Rex292 | $^1$H-NMR (CDCl3): 0.81 (3H, d, J = 6.4 Hz), 1.48 (3H, d, J = 6.6 Hz), 2.68 (2H, q, J = 11.0 Hz), 2.81 (2H, d, J = 4.9 Hz), 2.93 (1H, dd, J = 2.9 Hz, 12.9 Hz), 3.17 (1H, br-s), 3.29-3.44 (2H, m), 3.87 (2H, br-s), 6.83 (1H, dd, J = 2.7 Hz, 8.5 Hz), 6.89 (1H, d, J = 2.7 Hz), 7.29 (1H, d, J = 8.3 Hz). |
| 208 | Rex516 | $^1$H-NMR (CDCl3): 0.79 (3H, d, J = 6.3 Hz), 1.04 (3H, d, J = 6.4 Hz), 2.16-2.21 (1H, m), 2.28-2.34 (4H, m), 2.44-2.50 (1H, m), 2.86-2.90 (2H, m), 7.56 (1H, d, J = 8.8 Hz), 8.40 (1H, dd, J = 2.7 Hz, 8.8 Hz), 8.55 (1H, d, J = 2.7 Hz). |
| 209 | Rex353 | ESI+: 471 |
| 210 | Rex292 | EI: 219 |
| 211 | Rex516 | EI: 249 |
| 212 | Rex353 | ESI+: 403 |

TABLE 68

| Rex | Syn | Data |
|---|---|---|
| 213 | Rex292 | $^1$H-NMR (CDCl3): 1.52-1.55 (2H, m), 2.01 (2H, dt, J = 4.4 Hz, 8.4 Hz), 2.12-2.16 (2H, m), 2.84-2.94 (6H, m), 6.87 (1H, dd, J = 2.4 Hz, 8.4 Hz), 6.94 (1H, d, J = 2.4 Hz), 7.10-7.21 (4H, m), 7.29 (1H, d, J = 8.4 Hz). |
| 214 | Rex516 | $^1$H-NMR (CDCl3): 1.52-1.55 (2H, m), 2.01 (2H, dt, J = 4.4 Hz, 12.8 Hz), 2.12-2.16 (2H, m), 2.84-3.31 (6H, m), 6.86-6.89 (1H, m), 6.95 (1H, m), 7.10-7.19 (4H, m), 7.30 (1H, d, J = 8.4 Hz). |
| 215 | Rex353 | ESI−: 528 |
| 216 | Rex353 | ESI+: 403 |
| 217 | Rex292 | EI: 344 |
| 218 | Rex516 | EI: 374 |
| 219 | Rex353 | ESI−: 526 |
| 220 | Rex292 | $^1$H-NMR (CDCl3): 2.34 (3H, s), 2.51 (4H, t, J = 4.8 Hz), 3.17 (4H, t, J = 4.8 Hz), 3.63 (2H, br-s), 6.58 (2H, s). |
| 221 | Rex516 | $^1$H-NMR (CDCl3): 2.38 (3H, s), 2.58 (4H, m), 3.36 (4H, t, J = 4.8 Hz), 8.15 (2H, s). |
| 222 | Rex353 | ESI−: 441 |
| 223 | Rex292 | $^1$H-NMR (CDCl3): 1.41-1.53 (10H, m), 1.69 (2H, t, J = 7.1 Hz), 2.86 (2H, s), 3.10 (2H, t, J = 6.8 Hz), 3.59 (2H, br-s), 6.77 (1H, d, J = 2.7 Hz, 8.5 Hz), 6.90 (1H, dd, J = 2.5 Hz, 9.5 Hz), 7.08 (1H, d, J = 8.8 Hz). |
| 224 | Rex516 | $^1$H-NMR (CDCl3): 1.42-1.57 (10H, m), 1.85 (2H, t, J = 7.1 Hz), 3.33 (2H, s), 3.61 (2H, t, J = 7.0 Hz), 6.77 (1H, d, J = 9.5 Hz), 8.14 (1H, dd, J = 2.7 Hz, 9.5 Hz), 8.53 (1H, d, J = 2.9 Hz). |

TABLE 69

| Rex | Syn | Data |
|---|---|---|
| 225 | Rex353 | $^1$H-NMR (CDCl3): 1.28 (3H, t, J = 7.6 Hz), 1.43-1.55 (10H, m), 2.32 (3H, s), 1.75 (2H, t, J = 7.1 Hz), 2.85 (2H, q, J = 7.6 Hz), 3.06 (2H, s), |

TABLE 69-continued

| Rex | Syn | Data |
|---|---|---|
|  |  | 3.32 (2H, t, J = 6.8 Hz), 5.50 (1H, br-s), 7.02 (1H, d, J = 9.0 Hz), 7.69-7.71 (2H, m), 7.80 (1H, d, J = 2.7 Hz), 10.61 (1H, br-s). |
| 226 | Rex353 | $^1$H-NMR (CDCl3): 1.29 (3H, t, J = 7.6 Hz), 1.49 (9H, s), 2.85 (2H, q, J = 7.6 Hz), 2.98 (4H, m), 3.61 (4H, t, J = 5.1 Hz), 3.90 (3H, s), 5.52 (1H, br-s), 6.87 (1H, d, J = 8.5 Hz), 7.14 (1H, dd, J = 2.4 Hz, 8.5 Hz), 7.38 (1H, d, J = 2.2 Hz), 7.73 (1H, br-s), 10.70 (1H, br-s). |
| 227 | Rex353 | ESI+: 370 |
| 228 | Rex413 | ESI−: 343 |
| 229 | Rex412 | $^1$H-NMR (CDCl3): 1.50 (9H, s), 2.37 (2H, m), 3.63-3.65 (2H, m), 4.06 (2H, m), 5.66 (1H, m), 7.44 (1H, d, J = 8.3 Hz), 8.35 (1H, dd, J = 2.2 Hz, 8.3 Hz), 8.54 (1H, d, J = 2.2 Hz). |
| 230 | Rex353 | $^1$H-NMR (CDCl3): 1.30 (3H, t, J = 7.3 Hz), 1.49 (9H, s), 1.60-1.78 (2H, m), 2.81 (2H, m), 2.88 (2H, q, J = 7.3 Hz), 3.00-3.06 (1H, m), 4.24 (1H, m), 5.56 (1H, m), 7.37 (1H, d, J = 8.5 Hz), 7.74 (1H, m), 7.85 (1H, dd, J = 2.4 Hz, 8.5 Hz), 7.92 (1H, d, J = 2.4 Hz), 10.90 (1H, br-s). |
| 231 | Rex353 | ESI+: 403 |
| 232 | Rex353 | ESI+: 392 |
| 233 | Rex353 | ESI+: 390 |
| 234 | Rex292 | $^1$H-NMR (CDCl3): 2.18 (3H, s), 2.38 (3H, s), 2.58 (4H, br-s), 2.83 (4H, br-s), 3.63 (2H, br-s), 6.35 (1H, dd, J = 2.8 Hz, 8.4 Hz), 6.98 (1H, d, J = 8.4 Hz), 7.81 (1H, d, J = 2.8 Hz), 8.66 (1H, br-s). |

TABLE 70

| Rex | Syn | Data |
|---|---|---|
| 235 | Rex353 | ESI+: 432 |
| 236 | Rex292 | $^1$H-NMR (CDCl3 + CD3OD): 2.42 (3H, s), 2.69 (4H, br-s), 2.86 (4H, br-s), 3.05 (3H, s), 6.44 (1H, dd, J = 2.8 Hz, 8.4 Hz), 6.87 (1H, d, J = 2.8 Hz), 7.08 (1H, d, J = 8.8 Hz). |
| 237 | Rex516 | $^1$H-NMR (CDCl3): 2.39 (3H, s), 2.64 (4H, br-s), 2.97 (4H, t, J = 4.8 Hz), 3.19 (3H, s), 7.28 (1H, d, J = 8.8 Hz), 7.53 (1H, br-s), 7.97 (1H, dd, J = 2.4 Hz, 8.4 Hz), 8.31 (1H, d, J = 2.4 Hz). |
| 238 | Rex353 | ESI+: 468 |
| 239 | Rex292 | $^1$H-NMR (CDCl3): 2.35 (3H, s), 2.45 (4H, br-s), 2.85 (4H, t, J = 4.8 Hz), 3.54 (2H, br-s), 6.62-6.65 (2H, m), 6.92 (1H, d, J = 9.2 Hz), 7.29 (1H, t, J = 7.6 Hz), 7.36 (2H, t, J = 7.6 Hz), 7.57 (2H, d, J = 7.2 Hz). |
| 240 | Rex240 | $^1$H-NMR (CDCl3): 2.27 (3H, s), 2.34 (4H, s), 2.99 (4H, t, J = 4.8 Hz), 7.01 (1H, d, J = 9.2 Hz), 7.35 (1H, t, J = 7.2 Hz), 7.44 (2H, t, J = 7.2 Hz), 7.58 (2H, d, J = 7.2 Hz), 8.08 (1H, d, J = 2.8 Hz), 8.14 (1H, dd, J = 2.8 Hz, 9.2 Hz). |
| 241 | Rex516 | ESI+: 348 |
| 242 | Rex353 | ESI+: 451 |
| 243 | Rex292 | $^1$H-NMR (CDCl3): 1.91 (3H, s), 2.34 (3H, s), 2.55 (4H, br-s), 2.87 (4H, m), 3.22 (3H, s), 3.64 (2H, br-s), 6.47 (1H, s), 6.66 (1H, d, J = 8.8 Hz), 6.95 (1H, d, J = 8.4 Hz). |
| 244 | Rex244 | $^1$H-NMR (CDCl3): 1.98 (3H, s), 2.35 (3H, s), 2.56 (4H, t, J = 4.8 Hz), 3.18 (4H, dd, J = 3.6 Hz, 5.6 Hz), 3.26 (3H, s), 7.05 (1H, d, J = 9.2 Hz), 7.98 (1H, d, J = 2.4 Hz), 8.14 (1H, dd, J = 2.4 Hz, 8.8 Hz). |

TABLE 71

| Rex | Syn | Data |
|---|---|---|
| 245 | Rex353 | ESI+: 446 |
| 246 | Rex246 | $^1$H-NMR (CDCl3): 0.90 (3H, t, J = 7.8 Hz), 1.40-1.55 (15H, m), 1.61-1.64 (2H, m), 1.78-1.82 (2H, m), 3.39 (1H, m), 4.42 (1H, m). |

TABLE 71-continued

| Rex | Syn | Data |
|---|---|---|
| 247 | Rex247 | $^1$H-NMR (CD3OD): 0.90 (3H, t, J = 7.6 Hz), 1.30-1.54 (6H, m), 1.62-1.65 (3H, m), 2.52-2.58 (1H, m). |
| 248 | Rex246 | $^1$H-NMR (CDCl3): 0.91 (3H, t, J = 7.6 Hz), 1.32-1.49 (13H, m), 1.54 (2H, q, J = 7.6 Hz), 1.60-1.66 (2H, m), 1.88-1.93 (2H, m), 3.59 (1H, m), 4.55 (1H, m). |
| 249 | Rex249 | $^1$H-NMR (CD3OD): 0.89 (3H, t, J = 7.6 Hz), 1.20-1.31 (2H, m), 1.38-1.45 (2H, m), 1.55 (2H, q, J = 7.6 Hz), 1.68-1.81 (4H, m), 2.70-2.75 (1H, m). |
| 250 | Rex250 | $^1$H-NMR (CDCl3): 0.91 (6H, d, J = 6.8 Hz), 1.43-1.49 (11H, m), 1.51-1.63 (5H, m), 1.81-1.83 (2H, m), 3.37 (1H, m), 4.41 (1H, m). |
| 251 | Rex251 | $^1$H-NMR (DMSO-d6): 0.82 (6H, d, J = 6.8 Hz), 1.24-1.31 (2H, m), 1.43-1.53 (3H, m), 1.65-1.67 (4H, m), 2.85-2.89 (1H, m), 3.87 (1H, m), 7.88 (2H, m). |
| 252 | Rex250 | $^1$H-NMR (CDCl3): 0.92 (6H, d, J = 6.8 Hz), 1.43-1.45 (11H, m), 1.52-1.55 (2H, m), 1.64-1.76 (3H, m), 1.88-1.92 (2H, m), 3.68 (1H, m), 4.53 (1H, m). |
| 253 | Rex253 | $^1$H-NMR (DMSO-d6): 0.83 (6H, d, J = 6.8 Hz), 1.25-1.32 (2H, m), 1.48 (2H, m), 1.62-1.68 (3H, m), 1.82-1.88 (2H, m), 3.17 (1H, m), 3.92 (1H, m), 7.84 (2H, m). |
| 254 | Rex353 | ESI+: 453 |

TABLE 72

| Rex | Syn | Data |
|---|---|---|
| 255 | Rex292 | $^1$H-NMR (CDCl3): 1.48 (9H, s), 1.85-1.93 (2H, m), 2.23 (3H, s), 2.93-3.02 (4H, m), 3.45-3.59 (6H, m), 6.47 (1H, d, J = 8.3 Hz), 6.53 (1H, s), 6.86 (1H, d, J = 8.3 Hz). |
| 256 | Rex353 | $^1$H-NMR (CDCl3): 1.28 (3H, t, J = 7.3 Hz), 1.49 (9H, s), 1.91-1.96 (2H, m), 2.31 (3H, s), 2.84 (2H, q, J = 7.3 Hz), 3.00-3.08 (4H, m), 3.56-3.61 (4H, m), 5.50 (1H, br-s), 7.01-7.04 (1H, m), 7.34 (1H, s), 7.52 (1H, m), 7.71 (1H, br-s), 10.60 (1H, br-s). |
| 257 | Rex292 | $^1$H-NMR (CD3OD): 1.49 (9H, s), 2.02-2.20 (6H, m), 2.37 (3H, s), 2.77-2.86 (2H, m), 3.27-3.34 (6H, m), 3.48-3.65 (6H, m), 3.96 (1H, t, J = 15.4 Hz), 7.18-7.23 (3H, m). |
| 258 | Rex503 | $^1$H-NMR (CDCl3): 1.47 (9H, s), 1.69-1.90 (6H, m), 2.35 (3H, s), 2.61-2.80 (7H, m), 3.30-3.33 (2H, m), 3.42-3.50 (4H, m), 6.96 (1H, d, J = 8.3 Hz), 8.00-8.03 (2H, m). |
| 259 | Rex516 | ESI+: 235 |
| 260 | Rex292 | $^1$H-NMR (CDCl3): 1.63 (2H, m), 2.03-2.94 (21H, m), 3.63 (2H, br-s), 6.34 (1H, d, J = 8.4 Hz), 6.93 (1H, d, J = 8.4 Hz), 7.81 (1H, s), 8.61 (1H, br-s). |
| 261 | Rex503 | $^1$H-NMR (CDCl3): 1.64-1.73 (2H, m), 2.12 (2H, d, J = 12.8 Hz), 2.24 (3H, s), 2.29-2.38 (1H, m), 2.31 (3H, s), 2.50 (4H, br-s), 2.66 (4H, br-s), 2.75 (2H, t, J = 12.4 Hz), 3.15 (2H, d, J = 12.0 Hz), 7.16 (1H, d, J = 8.8 Hz), 7.92 (1H, dd, J = 2.8 Hz, 8.8 Hz), 8.07 (1H, br-s), 9.16 (1H, d, J = 2.4 Hz). |
| 262 | Rex516 | $^1$H-NMR (CDCl3): 2.29 (3H, s), 2.68 (4H, t, J = 6.0 Hz), 3.27 (4H, t, J = 6.0 Hz), 7.23 (1H, d, J = 8.8 Hz), 7.97 (1H, dd, J = 2.4 Hz, 8.8 Hz), 8.16 (1H, br-s), 9.22 (1H, br-s). |

TABLE 73

| Rex | Syn | Data |
|---|---|---|
| 263 | Rex353 | ESI+: 515 |
| 264 | Rex292 | $^1$H-NMR (CDCl3): 1.63 (2H, m), 1.89 (3H, s), 1.97 (2H, m), 2.56-3.21 (19H, m), 3.61 (2H, br-s), 6.47 (1H, d, J = 2.8 Hz), 6.61 (1H, dd, J = 2.8 Hz, 8.4 Hz), 6.91 (1H, d, J = 8.8 Hz). |

TABLE 73-continued

| Rex | Syn | Data |
|---|---|---|
| 265 | Rex244 | ¹H-NMR (CDCl3): 1.62 (2H, m), 1.96 (3H, s), 2.00 (2H, m), 2.29 (3H, s), 2.36 (1H, m), 2.48 (4H, br-s), 2.48 (4H, br-s), 2.61 (4H, br-s), 2.86 (4H, m), 3.48 (3H, s), 3.51 (2H, t, J = 10.8 Hz), 7.03 (1H, d, J = 9.2 Hz), 7.96 (1H, d, J = 2.8 Hz), 8.11 (1H, dd, J = 2.8 Hz, 9.2 Hz). |
| 266 | Rex353 | ESI+: 529 |
| 267 | Rex292 | ¹H-NMR (CDCl3): 0.62-0.66 (2H, m), 0.91-0.96 (2H, m), 2.35 (1H, m), 2.35 (3H, s), 2.57 (4H, br-s), 2.96 (4H, s), 3.42 (2H, br-s), 6.08 (1H, d, J = 2.4 Hz), 6.46 (1H, dd, J = 2.4 Hz, 8.4 Hz), 6.88 (1H, d, J = 8.4 Hz). |
| 268 | Rex240 | ¹H-NMR (CDCl3): 0.83 (2H, m), 1.09 (2H, m), 2.15 (1H, m), 2.38 (3H, s), 2.62 (4H, br-s), 3.21 (4H, br-s), 6.99 (1H, d, J = 8.4 Hz), 7.68 (1H, d, J = 2.8 Hz), 7.99 (1H, dd, J = 2.4 Hz, 8.8 Hz). |
| 269 | Rex353 | ESI+: 415 |
| 270 | Rex292 | EI: 251 |
| 271 | Rex516 | EI: 281 |
| 272 | Rex353 | ESI−: 433 |
| 273 | Rex353 | ESI+: 482 |
| 274 | Rex292 | ¹H-NMR (CD3OD): 2.54 (3H, s), 2.57 (3H, s), 2.90-2.94 (4H, m), 2.99-3.02 (4H, m), 6.80 (1H, dd, J = 2.4 Hz, 8.8 Hz), 7.09 (1H, d, J = 8.8 Hz), 7.22 (1H, d, J = 2.4 Hz). |

TABLE 74

| Rex | Syn | Data |
|---|---|---|
| 275 | Rex516 | ¹H-NMR (CDCl3): 2.39 (3H, s), 2.60 (4H, m), 3.04 (3H, d, J = 4.8 Hz), 3.12-3.15 (4H, m), 7.17 (1H, d, J = 8.8 Hz), 8.23 (1H, dd, J = 2.4 Hz, 8.8 Hz), 8.80 (1H, d, J = 2.4 Hz). |
| 276 | Rex353 | ESI+: 432 |
| 277 | Rex292 | ¹H-NMR (CD3OD): 1.69-1.71 (2H, m), 1.92-1.95 (2H, m), 2.35 (3H, s), 2.55 (3H, s), 2.57-2.82 (9H, m), 3.14 (2H, m), 3.31 (2H, m), 3.34 (6H, s), 6.86-6.88 (1H, m), 7.20-7.22 (2H, m). |
| 278 | Rex503 | ¹H-NMR (CDCl3): 1.71-1.80 (2H, m), 1.96-1.99 (2H, m), 2.30 (3H, m), 2.49-2.64 (9H, m), 2.80 (6H, s), 2.84 (2H, m), 3.57-3.60 (2H, m), 7.31 (1H, d, J = 9.2 Hz), 8.30 (1H, dd, J = 2.8 Hz, 9.2 Hz), 8.71 (1H, d, J = 2.8 Hz). |
| 279 | Rex516 | ¹H-NMR (CDCl3): 2.69-2.72 (4H, m), 2.86 (6H, s), 3.47-3.50 (4H, m), 7.39 (1H, d, J = 8.8 Hz), 8.36 (1H, dd, J = 2.4 Hz, 8.8 Hz), 8.71 (1H, d, J = 2.4 Hz). |
| 280 | Rex353 | ESI+: 565 |
| 281 | Rex292 | ¹H-NMR (CDCl3): 2.48 (3H, s), 2.98 (4H, m), 3.31 (7H, m), 6.90 (1H, dd, J = 2.8 Hz, 8.4 Hz), 7.21 (1H, d, J = 2.8 Hz), 7.27 (1H, d, J = 8.4 Hz). |
| 282 | Rex516 | EI: 328 |
| 283 | Rex353 | ESI+: 468 |
| 284 | Rex292 | ¹H-NMR (CDCl3): 2.88 (3H, s), 2.96 (3H, s), 3.14 (3H, s), 3.19-3.56 (8H, m), 7.09 (1H, s), 7.29 (2H, m). |
| 285 | Rex516 | ¹H-NMR (CDCl3): 2.34 (3H, s), 2.49-2.51 (4H, m), 2.88 (3H, s), 3.13-3.16 (2H, m), 3.15 (3H, s), 3.38 (2H, m), 6.64 (1H, d, J = 8.8 Hz), 8.14-8.18 (2H, m). |

TABLE 75

| Rex | Syn | Data |
|---|---|---|
| 286 | Rex353 | ESI+: 446 |
| 287 | Rex287 | EI: 211 |
| 288 | Rex291 | ESI+: 244 |
| 289 | Rex292 | FAB+: 214 |
| 290 | Rex287 | EI: 211 |
| 291 | Rex291 | FAB+: 244 |
| 292 | Rex292 | FAB+: 214 |

TABLE 75-continued

| Rex | Syn | Data |
|---|---|---|
| 293 | Rex298 | ESI+: 401 |
| 294 | Rex299 | ESI+: 383 |
| 295 | Rex298 | ESI+: 415 |
| 296 | Rex298 | ESI+: 415 |
| 297 | Rex299 | ESI+: 397 |
| 298 | Rex298 | ESI−: 371 |
| 299 | Rex299 | ESI−: 353 |
| 300 | Rex298 | ESI−: 371 |
| 301 | Rex299 | ESI−: 354 |
| 302 | Rex299 | ESI+: 397 |
| 303 | Rex298 | ESI+: 310 |
| 304 | Rex304 | ESI+: 306 |
| 305 | Rex298 | ESI+: 352 |
| 306 | Rex299 | FAB+: 334 |
| 307 | Rex298 | ESI+: 338 |
| 308 | Rex298 | ESI+: 330, 332 |
| 309 | Rex298 | ESI+: 366 |
| 310 | Rex299 | ESI+: 348 |
| 311 | Rex311 | FAB+: 350 |
| 312 | Rex299 | ESI−: 318 |
| 313 | Rex298 | ESI+: 374 |
| 314 | Rex299 | ESI+: 356 |
| 315 | Rex298 | ESI+: 387 |
| 316 | Rex298 | ESI+: 401 |

TABLE 76

| Rex | Syn | Data |
|---|---|---|
| 317 | Rex339 | ESI+: 292 |
| 318 | Rex304 | ESI+: 326, 328 |
| 319 | Rex339 | ESI+: 310 |
| 320 | Rex299 | APCI−: 367 |
| 321 | Rex299 | ESI−: 381 |
| 322 | Rex298 | APCI−: 400 |
| 323 | Rex298 | ESI−: 336 |
| 324 | Rex298 | ESI+: 364 |
| 325 | Rex299 | ESI+: 384 |
| 326 | Rex298 | ESI+: 388 |
| 327 | Rex299 | APCI−: 368 |
| 328 | Rex298 | ESI+: 392 |
| 329 | Rex298 | ESI+: 404 |
| 330 | Rex298 | ESI+: 326 |
| 331 | Rex299 | ESI−: 318 |
| 332 | Rex298 | ESI+: 388 |
| 333 | Rex298 | ESI+: 427 |
| 334 | Rex299 | ESI−: 344 |
| 335 | Rex299 | ESI−: 386 |
| 336 | Rex299 | ESI−: 373 |
| 337 | Rex304 | ESI+: 322 |
| 338 | Rex299 | ESI−: 407 |
| 339 | Rex339 | ESI+: 308 |
| 340 | Rex346 | ESI+: 412 |
| 341 | Rex349 | ESI+: 370 |
| 342 | Rex342 | ESI+: 387, 389 |
| 343 | Rex342 | FAB+: 369 |
| 344 | Rex298 | ESI+: 346 |
| 345 | Rex298 | ESI+: 372 |
| 346 | Rex346 | ESI+: 370 |
| 347 | Rex346 | ESI+: 396 |

TABLE 77

| Rex | Syn | Data |
|---|---|---|
| 348 | Rex349 | ESI+: 354 |
| 349 | Rex349 | ESI+: 328 |
| 350 | Rex298 | ESI+: 372 |
| 351 | Rex298 | ESI+: 407, 409 |
| 352 | Rex298 | ESI+: 330 |
| 353 | Rex353 | ESI+: 355 |
| 354 | Rex299 | ESI+: 389, 391 |
| 355 | Rex346 | ESI+: 396 |

TABLE 77-continued

| Rex | Syn | Data |
| --- | --- | --- |
| 356 | Rex298 | ESI+: 330 |
| 357 | Rex346 | ESI+: 354 |
| 358 | Rex349 | ESI+: 354 |
| 359 | Rex298 | ESI+: 310, 312 |
| 360 | Rex353 | ESI+: 308, 310 |
| 361 | Rex346 | ESI+: 354 |
| 362 | Rex349 | ESI+: 312 |
| 363 | Rex349 | ESI+: 312 |
| 364 | Rex364 | ESI+: 292 |
| 365 | Rex298 | ESI+: 364 |
| 366 | Rex346 | ESI+: 388 |
| 367 | Rex298 | ESI+: 364 |
| 368 | Rex346 | ESI+: 388 |
| 369 | Rex349 | ESI+: 346 |
| 370 | Rex349 | ESI+: 346 |
| 371 | Rex298 | ESI+: 372 |
| 372 | Rex346 | ESI+: 396 |
| 373 | Rex349 | ESI+: 354 |
| 374 | Rex298 | ESI+: 296 |
| 375 | Rex298 | ESI+: 374 |
| 376 | Rex298 | ESI+: 330 |
| 377 | Rex298 | ESI+: 330 |
| 378 | Rex298 | ESI+: 398 |

TABLE 78

| Rex | Syn | Data |
| --- | --- | --- |
| 379 | Rex353 | FAB+: 327 |
| 380 | Rex346 | ESI+: 422 |
| 381 | Rex346 | ESI−: 396 |
| 382 | Rex346 | ESI+: 320 |
| 383 | Rex346 | ESI+: 354 |
| 384 | Rex346 | ESI+: 354 |
| 385 | Rex349 | ESI+: 380 |
| 386 | Rex349 | ESI+: 356 |
| 387 | Rex349 | ESI+: 278 |
| 388 | Rex349 | ESI+: 312 |
| 389 | Rex349 | ESI+: 312 |
| 390 | Rex353 | ESI+: 278 |
| 391 | Rex353 | ESI+: 369, 371 |
| 392 | Rex353 | ESI+: 361, 363 |
| 393 | Rex353 | ESI+: 323 |
| 394 | Rex353 | ESI+: 323 |
| 395 | Rex353 | ESI+: 292 |
| 396 | Rex397 | ESI+: 355 |
| 397 | Rex397 | ESI+: 355 |
| 398 | Rex398 | ESI+: 234, 236 |
| 399 | Rex399 | ESI+: 229 |
| 400 | Rex400 | ESI+: 129 |
| 401 | Rex353 | ESI+: 328 |
| 402 | Rex353 | ESI−: 343 |
| 403 | Rex353 | ESI+: 317 |
| 404 | Rex353 | ESI+: 333 |
| 405 | Rex353 | ESI+: 328 |
| 406 | Rex516 | ESI+: 335 |
| 407 | Rex292 | ESI+: 305 |
| 408 | Rex353 | ESI+: 322 |
| 409 | Rex353 | ESI+: 368 |

TABLE 79

| Rex | Syn | Data |
| --- | --- | --- |
| 410 | Rex353 | ESI+: 348 |
| 411 | Rex353 | ESI+: 361 |
| 412 | Rex412 | FAB+: 335 |
| 413 | Rex413 | ESI+: 306 |
| 414 | Rex353 | ESI+: 375 |
| 415 | Rex353 | ESI+: 405 |
| 416 | Rex353 | ESI+: 405 |
| 417 | Rex417 | ESI+: 387 |
| 418 | Rex353 | ESI+: 458 |

TABLE 79-continued

| Rex | Syn | Data |
| --- | --- | --- |
| 419 | Rex353 | ESI+: 433 |
| 420 | Rex353 | ESI+: 375 |
| 421 | Rex516 | ESI+: 349 |
| 422 | Rex292 | ESI+: 319 |
| 423 | Rex353 | ESI+: 488, 490 |
| 424 | Rex353 | ESI+: 443 |
| 425 | Rex353 | ESI+: 460 |
| 426 | Rex516 | ESI+: 373 |
| 427 | Rex353 | ESI+: 405 |
| 428 | Rex353 | ESI+: 362 |
| 429 | Rex353 | ESI+: 360 |
| 430 | Rex430 | EI: 256, 258 |
| 431 | Rex430 | EI: 270, 272 |
| 432 | Rex432 | ESI+: 321 |
| 433 | Rex432 | ESI+: 335 |
| 434 | Rex292 | ESI+: 291 |
| 435 | Rex292 | ESI+: 305 |
| 436 | Rex292 | ESI+: 343 |
| 437 | Rex353 | FAB+: 489 491 |
| 438 | Rex454 | ESI−: 409 |
| 439 | Rex353 | ESI+: 405 |
| 440 | Rex440 | ESI+: 538 |

TABLE 80

| Rex | Syn | Data |
| --- | --- | --- |
| 441 | Rex455 | ESI+: 311 |
| 442 | Rex353 | ESI+: 443 |
| 443 | Rex353 | ESI+: 374 |
| 444 | Rex444 | ESI+: 252 |
| 445 | Rex292 | ESI+: 222 |
| 446 | Rex353 | ESI+: 355, 357 |
| 447 | Rex353 | ESI+: 405 |
| 448 | Rex464 | ESI+: 408 |
| 449 | Rex468 | ESI+: 274 |
| 450 | Rex353 | ESI+: 457 |
| 451 | Rex516 | ESI+: 305 |
| 452 | Rex292 | ESI+: 275 |
| 453 | Rex353 | ESI+: 458 |
| 454 | Rex454 | ESI+: 441 |
| 455 | Rex455 | ESI+: 341 |
| 456 | Rex516 | ESI+: 290 |
| 457 | Rex292 | ESI+: 260 |
| 458 | Rex353 | ESI+: 443 |
| 459 | Rex516 | ESI+: 379 |
| 460 | Rex292 | ESI+: 349 |
| 461 | Rex353 | ESI+: 405 |
| 462 | Rex454 | ESI+: 441 |
| 463 | Rex455 | APCI/ESI+: 341 |
| 464 | Rex464 | ESI+: 355 |
| 465 | Rex464 | ESI+: 438 |
| 466 | Rex467 | ESI+: 277 |
| 467 | Rex467 | ESI+: 291 |
| 468 | Rex468 | ESI+: 221 |
| 469 | Rex468 | ESI+: 304 |
| 470 | Rex353 | ESI+: 404, 406 |
| 471 | Rex353 | ESI+: 487, 489 |

TABLE 81

| Rex | Syn | Data |
| --- | --- | --- |
| 472 | Rex472 | ESI+: 275 |
| 473 | Rex473 | APCI/ESI+: 279 |
| 474 | Rex292 | APCI/ESI+: 249 |
| 475 | Rex516 | APCI/ESI+: 237 |
| 476 | Rex353 | APCI/ESI+: 432, 434 |
| 477 | Rex292 | APCI/ESI+: 207 |
| 478 | Rex454 | FAB+: 411 |
| 479 | Rex455 | ESI+: 311 |
| 480 | Rex464 | ESI+: 325 |
| 481 | Rex468 | ESI+: 191 |

TABLE 81-continued

| Rex | Syn | Data |
|---|---|---|
| 482 | Rex464 | ESI+: 408 |
| 483 | Rex464 | ESI+: 438 |
| 484 | Rex468 | ESI+: 274 |
| 485 | Rex353 | ESI+: 409 |
| 486 | Rex468 | ESI+: 304 |
| 487 | Rex353 | ESI+: 404 |
| 488 | Rex353 | ESI+: 374 |
| 489 | Rex353 | ESI+: 487 |
| 490 | Rex353 | ESI+: 457 |
| 491 | Rex353 | APCI/ESI+: 390, 392 |
| 492 | Rex502 | EI: 220 |
| 493 | Rex503 | ESI+: 419 |
| 494 | Rex455 | ESI+: 319 |
| 495 | Rex444 | ESI+: 295 |
| 496 | Rex464 | ESI+: 333 |
| 497 | Rex292 | ESI+: 265 |
| 498 | Rex292 | ESI+: 303 |
| 499 | Rex444 | ESI+: 279 |
| 500 | Rex353 | APCI/ESI+: 486, 488 |
| 501 | Rex353 | ESI+: 420 |
| 502 | Rex502 | APCI/ESI+: 251 |

TABLE 82

| Rex | Syn | Data |
|---|---|---|
| 503 | Rex503 | APCI/ESI+: 335 |
| 504 | Rex292 | APCI/ESI+: 305 |
| 505 | Rex353 | APCI/ESI+: 406 |
| 506 | Rex353 | APCI/ESI+: 433 |
| 507 | Rex353 | APCI/ESI+: 420 |
| 508 | Rex353 | APCI/ESI+: 419 |
| 509 | Rex353 | APCI/ESI+: 488 |
| 510 | Rex502 | APCI/ESI+: 235 |
| 511 | Rex503 | APCI/ESI+: 319 |
| 512 | Rex292 | APCI/ESI+: 239 |
| 513 | Rex353 | ESI+: 472 |
| 514 | Rex432 | ESI+: 308 |
| 515 | Rex432 | ESI+: 322 |
| 516 | Rex516 | ESI+: 279 |
| 517 | Rex292 | ESI+: 249 |
| 518 | Rex516 | ESI+: 295 |
| 519 | Rex292 | APCI/ESI+: 265 |
| 520 | Rex353 | ESI+: 404 |
| 521 | Rex353 | ESI+: 420 |
| 522 | Rex292 | ESI+: 292 |
| 523 | Rex292 | ESI+: 278 |
| 524 | Rex353 | ESI+: 475, 477 |
| 525 | Rex353 | ESI+: 488, 490 |
| 526 | Rex353 | ESI+: 502, 504 |
| 527 | Rex353 | ESI+: 474, 476 |
| 528 | Rex353 | ESI+: 474 |
| 529 | Rex353 | ESI+: 461 |
| 530 | Rex467 | ESI+: 278 |
| 531 | Rex353 | ESI+: 461, 463 |
| 532 | Rex353 | ESI+: 460, 462 |
| 533 | Rex430 | EI: 270, 272 |

TABLE 83

| Rex | Syn | Data |
|---|---|---|
| 534 | Rex432 | ESI+: 335 |
| 535 | Rex292 | ESI+: 305 |
| 536 | Rex353 | ESI+: 488, 490 |
| 537 | Rex432 | ESI+: 322 |
| 538 | Rex292 | ESI+: 292 |
| 539 | Rex353 | ESI+: 475, 477 |
| 540 | Rex353 | ESI+: 532, 534 |
| 541 | Rex516 | ESI+: 319 |
| 542 | Rex292 | ESI+: 289 |
| 543 | Rex545 | ESI+: 389 |
| 544 | Rex353 | ESI+: 435 |

TABLE 83-continued

| Rex | Syn | Data |
|---|---|---|
| 545 | Rex545 | APCI/ESI+: 419 |
| 546 | Rex417 | ESI+: 470 |
| 547 | Rex353 | APCI/ESI+: 488 |
| 548 | Rex353 | 1H-NMR (CDCl3): 1.28 (3H, t, J = 7.3 Hz), 2.36 (3H, S), 2.62 (4H, br-s), 2.85 (2H, q, J = 7.6 Hz), 3.10 (4H, br-s), 5.50 (1H, br-s), 6.91-6.99 (1H, m), 7.25 (1H, br-s), 7.53 (1H, d, J = 14.4 Hz), 7.71 (1H, br-s), 10.71 (1H, br-s) |
| 549 | Rex353 | ESI+: 506 |
| 550 | Rex545 | ESI+: 490 |
| 551 | Rex516 | ESI+: 319 |
| 552 | Rex292 | ESI+: 289 |
| 553 | Rex353 | ESI+: 472 |
| 554 | Rex516 | 1H-NMR (CDCl3): 1.71-2.17 (6H, m), 2.35 (4H, m), 2.72-2.75 (4H, m), 2.99-3.02 (2H, m), 3.30-3.32 (4H, m), 6.87-6.92 (1H, m), 7.87-7.99 (2H, m) |
| 555 | Rex292 | ESI+: 293 |

TABLE 84

| Rex | Syn | Data |
|---|---|---|
| 556 | Rex353 | 1H-NMR (CDCl3): 1.26-1.32 (3H, m), 1.56-1.65 (2H, m), 1.84-1.97 (4H, m), 2.30 (4H, m), 2.72-3.09 (12H, m), 5.49 (1H, br-s), 6.90-6.95 (1H, m), 7.17-7.29 (1H, m), 7.52-7.56 (1H, m), 7.71 (1H, br-s), 10.71 (1H, br-s) |
| 557 | Rex516 | 1H-NMR (CDCl3): 1.59 (2H, m), 1.82-1.85 (2H, m), 1.93-1.98 (2H, m), 2.27 (4H, br-s), 2.75 (4H, t, J = 4.6 Hz), 2.91-2.94 (2H, m), 3.24-3.26 (4H, m), 3.95 (3H, s), 6.87 (1H, d, J = 9.0 Hz), 7.70 (1H, d, J = 2.4 Hz), 7.85 (1H, dd, J = 2.7, 9.0 Hz) |
| 558 | Rex292 | 1H-NMR (CDCl3): 1.65-2.00 (8H, m), 2.29 (4H, br-s), 2.75-2.76 (4H, m), 2.93-3.03 (6H, m), 3.83 (3H, s), 6.23-6.26 (2H, m), 6.76 (1H, d, J = 8.1 Hz) |
| 559 | Rex353 | 1H-NMR (CDCl3): 1.57-1.98 (11H, m), 2.29 (5H, m), 2.78 (4H, br-s), 2.94-2.96 (2H, m), 3.09 (4H, br-s), 3.71 (1H, br-s), 3.90 (3H, s), 5.56 (1H, br-s), 6.91 (1H, d, J = 8.5 Hz), 7.13 (1H, dd, J = 2.4, 8.5 Hz), 7.36 (1H, d, J = 2.4 Hz), 7.41 (1H, br-s), 10.76 (1H, br-s) |
| 560 | Rex545 | ESI+: 502 |
| 561 | Rex353 | ESI+: 423 |
| 562 | Rex545 | 1H-NMR (CDCl3): 1.26 (6H, d, J = 6.8 Hz), 2.37 (3H, S), 2.62 (4H, br-s), 3.10 (4H, br-s), 3.40-3.47 (1H, m), 5.52 (1H, br-s), 6.91-6.96 (1H, m), 7.24-7.26 (1H, m), 7.53 (1H, dd, J = 2.7, 14.6 Hz), 7.69 (1H, br-s), 10.70 (1H, br-s) |

TABLE 85

| Ex | Structure |
|---|---|
| 1 | 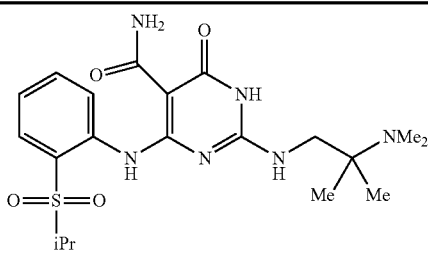 |

TABLE 85-continued

| Ex | Structure |
|---|---|
| 2 | (chemical structure) |
| 3 | (chemical structure) |
| 4 | (chemical structure) |
| 5 | (chemical structure) |
| 6 | (chemical structure) |

TABLE 86

| Ex | Structure |
|---|---|
| 7 | (chemical structure) |
| 8 | (chemical structure) |
| 9 | (chemical structure) |
| 10 | (chemical structure) |
| 11 | (chemical structure) |

TABLE 86-continued

| Ex | Structure |
|---|---|
| 12 | (structure) |
| 13 | (structure) |

TABLE 87

| Ex | Structure |
|---|---|
| 14 | (structure) |
| 15 | (structure) |
| 16 | (structure) |
| 17 | (structure) |
| 18 | (structure) |
| 19 | (structure) |

TABLE 88

| Ex | Structure |
|---|---|
| 20 | (structure) |

TABLE 88-continued

| Ex | Structure |
|---|---|
| 21 | (structure) |
| 22 | (structure) |
| 23 | (structure) |
| 24 | (structure) |
| 25 | (structure) |
| 26 | (structure) |

TABLE 89

| Ex | Structure |
|---|---|
| 27 | (structure) |
| 28 | (structure) |
| 29 | (structure) 2HCl |
| 30 | (structure) |
| 31 | (structure) |
| 32 | (structure) |

TABLE 89-continued

| Ex | Structure |
|---|---|
| 33 | (structure) |

TABLE 90

| Ex | Structure |
|---|---|
| 34 | (structure) |
| 35 | (structure) |
| 36 | (structure) |
| 37 | (structure) |

TABLE 90-continued

| Ex | Structure |
|---|---|
| 38 | (structure) |
| 39 | (structure) |
| 40 | (structure) |

TABLE 91

| Ex | Structure |
|---|---|
| 41 | (structure) |
| 42 | (structure) |
| 43 | (structure) |
| 44 | (structure) |
| 45 | (structure) |
| 46 | (structure) |
| 47 | (structure) |

TABLE 92

| Ex | Structure |
|---|---|
| 48 | (structure) |

TABLE 92-continued

| Ex | Structure |
|---|---|
| 49 | (structure) |
| 50 | (structure) |
| 51 | (structure) |
| 52 | (structure) |
| 53 | (structure) |
| 54 | (structure) |

TABLE 93

| Ex | Structure |
|---|---|
| 55 | (structure) |
| 56 | (structure) |
| 57 | (structure) |
| 58 | (structure) |
| 59 | (structure) |
| 60 | (structure) |

TABLE 93-continued
| Ex | Structure |
|---|---|
| 61 | 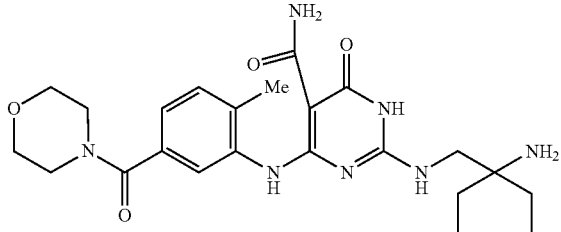 |
TABLE 94
| Ex | Structure |
|---|---|
| 62 | 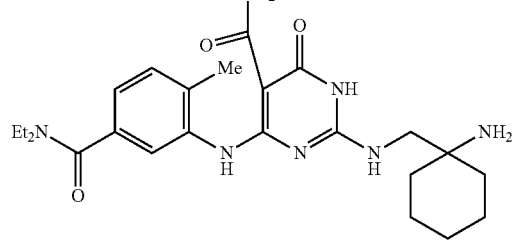 |
| 63 | 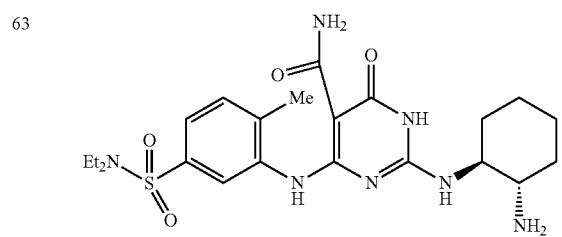 |
| 64 | 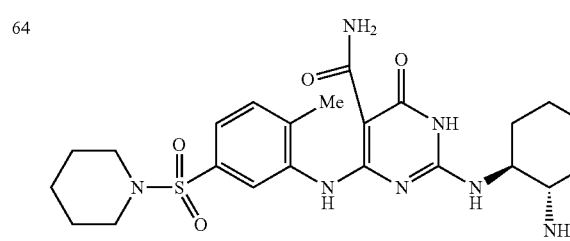 |
| 65 | 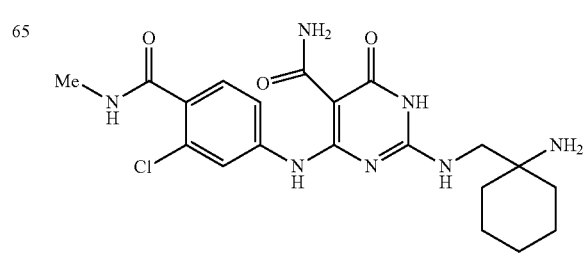 |
TABLE 94-continued
| Ex | Structure |
|---|---|
| 66 | 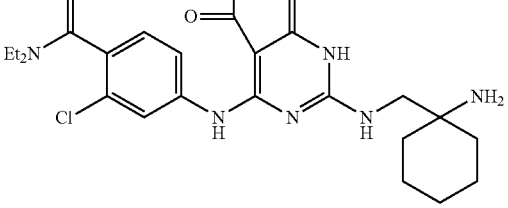 |
| 67 | 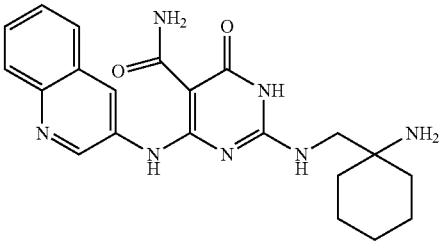 [SMILES: NC(=O)c1c(Nc2cnc3ccccc3c2)nc(NCC2(N)CCCCC2)[nH]c1=O] |
| 68 | 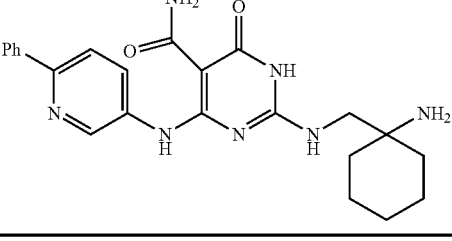 |
TABLE 95
| Ex | Structure |
|---|---|
| 69 | 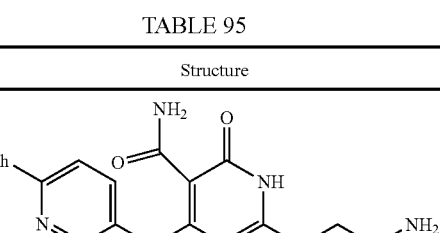 |
| 70 | 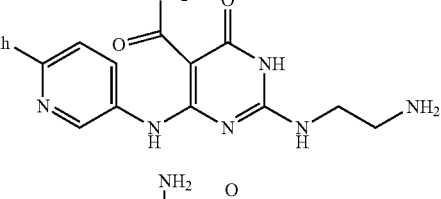 |
| 71 | 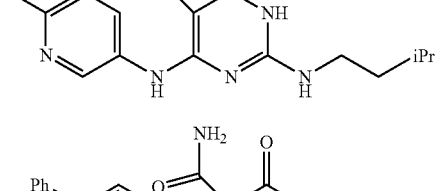 |
| 72 | 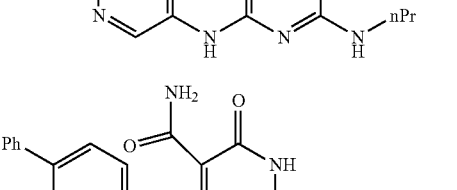 |

TABLE 95-continued

| Ex | Structure |
|---|---|
| 73 | 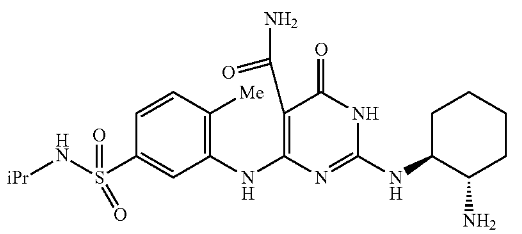 [SMILES: Cc1ccc(S(=O)(=O)NC(C)C)cc1Nc1nc(N[C@H]2CCCC[C@@H]2N)[nH]c(=O)c1C(N)=O] |
| 74 | 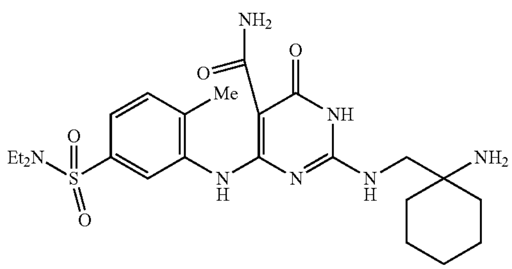 |
| 75 | 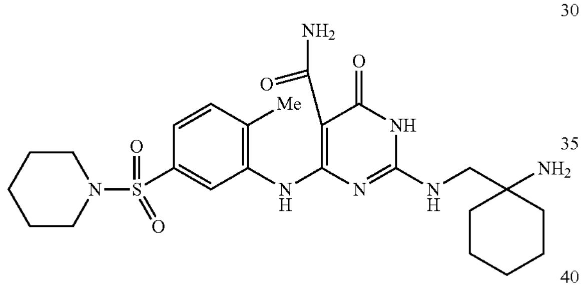 |

TABLE 96

| Ex | Structure |
|---|---|
| 76 | 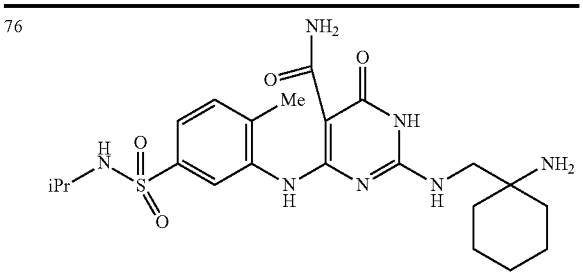 |
| 77 | 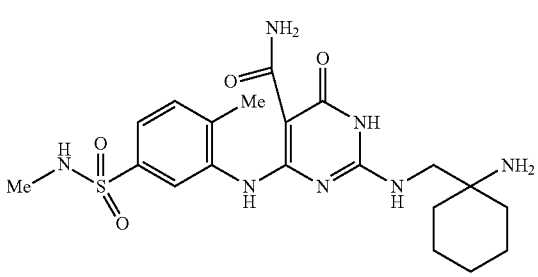 [SMILES: CNS(=O)(=O)c1ccc(C)c(Nc2nc(NCC3(N)CCCCC3)[nH]c(=O)c2C(N)=O)c1] |

TABLE 96-continued

| Ex | Structure |
|---|---|
| 78 | 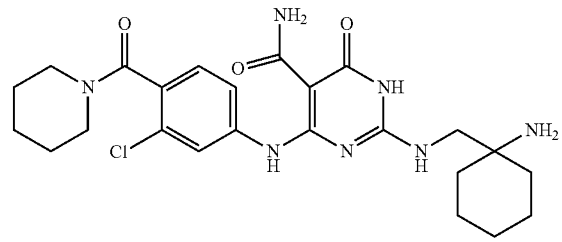 [SMILES: NC(=O)c1c(Nc2ccc(C(=O)N3CCCCC3)c(Cl)c2)nc(NCC2(N)CCCCC2)[nH]c1=O] |
| 79 | 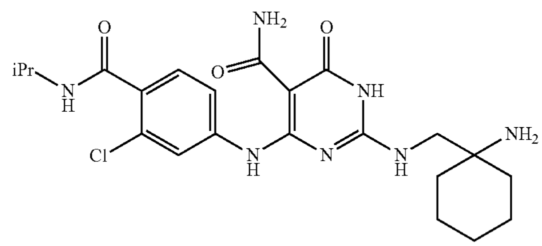 [SMILES: CC(C)NC(=O)c1ccc(Nc2nc(NCC3(N)CCCCC3)[nH]c(=O)c2C(N)=O)cc1Cl] |
| 80 | 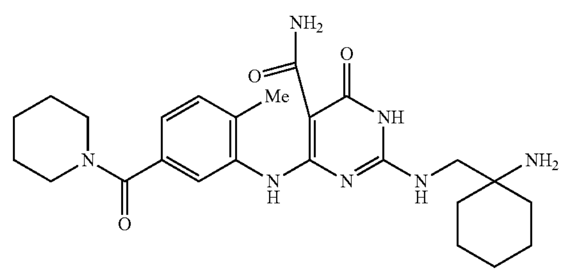 [SMILES: Cc1ccc(C(=O)N2CCCCC2)cc1Nc1nc(NCC2(N)CCCCC2)[nH]c(=O)c1C(N)=O] |
| 81 | 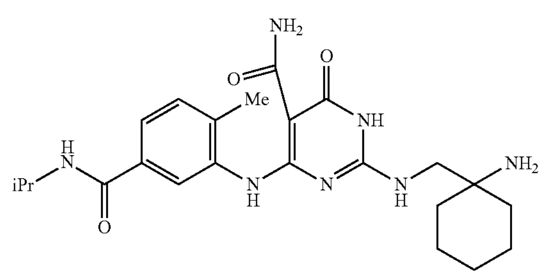 [SMILES: Cc1ccc(C(=O)NC(C)C)cc1Nc1nc(NCC2(N)CCCCC2)[nH]c(=O)c1C(N)=O] |
| 82 | 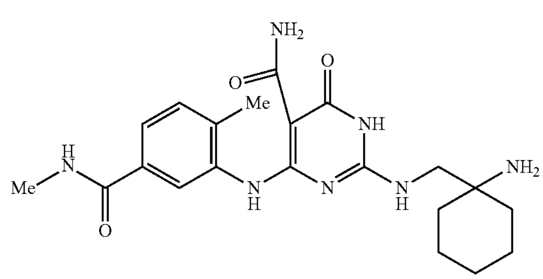 [SMILES: CNC(=O)c1ccc(C)c(Nc2nc(NCC3(N)CCCCC3)[nH]c(=O)c2C(N)=O)c1] |

TABLE 97

| Ex | Structure |
|---|---|
| 83 | (chemical structure) |
| 84 | (chemical structure) |
| 85 | (chemical structure) |
| 86 | (chemical structure) |
| 87 | (chemical structure) |
| 88 | (chemical structure) |

TABLE 97-continued

| Ex | Structure |
|---|---|
| 89 | (chemical structure) |

TABLE 98

| Ex | Structure |
|---|---|
| 90 | (chemical structure) |
| 91 | (chemical structure) |
| 92 | (chemical structure) |
| 93 | (chemical structure) |
| 94 | (chemical structure) |

TABLE 98-continued

| Ex | Structure |
|---|---|
| 95 | (structure) |
| 96 | (structure) |
| 97 | (structure) |

TABLE 99

| Ex | Structure |
|---|---|
| 98 | (structure) |
| 99 | (structure) |
| 100 | (structure) |

TABLE 99-continued

| Ex | Structure |
|---|---|
| 101 | (structure) |
| 102 | (structure) |
| 103 | (structure) |
| 104 | (structure) |

TABLE 100

| Ex | Structure |
|---|---|
| 105 | (structure) |
| 106 | (structure) |

TABLE 100-continued

| Ex | Structure |
|---|---|
| 107 | 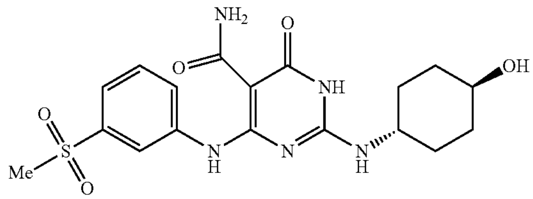 [SMILES: CS(=O)(=O)c1cccc(Nc2nc(N[C@H]3CC[C@H](O)CC3)[nH]c(=O)c2C(N)=O)c1] |
| 108 | 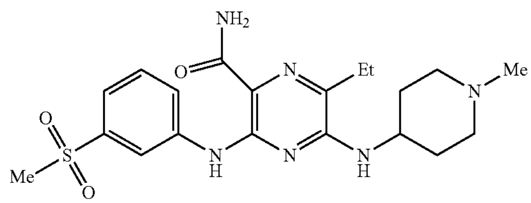 [SMILES: CCc1nc(C(N)=O)c(Nc2cccc(S(C)(=O)=O)c2)nc1NC1CCN(C)CC1] |
| 109 | 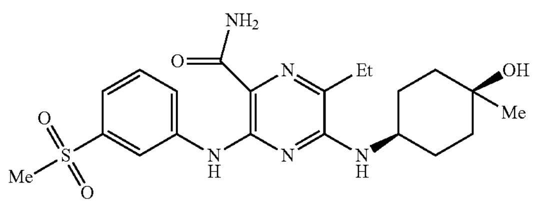 [SMILES: CCc1nc(C(N)=O)c(Nc2cccc(S(C)(=O)=O)c2)nc1N[C@H]1CC[C@@](C)(O)CC1] |
| 110 | 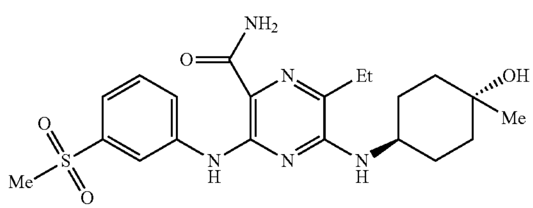 [SMILES: CCc1nc(C(N)=O)c(Nc2cccc(S(C)(=O)=O)c2)nc1N[C@H]1CC[C@](C)(O)CC1] |
| 111 | 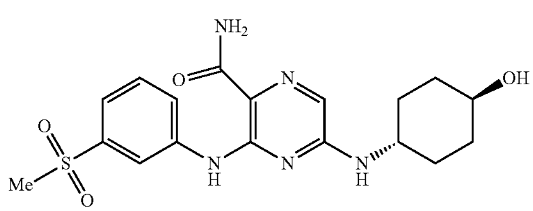 [SMILES: CS(=O)(=O)c1cccc(Nc2nc(N[C@H]3CC[C@H](O)CC3)cnc2C(N)=O)c1] |
| 112 | 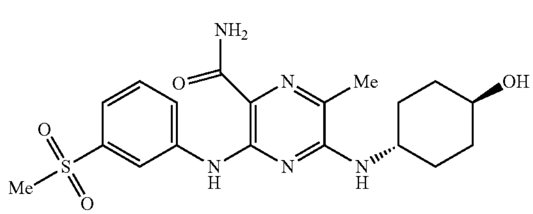 |

TABLE 101

| Ex | Structure |
|---|---|
| 113 | 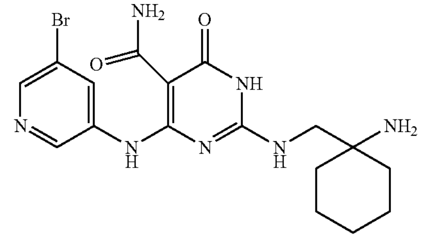 [SMILES: NC(=O)c1c(Nc2cncc(Br)c2)nc(NCC2(N)CCCCC2)[nH]c1=O] |
| 114 | 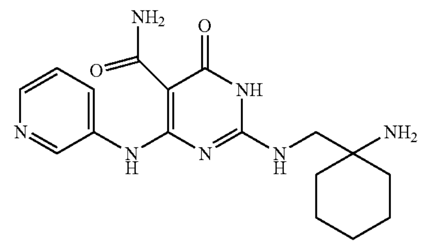 [SMILES: NC(=O)c1c(Nc2cccnc2)nc(NCC2(N)CCCCC2)[nH]c1=O] |
| 115 | 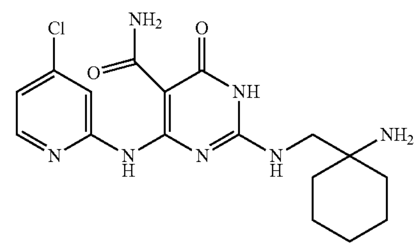 [SMILES: NC(=O)c1c(Nc2cc(Cl)ccn2)nc(NCC2(N)CCCCC2)[nH]c1=O] |
| 116 | 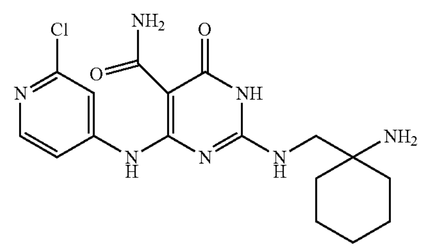 [SMILES: NC(=O)c1c(Nc2ccnc(Cl)c2)nc(NCC2(N)CCCCC2)[nH]c1=O] |
| 117 | 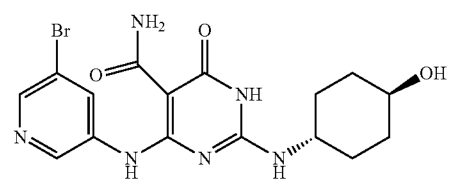 [SMILES: NC(=O)c1c(Nc2cncc(Br)c2)nc(N[C@H]2CC[C@H](O)CC2)[nH]c1=O] |
| 118 | 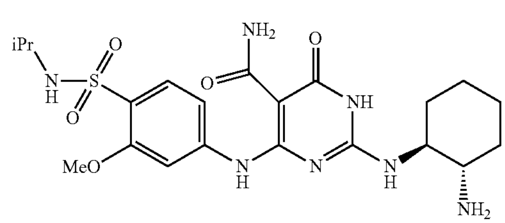 [SMILES: COc1cc(Nc2nc(N[C@H]3CCCC[C@@H]3N)[nH]c(=O)c2C(N)=O)ccc1S(=O)(=O)NC(C)C] |

TABLE 101-continued
| Ex | Structure |
|---|---|
| 119 | 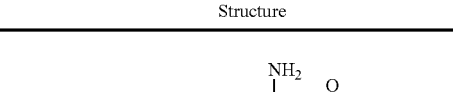 |
TABLE 102
| Ex | Structure |
|---|---|
| 120 | 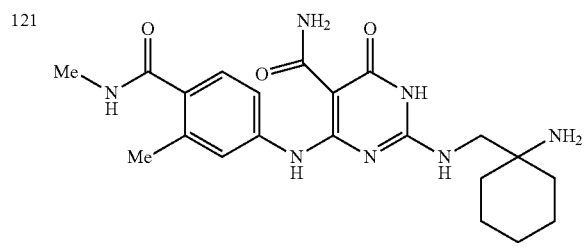 |
| 121 | 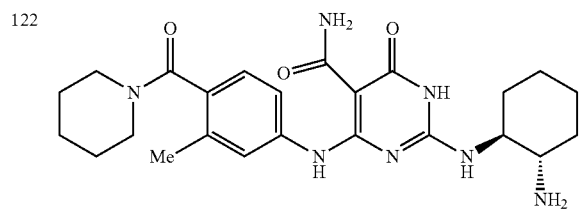 |
| 122 | 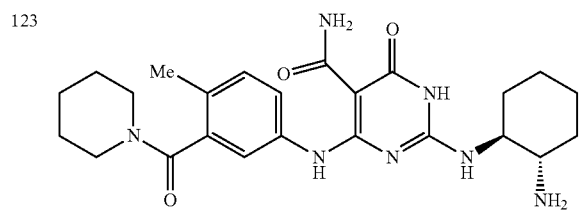 |
| 123 | 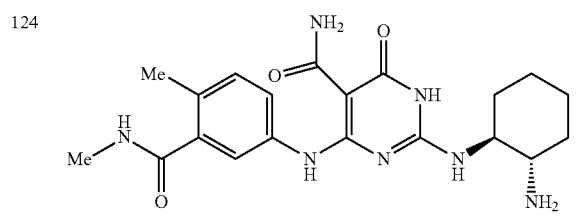 |
| 124 | 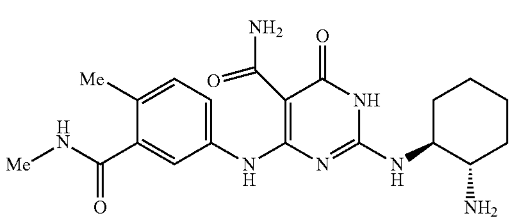 |
TABLE 102-continued
| Ex | Structure |
|---|---|
| 125 | 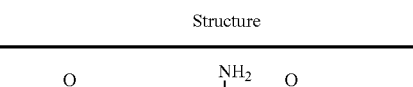 |
| 126 | 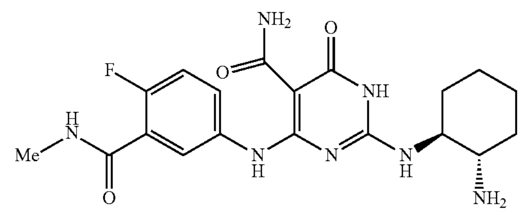 [SMILES: CNC(=O)c1cc(Nc2nc(N[C@H]3CCCC[C@@H]3N)[nH]c(=O)c2C(N)=O)ccc1F] |
TABLE 103
| Ex | Structure |
|---|---|
| 127 | 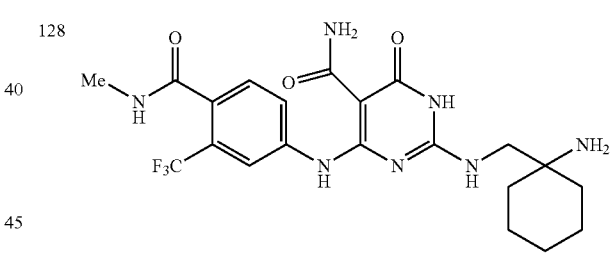 |
| 128 | 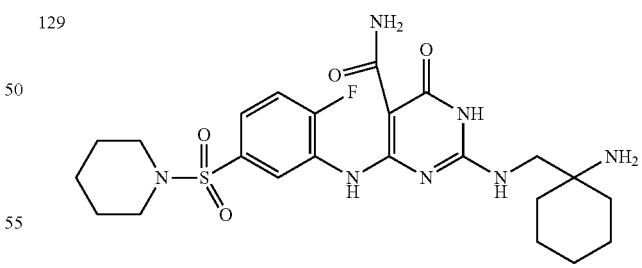 |
| 129 | 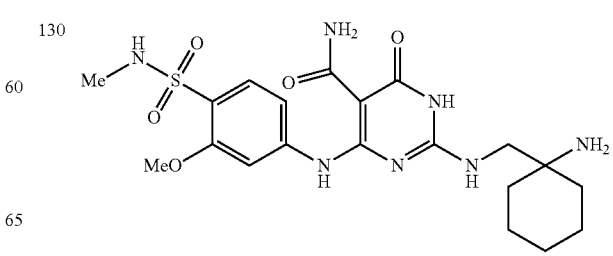 |
| 130 | 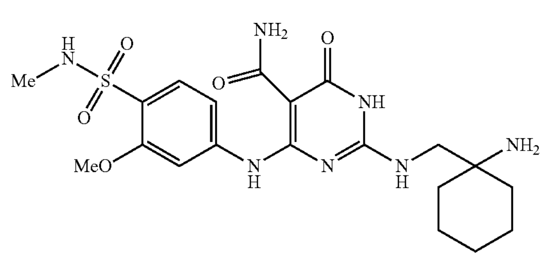 [SMILES: CNS(=O)(=O)c1ccc(Nc2nc(NCC3(N)CCCCC3)[nH]c(=O)c2C(N)=O)cc1OC] |

TABLE 103-continued

| Ex | Structure |
|---|---|
| 131 | (structure) |
| 132 | (structure) |
| 133 | (structure) |

TABLE 104

| Ex | Structure |
|---|---|
| 134 | (structure) |
| 135 | (structure) |
| 136 | (structure) |
| 137 | (structure) |
| 138 | (structure) |
| 139 | (structure) |
| 140 | (structure) |

TABLE 105

| Ex | Structure |
|---|---|
| 141 | (structure) |
| 142 | (structure) |

TABLE 105-continued

татtable of chemical structures (Ex 143–148)

TABLE 106 table of chemical structures (Ex 149–156)

TABLE 107

| Ex | Structure |
|---|---|
| 157 | (structure) |
| 158 | (structure) |
| 159 | (structure) |
| 160 | (structure) |
| 161 | (structure) |
| 162 | (structure) |
| 163 | (structure) |

TABLE 107-continued

| Ex | Structure |
|---|---|
| 164 | (structure) |
| 165 | (structure) |

TABLE 108

| Ex | Structure |
|---|---|
| 166 | (structure) |
| 167 | (structure) |
| 168 | (structure) |
| 169 | (structure) |
| 170 | (structure) |

TABLE 108-continued

| Ex | Structure |
|---|---|
| 171 | (structure) |
| 172 | (structure) |
| 173 | (structure) |

TABLE 109

| Ex | Structure |
|---|---|
| 174 | (structure) |
| 175 | (structure) |
| 176 | (structure) |
| 177 | (structure) |

TABLE 109-continued

| Ex | Structure |
|---|---|
| 178 | (structure) |
| 179 | (structure) |
| 180 | (structure) |
| 181 | (structure) |
| 182 | (structure) |

TABLE 110

| Ex | Structure |
|---|---|
| 183 | (structure) |
| 184*[5] | (structure) |
| 185*[5] | (structure) |

TABLE 110-continued

| Ex | Structure |
|---|---|
| 186 | 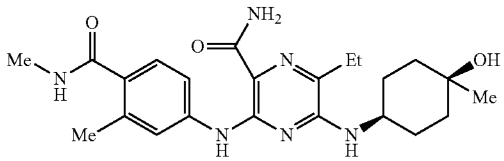 [SMILES: CCc1nc(C(N)=O)c(Nc2ccc(C(=O)NC)c(C)c2)nc1N[C@H]1CC[C@@](C)(O)CC1] |
| 187 | 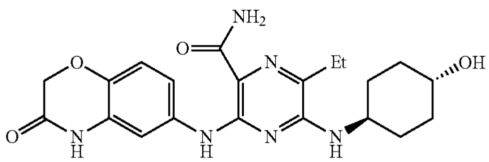 [SMILES: CCc1nc(C(N)=O)c(Nc2ccc3c(c2)NC(=O)CO3)nc1N[C@H]1CC[C@H](O)CC1] |
| 188 | 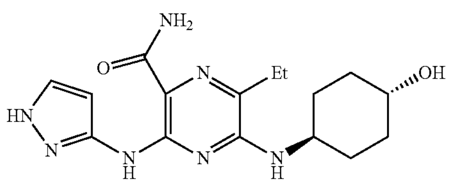 [SMILES: CCc1nc(C(N)=O)c(Nc2cc[nH]n2)nc1N[C@H]1CC[C@H](O)CC1] |
| 189 | 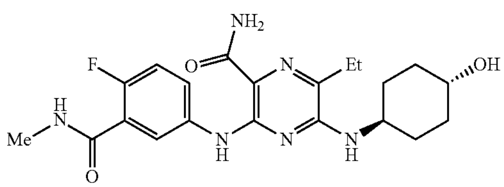 [SMILES: CCc1nc(C(N)=O)c(Nc2ccc(F)c(C(=O)NC)c2)nc1N[C@H]1CC[C@H](O)CC1] |
| 190 | 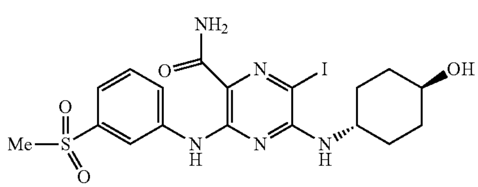 [SMILES: CS(=O)(=O)c1cccc(Nc2nc(N[C@H]3CC[C@H](O)CC3)c(I)nc2C(N)=O)c1] |
| 191 | 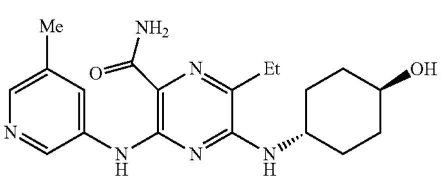 [SMILES: CCc1nc(C(N)=O)c(Nc2cncc(C)c2)nc1N[C@H]1CC[C@H](O)CC1] |

TABLE 111

| Ex | Structure |
|---|---|
| 192 | |
| 193 | 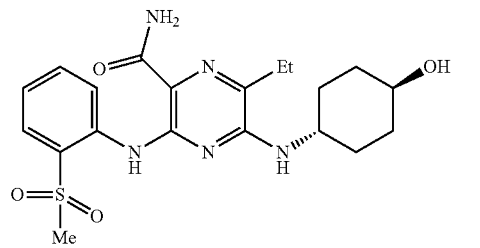 [SMILES: CCc1nc(C(N)=O)c(Nc2ccccc2S(C)(=O)=O)nc1N[C@H]1CC[C@H](O)CC1] |
| 194 | 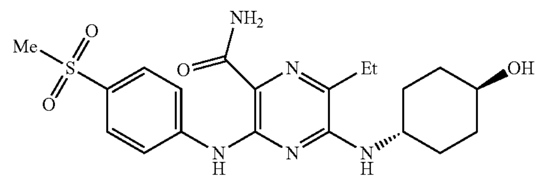 [SMILES: CCc1nc(C(N)=O)c(Nc2ccc(S(C)(=O)=O)cc2)nc1N[C@H]1CC[C@H](O)CC1] |
| 195 | 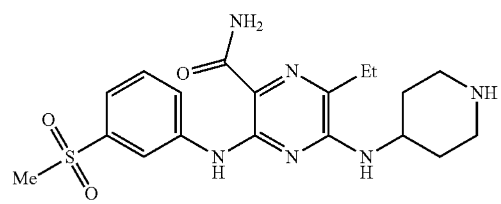 [SMILES: CCc1nc(C(N)=O)c(Nc2cccc(S(C)(=O)=O)c2)nc1NC1CCNCC1] |
| 196 | 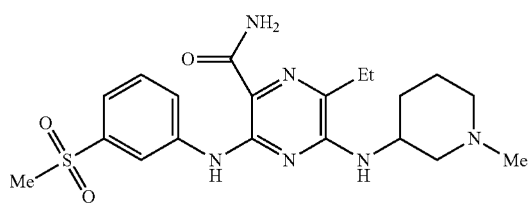 [SMILES: CCc1nc(C(N)=O)c(Nc2cccc(S(C)(=O)=O)c2)nc1NC1CCCN(C)C1] |
| 197 | 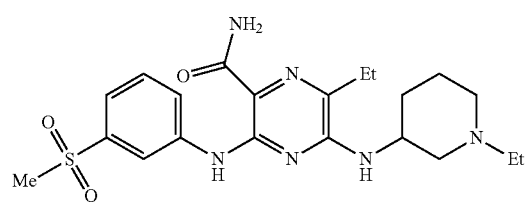 [SMILES: CCc1nc(C(N)=O)c(Nc2cccc(S(C)(=O)=O)c2)nc1NC1CCCN(CC)C1] |
| 198 | 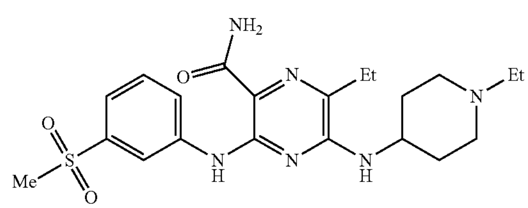 [SMILES: CCc1nc(C(N)=O)c(Nc2cccc(S(C)(=O)=O)c2)nc1NC1CCN(CC)CC1] |
| 199 | 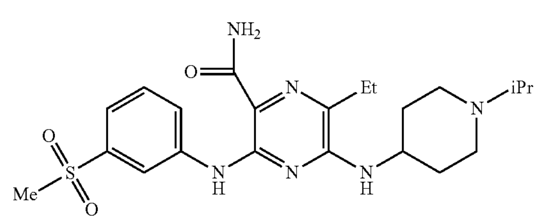 [SMILES: CCc1nc(C(N)=O)c(Nc2cccc(S(C)(=O)=O)c2)nc1NC1CCN(C(C)C)CC1] |

TABLE 112
| Ex | Structure |
|---|---|
| 200 | 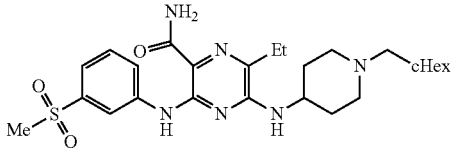 |
| 201 | 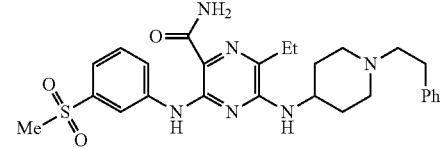 [SMILES: CCc1nc(C(N)=O)c(Nc2cccc(S(C)(=O)=O)c2)nc1NC1CCN(CCc2ccccc2)CC1] |
| 202 | 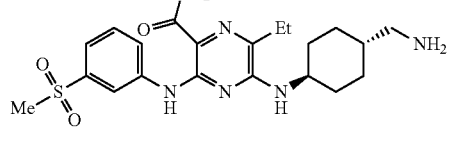 |
| 203 | 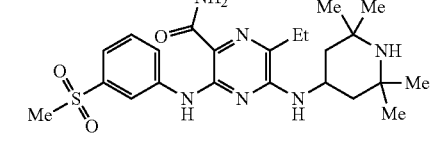 |
| 204 | 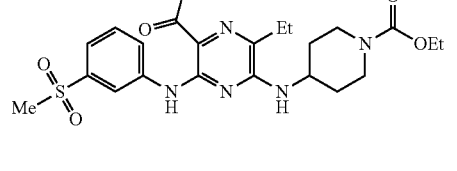 |
| 205 | 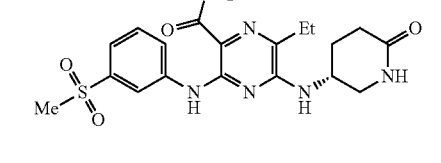 |
| 206 | 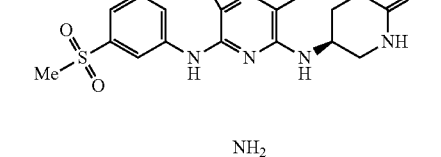 |
| 207 | 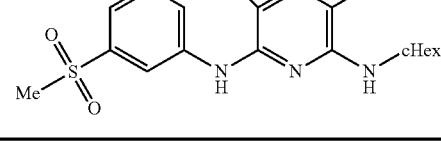 |
TABLE 113
| Ex | Structure |
|---|---|
| 208 | 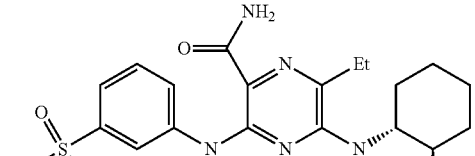 |
| 209 | 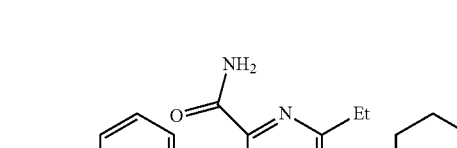 |
| 210 | 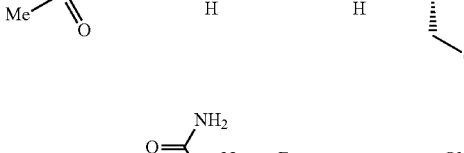 |
| 211 | 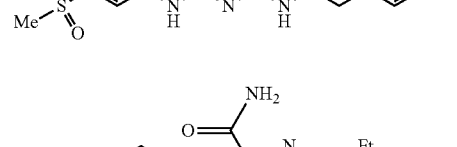 |
| 212 | 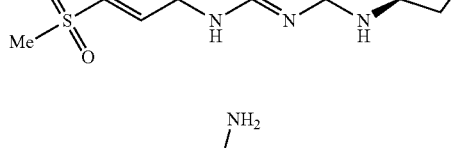 |
| 213 | 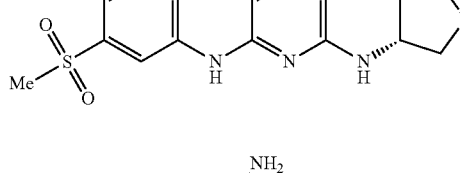 |
| 214 | 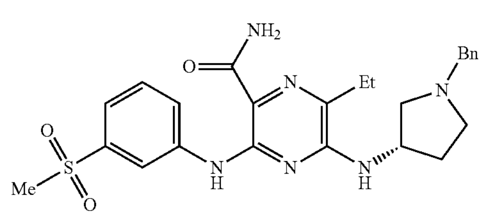 [SMILES: CCc1nc(C(N)=O)c(Nc2cccc(S(C)(=O)=O)c2)nc1NC1CCN(C)C1] |

TABLE 113-continued

| Ex | Structure |
|---|---|
| 215 | (pyrazine-2-carboxamide core with 3-(methylsulfonyl)phenylamino, Et, and (S)-1-benzylpyrrolidin-3-ylamino substituents) |

TABLE 114

| Ex | Structure |
|---|---|
| 216 | (pyrazine-2-carboxamide with 3-(methylsulfonyl)phenylamino, Et, and trans-2-aminocyclopentylamino substituents) |
| 217 | (pyrazine-2-carboxamide with 3-(methylsulfonyl)phenylamino, Et, and 2-carbamoylcyclopentylamino substituents) |
| 218 | (pyrazine-2-carboxamide with 3-(methylsulfonyl)phenylamino, Et, and 2-hydroxycyclopentylamino substituents) |
| 219 | (pyrazine-2-carboxamide with 3-(methylsulfonyl)phenylamino, Et, and 1-(hydroxymethyl)cyclopentylamino substituents) |
| 220 | (pyrazine-2-carboxamide with 3-(methylsulfonyl)phenylamino, Et, and 4-hydroxytetrahydrothiophen-3-ylamino substituents) |

TABLE 114-continued

| Ex | Structure |
|---|---|
| 221 | (pyrazine-2-carboxamide with 3-(methylsulfonyl)phenylamino, Et, and azetidin-3-ylamino substituents) |
| 222 | (pyrazine-2-carboxamide with 3-(methylsulfonyl)phenylamino, Et, and piperazin-1-yl substituents) |

TABLE 115

| Ex | Structure |
|---|---|
| 223 | (pyrazine-2-carboxamide with 3-(methylsulfonyl)phenylamino, Et, and 8-methyl-8-azabicyclo[3.2.1]octan-3-ylamino substituents) |
| 224 | (pyrazine-2-carboxamide with 3-(methylsulfonyl)phenylamino, Et, and (1-methylpiperidin-2-yl)methylamino substituents) |
| 225 | (pyrazine-2-carboxamide with 3-(methylsulfonyl)phenylamino, Et, and (1-methylpiperidin-4-yl)methylamino substituents) |
| 226 | (pyrazine-2-carboxamide with 3-(methylsulfonyl)phenylamino, Et, and (4-methylmorpholin-2-yl)methylamino substituents) |

TABLE 115-continued

| Ex | Structure |
|---|---|
| 227 | (structure) |
| 228 | (structure) |
| 229 | (structure) |

TABLE 116

| Ex | Structure |
|---|---|
| 230 | (structure) |
| 231 | (structure) |
| 232 | (structure) |
| 233 | (structure) |

TABLE 116-continued

| Ex | Structure |
|---|---|
| 234 | (structure) |
| 235 | (structure) |
| 236 | (structure) |
| 237 | (structure) |

TABLE 117

| Ex | Structure |
|---|---|
| 238 | (structure) |
| 239 | (structure) |

TABLE 117-continued

| Ex | Structure |
|---|---|
| 240 | (structure) |
| 241 | (structure) |
| 242 | (structure) |
| 243 | (structure) |
| 244 | (structure) |
| 245 | (structure) |

TABLE 118

| Ex | Structure |
|---|---|
| 246 | (structure) |
| 247 | (structure) |
| 248 | (structure) |
| 249 | (structure) |
| 250 | (structure) |
| 251 | (structure) |
| 252 | (structure) |
| 253 | (structure) |

TABLE 119

| Ex | Structure |
|---|---|
| 254 | pyrazine-2-carboxamide, 3-[(3-methylsulfonylphenyl)amino]-5-ethyl-6-[[2-(tetrahydrofuran-2-yl)ethyl]amino] |
| 255 | pyrazine-2-carboxamide, 3-[(3-methylsulfonylphenyl)amino]-5-ethyl-6-[(2-aminoethyl)amino] |
| 256 | pyrazine-2-carboxamide, 3-[(3-methylsulfonylphenyl)amino]-5-ethyl-6-[[2-(methylamino)ethyl]amino] |
| 257 | pyrazine-2-carboxamide, 3-[(3-methylsulfonylphenyl)amino]-5-ethyl-6-[[2-(dimethylamino)ethyl]amino] |
| 258 | pyrazine-2-carboxamide, 3-[(3-methylsulfonylphenyl)amino]-5-ethyl-6-[[3-(dimethylamino)propyl]amino] |
| 259 | pyrazine-2-carboxamide, 3-[(3-methylsulfonylphenyl)amino]-5-ethyl-6-[[1-methyl-2-(dimethylamino)ethyl]amino] |
| 260 | pyrazine-2-carboxamide, 3-[(3-methylsulfonylphenyl)amino]-5-ethyl-6-[(2-acetamidoethyl)amino] |
| 261 | pyrazine-2-carboxamide, 3-[(3-methylsulfonylphenyl)amino]-5-ethyl-6-[(2-carbamoylethyl)amino] |

TABLE 120

| Ex | Structure |
|---|---|
| 262 | pyrazine-2-carboxamide, 3-[(3-methylsulfonylphenyl)amino]-5-ethyl-6-[(2-hydroxyethyl)amino] |
| 263 | pyrazine-2-carboxamide, 3-[(3-methylsulfonylphenyl)amino]-5-ethyl-6-[(3-hydroxypropyl)amino] |
| 264 | pyrazine-2-carboxamide, 3-[(3-methylsulfonylphenyl)amino]-5-ethyl-6-[(4-hydroxybutyl)amino] |
| 265 | pyrazine-2-carboxamide, 3-[(3-methylsulfonylphenyl)amino]-5-ethyl-6-[(1-hydroxymethyl-ethyl)amino] |
| 266 | pyrazine-2-carboxamide, 3-[(3-methylsulfonylphenyl)amino]-5-ethyl-6-[(2,3-dihydroxypropyl)amino] |
| 267 | pyrazine-2-carboxamide, 3-[(3-methylsulfonylphenyl)amino]-5-ethyl-6-[(2-methoxyethyl)amino] |
| 268 | pyrazine-2-carboxamide, 3-[(3-methylsulfonylphenyl)amino]-5-ethyl-6-[[1-(methoxymethyl)-2-methoxyethyl]amino] |

TABLE 120-continued

| Ex | Structure |
|---|---|
| 269 | 3-(methylsulfonyl)phenylamino-6-ethyl-5-(4-methylpiperazin-1-yl)pyrazine-2-carboxamide |

TABLE 121

| Ex | Structure |
|---|---|
| 270 | 3-(methylsulfonyl)phenylamino-6-ethyl-5-(4-phenylpiperazin-1-yl)pyrazine-2-carboxamide |
| 271 | 3-(methylsulfonyl)phenylamino-6-ethyl-5-(morpholin-4-yl)pyrazine-2-carboxamide |
| 272 | 3-(methylsulfonyl)phenylamino-6-ethyl-5-(4-methoxypiperidin-1-yl)pyrazine-2-carboxamide |

TABLE 121-continued

| Ex | Structure |
|---|---|
| 273 | 3-(methylsulfonyl)phenylamino-6-ethyl-5-[N-methyl-N-(2-dimethylaminoethyl)amino]pyrazine-2-carboxamide |
| 274 | 3-(methylsulfonyl)phenylamino-6-ethyl-5-[N-methyl-N-(2-hydroxyethyl)amino]pyrazine-2-carboxamide |
| 275 | 3-(methylsulfonyl)phenylamino-6-ethyl-5-(4-methoxyphenylamino)pyrazine-2-carboxamide |
| 276 | 3-(methylsulfonyl)phenylamino-6-ethyl-5-(pyridin-4-ylamino)pyrazine-2-carboxamide |
| 277 | 3-(methylsulfonyl)phenylamino-6-ethyl-5-(benzylamino)pyrazine-2-carboxamide |

TABLE 122

| Ex | Structure |
|---|---|
| 278 | 3-(methylsulfonyl)phenylamino-6-ethyl-5-(4-methoxybenzylamino)pyrazine-2-carboxamide |

TABLE 122-continued
| Ex | Structure |
|---|---|
| 279 | 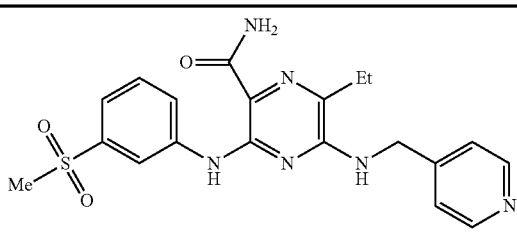 |
| 280 | 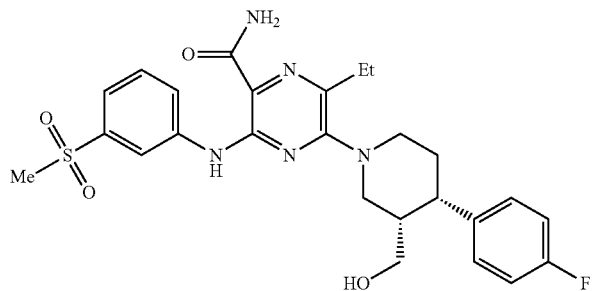 [SMILES: CCc1nc(C(N)=O)c(Nc2cccc(S(C)(=O)=O)c2)nc1N1CC[C@H](c2ccc(F)cc2)[C@H](CO)C1] |
| 281 | 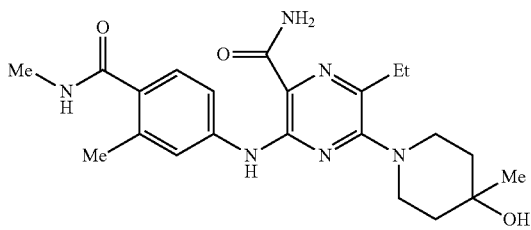 [SMILES: CCc1nc(C(N)=O)c(Nc2ccc(C(=O)NC)c(C)c2)nc1N1CCC(C)(O)CC1] |
| 282* | 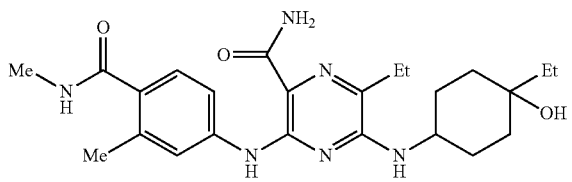 [SMILES: CCc1nc(C(N)=O)c(Nc2ccc(C(=O)NC)c(C)c2)nc1NC1CCC(O)(CC)CC1] |
| 283 | 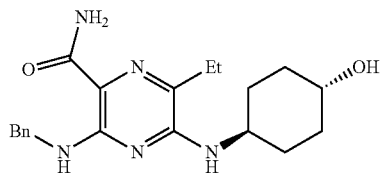 [SMILES: CCc1nc(C(N)=O)c(NCc2ccccc2)nc1N[C@H]1CC[C@H](O)CC1] |
| 284 | 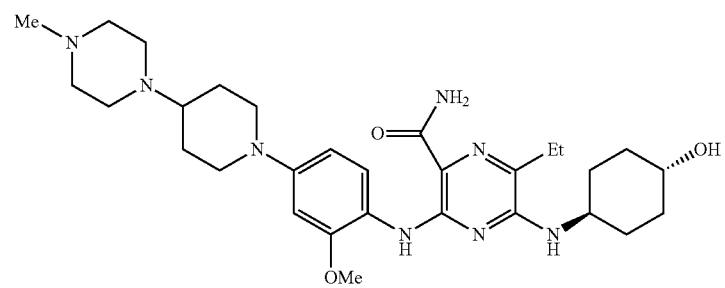 [SMILES: CCc1nc(C(N)=O)c(Nc2ccc(N3CCC(N4CCN(C)CC4)CC3)cc2OC)nc1N[C@H]1CC[C@H](O)CC1] |

TABLE 122-continued

| Ex | Structure |
|---|---|
| 285 | (structure) |

TABLE 123

| Ex | Structure |
|---|---|
| 286 | (structure) |
| 287 | (structure) |
| 288 | (structure) |
| 289 | (structure) |
| 290 | (structure) |
| 291 | (structure) |
| 292 | (structure) |
| 293 | (structure) |

TABLE 123-continued

| Ex | Structure |
|---|---|
| 294 | (structure) |

TABLE 124

| Ex | Structure |
|---|---|
| 295 | (structure) |
| 296 | (structure) |
| 297 | (structure) |
| 298 | (structure) |
| 299 | (structure) |

TABLE 124-continued

| Ex | Structure |
|---|---|
| 300 | (structure) |
| 301* | (structure) |
| 302* | (structure) |
| 303 | (structure) |

TABLE 125

| Ex | Structure |
|---|---|
| 304 | (structure) |
| 305 | (structure) |
| 306 | (structure) |
| 307 | (structure) |

TABLE 125-continued

| Ex | Structure |
|---|---|
| 308 | (structure) |
| 309 | (structure) |
| 310 | (structure) |
| 311 | (structure) |
| 312 | (structure) |

TABLE 126

| Ex | Structure |
|---|---|
| 313 | (structure) |
| 314* | (structure) |
| 315 | (structure) |
| 316* | (structure) |

TABLE 126-continued

| Ex | Structure |
|---|---|
| 317* | (structure) |
| 318* | (structure) |
| 319 | (structure) |
| 320 | (structure) |
| 321 | (structure) |

TABLE 127

| Ex | Structure |
|---|---|
| 322 | (structure) |
| 323 | (structure) |
| 324 | (structure) |
| 325 | (structure) |
| 326 | (structure) |

TABLE 127-continued

| Ex | Structure |
|---|---|
| 327 | 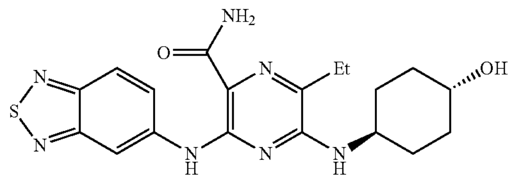 [SMILES: CCc1nc(C(N)=O)c(Nc2ccc3nsnc3c2)nc1N[C@H]1CC[C@H](O)CC1] |
| 328 | 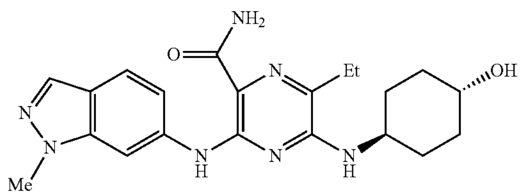 [SMILES: CCc1nc(C(N)=O)c(Nc2ccc3cnn(C)c3c2)nc1N[C@H]1CC[C@H](O)CC1] |
| 329 | 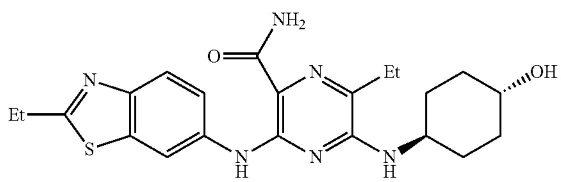 [SMILES: CCc1nc2ccc(Nc3nc(N[C@H]4CC[C@H](O)CC4)c(CC)nc3C(N)=O)cc2s1] |
| 330 | 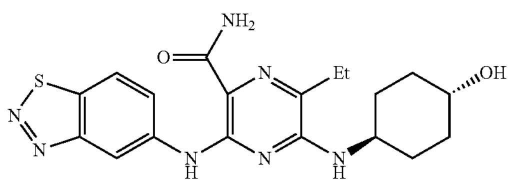 [SMILES: CCc1nc(C(N)=O)c(Nc2ccc3snnc3c2)nc1N[C@H]1CC[C@H](O)CC1] |

TABLE 128

| Ex | Structure |
|---|---|
| 331 | 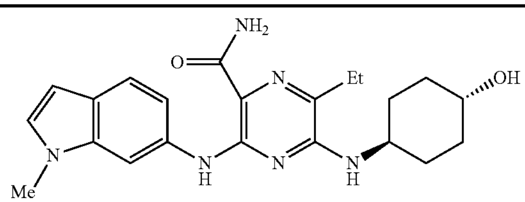 |
| 332 | 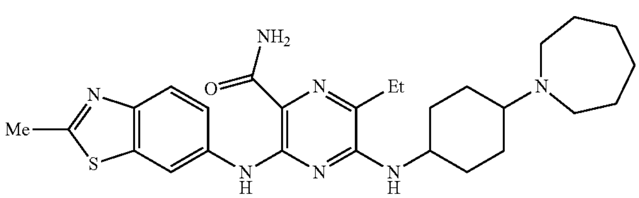 [SMILES: CCc1nc(C(N)=O)c(Nc2ccc3nc(C)sc3c2)nc1NC1CCC(N2CCCCCC2)CC1] |
| 333 | 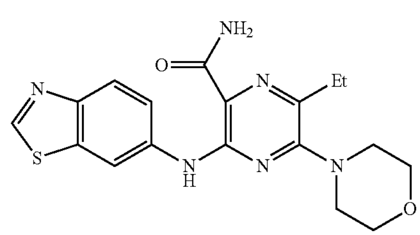 [SMILES: CCc1nc(C(N)=O)c(Nc2ccc3ncsc3c2)nc1N1CCOCC1] |

TABLE 128-continued
| Ex | Structure |
|---|---|
| 334 | 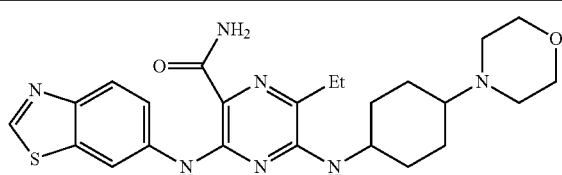 |
| 335 | 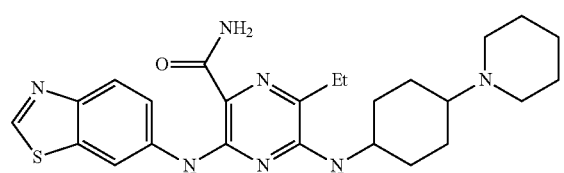 |
| 336* | 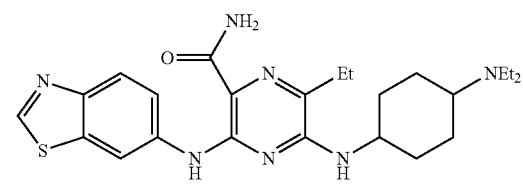 |
| 337 | 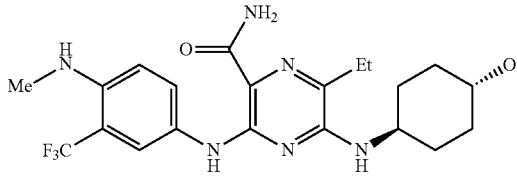 |
| 338 | 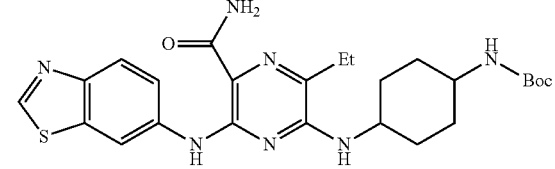 [SMILES: CCc1nc(C(N)=O)c(Nc2ccc3ncsc3c2)nc1NC1CCC(NC(=O)OC(C)(C)C)CC1] |
TABLE 129
| Ex | Structure |
|---|---|
| 339 | 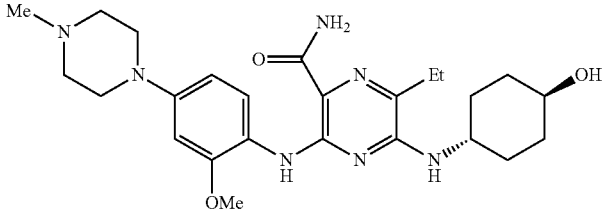 [SMILES: CCc1nc(C(N)=O)c(Nc2ccc(N3CCN(C)CC3)cc2OC)nc1N[C@H]1CC[C@H](O)CC1] |
| 340 | 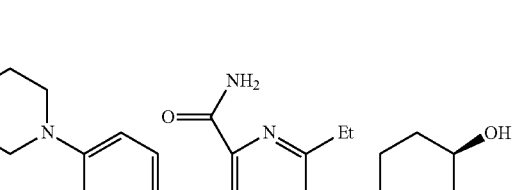 |

TABLE 129-continued

| Ex | Structure |
|---|---|
| 341 | (4-methylpiperazinyl)-piperidinyl-phenyl-NH-pyrazine(CONH2)(Et)-NH-cyclohexyl-OH |
| 342 | (4-methylpiperazinyl)-phenyl-NH-pyrazine(CONH2)(C(=CH2)Me)-NH-cyclohexyl-OH |
| 343 | (4-methylpiperazinyl)-phenyl-NH-pyrazine(CONH2)(iPr)-NH-cyclohexyl-OH |
| 344 | Boc-piperazinyl-phenyl-NH-pyrazine(CONH2)-NH-cyclohexyl-OH |
| 345 | Boc-piperazinyl-phenyl-NH-pyrazine(CONH2)(Cl)-NH-cyclohexyl-OH |
| 346 | HN-piperazinyl-phenyl-NH-pyrazine(CONH2)(Cl)-NH-cyclohexyl-OH |

TABLE 130

| Ex | Structure |
|---|---|
| 347 | (4-methylpiperazinyl)-phenyl(meta)-NH-pyrazine(CONH2)(Et)-NH-cyclohexyl-OH |

TABLE 130-continued

| Ex | Structure |
|---|---|
| 348 | (structure: 4-methylpiperazinyl-piperidinyl-(2-methoxyphenyl)amino-pyrazine carboxamide with ethyl and (4-hydroxy-4-methylcyclohexyl)amino substituents) |
| 349 | (structure: 4-methylpiperazinyl-piperidinyl-(2-methoxyphenyl)amino-pyrazine carboxamide with ethyl and (4-hydroxy-4-methylcyclohexyl)amino substituents) |
| 350 | (structure: 3,4-dihydroxypyrrolidinyl-piperidinyl-(2-methoxyphenyl)amino-pyrazine carboxamide with ethyl and (4-hydroxycyclohexyl)amino substituents) |
| 351 | (structure: 4-methylpiperazinyl-piperidinyl-(2-methoxyphenyl)amino-pyrazine with cyano, ethyl, and (4-hydroxycyclohexyl)amino substituents) |
| 352 | (structure: 2-methylbenzothiazol-6-ylamino-pyrazine carboxamide with ethyl and (4-methoxybenzyl)amino substituents) |

TABLE 131

| Ex | Structure |
|---|---|
| 353 | (structure) |
| 354 | (structure) |
| 355 | (structure) |
| 356 | (structure) |
| 357 | (structure) |
| 358 | (structure) |
| 359 | (structure) |

TABLE 131-continued

| Ex | Structure |
|---|---|
| 360 | (structure) |

TABLE 132

| Ex | Structure |
|---|---|
| 361 | (structure) |
| 362 | (structure) |
| 363 | (structure) |
| 364 | (structure) |
| 365 | (structure) |

TABLE 132-continued

| Ex | Structure |
|---|---|
| 366 | *(structure)* |
| 367 | *(structure)* |

TABLE 133

| Ex | Structure |
|---|---|
| 368 | *(structure)* |
| 369 | *(structure)* |
| 370 | *(structure)* |
| 371 | *(structure)* |

TABLE 133-continued

| Ex | Structure |
|---|---|
| 372 | 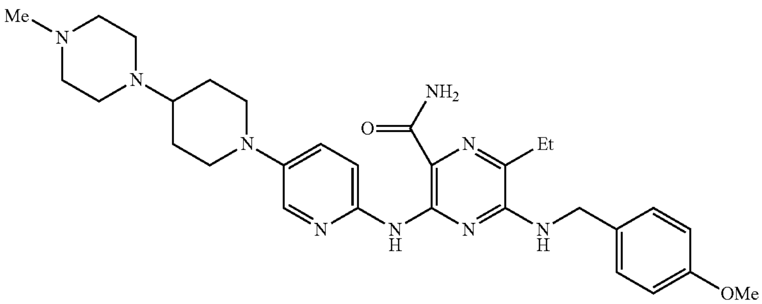 [SMILES: CCc1nc(C(N)=O)c(Nc2ccc(N3CCC(N4CCN(C)CC4)CC3)cn2)nc1NCc1ccc(OC)cc1] |
| 373 | 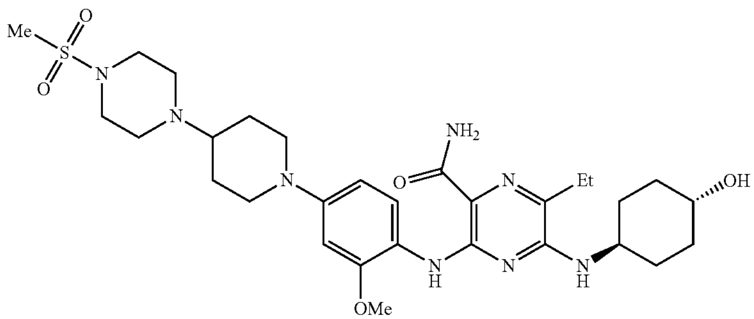 [SMILES: CCc1nc(C(N)=O)c(Nc2ccc(N3CCC(N4CCN(S(C)(=O)=O)CC4)CC3)cc2OC)nc1N[C@H]1CC[C@H](O)CC1] |
| 374 | 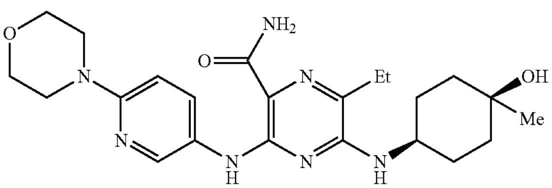 [SMILES: CCc1nc(C(N)=O)c(Nc2ccc(N3CCOCC3)cc2)nc1N[C@H]1CC[C@@](C)(O)CC1] |

TABLE 134

| Ex | Structure |
|---|---|
| 375 | 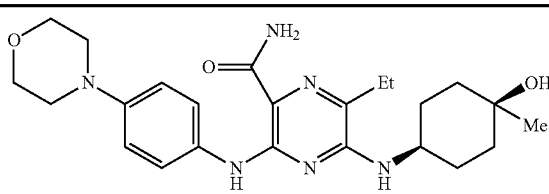 |
| 376 | 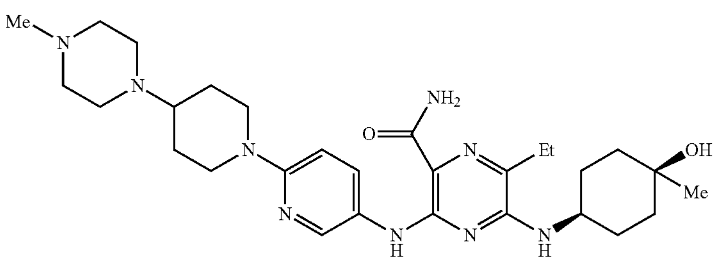 [SMILES: CCc1nc(C(N)=O)c(Nc2ccc(N3CCC(N4CCN(C)CC4)CC3)nc2)nc1N[C@H]1CC[C@@](C)(O)CC1] |
| 377 | 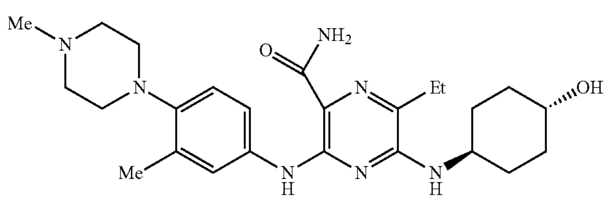 [SMILES: CCc1nc(C(N)=O)c(Nc2ccc(N3CCN(C)CC3)c(C)c2)nc1N[C@H]1CC[C@H](O)CC1] |

TABLE 134-continued
| Ex | Structure |
|---|---|
| 378 | 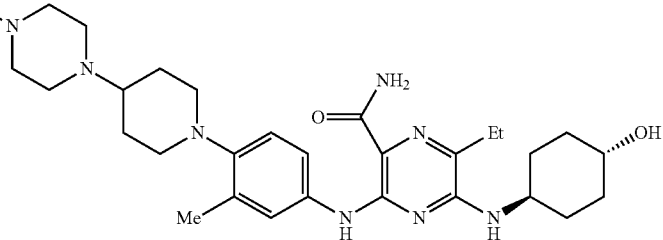 |
| 379 | 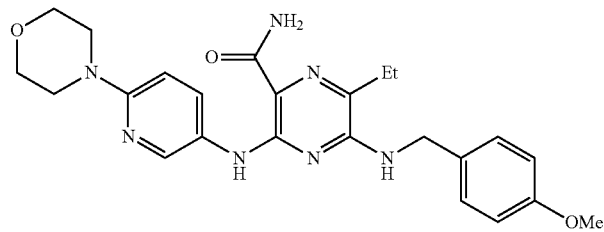 [SMILES: CCc1nc(C(N)=O)c(Nc2ccc(N3CCOCC3)nc2)nc1NCc1ccc(OC)cc1] |
| 380 | 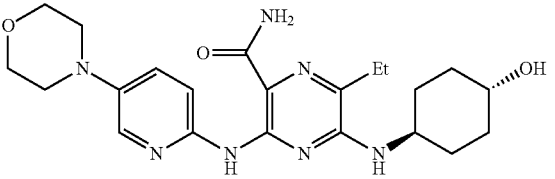 [SMILES: CCc1nc(C(N)=O)c(Nc2ccc(N3CCOCC3)cn2)nc1N[C@H]1CC[C@H](O)CC1] |
| 381 | 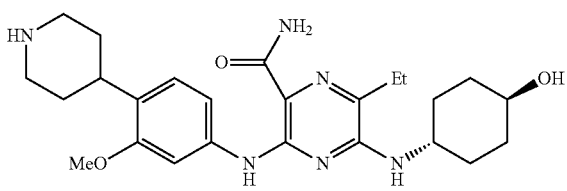 [SMILES: CCc1nc(C(N)=O)c(Nc2ccc(C3CCNCC3)c(OC)c2)nc1N[C@H]1CC[C@H](O)CC1] |
| 382 | 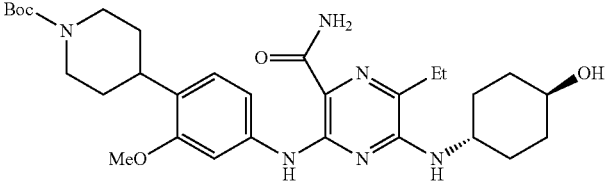 [SMILES: CCc1nc(C(N)=O)c(Nc2ccc(C3CCN(C(=O)OC(C)(C)C)CC3)c(OC)c2)nc1N[C@H]1CC[C@H](O)CC1] |
TABLE 135
| Ex | Structure |
|---|---|
| 383 | 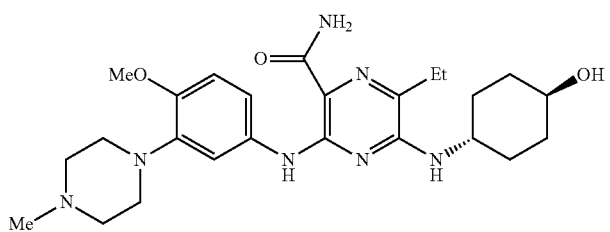 |

TABLE 135-continued

| Ex | Structure |
|---|---|
| 384 | 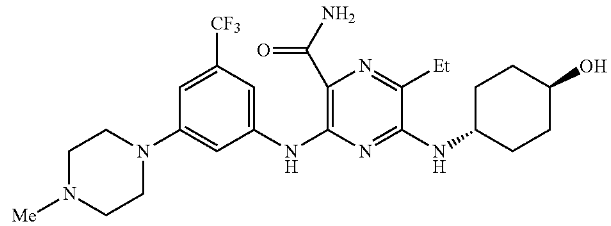 [SMILES: CCc1nc(C(N)=O)c(Nc2cc(N3CCN(C)CC3)cc(C(F)(F)F)c2)nc1N[C@H]1CC[C@H](O)CC1] |
| 385 | 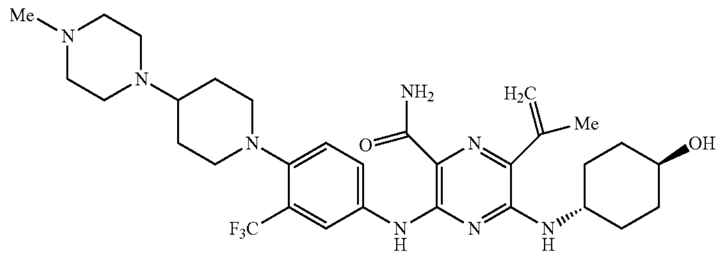 [SMILES: C=C(C)c1nc(C(N)=O)c(Nc2ccc(N3CCC(N4CCN(C)CC4)CC3)c(C(F)(F)F)c2)nc1N[C@H]1CC[C@H](O)CC1] |
| 386 | 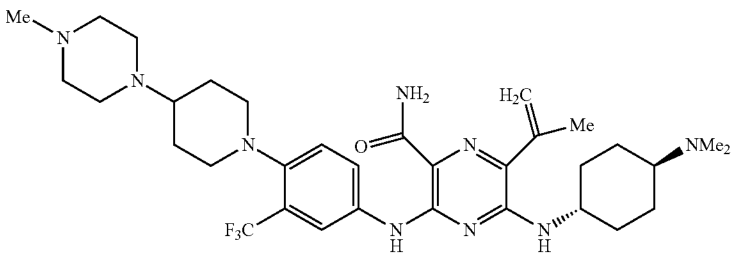 [SMILES: C=C(C)c1nc(C(N)=O)c(Nc2ccc(N3CCC(N4CCN(C)CC4)CC3)c(C(F)(F)F)c2)nc1N[C@H]1CC[C@H](N(C)C)CC1] |
| 387 | 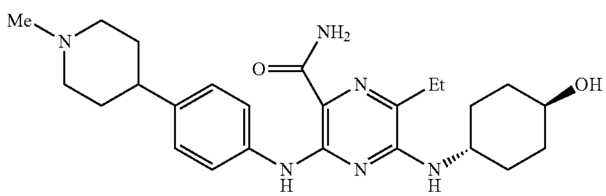 [SMILES: CCc1nc(C(N)=O)c(Nc2ccc(C3CCN(C)CC3)cc2)nc1N[C@H]1CC[C@H](O)CC1] |
| 388 | 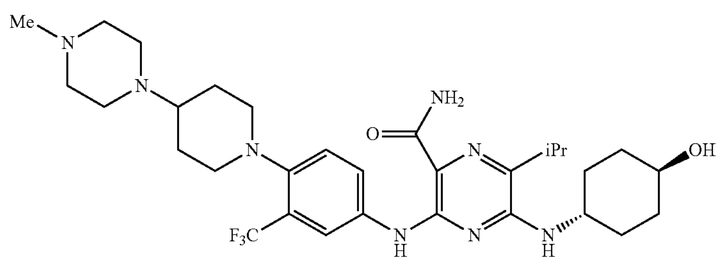 [SMILES: CC(C)c1nc(C(N)=O)c(Nc2ccc(N3CCC(N4CCN(C)CC4)CC3)c(C(F)(F)F)c2)nc1N[C@H]1CC[C@H](O)CC1] |
| 389 | 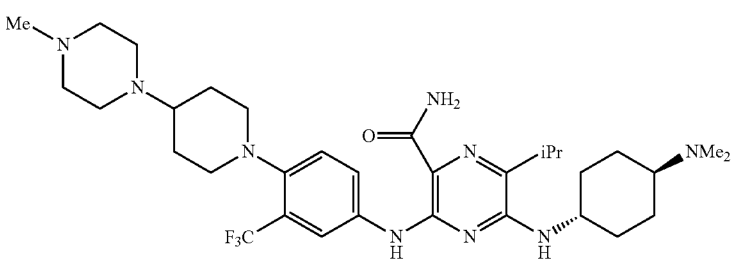 [SMILES: CC(C)c1nc(C(N)=O)c(Nc2ccc(N3CCC(N4CCN(C)CC4)CC3)c(C(F)(F)F)c2)nc1N[C@H]1CC[C@H](N(C)C)CC1] |

TABLE 136
| Ex | Structure |
|---|---|
| 390 | 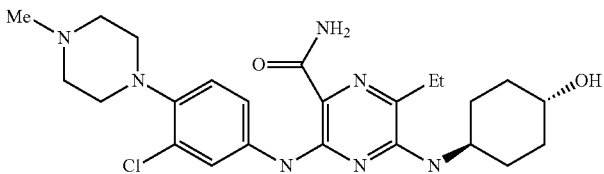 |
| 391 | 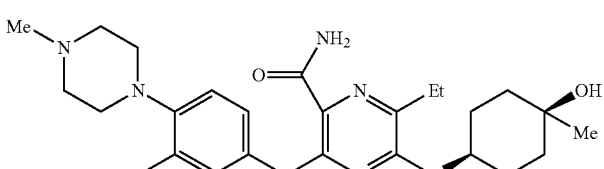 |
| 392 | 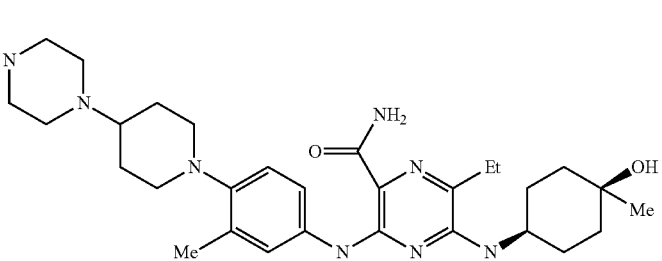 |
| 393 | 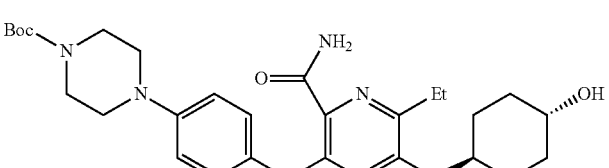 |
| 394 | 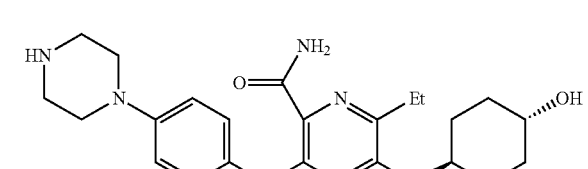 |
| 395 | 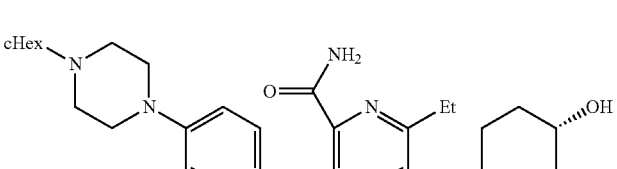 |
| 396 | 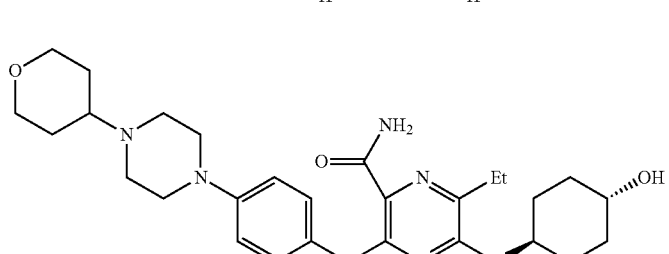 |

TABLE 136-continued

| Ex | Structure |
|---|---|
| 397 | (chemical structure) |

TABLE 137

| Ex | Structure |
|---|---|
| 398 | (chemical structure) |
| 399 | (chemical structure) |
| 400 | (chemical structure) |
| 401 | (chemical structure) |
| 402 | (chemical structure) |

TABLE 137-continued

| Ex | Structure |
|---|---|
| 403 | 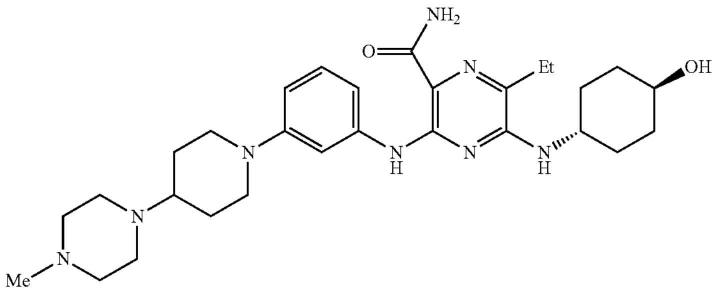 [SMILES: CCc1nc(C(N)=O)c(Nc2cccc(N3CCC(N4CCN(C)CC4)CC3)c2)nc1N[C@H]1CC[C@H](O)CC1] |
| 404 | 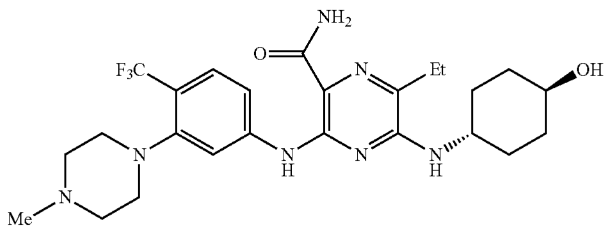 |
| 405 | 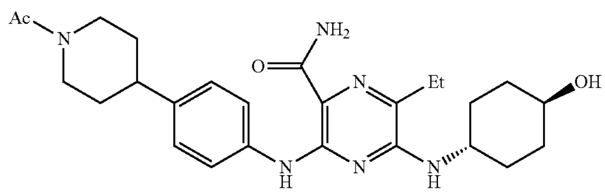 [SMILES: CCc1nc(C(N)=O)c(Nc2ccc(C3CCN(C(C)=O)CC3)cc2)nc1N[C@H]1CC[C@H](O)CC1] |

TABLE 138

| Ex | Structure |
|---|---|
| 406 | 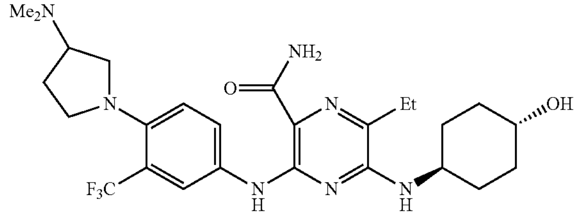 [SMILES: CCc1nc(C(N)=O)c(Nc2ccc(N3CCC(N(C)C)C3)c(C(F)(F)F)c2)nc1N[C@H]1CC[C@H](O)CC1] |
| 407 | 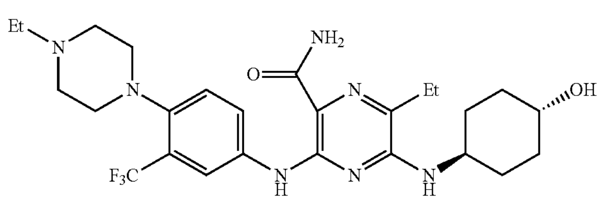 [SMILES: CCc1nc(C(N)=O)c(Nc2ccc(N3CCN(CC)CC3)c(C(F)(F)F)c2)nc1N[C@H]1CC[C@H](O)CC1] |
| 408 | 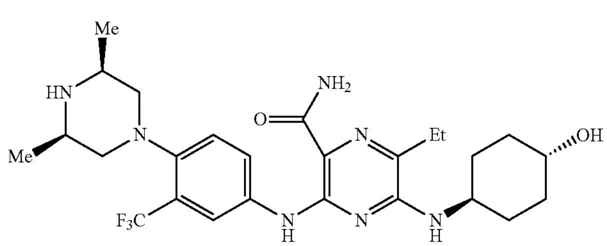 [SMILES: CCc1nc(C(N)=O)c(Nc2ccc(N3C[C@@H](C)N[C@@H](C)C3)c(C(F)(F)F)c2)nc1N[C@H]1CC[C@H](O)CC1] |

TABLE 138-continued

| Ex | Structure |
|---|---|
| 409 | (structure) |
| 410 | (structure) |
| 411 | (structure) |
| 412 | (structure) |

TABLE 139

| Ex | Structure |
|---|---|
| 413 | (structure) |
| 414 | (structure) |

TABLE 139-continued
| Ex | Structure |
|---|---|
| 415 | 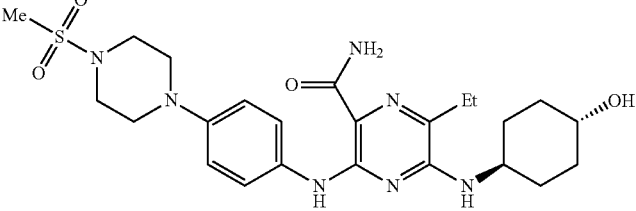 |
| 416 | 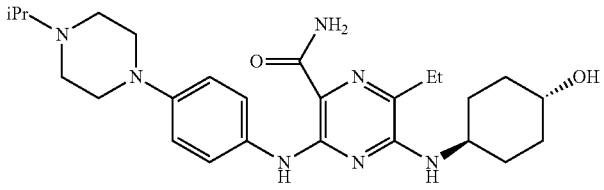 [SMILES: CCc1nc(C(N)=O)c(Nc2ccc(N3CCN(C(C)C)CC3)cc2)nc1N[C@H]1CC[C@H](O)CC1] |
| 417 | 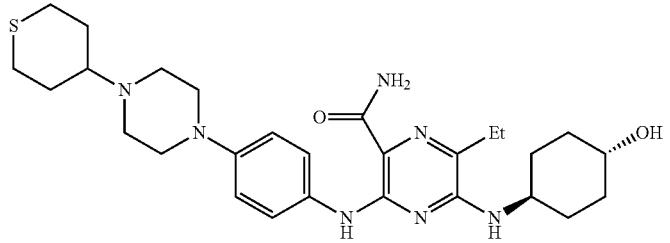 [SMILES: CCc1nc(C(N)=O)c(Nc2ccc(N3CCN(C4CCSCC4)CC3)cc2)nc1N[C@H]1CC[C@H](O)CC1] |
| 418 | 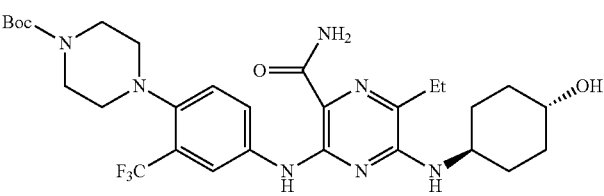 [SMILES: CCc1nc(C(N)=O)c(Nc2ccc(N3CCN(C(=O)OC(C)(C)C)CC3)c(C(F)(F)F)c2)nc1N[C@H]1CC[C@H](O)CC1] |
| 419 | 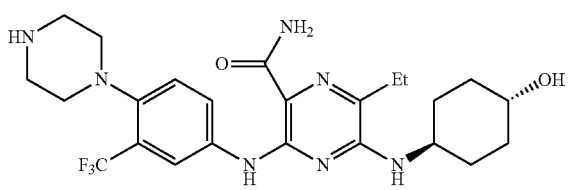 [SMILES: CCc1nc(C(N)=O)c(Nc2ccc(N3CCNCC3)c(C(F)(F)F)c2)nc1N[C@H]1CC[C@H](O)CC1] |
| 420 | 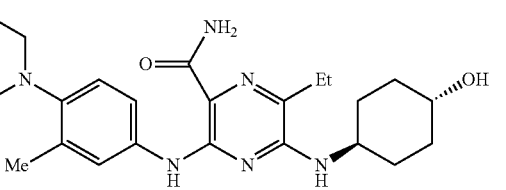 |
TABLE 140
| Ex | Structure |
|---|---|
| 421 | 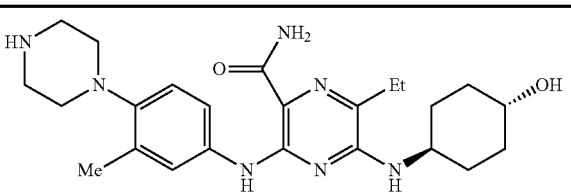 |

TABLE 140-continued

| Ex | Structure |
|---|---|
| 422 | (structure) |
| 423 | (structure) |
| 424 | (structure) |
| 425 | (structure) |
| 426 | (structure) |
| 427 | (structure) |
| 428 | (structure) |

TABLE 141

| Ex | Structure |
|---|---|
| 429 | 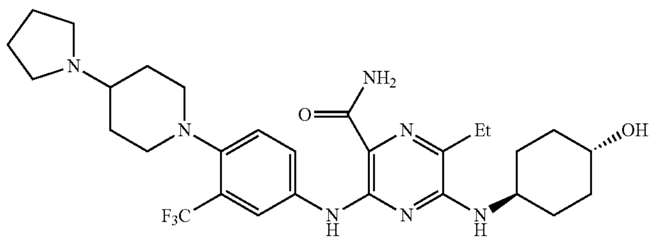 [SMILES: CCc1nc(C(N)=O)c(Nc2ccc(N3CCC(N4CCCC4)CC3)c(C(F)(F)F)c2)nc1N[C@H]1CC[C@H](O)CC1] |
| 430 | 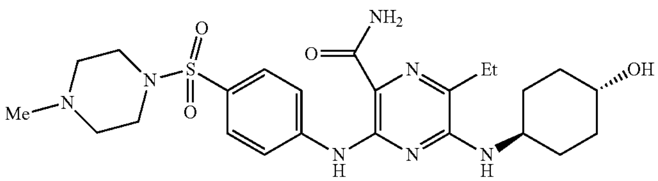 [SMILES: CCc1nc(C(N)=O)c(Nc2ccc(S(=O)(=O)N3CCN(C)CC3)cc2)nc1N[C@H]1CC[C@H](O)CC1] |
| 431 | 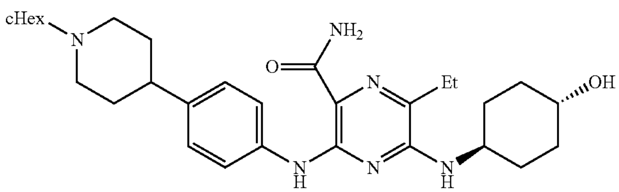 |
| 432 | 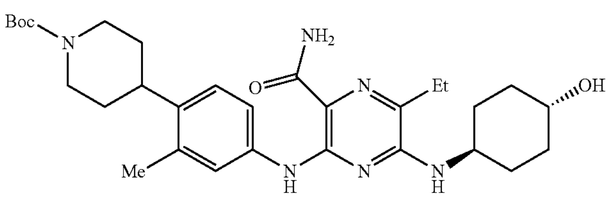 [SMILES: CCc1nc(C(N)=O)c(Nc2ccc(C3CCN(C(=O)OC(C)(C)C)CC3)c(C)c2)nc1N[C@H]1CC[C@H](O)CC1] |
| 433 | 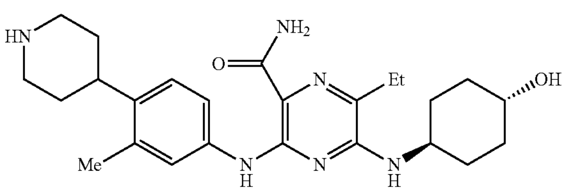 |
| 434 | 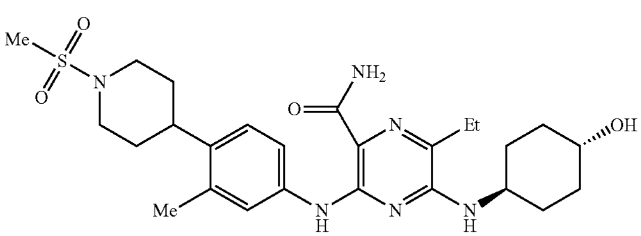 [SMILES: CCc1nc(C(N)=O)c(Nc2ccc(C3CCN(S(C)(=O)=O)CC3)c(C)c2)nc1N[C@H]1CC[C@H](O)CC1] |
| 435 | 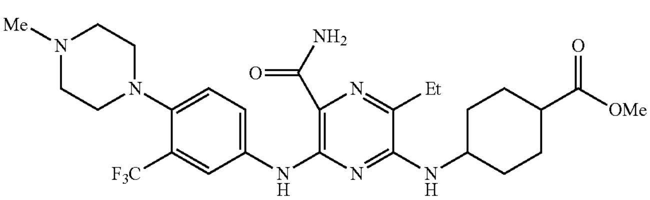 [SMILES: CCc1nc(C(N)=O)c(Nc2ccc(N3CCN(C)CC3)c(C(F)(F)F)c2)nc1NC1CCC(C(=O)OC)CC1] |

TABLE 141-continued
| Ex | Structure |
|---|---|
| 436*6 | 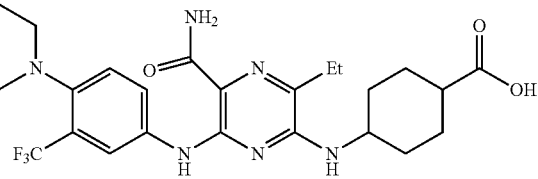 |
TABLE 142
| Ex | Structure |
|---|---|
| 437*6 | 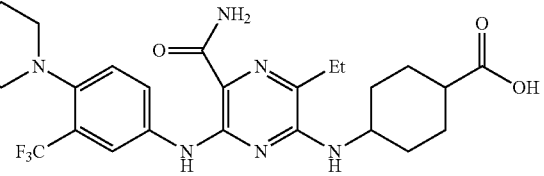 |
| 438*7 | 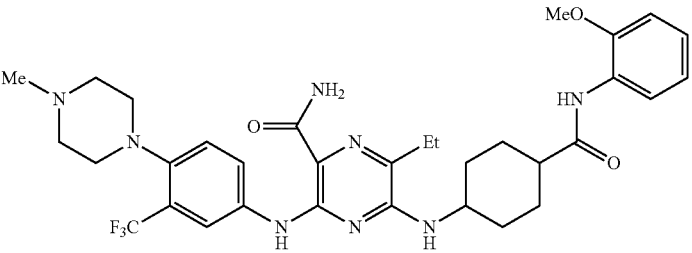 [SMILES: CCc1nc(C(N)=O)c(Nc2ccc(N3CCN(C)CC3)c(C(F)(F)F)c2)nc1NC1CCC(C(=O)Nc2ccccc2OC)CC1] |
| 439*7 | 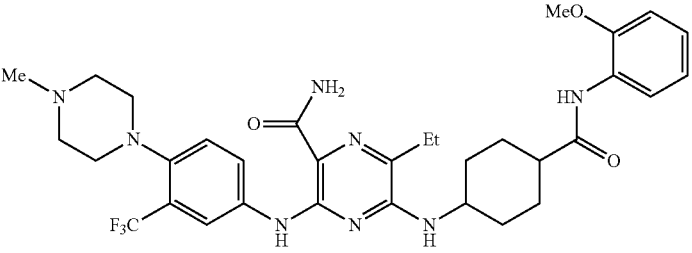 [SMILES: CCc1nc(C(N)=O)c(Nc2ccc(N3CCN(C)CC3)c(C(F)(F)F)c2)nc1NC1CCC(C(=O)Nc2ccccc2OC)CC1] |
| 440 | 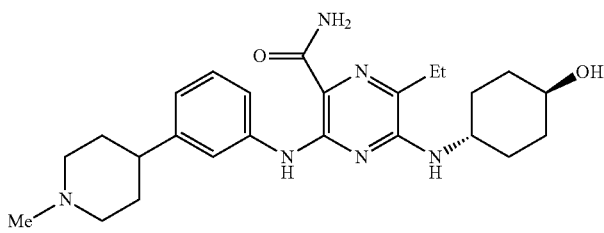 |
| 441 | 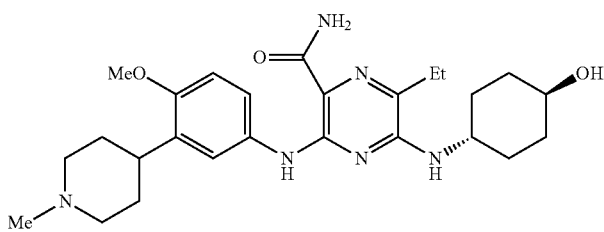 [SMILES: CCc1nc(C(N)=O)c(Nc2ccc(OC)c(C3CCN(C)CC3)c2)nc1N[C@H]1CC[C@H](O)CC1] |

TABLE 142-continued

| Ex | Structure |
|---|---|
| 442 | (structure) |
| 443 | (structure) |

TABLE 143

| Ex | Structure |
|---|---|
| 444 | (structure) |
| 445 | (structure) |
| 446 | (structure) |
| 447 | (structure) |

TABLE 143-continued

| Ex | Structure |
|---|---|
| 448 | (chemical structure) |
| 449 | (chemical structure) |
| 450 | (chemical structure) |

TABLE 144

| Ex | Structure |
|---|---|
| 451 | (chemical structure) |
| 452 | (chemical structure) |

TABLE 144-continued

| Ex | Structure |
|---|---|
| 453 | 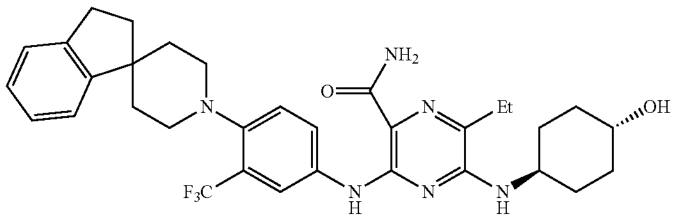 [SMILES: CCc1nc(C(N)=O)c(Nc2ccc(N3CCC4(CCc5ccccc54)CC3)c(C(F)(F)F)c2)nc1N[C@H]1CC[C@H](O)CC1] |
| 454 | 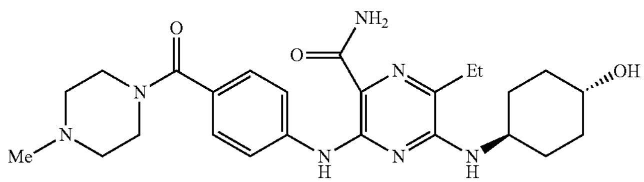 [SMILES: CCc1nc(C(N)=O)c(Nc2ccc(C(=O)N3CCN(C)CC3)cc2)nc1N[C@H]1CC[C@H](O)CC1] |
| 455 | 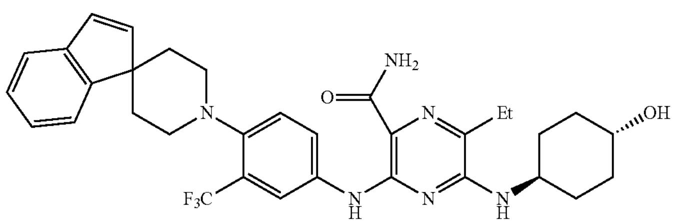 [SMILES: CCc1nc(C(N)=O)c(Nc2ccc(N3CCC4(C=Cc5ccccc54)CC3)c(C(F)(F)F)c2)nc1N[C@H]1CC[C@H](O)CC1] |
| 456 | 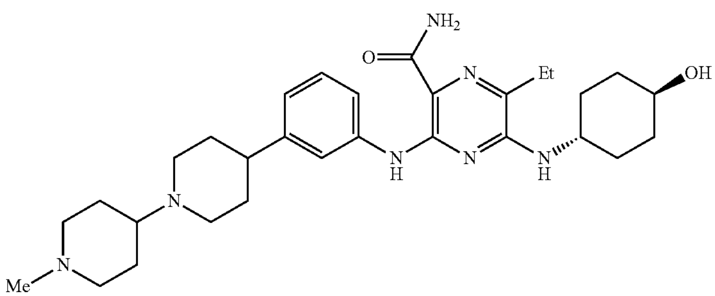 [SMILES: CCc1nc(C(N)=O)c(Nc2cccc(C3CCN(C4CCN(C)CC4)CC3)c2)nc1N[C@H]1CC[C@H](O)CC1] |
| 457 | 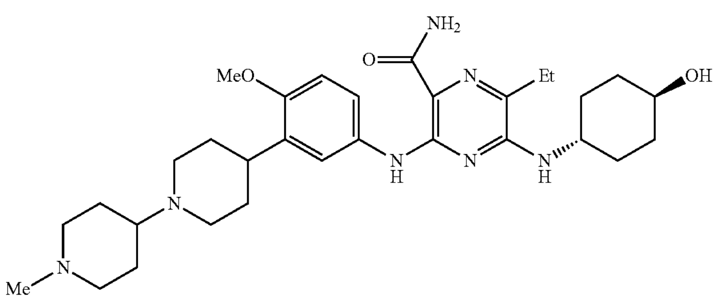 [SMILES: CCc1nc(C(N)=O)c(Nc2ccc(OC)c(C3CCN(C4CCN(C)CC4)CC3)c2)nc1N[C@H]1CC[C@H](O)CC1] |

TABLE 145

| Ex | Structure |
|---|---|
| 458 | 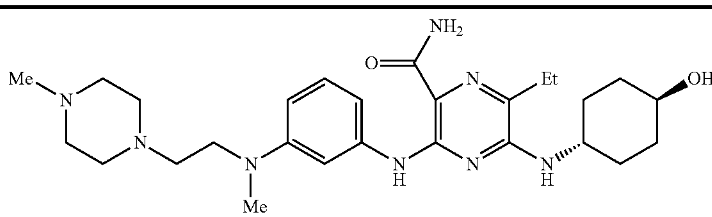 |

TABLE 145-continued
| Ex | Structure |
|---|---|
| 459 | 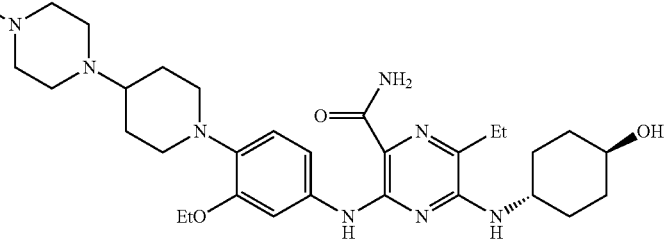 |
| 460 | 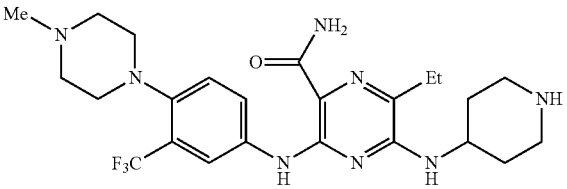 [SMILES: CCc1nc(C(N)=O)c(Nc2ccc(N3CCN(C)CC3)c(C(F)(F)F)c2)nc1NC1CCNCC1] |
| 461 | 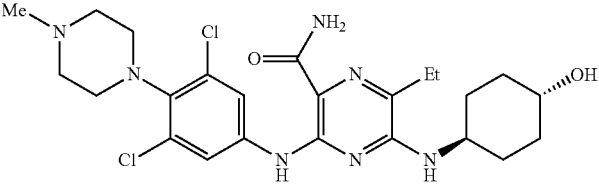 |
| 462 | 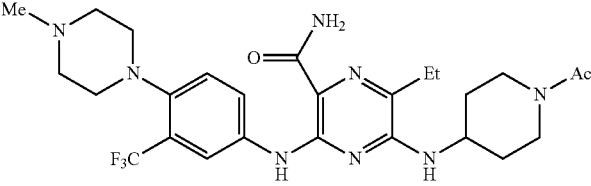 |
| 463 | 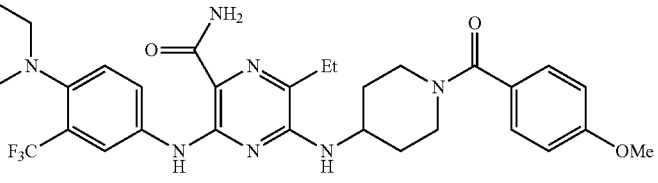 |
| 464 | 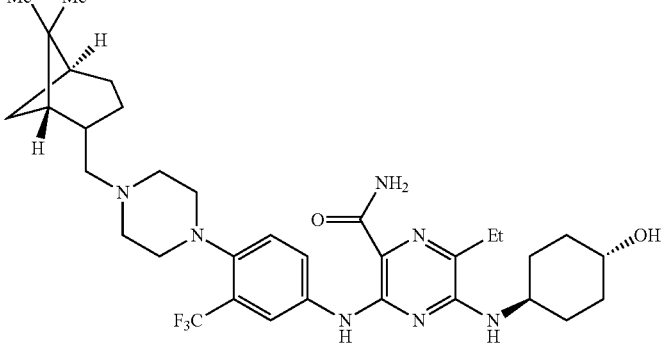 |

TABLE 146

| Ex | Structure |
|---|---|
| 465 | (structure) |
| 466 | (structure) |
| 467 | (structure) |
| 468 | (structure) |
| 469 | (structure) |
| 470 | (structure) |
| 471 | (structure) |

TABLE 146-continued

| Ex | Structure |
|---|---|
| 472 | (structure) |

TABLE 147

| Ex | Structure |
|---|---|
| 473 | (structure) |
| 474 | (structure) |
| 475 | (structure) |
| 476 | (structure) |
| 477 | (structure) |
| 478 | (structure) |

TABLE 147-continued
| Ex | Structure |
|---|---|
| 479 | 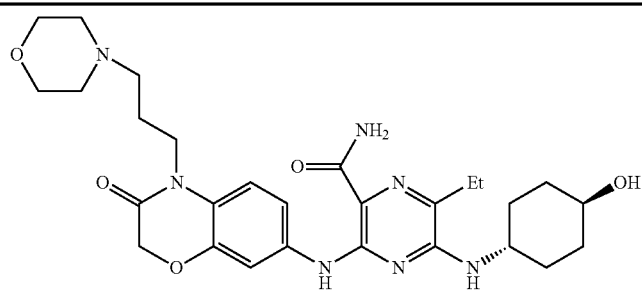 |
| 480 | 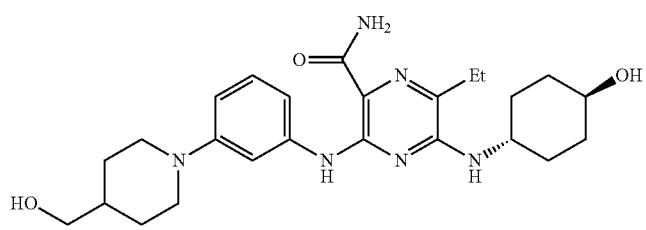 [SMILES: CCc1nc(C(N)=O)c(Nc2cccc(N3CCC(CO)CC3)c2)nc1N[C@H]1CC[C@H](O)CC1] |
TABLE 148
| Ex | Structure |
|---|---|
| 481 | 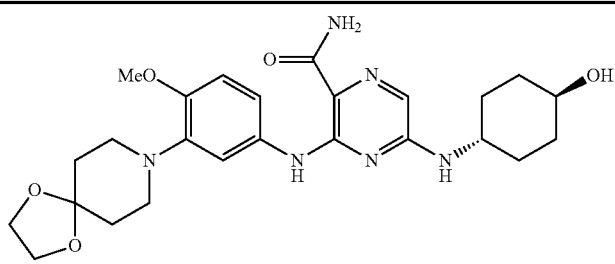 |
| 482 | 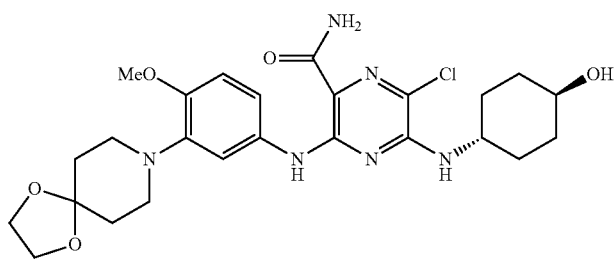 [SMILES: COc1ccc(Nc2nc(N[C@H]3CC[C@H](O)CC3)c(Cl)nc2C(N)=O)cc1N1CCC2(CC1)OCCO2] |
| 483 | 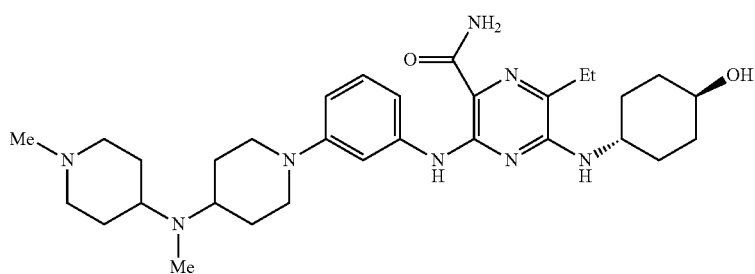 [SMILES: CCc1nc(C(N)=O)c(Nc2cccc(N3CCC(N(C)C4CCN(C)CC4)CC3)c2)nc1N[C@H]1CC[C@H](O)CC1] |

TABLE 148-continued

| Ex | Structure |
|----|-----------|
| 484 | 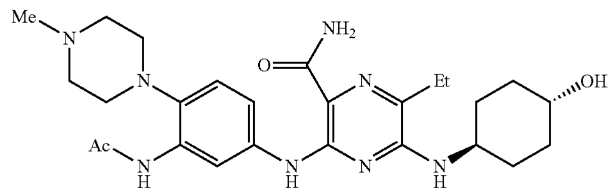 [SMILES: CCc1nc(C(N)=O)c(Nc2ccc(N3CCN(C)CC3)c(NC(C)=O)c2)nc1N[C@H]1CC[C@H](O)CC1] |
| 485 | 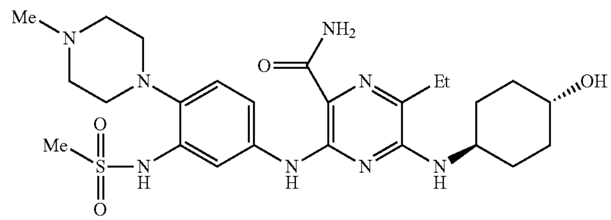 [SMILES: CCc1nc(C(N)=O)c(Nc2ccc(N3CCN(C)CC3)c(NS(C)(=O)=O)c2)nc1N[C@H]1CC[C@H](O)CC1] |
| 486 | 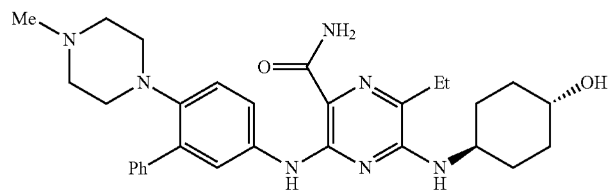 |
| 487 | 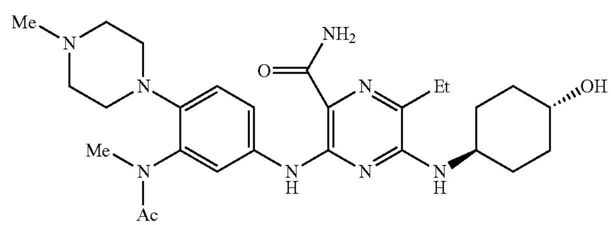 [SMILES: CCc1nc(C(N)=O)c(Nc2ccc(N3CCN(C)CC3)c(N(C)C(C)=O)c2)nc1N[C@H]1CC[C@H](O)CC1] |

TABLE 149

| Ex | Structure |
|----|-----------|
| 488 | 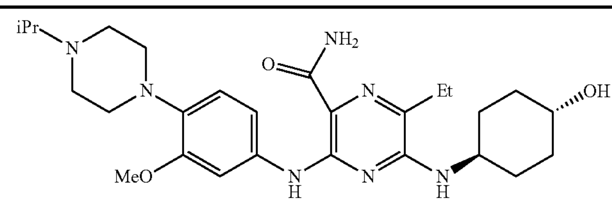 |
| 489 | 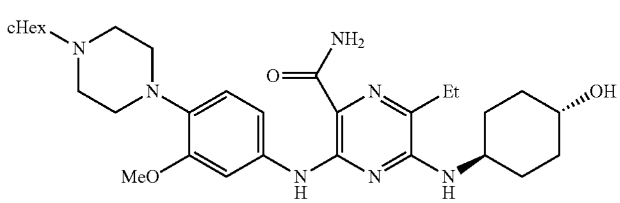 |

TABLE 149-continued

| Ex | Structure |
|---|---|
| 490*8 | (structure) |
| 491*8 | (structure) |
| 492 | (structure) |
| 493*9 | (structure) |
| 494*9 | (structure) |

TABLE 150

| Ex | Structure |
|---|---|
| 495 | (structure) |
| 496 | (structure) |
| 497 | (structure) |
| 498 | (structure) |
| 499 | (structure) |

TABLE 150-continued
| Ex | Structure |
|---|---|
| 500 | 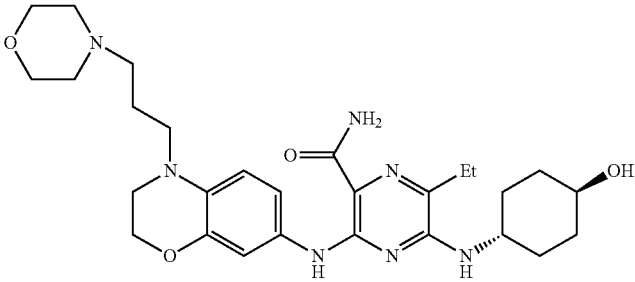 [SMILES: CCc1nc(C(N)=O)c(Nc2ccc3c(c2)OCCN3CCCN2CCOCC2)nc1N[C@H]1CC[C@H](O)CC1] |
TABLE 151
| Ex | Structure |
|---|---|
| 501 | 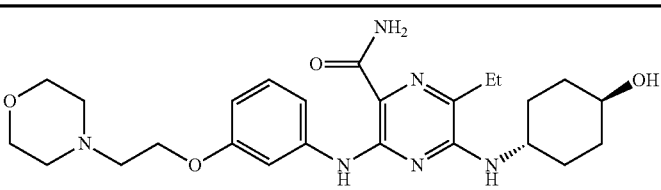 |
| 502 | 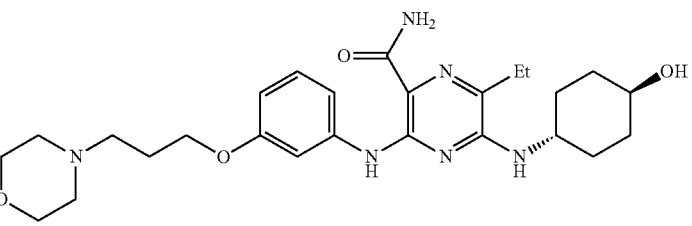 [SMILES: CCc1nc(C(N)=O)c(Nc2cccc(OCCCN3CCOCC3)c2)nc1N[C@H]1CC[C@H](O)CC1] |
| 503 | 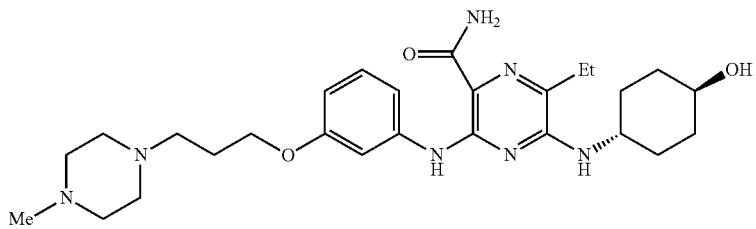 [SMILES: CCc1nc(C(N)=O)c(Nc2cccc(OCCCN3CCN(C)CC3)c2)nc1N[C@H]1CC[C@H](O)CC1] |
| 504 | 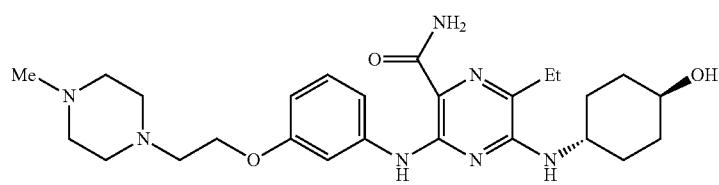 [SMILES: CCc1nc(C(N)=O)c(Nc2cccc(OCCN3CCN(C)CC3)c2)nc1N[C@H]1CC[C@H](O)CC1] |
| 505 | 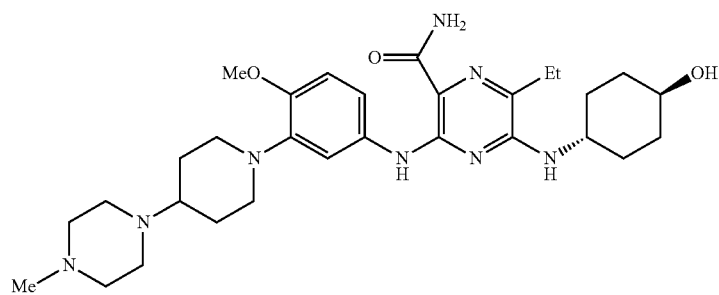 [SMILES: CCc1nc(C(N)=O)c(Nc2ccc(OC)c(N3CCC(N4CCN(C)CC4)CC3)c2)nc1N[C@H]1CC[C@H](O)CC1] |

TABLE 151-continued

| Ex | Structure |
|---|---|
| 506 | (structure) |
| 507 | (structure) |

TABLE 152

| Ex | Structure |
|---|---|
| 508 | (structure) |
| 509 | (structure) |
| 510 | (structure) |

TABLE 152-continued

| Ex | Structure |
|---|---|
| 511 | 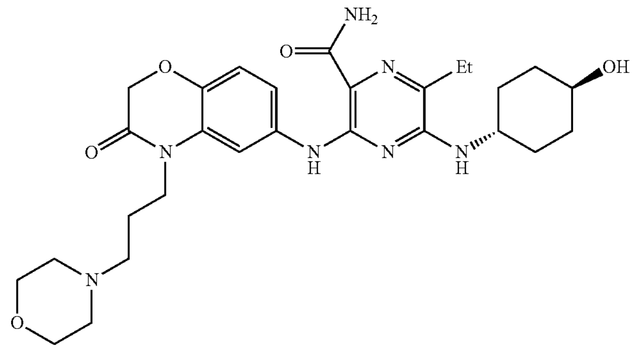 [SMILES: CCc1nc(C(N)=O)c(Nc2ccc3c(c2)N(CCCN2CCOCC2)C(=O)CO3)nc1N[C@H]1CC[C@H](O)CC1] |
| 512 | 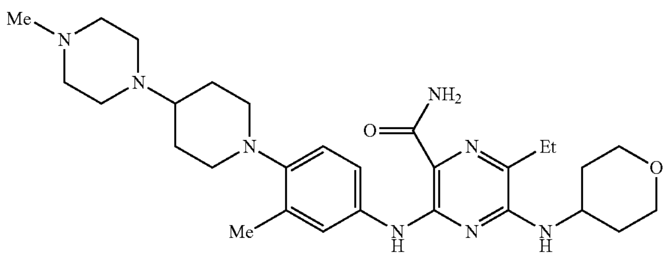 [SMILES: CCc1nc(C(N)=O)c(Nc2ccc(N3CCC(N4CCN(C)CC4)CC3)c(C)c2)nc1NC1CCOCC1] |
| 513 | 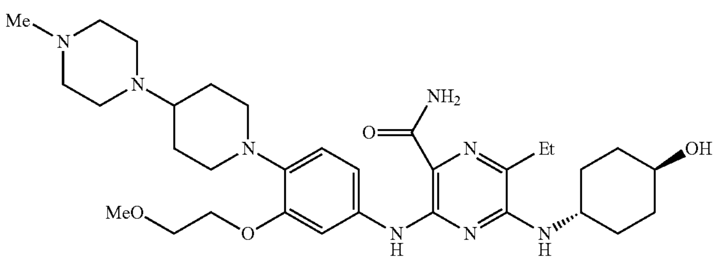 [SMILES: CCc1nc(C(N)=O)c(Nc2ccc(N3CCC(N4CCN(C)CC4)CC3)c(OCCOC)c2)nc1N[C@H]1CC[C@H](O)CC1] |

TABLE 153

| Ex | Structure |
|---|---|
| 514 | 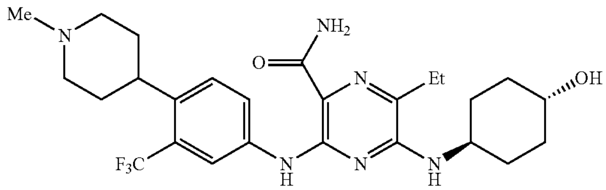 |
| 515 | 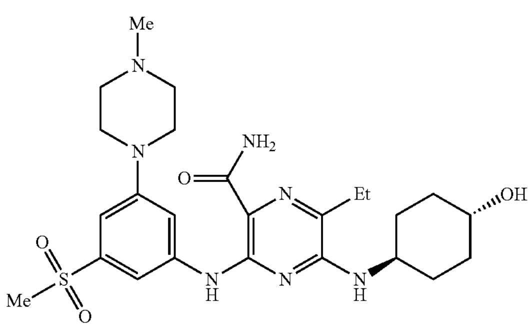 [SMILES: CCc1nc(C(N)=O)c(Nc2cc(N3CCN(C)CC3)cc(S(C)(=O)=O)c2)nc1N[C@H]1CC[C@H](O)CC1] |

275 276
TABLE 153-continued
| Ex | Structure |
|---|---|
| 516 | 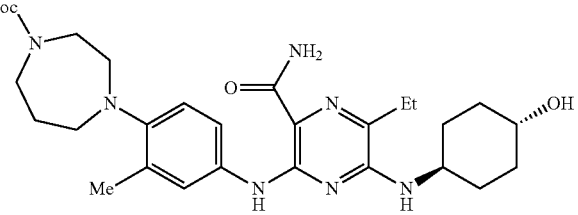 |
| 517 | 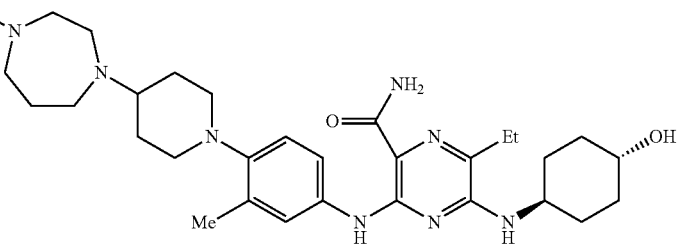 |
| 518 | 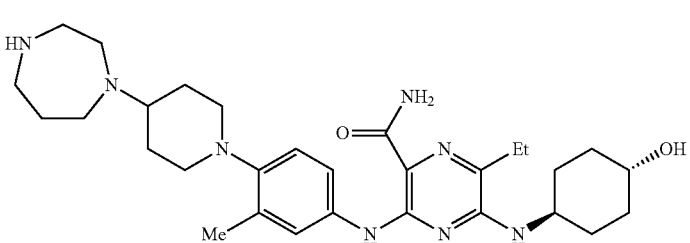 |
| 519 | 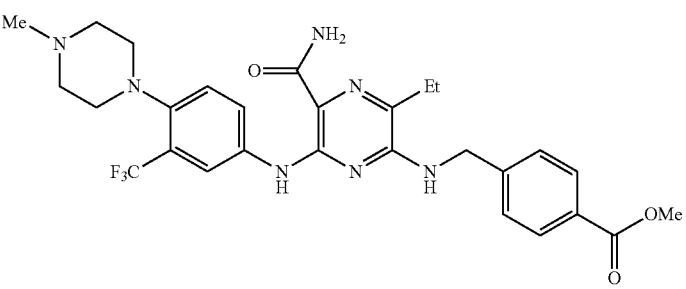 [SMILES: CCc1nc(C(N)=O)c(Nc2ccc(N3CCN(C)CC3)c(C(F)(F)F)c2)nc1NCc1ccc(C(=O)OC)cc1] |
TABLE 154
| Ex | Structure |
|---|---|
| 520 | 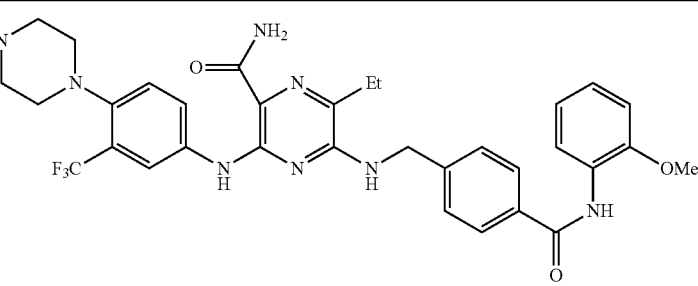 |

TABLE 154-continued

| Ex | Structure |
|---|---|
| 521 | (structure) |
| 522 | (structure) |
| 523 | (structure) |
| 524 | (structure) |
| 525 | (structure) |
| 526 | (structure) |

TABLE 155
| Ex | Structure |
|---|---|
| 527 | 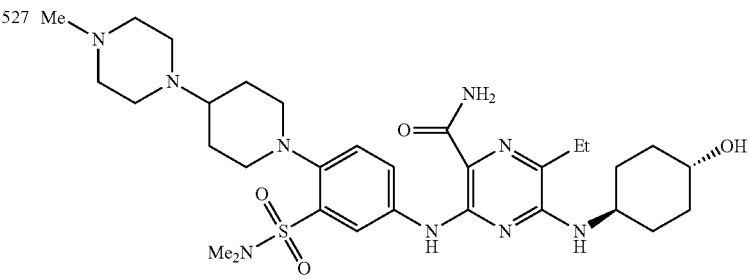 |
| 528 | 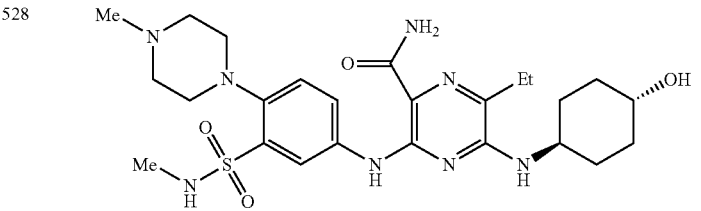 |
| 529 | 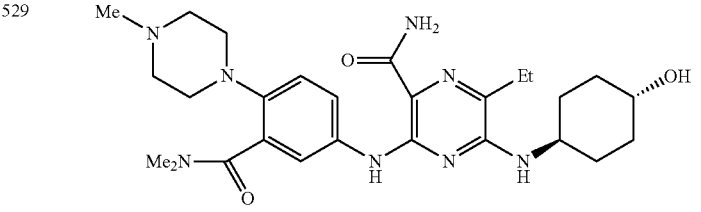 |
| 530 | 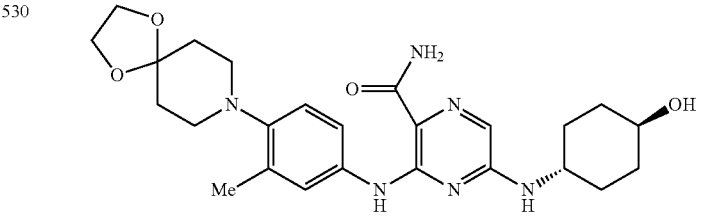 |
| 531 | 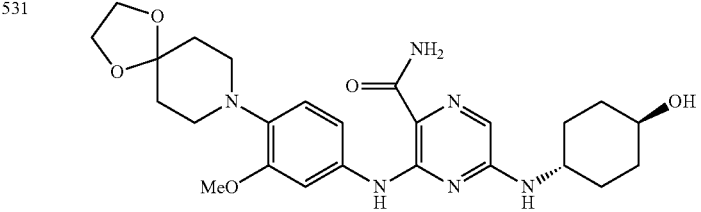 |
| 532 | 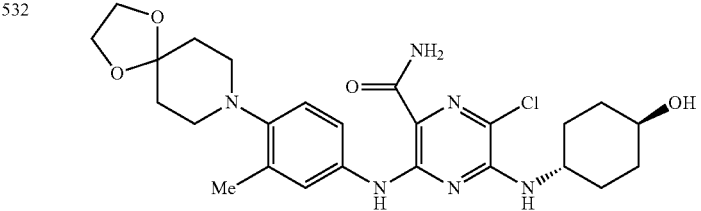 |

TABLE 155-continued

| Ex | Structure |
|---|---|
| 533 | (structure) |

TABLE 156

| Ex | Structure |
|---|---|
| 534 | (structure) |
| 535 | (structure) |
| 536 | (structure) |
| 537 | (structure) |
| 538 | (structure) |

TABLE 156-continued
| Ex | Structure |
|---|---|
| 539 | 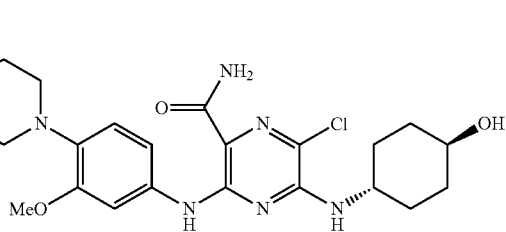 |
| 540 | 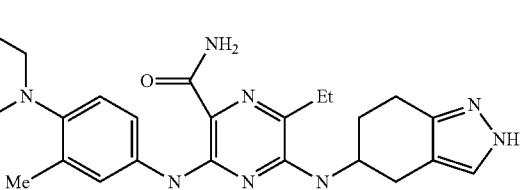 |
TABLE 157
| EX | STRUCTURE |
|---|---|
| 541 | 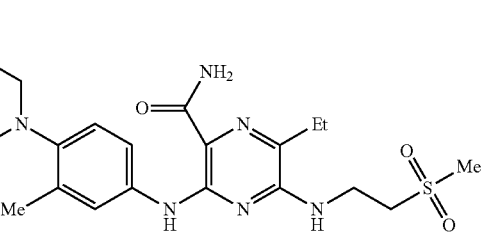 |
| 542 | 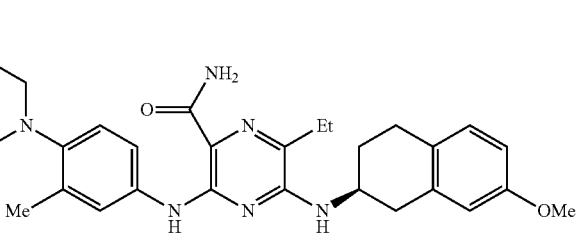  2TsOH |
| 543 | 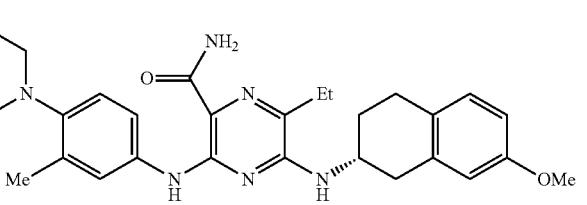  2TsOH |

TABLE 157-continued
| EX | STRUCTURE |
|----|-----------|
| 544 | 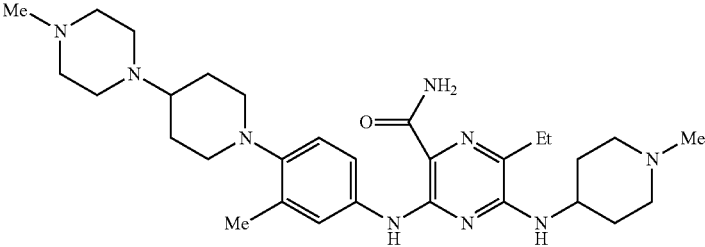 [SMILES: CCc1nc(C(N)=O)c(Nc2ccc(N3CCC(N4CCN(C)CC4)CC3)c(C)c2)nc1NC1CCN(C)CC1] |
| 545 | 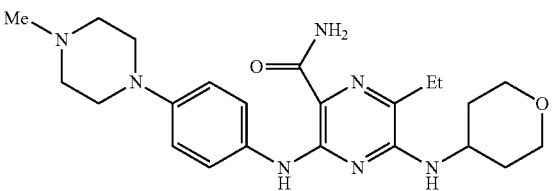 [SMILES: CCc1nc(C(N)=O)c(Nc2ccc(N3CCN(C)CC3)cc2)nc1NC1CCOCC1] |
| 546 | 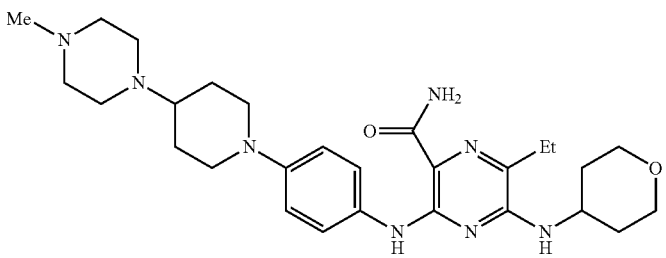 [SMILES: CCc1nc(C(N)=O)c(Nc2ccc(N3CCC(N4CCN(C)CC4)CC3)cc2)nc1NC1CCOCC1] |
| 547 | 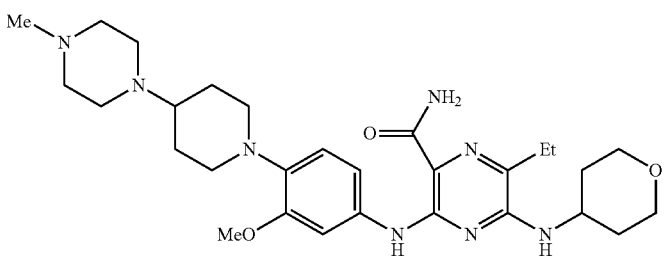 [SMILES: CCc1nc(C(N)=O)c(Nc2ccc(N3CCC(N4CCN(C)CC4)CC3)c(OC)c2)nc1NC1CCOCC1] |
TABLE 158
| EX | STRUCTURE |
|----|-----------|
| 548 | 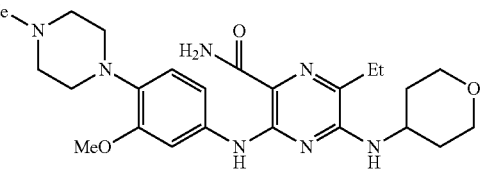 |
| 549 | 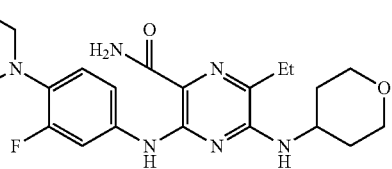 |
| 550 | 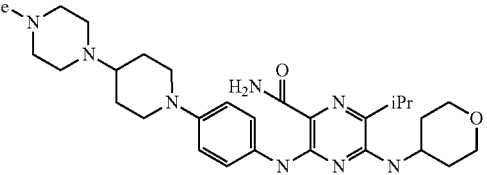 |
| 551 | 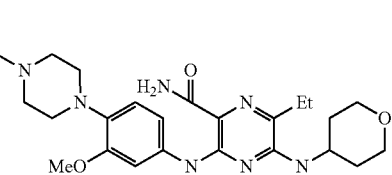 |

TABLE 158-continued
| EX | STRUCTURE |
|---|---|
| 552 | 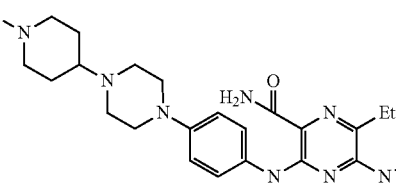 |
| 553 | 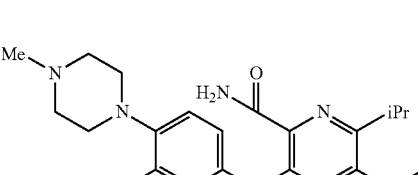 |
TABLE 159
| EX | STRUCTURE |
|---|---|
| 554 | 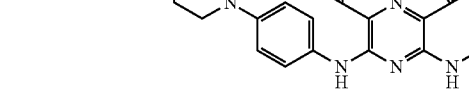 |
| 555 | 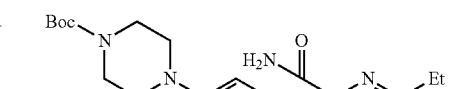 |
| 556 | 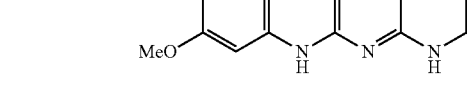 |
| 557 | 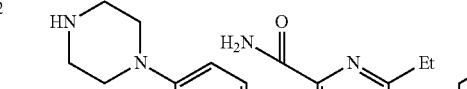 |
TABLE 159-continued
| EX | STRUCTURE |
|---|---|
| 558 | 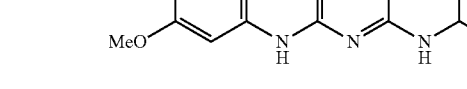 |
TABLE 160
| EX | STRUCTURE |
|---|---|
| 559 | 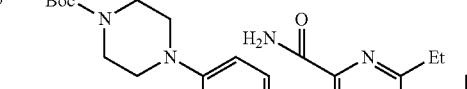 |
| 560 | 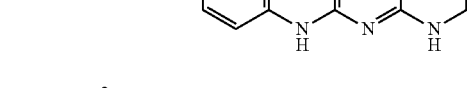 |
| 561 | 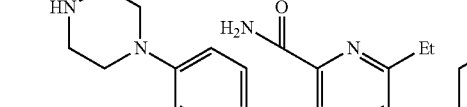 |
| 562 | 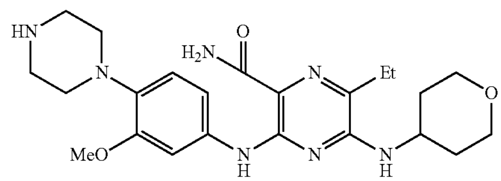 [SMILES: CCc1nc(C(N)=O)c(Nc2ccc(N3CCNCC3)c(OC)c2)nc1NC1CCOCC1] |
| 563 | 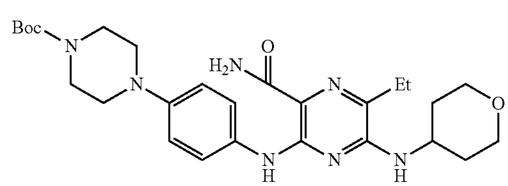 [SMILES: CCc1nc(C(N)=O)c(Nc2ccc(N3CCN(C(=O)OC(C)(C)C)CC3)cc2)nc1NC1CCOCC1] |
| 564 | 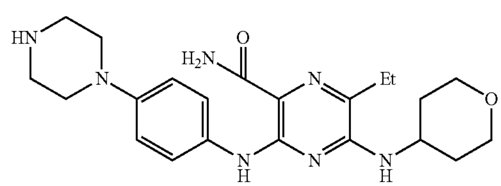 [SMILES: CCc1nc(C(N)=O)c(Nc2ccc(N3CCNCC3)cc2)nc1NC1CCOCC1] |

TABLE 161

| EX | STRUCTURE |
|---|---|
| 565 | (structure) HFM |
| 566 | (structure) HFM |
| 567 | (structure) HFM |
| 568 | (structure) HFM |
| 569 | (structure) HFM |

TABLE 162

| EX | STRUCTURE |
|---|---|
| 570 | (structure) HFM |

TABLE 162-continued
| EX | STRUCTURE |
|---|---|
| 571 | 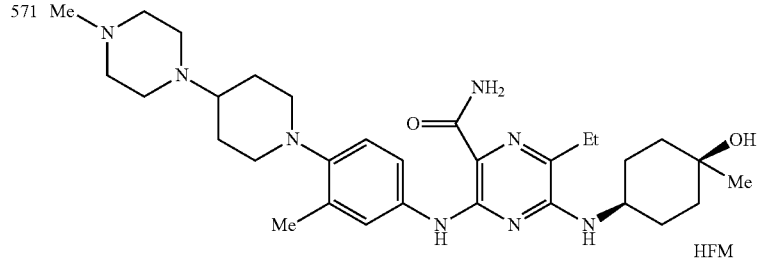 HFM |
| 572 | 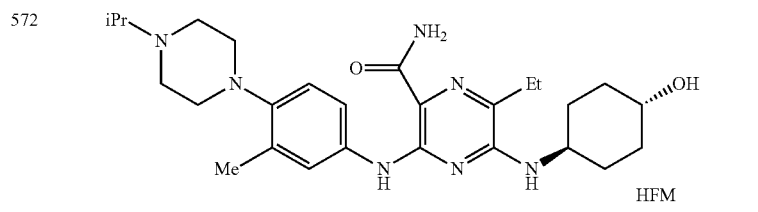 HFM |
| 573 | 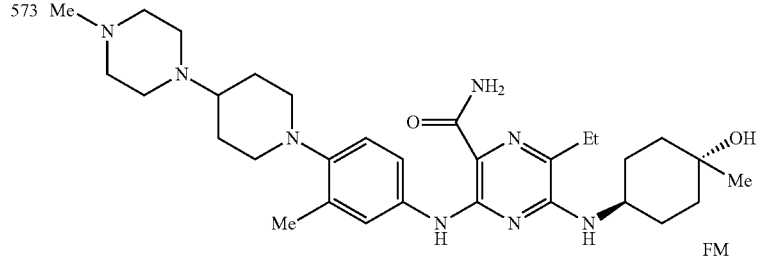 FM |
| 574 | 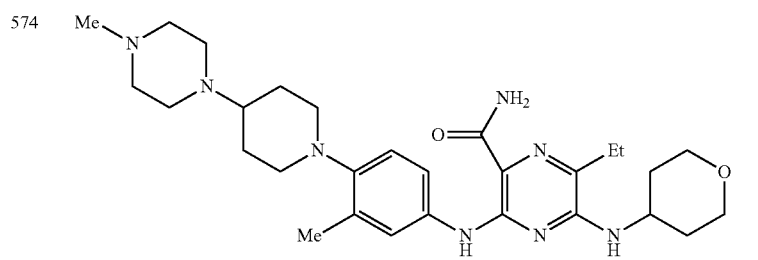 HFM |
TABLE 163
| EX | STRUCTURE |
|---|---|
| 575 | 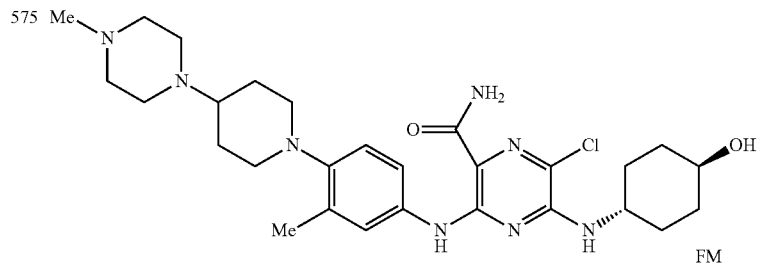 FM |

TABLE 163-continued
| EX | STRUCTURE |
|---|---|
| 576 | 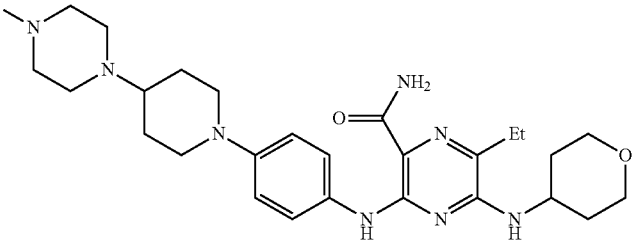 HFM |
| 577 | 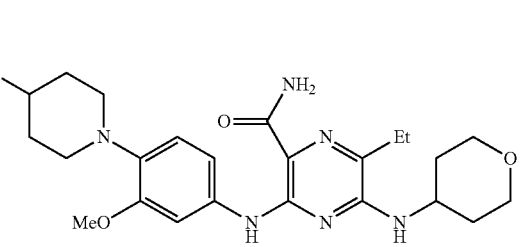 HFM |
| 578 | 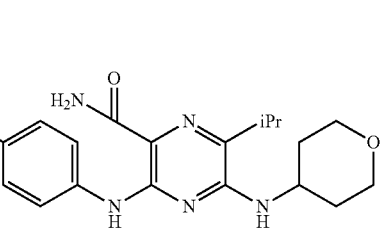 HFM |
| 579 | 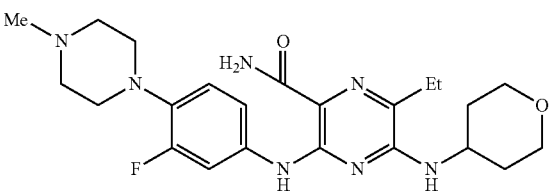 HFM |
| TABLE 164 | | TABLE 164-continued | |
|---|---|---|---|
| EX | STRUCTURE | EX | STRUCTURE |
| 580 | 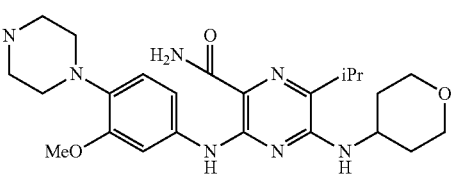 HFM | 581 | 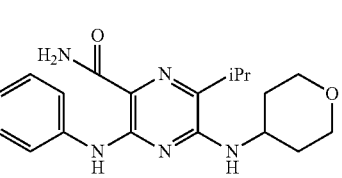 HFM |

TABLE 164-continued

| EX | STRUCTURE |
|---|---|
| 582 | Me-N-piperidine-N-piperazine-phenyl(Me)-NH-pyrazine(CONH2)(Et)-NH-tetrahydropyran  HFM |

TABLE 165

| Ex | Syn | Data |
|---|---|---|
| 1 | Ex4 | ESI+: 451 |
| 2 | Ex4 | ESI+: 463 |
| 3 | Ex4 | ESI+: 477 |
| 4 | Ex4 | ESI+: 491 |
| 5 | Ex4 | ESI+: 493 |
| 6 | Ex4 | ESI+: 509 |
| 7 | Ex4 | ESI+: 423 |
| 8 | Ex4 | ESI+: 449 |
| 9 | Ex4 | ESI+: 477 |
| 10 | Ex4 | FAB+: 450 |
| 11 | Ex4 | FAB+: 450 |
| 12 | Ex4 | FAB+: 449 |
| 13 | Ex4 | ESI+: 449 |
| 14 | Ex4 | ESI+: 449 |
| 15 | Ex4 | ESI+: 449 |
| 16 | Ex4 | ESI+: 436 |
| 17 | Ex4 | ESI+: 436 |
| 18 | Ex4 | ESI+: 436 |
| 19 | Ex19 | ESI+: 449 |
| 20 | Ex4 | ESI+: 435 |
| 21 | Ex4 | ESI+: 435 |
| 22 | Ex4 | ESI+: 463 |
| 23 | Ex37 | ESI+: 639 |
| 24 | Ex4 | ESI+: 435 |
| 25 | Ex4 | ESI+: 435 |
| 26 | Ex4 | ESI+: 421 |
| 27 | Ex4 | ESI+: 421 |
| 28 | Ex37 | ESI+: 535 |
| 29 | Ex29 | ESI+: 435 |
| 30 | Ex405 | FAB+: 477 |
| 31 | Ex31 | FAB+: 513 |
| 32 | Ex4 | ESI+: 477 |
| 33 | Ex4 | ESI+: 477 |
| 34 | Ex4 | ESI+: 372 |
| 35 | Ex4 | FAB+: 436 |
| 36 | Ex4 | ESI+: 400 |
| 37 | Ex37 | ESI+: 414 |
| 38 | Ex4 | ESI+: 428 |
| 39 | Ex4 | ESI+: 449 |
| 40 | Ex4 | ESI+: 463 |
| 41 | Ex4 | ESI+: 437 |
| 42 | Ex4 | ESI+: 436 |
| 43 | Ex4 | ESI−: 400 |
| 44 | Ex4 | ESI+: 463 |
| 45 | Ex4 | ESI+: 449 |
| 46 | Ex4 | ESI+: 464 |
| 47 | Ex4 | ESI+: 392 |
| 48 | Ex4 | ESI+: 450 |
| 49 | Ex4 | ESI+: 426 |
| 50 | Ex4 | ESI+: 468 |
| 51 | Ex4 | ESI+: 454 |
| 52 | Ex4 | ESI+: 489 |
| 53 | Ex4 | FAB+: 388 |
| 54 | Ex4 | FAB+: 450 |
| 55 | Ex4 | ESI+: 449 |
| 56 | Ex4 | ESI+: 470 |
| 57 | Ex4 | ESI+: 456 |
| 58 | Ex4 | ESI+: 468 |
| 59 | Ex4 | ESI+: 442 |
| 60 | Ex4 | ESI+: 414 |
| 61 | Ex4 | ESI+: 484 |
| 62 | Ex4 | ESI+: 470 |
| 63 | Ex4 | ESI+: 492 |
| 64 | Ex4 | ESI+: 504 |
| 65 | Ex4 | ESI+: 448 |
| 66 | Ex4 | ESI+: 490 |

TABLE 166

| Ex | Syn | Data |
|---|---|---|
| 67 | Ex4 | ESI+: 408 |
| 68 | Ex4 | ESI+: 434 |
| 69 | Ex4 | FAB+: 382 |
| 70 | Ex4 | FAB+: 409 |
| 71 | Ex4 | ESI+: 381 |
| 72 | Ex4 | FAB+: 410 |
| 73 | Ex4 | ESI+: 478 |
| 74 | Ex4 | ESI+: 506 |
| 75 | Ex4 | ESI+: 518 |
| 76 | Ex4 | ESI+: 492 |
| 77 | Ex4 | ESI+: 464 |
| 78 | Ex4 | ESI+: 502 |
| 79 | Ex4 | ESI+: 476 |
| 80 | Ex4 | ESI+: 482 |
| 81 | Ex4 | ESI+: 456 |
| 82 | Ex4 | ESI+: 428 |
| 83 | Ex4 | ESI+: 469, 471 |
| 84 | Ex84 | ESI+: 447 |
| 85 | Ex84 | ESI+: 433 |
| 86 | Ex84 | ESI+: 434 |
| 87 | Ex4 | ESI+: 434 |
| 88 | Ex4 | ESI+: 392 |
| 89 | Ex84 | ESI+: 400 |
| 90 | Ex4 | ESI+: 372 |
| 91 | Ex4 | ESI+: 520 |
| 92 | Ex4 | ESI+: 508 |
| 93 | Ex4 | ESI+: 488 |
| 94 | Ex4 | ESI+: 434 |
| 95 | Ex4 | ESI+: 462 |
| 96 | Ex4 | ESI+: 446 |
| 97 | Ex4 | ESI+: 472 |
| 98 | Ex4 | ESI+: 474 |
| 99 | Ex4 | ESI+: 460 |
| 100 | Ex4 | ESI+: 392 |
| 101 | Ex84 | FAB+: 419 |
| 102 | Ex84 | FAB+: 475 |
| 103 | Ex84 | FAB+: 448 |
| 104 | Ex4 | ESI+: 426 |
| 105 | Ex4 | ESI+: 426 |
| 106 | Ex4 | ESI+: 434 |
| 107 | Ex4 | ESI+: 422 |
| 108 | Ex84 | ESI+: 433 |
| 109 | Ex84 | ESI+: 448 |
| 110 | Ex84 | ESI+: 448 |
| 111 | Ex84 | FAB+: 406 |
| 112 | Ex146 | ESI+: 420 |
| 113 | Ex4 | ESI+: 436 |
| 114 | Ex4 | ESI+: 358 |
| 115 | Ex4 | ESI+: 392 |
| 116 | Ex4 | ESI+: 392 |
| 117 | Ex84 | ESI+: 423 |
| 118 | Ex4 | ESI+: 494 |
| 119 | Ex4 | ESI+: 508 |
| 120 | Ex4 | ESI+: 482 |
| 121 | Ex4 | ESI+: 428 |
| 122 | Ex4 | ESI+: 484 |
| 123 | Ex4 | ESI+: 468 |
| 124 | Ex4 | ESI+: 414 |
| 125 | Ex4 | ESI+: 468 |
| 126 | Ex4 | ESI+: 418 |
| 127 | Ex4 | ESI+: 486 |
| 128 | Ex4 | ESI+: 482 |
| 129 | Ex4 | ESI+: 522 |
| 130 | Ex4 | ESI+: 480 |

TABLE 166-continued

| Ex | Syn | Data |
| --- | --- | --- |
| 131 | Ex4 | FAB+: 508 |
| 132 | Ex4 | ESI+: 468 |

TABLE 167

| Ex | Syn | Data |
| --- | --- | --- |
| 133 | Ex4 | FAB+: 414 |
| 134 | Ex4 | ESI+: 522 |
| 135 | Ex4 | FAB+: 534 |
| 136 | Ex4 | FAB+: 444 |
| 137 | Ex4 | ESI+: 498 |
| 138 | Ex4 | ESI+: 482 |
| 139 | Ex4 | FAB+: 428 |
| 140 | Ex4 | ESI+: 536 |
| 141 | Ex4 | ESI+: 460 |
| 142 | Ex4 | ESI+: 432 |
| 143 | Ex4 | ESI+: 488 |
| 144 | Ex4 | ESI+: 474 |
| 145 | Ex4 | ESI+: 460 |
| 146 | Ex146 | ESI+: 468 |
| 147 | Ex84 | ESI+: 486 |
| 148 | Ex84 | ESI+: 448 |
| 149 | Ex84 | ESI+: 434 |
| 150 | Ex84 | ESI+: 427 |
| 151 | Ex84 | ESI+: 535 |
| 152 | Ex84 | ESI+: 427 |
| 153 | Ex84 | ESI+: 427 |
| 154 | Ex4 | ESI+: 448 |
| 155 | Ex84 | ESI+: 447 |
| 156 | Ex84 | ESI+: 443 |
| 157 | Ex84 | ESI+: 433 |
| 158 | Ex84 | ESI+: 433 |
| 159 | Ex159 | ESI+: 440 |
| 160 | Ex84 | ESI+: 427 |
| 161 | Ex84 | ESI+: 481 |
| 162 | Ex84 | ESI+: 427 |
| 163 | Ex84 | ESI+: 447 |
| 164 | Ex84 | ESI+: 406 |
| 165 | Ex146 | ESI+: 448 |
| 166 | Ex84 | ESI+: 434 |
| 167 | Ex84 | ESI+: 461 |
| 168 | Ex84 | ESI+: 497 |
| 169 | Ex84 | ESI+: 461 |
| 170 | Ex84 | ESI+: 448 |
| 171 | Ex84 | FAB+: 431 |
| 172 | Ex84 | FAB+: 447 |
| 173 | Ex4 | FAB−: 405 |
| 174 | Ex84 | FAB−: 404 |
| 175 | Ex84 | FAB+: 479 |
| 176 | Ex84 | FAB+: 413 |
| 177 | Ex84 | ESI+: 454 |
| 178 | Ex146 | ESI+: 407 |
| 179 | Ex84 | ESI+: 454 |
| 180 | Ex159 | ESI+: 488 |
| 181 | Ex181 | ESI+: 484, 486 |
| 182 | Ex84 | ESI+: 357 |
| 183 | Ex84 | ESI+: 441 |
| 184 | Ex84 | ESI+: 469 |
| 185 | Ex84 | ESI+: 469 |
| 186 | Ex84 | ESI+: 441 |
| 187 | Ex84 | ESI+: 427 |
| 188 | Ex84 | ESI+: 346 |
| 189 | Ex84 | ESI+: 431 |
| 190 | Ex190 | ESI+: 532 |
| 191 | Ex84 | ESI+: 371 |
| 192 | Ex146 | APCI/ESI+: 371 |
| 193 | Ex84 | ESI+: 434 |
| 194 | Ex84 | ESI+: 434 |
| 195 | Ex196 | ESI+: 419 |
| 196 | Ex196 | ESI+: 433 |
| 197 | Ex196 | ESI+: 447 |
| 198 | Ex196 | ESI+: 447 |

TABLE 168

| Ex | Syn | Data |
| --- | --- | --- |
| 199 | Ex196 | ESI+: 461 |
| 200 | Ex196 | ESI+: 515 |
| 201 | Ex196 | ESI+: 523 |
| 202 | Ex196 | ESI+: 447 |
| 203 | Ex196 | ESI+: 475 |
| 204 | Ex196 | ESI+: 491 |
| 205 | Ex196 | ESI+: 433 |
| 206 | Ex196 | ESI+: 433 |
| 207 | Ex196 | ESI+: 418 |
| 208 | Ex196 | ESI+: 448 |
| 209 | Ex196 | ESI+: 448 |
| 210 | Ex196 | ESI+: 496 |
| 211 | Ex196 | ESI+: 405 |
| 212 | Ex196 | ESI+: 405 |
| 213 | Ex196 | ESI+: 419 |
| 214 | Ex196 | ESI+: 495 |
| 215 | Ex196 | ESI+: 495 |
| 216 | Ex196 | ESI+: 419 |
| 217 | Ex196 | ESI+: 447 |
| 218 | Ex196 | ESI+: 420 |
| 219 | Ex196 | ESI+: 434 |
| 220 | Ex196 | ESI+: 438 |
| 221 | Ex196 | ESI+: 391 |
| 222 | Ex196 | ESI+: 405 |
| 223 | Ex196 | ESI+: 473 |
| 224 | Ex196 | ESI+: 447 |
| 225 | Ex196 | ESI+: 447 |
| 226 | Ex196 | ESI+: 449 |
| 227 | Ex196 | ESI+: 463 |
| 228 | Ex196 | ESI+: 515 |
| 229 | Ex196 | ESI+: 523 |
| 230 | Ex196 | ESI+: 433 |
| 231 | Ex196 | ESI+: 433 |
| 232 | Ex196 | ESI+: 433 |
| 233 | Ex196 | ESI+: 433 |
| 234 | Ex196 | ESI+: 433 |
| 235 | Ex196 | ESI+: 434 |
| 236 | Ex196 | ESI+: 434 |
| 237 | Ex196 | ESI+: 436 |
| 238 | Ex196 | ESI+: 448 |
| 239 | Ex196 | ESI+: 448 |
| 240 | Ex196 | ESI+: 447 |
| 241 | Ex196 | ESI+: 447 |
| 242 | Ex196 | ESI+: 420 |
| 243 | Ex196 | ESI+: 420 |
| 244 | Ex196 | ESI+: 405 |
| 245 | Ex196 | ESI+: 406 |
| 246 | Ex196 | ESI+: 462 |
| 247 | Ex196 | ESI+: 476 |
| 248 | Ex196 | ESI+: 447 |
| 249 | Ex196 | ESI+: 462 |
| 250 | Ex196 | ESI+: 463 |
| 251 | Ex196 | ESI+: 448 |
| 252 | Ex196 | ESI+: 433 |
| 253 | Ex196 | ESI+: 447 |
| 254 | Ex196 | ESI+: 434 |
| 255 | Ex196 | ESI+: 379 |
| 256 | Ex196 | ESI+: 393 |
| 257 | Ex196 | ESI+: 407 |
| 258 | Ex196 | ESI+: 421 |
| 259 | Ex196 | ESI+: 421 |
| 260 | Ex196 | ESI+: 421 |
| 261 | Ex196 | ESI+: 407 |
| 262 | Ex196 | ESI+: 380 |
| 263 | Ex196 | ESI+: 394 |
| 264 | Ex196 | ESI+: 408 |

TABLE 169

| Ex | Syn | Data |
| --- | --- | --- |
| 265 | Ex196 | ESI+: 394 |
| 266 | Ex196 | ESI+: 410 |
| 267 | Ex196 | ESI+: 394 |
| 268 | Ex196 | ESI+: 438 |

TABLE 169-continued

| Ex | Syn | Data |
|---|---|---|
| 269 | Ex196 | ESI+: 419 |
| 270 | Ex196 | ESI+: 481 |
| 271 | Ex196 | ESI+: 406 |
| 272 | Ex196 | ESI+: 434 |
| 273 | Ex196 | ESI+: 421 |
| 274 | Ex196 | ESI+: 394 |
| 275 | Ex196 | ESI+: 442 |
| 276 | Ex196 | ESI+: 413 |
| 277 | Ex196 | ESI+: 426 |
| 278 | Ex196 | ESI+: 456 |
| 279 | Ex196 | ESI+: 427 |
| 280 | Ex196 | ESI+: 528 |
| 281 | Ex84 | ESI+: 427 |
| 282 | Ex84 | ESI+: 455 |
| 283 | Ex84 | ESI+: 370 |
| 284 | Ex84 | ESI+: 567 |
| 285 | Ex84 | ESI+: 463 |
| 286 | Ex84 | ESI+: 483 |
| 287 | Ex84 | ESI+: 447 |
| 288 | Ex84 | ESI+: 443 |
| 289 | Ex84 | ESI+: 463 |
| 290 | Ex84 | ESI+: 535 |
| 291 | Ex84 | ESI+: 427 |
| 292 | Ex84 | ESI+: 396 |
| 293 | Ex84 | ESI+: 414 |
| 294 | Ex84 | ESI+: 525 |
| 295 | Ex84 | ESI+: 549 |
| 296 | Ex146 | ESI+: 448 |
| 297 | Ex84 | ESI+: 433 |
| 298 | Ex84 | ESI+: 407 |
| 299 | Ex84 | ESI+: 378 |
| 300 | Ex84 | ESI+: 404 |
| 301 | Ex84 | ESI+: 461 |
| 302 | Ex302 | ESI+: 489 |
| 303 | Ex84 | ESI+: 424 |
| 304 | Ex84 | ESI+: 396 |
| 305 | Ex84 | ESI+: 412 |
| 306 | Ex84 | ESI+: 407 |
| 307 | Ex84 | ESI+: 547 |
| 308 | Ex84 | ESI+: 429 |
| 309 | Ex309 | ESI+: 399 |
| 310 | Ex310 | ESI+: 453 |
| 311 | Ex84 | ESI+: 549 |
| 312 | Ex84 | ESI+: 428 |
| 313 | Ex84 | ESI+: 496 |
| 314 | Ex84 | ESI+: 494 |
| 315 | Ex84 | ESI+: 427 |
| 316 | Ex84 | ESI+: 480 |
| 317 | Ex84 | ESI+: 466 |
| 318 | Ex84 | ESI+: 494 |
| 319 | Ex84 | ESI+: 401 |
| 320 | Ex84 | ESI+: 447 |
| 321 | Ex84 | ESI+: 440 |
| 322 | Ex302 | ESI+: 468 |
| 323 | Ex146 | ESI+: 502 |
| 324 | Ex84 | ESI+: 440 |
| 325 | Ex84 | ESI+: 454 |
| 326 | Ex84 | ESI+: 526 |
| 327 | Ex84 | ESI+: 414 |
| 328 | Ex84 | ESI+: 410 |
| 329 | Ex84 | ESI+: 441 |
| 330 | Ex84 | ESI+: 414 |

TABLE 170

| Ex | Syn | Data |
|---|---|---|
| 331 | Ex84 | ESI+: 409 |
| 332 | Ex84 | ESI+: 508 |
| 333 | Ex84 | ESI+: 385 |
| 334 | Ex84 | ESI+: 482 |
| 335 | Ex84 | ESI+: 480 |
| 336 | Ex84 | ESI+: 468 |
| 337 | Ex84 | ESI+: 453 |
| 338 | Ex84 | ESI+: 512 |

TABLE 170-continued

| Ex | Syn | Data |
|---|---|---|
| 339 | Ex84 | ESI+: 484 |
| 340 | Ex84 | ESI+: 567 |
| 341 | Ex84 | ESI+: 537 |
| 342 | Ex84 | ESI+: 466 |
| 343 | Ex343 | ESI+: 468 |
| 344 | Ex84 | ESI+: 512 |
| 345 | Ex159 | ESI+: 546 |
| 346 | Ex381 | ESI+: 446 |
| 347 | Ex84 | ESI+: 454 |
| 348 | Ex84 | ESI+: 581 |
| 349 | Ex84 | ESI+: 581 |
| 350 | Ex84 | ESI+: 570 |
| 351 | Ex146 | ESI+: 549 |
| 352 | Ex84 | ESI+: 449 |
| 353 | Ex84 | ESI+: 463 |
| 354 | Ex84 | ESI+: 522 |
| 355 | Ex84 | ESI+: 484 |
| 356 | Ex84 | ESI+: 539 |
| 357 | Ex84 | ESI+: 441 |
| 358 | Ex381 | ESI+: 439 |
| 359 | Ex84 | ESI+: 439 |
| 360 | Ex84 | ESI+: 636 |
| 361 | Ex84 | ESI+: 469 |
| 362 | Ex84 | ESI+: 468 |
| 363 | Ex84 | ESI+: 538 |
| 364 | Ex84 | ESI+: 560 |
| 365 | Ex84 | ESI+: 455 |
| 366 | Ex84 | ESI+: 476 |
| 367 | Ex84 | ESI+: 455 |
| 368 | Ex84 | ESI+: 442 |
| 369 | Ex84 | ESI+: 477 |
| 370 | Ex146 | ESI+: 605 |
| 371 | Ex84 | ESI+: 538 |
| 372 | Ex84 | ESI+: 560 |
| 373 | Ex84 | ESI+: 631 |
| 374 | Ex84 | ESI+: 456 |
| 375 | Ex84 | ESI+: 455 |
| 376 | Ex84 | ESI+: 552 |
| 377 | Ex84 | ESI+: 468 |
| 378 | Ex84 | ESI+: 551 |
| 379 | Ex84 | ESI+: 464 |
| 380 | Ex84 | ESI+: 442 |
| 381 | Ex381 | ESI+: 469 |
| 382 | Ex84 | ESI+: 569 |
| 383 | Ex84 | ESI+: 484 |
| 384 | Ex84 | ESI+: 522 |
| 385 | Ex84 | ESI+: 617 |
| 386 | Ex84 | ESI+: 644 |
| 387 | Ex84 | ESI+: 453 |
| 388 | Ex343 | ESI+: 619 |
| 389 | Ex343 | ESI+: 646 |
| 390 | Ex84 | ESI−: 488 |
| 391 | Ex84 | ESI+: 482 |
| 392 | Ex84 | ESI+: 565 |
| 393 | Ex84 | ESI+: 540 |
| 394 | Ex381 | ESI+: 440 |
| 395 | Ex302 | ESI+: 522 |
| 396 | Ex302 | ESI+: 524 |

TABLE 171

| Ex | Syn | Data |
|---|---|---|
| 397 | Ex84 | ESI+: 543 |
| 398 | Ex84 | ESI−: 479 |
| 399 | Ex84 | ESI+: 562 |
| 400 | Ex84 | ESI+: 434, 436 |
| 401 | Ex84 | ESI+: 484 |
| 402 | Ex84 | ESI+: 536 |
| 403 | Ex84 | ESI+: 537 |
| 404 | Ex84 | ESI+: 522 |
| 405 | Ex405 | ESI+: 481 |
| 406 | Ex84 | ESI+: 536 |
| 407 | Ex84 | ESI+: 536 |
| 408 | Ex84 | ESI+: 536 |

TABLE 171-continued

| Ex | Syn | Data |
|---|---|---|
| 409 | Ex84 | ESI+: 550 |
| 410 | Ex84 | ESI+: 484 |
| 411 | Ex84 | ESI+: 441 |
| 412 | Ex84 | ESI+: 456 |
| 413 | Ex84 | ESI+: 468 |
| 414 | Ex84 | ESI+: 482 |
| 415 | Ex31 | ESI+: 518 |
| 416 | Ex302 | ESI+: 482 |
| 417 | Ex302 | ESI+: 540 |
| 418 | Ex84 | ESI+: 607 |
| 419 | Ex381 | ESI+: 508 |
| 420 | Ex84 | ESI+: 554 |
| 421 | Ex381 | ESI+: 454 |
| 422 | Ex146 | ESI+: 535 |
| 423 | Ex302 | ESI+: 590 |
| 424 | Ex302 | ESI+: 536 |
| 425 | Ex302 | ESI+: 550 |
| 426 | Ex302 | ESI+: 496 |
| 427 | Ex84 | ESI+: 496 |
| 428 | Ex84 | ESI+: 555 |
| 429 | Ex84 | ESI+: 576 |
| 430 | Ex84 | ESI+: 518 |
| 431 | Ex302 | ESI+: 521 |
| 432 | Ex84 | ESI+: 553 |
| 433 | Ex381 | ESI+: 453 |
| 434 | Ex31 | ESI+: 531 |
| 435 | Ex84 | ESI+: 564 |
| 436 | Ex436 | ESI+: 550 |
| 437 | Ex436 | ESI+: 550 |
| 438 | Ex438 | ESI+: 655 |
| 439 | Ex438 | ESI+: 655 |
| 440 | Ex84 | ESI+: 453 |
| 441 | Ex84 | ESI+: 483 |
| 442 | Ex84 | ESI+: 488 |
| 443 | Ex84 | ESI+: 483 |
| 444 | Ex84 | ESI+: 566 |
| 445 | Ex84 | ESI+: 544 |
| 446 | Ex84 | ESI+: 597 |
| 447 | Ex302 | ESI+: 602 |
| 448 | Ex84 | ESI+: 550 |
| 449 | Ex302 | ESI+: 642 |
| 450 | Ex302 | ESI−: 636 |
| 451 | Ex302 | ESI+: 467 |
| 452 | Ex84 | ESI+: 482 |
| 453 | Ex84 | ESI+: 609 |
| 454 | Ex84 | ESI+: 482 |
| 455 | Ex84 | ESI+: 607 |
| 456 | Ex84 | ESI+: 536 |
| 457 | Ex84 | ESI+: 566 |
| 458 | Ex84 | APCI/ESI+: 511 |
| 459 | Ex84 | ESI+: 581 |
| 460 | Ex534 | ESI+: 507 |
| 461 | Ex84 | ESI+: 522 |
| 462 | Ex405 | ESI+: 549 |

TABLE 172

| Ex | Syn | Data |
|---|---|---|
| 463 | Ex405 | ESI+: 641 |
| 464 | Ex302 | ESI+: 644 |
| 465 | Ex84 | ESI+: 561 |
| 466 | Ex84 | ESI+: 565 |
| 467 | Ex84 | ESI+: 570 |
| 468 | Ex381 | ESI+: 470 |
| 469 | Ex302 | ESI+: 495 |
| 470 | Ex302 | ESI+: 535 |
| 471 | Ex302 | ESI+: 449 |
| 472 | Ex84 | ESI+: 449 |
| 473 | Ex84 | ESI+: 607 |
| 474 | Ex381 | ESI+: 507 |
| 475 | Ex84 | ESI+: 482 |
| 476 | Ex84 | ESI+: 471 |
| 477 | Ex84 | ESI+: 469 |
| 478 | Ex84 | ESI+: 567 |

TABLE 172-continued

| Ex | Syn | Data |
|---|---|---|
| 479 | Ex84 | ESI+: 554 |
| 480 | Ex84 | ESI+: 469 |
| 481 | Ex84 | ESI+: 499 |
| 482 | Ex159 | ESI+: 533 |
| 483 | Ex84 | ESI+: 565 |
| 484 | Ex84 | ESI+: 511 |
| 485 | Ex84 | ESI+: 547 |
| 486 | Ex84 | ESI+: 530 |
| 487 | Ex84 | ESI+: 525 |
| 488 | Ex302 | ESI+: 512 |
| 489 | Ex302 | ESI+: 552 |
| 490 | Ex84 | ESI+: 579 |
| 491 | Ex84 | ESI+: 579 |
| 492 | Ex302 | ESI+: 608 |
| 493 | Ex84 | ESI+: 593 |
| 494 | Ex84 | ESI+: 593 |
| 495 | Ex495 | ESI+: 489 |
| 496 | Ex84 | FAB+: 553 |
| 497 | Ex84 | ESI+: 553 |
| 498 | Ex84 | ESI+: 540 |
| 499 | Ex499 | ESI+: 573 |
| 500 | Ex84 | FAB+: 540 |
| 501 | Ex84 | ESI+: 485 |
| 502 | Ex84 | ESI+: 499 |
| 503 | Ex84 | ESI+: 512 |
| 504 | Ex84 | ESI+: 498 |
| 505 | Ex84 | ESI+: 567 |
| 506 | Ex84 | ESI+: 551 |
| 507 | Ex84 | APCI/ESI+: 626 |
| 508 | Ex508 | APCI/ESI+: 446 |
| 509 | Ex84 | ESI+: 539 |
| 510 | Ex84 | ESI+: 567 |
| 511 | Ex84 | ESI+: 554 |
| 512 | Ex84 | ESI+: 537 |
| 513 | Ex84 | ESI+: 611 |
| 514 | Ex302 | ESI+: 521 |
| 515 | Ex84 | ESI+: 532 |
| 516 | Ex84 | ESI+: 568 |
| 517 | Ex146 | ESI+: 651 |
| 518 | Ex381 | ESI+: 551 |
| 519 | Ex84 | ESI+: 572 |
| 520 | Ex84 | ESI+: 663 |
| 521 | Ex84 | ESI+: 594 |
| 522 | Ex84 | ESI+: 608 |
| 523 | Ex84 | ESI+: 494 |
| 524 | Ex84 | ESI+: 514 |
| 525 | Ex84 | ESI+: 561 |
| 526 | Ex84 | ESI+: 511 |
| 527 | Ex84 | ESI+: 644 |
| 528 | Ex84 | ESI+: 547 |

TABLE 173

| Ex | Syn | Data |
|---|---|---|
| 529 | Ex84 | ESI+: 525 |
| 530 | Ex84 | ESI+: 483 |
| 531 | Ex84 | ESI+: 499 |
| 532 | Ex159 | ESI+: 517 |
| 533 | Ex159 | ESI+: 533 |
| 534 | Ex534 | ESI+: 536 |
| 535 | Ex84 | ESI+: 564 |
| 536 | Ex495 | ESI+: 473 |
| 537 | Ex495 | ESI+: 489 |
| 538 | Ex499 | ESI+: 557 |
| 539 | Ex499 | ESI+: 573 |
| 540 | Ex84 | ESI+: 573 |
| 541 | Ex84 | ESI+: 559 |
| 542 | Ex84 | APCI/ESI+: 613 |
| 543 | Ex84 | ESI+: 613 |
| 544 | Ex84 | ESI+: 550 |
| 545 | Ex84 | ESI+: 440 |
| 546 | Ex84 | ESI+: 523 |
| 547 | Ex84 | ESI+: 553 |
| 548 | Ex84 | ESI+: 470 |

TABLE 173-continued

| Ex | Syn | Data |
|---|---|---|
| 549 | Ex343 | ESI+: 537 |
| 550 | Ex84 | ESI+: 458 |
| 551 | Ex302 | ESI+: 553 |
| 552 | Ex302 | ESI+: 523 |
| 553 | Ex84 | ESI+: 484 |
| 554 | Ex84 | ESI+: 454 |
| 555 | Ex84 | ESI+: 472 |
| 556 | Ex84 | ESI+: 567 |
| 557 | Ex84 | ESI+: 541 |
| 558 | Ex84 | ESI+: 537 |
| 559 | Ex84 | ESI+: 555 |
| 560 | Ex84 | APCI/ESI+: 535 |
| 561 | Ex84 | ESI+: 556 |
| 562 | Ex381 | ESI+: 456 |
| 563 | Ex84 | ESI+: 524 |
| 564 | Ex381 | ESI+: 426 |
| 565 | Ex84 | ESI+: 454 |
| 566 | Ex84 | ESI+: 537 |
| 567 | Ex343 | ESI+: 468 |
| 568 | Ex146 | ESI+: 605 |
| 569 | Ex84 | ESI+: 551 |
| 570 | Ex343 | ESI+: 619 |
| 571 | Ex84 | ESI+: 565 |
| 572 | Ex302 | ESI+: 496 |
| 573 | Ex84 | ESI+: 565 |
| 574 | Ex84 | ESI+: 537 |
| 575 | Ex499 | ESI+: 557 |
| 576 | Ex84 | ESI+: 523 |
| 577 | Ex84 | ESI+: 553 |
| 578 | Ex343 | ESI+: 537 |
| 579 | Ex84 | ESI+: 441 |
| 580 | Ex84 | ESI+: 484 |
| 581 | Ex84 | ESI+: 454 |
| 582 | Ex84 | ESI+: 537 |

TABLE 174

| Ex | Data |
|---|---|
| 86 | $^1$H-NMR (DMSO-d6): 1.19 (3H, t, J = 7.8 Hz), 1..33-1.50 (4H, m), 1.79-1.95 (4H, m), 2.60 (2H, q, J = 7.8 Hz), 3.21 (3H, s), 3.37-3.49 (1H, m), 3.89-4.01 (1H, m), 4.54 (1H, d, J = 4.4 Hz), 6.76 (1H, d, J = 7.9 Hz), 7.33-7.42 (1H, m), 7.44-7.57 (2H, m), 7.58-7.65 (1H, m), 7.96-8.03 (1H, m), 8.15-8.21 (1H, m), 11.59 (1H, s). |
| 110 | $^1$H-NMR (DMSO-d6): 1.13-1.25 (6H, m), 1.46-1.64 (6H, m), 1.79-1.91 (2H, m), 2.61 (2H, q, J = 7.4 Hz), 3.21 (3H, s), 3.94-4.09 (1H, m), 4.26 (1H, s), 6.72 (1H, d, J = 7.9 Hz), 7.33-7.42 (1H, m), 7.44-7.58 (2H, m), 7.59-7.66 (1H, m), 7.98-8.04 (1H, m), 8.16-8.20 (1H, m), 11.58 (1H, s). |
| 284 | $^1$H-NMR (CDCl3): 1.26-1.36 (5H, m), 1.48-1.56 (2H, m), 1.68-1.76 (2H, m), 1.95 (2H, d, J = 11.6 Hz), 2.08 (2H, d, J = 10.4 Hz), 2.26 (2H, d, J = 11.6 Hz), 2.30 (3H, s), 2.30-2.73 (13H, m), 3.64-3.74 (4H, m), 3.93-3.97 (4H, m), 4.52 (1H, d, J = 7.2 Hz), 5.13 (1H, br-s), 6.50 (1H, dd, J = 2.4 Hz, 9.2 Hz), 6.58 (1H, d, J = 2.4 Hz), 7.46 (1H, br-s), 8.39 (1H, d, J = 8.8 Hz), 10.98 (1H, s). |
| 325 | $^1$H-NMR (DMSO-d6): 1.17 (3H, t, J = 7.4 Hz), 1.22-1.48 (4H, m), 1.84-2.00 (4H, m), 2.25 (3H, s), 2.44-2.59 (6H, m), 3.00-3.12 (4H, m), 3.43 (1H, m), 3.80 (1H, m), 4.56 (1H, d, J = 4.7 Hz), 6.63 (1H, d, J = 8.0 Hz), 6.87 (2H, d, J = 9.2 Hz), 7.13 (1H, br), 7.47 (1H, br), 7.51 (2H, d, J = 9.2 Hz), 10.9 (1H, s). |
| 328 | $^1$H-NMR (CDCl3): 1.25-1.67 (7H, m), 2.04 (2H, m), 2.17-2.22 (2H, m), 2.48-2.55 (2H, m), 3.72 (1H, m), 4.03 (3H, s), 4.05 (1H, m), 4.60 (1H, m), 5.19 (1H, m), 7.44 (1H, m), 7.51 (1H, m), 7.62 (1H, m), 7.78 (1H, s), 7.88 (1H, s), 11.14 (1H, br-s). |
| 340 | $^1$H-NMR (CDCl3): 1.22-1.54 (7H, m), 1.74-1.94 (4H, m), 2.01-2.10 (2H, m), 2.16-2.26 (2H, m), 2.30 (3H, s), 2.32-2.74 (13H, m), 3.50 (2H, d, J = 11.4 Hz), 3.65-3.76 (1H, m), 3.87 (3H, s), 3.92-4.03 (1H, m), 4.52 (1H, d, J = 7.3 Hz), 5.12 (1H, br-s), 6.71 (1H, s), 6.84-6.90 (2H, m), 7.45-7.55 (2H, m), 10.74 (1H, s). |

TABLE 175

| Ex | Data |
|---|---|
| 341 | $^1$H-NMR (DMSO-d6): 1.17 (3H, t, J = 7.4 Hz), 1.21-1.60 (6H, m), 1.75-2.00 (6H, m), 2.14 (3H, s), 2.20-2.72 (13H, m), 3.43 (1H, m), 3.58 (2H, m), 3.80 (1H, m), 4.57 (1H, d, J = 4.4 Hz), 6.63 (1H, d, J = 7.3 Hz), 6.86 (2H, d, J = 8.7 Hz), 7.13 (1H, br-s), 7.40-7.60 (3H, m), 10.92 (1H, s). |
| 343 | $^1$H-NMR (DMSO-d6): 1.14 (6H, d, J = 6.6 Hz), 1.21-1.48 (4H, m), 1.85-1.98 (4H, m), 2.22 (3H, s), 2.41-2.48 (4H, m), 2.99-3.18 (5H, m), 3.37-3.48 (1H, m), 3.74-3.87 (1H, m), 4.56 (1H, d, J = 4.7 Hz), 6.67 (1H, d, J = 7.6 Hz), 6.86 (2H, d, J = 9.0 Hz), 7.11-7.18 (1H, m), 7.40-7.47 (1H, m), 7.50 (2H, d, J = 9.0 Hz), 10.91 (1H, s) |
| 347 | $^1$H-NMR (DMSO-d6): 1.10-1.49 (7H, m), 1.80-1.96 (4H, m), 2.22 (3H, s), 2.40-2.61 (6H, m), 3.06-3.18 (4H, m), 3.43 (1H, m), 3.86 (1H, m), 4.56 (1H, d, J = 4.3 Hz), 6.57 (1H, m), 6.63 (1H, d, J = 7.6 Hz), 6.91 (1H, m), 7.10 (1H, m), 7.18 (1H, br), 7.29 (1H, m), 7.51 (1H, br-s), 11.09 (1H, s). |

TABLE 175-continued

| Ex | Data |
|---|---|
| 354 | $^1$H-NMR (DMSO-d6): 1.12-1.32 (5H, m), 1.36-1.50 (2H, m), 1.78-1.96 (4H, m), 2.22 (3H, s), 2.35-2.63 (6H, m), 2.78-2.88 (4H, m), 3.41 (1H, m), 3.87 (1H, m), 4.55 (1H, d, J = 3.9 Hz), 6.68 (1H, d, J = 7.9 Hz), 7.27 (1H, br-s), 7.46 (1H, d, J = 8.7 Hz), 7.56 (1H, br-s), 7.61 (1H, m), 8.18 (1H, m), 11.37 (1H, s) |
| 355 | $^1$H-NMR (DMSO-d6): 1.10-1.32 (5H, m), 1.32-1.50 (2H, m), 1.82-1.96 (4H, m), 2.21 (3H, s), 2.35-2.60 (6H, m), 2.84-2.99 (4H, m), 3.42 (1H, m), 3.81 (3H, s), 3.87 (1H, m), 4.56 (1H, d, J = 4.6 Hz), 6.61 (1H, d, J = 7.8 Hz), 6.79 (1H, d, J = 8.6 Hz), 7.09 (1H, d, J = 2.2 Hz), 7.16 (1H, br-s), 7.24 (1H, dd, J = 8.6, 2.2 Hz), 7.49 (1H, br-s), 11.03 (1H, s) |
| 357 | $^1$H-NMR (DMSO-d6): 1.17 (3H, t, J = 7.4 Hz), 1.21-1.48 (4H, m), 1.84-2.00 (4H, m), 2.55 (2H, q, J = 7.4 Hz), 3.00-3.06 (4H, m), 3.42 (1H, m), 3.69-3.86 (5H, m), 4.58 (1H, d, J = 4.8 Hz), 6.65 (1H, d, J = 7.4 Hz), 6.84-6.90 (2H, m), 7.16 (1H, m), 7.44-7.56 (3H, m), 10.95 (1H, s) |

TABLE 176

| Ex | Data |
|---|---|
| 370 | $^1$H-NMR (DMSO-d6): 1.10-1.32 (5H, m), 1.36-1.58 (4H, m), 1.75-1.93 (6H, m), 2.14 (3H, s), 2.22-2.38 (4H, m), 2.40-2.62 (5H, m), 2.65-2.78 (2H, m), 2.87-2.97 (2H, m), 3.20-3.48 (3H, m), 3.87 (1H, m), 4.56 (1H, d, J = 3.9 Hz), 6.67 (1H, d, J = 7.9 Hz), 7.27 (1H, br-s), 7.42 (1H, d, J = 8.7 Hz), 7.55 (1H, br-s), 7.62 (1H, m), 8.15 (1H, m), 11.37 (1H, s) |
| 377 | $^1$H-NMR (CDCl3): 1.24-1.35 (5H, m), 1.43-1.50 (2H, m), 2.04-2.07 (2H, m), 2.17-2.24 (2H, m), 2.32 (3H, s), 2.36 (3H, s), 2.47 (2H, q, J = 7.1 Hz), 2.58 (4H, br-s), 2.92-2.94 (4H, m), 3.70 (1H, m), 3.95-3.99 (1H, m), 4.51 (1H, d, J = 7.1 Hz), 5.11 (1H, br-s), 6.98 (1H, d, J = 8.3 Hz), 7.48-7.52 (3H, m), 10.70 (1H, br-s). |
| 378 | $^1$H-NMR (CDCl3): 1.23-1.32 (5H, m), 1.45-1.72 (4H, m), 1.92-2.08 (4H, m), 2.17-2.30 (8H, m), 2.45-2.67 (13H, m), 3.15 (2H, m), 3.71-3.73 (1H, m), 3.98 (1H, m), 4.51 (1H, d, J = 7.1 Hz), 5.11 (1H, m), 6.93 (1H, d, J = 8.5 Hz), 7.46-7.52 (3H, m), 10.70 (1H, br-s). |
| 383 | $^1$H-NMR (DMSO-d6): 1.17 (3H, t, J = 7.4 Hz), 1.20-1.32 (2H, m), 1.35-1.48 (2H, m), 1.81-1.93 (4H, m), 2.22 (3H, s), 2.40-2.60 (6H, m), 2.94-3.04 (4H, m), 3.36-3.47 (1H, m), 3.76 (3H, s), 3.80-3.93 (1H, m), 4.53 (1H, d, J = 4.3 Hz), 6.58 (1H, d, J = 7.7 Hz), 6.82 (1H, d, J = 8.6 Hz), 6.86 (1H, d, J = 2.0 Hz), 7.10-7.17 (1H, m), 7.37 (1H, dd, J = 2.0, 8.6 Hz), 7.44-7.51 (1H, m), 10.93 (1H, s) |
| 387 | $^1$H-NMR (DMSO-d6): 1.17 (3H, t, J = 7.3 Hz), 1.22-1.52 (4H, m), 1.54-1.78 (4H, m), 1.85-2.03 (6H, m), 2.18 (3H, s), 2.40 (1H, m), 2.56 (2H, q, J = 7.3 Hz), 2.80-2.90 (2H, m), 3.43 (1H, m), 3.82 (1H, m), 4.58 (1H, d, J = 4.7 Hz), 6.70 (1H, d, J = 7.3 Hz), 7.13 (2H, d, J = 8.5 Hz), 7.19 (1H, br), 7.50 (1H, br), 7.59 (2H, d, J = 8.5 Hz), 11.11 (1H, s) |

TABLE 177

| Ex | Data |
|---|---|
| 388 | 1H-NMR (DMSO-d6): 1.15 (6H, d, J = 6.7 Hz), 1.18-1.33 (2H, m), 1.36-1.59 (4H, m), 1.75-1.91 (6H, m), 2.14 (3H, s), 2.21-2.56 (9H, m), 2.64-2.79 (2H, m), 2.87-2.98 (2H, m), 3.09-3.21 (1H, m), 3.36-3.48 (1H, m), 3.79-3.96 (1H, m), 4.56 (1H, d, J = 3.9 Hz), 6.72 (1H, d, J = 7.3 Hz), 7.22-7.33 (1H, m), 7.42 (1H, d, J = 9.0 Hz), 7.48-7.56 (1H, m), 7.58-7.66 (1H, m), 8.14 (1H, d, J = 2.3 Hz), 11.35 (1H, s). |
| 391 | 1H-NMR (CDCl3): 1.26-1.30 (6H, m), 1.49-1.76 (6H, m), 1.97-2.01 (2H, m), 2.30 (3H, s), 2.36 (3H, s), 2.48 (2H, q, J = 7.3 Hz), 2.59 (4H, br-s), 2.91-2.94 (4H, m), 3.73-3.97 (1H, m), 4.61 (1H, d, J = 7.5 Hz), 5.10 (1H, br-s), 6.96 (1H, d, J = 8.5 Hz), 7.48-7.53 (3H, m), 10.69 (1H, br-s). |
| 392 | 1H-NMR (CDCl3): 1.26-1.32 (6H, m), 1.54-1.76 (8H, m), 1.92-2.00 (4H, m), 2.28 (3H, s), 2.30 (3H, s), 2.47 (2H, q, J = 7.3 Hz), 2.60-2.66 (11H, m), 3.12-3.15 (2H, m), 3.94-3.97 (1H, m), 4.60 (1H, d, J = 7.3 Hz), 5.10 (1H, br-s), 6.91 (1H, d, J = 8.5 Hz), 7.41-7.71 (3H, m), 10.69 (1H, br-s). |
| 399 | 1H-NMR (CDCl3): 0.13-0.16 (2H, m), 0.52-0.57 (2H, m), 0.92 (1H, m), 1.24-1.58 (7H, m), 2.03 (2H, m), 2.18 (2H, m), 2.33 (2H, m), 2.49 (2H, q, J = 7.6 Hz), 2.68 (4H, br-s), 2.98 (4H, m), 3.66 (1H, m), 4.00 (1H, m), 4.56 (1H, d, J = 7.6 Hz), 5.16 (1H, m), 7.34 (1H, d, J = 8.8 Hz), 7.51 (1H, m), 7.62 (1H, dd, J = 8.8, 2.4 Hz), 8.18 (1H, d, J = 2.4 Hz), 10.96 (1H, br-s). |
| 406 | 1H-NMR (CDCl3): 1.29 (3H, t, J = 7.3 Hz), 1.43-1.52 (4H, m), 1.85-1.90 (2H, m), 2.01-2.04 (2H, m), 2.12-2.18 (3H, m), 2.29 (6H, s), 2.46 (2H, q, J = 7.3 Hz), 2.86-2.90 (1H, m), 3.16-3.37 (4H, m), 3.66 (1H, m), 3.97-4.00 (1H, m), 4.53 (1H, d, J = 7.6 Hz), 5.15 (1H, br-s), 7.11 (1H, d, J = 8.8 Hz), 7.48-7.55 (2H, m), 8.15 (1H, d, J = 2.4 Hz), 10.84 (1H, br-s). |

TABLE 178

| Ex | Data |
|---|---|
| 426 | 1H-NMR (CDCl3): 1.11 (6H, d, J = 6.3 Hz), 1.24-1.32 (5H, m), 1.39-1.52 (2H, m), 2.05-2.07 (2H, m), 2.20-2.23 (2H, m), 2.32 (3H, s), 2.47 (2H, q, J = 7.3 Hz), 2.70-2.78 (5H, m), 2.94-2.96 (5H, m), 3.66-3.71 (1H, m), 3.93-3.98 (1H, m), 4.54 (1H, d, J = 7.1 Hz), 5.19 (1H, br-s), 6.99 (1H, d, J = 8.5 Hz), 7.44-7.55 (3H, m), 10.68 (1H, br-s). |
| 459 | 1H-NMR (CDCl3): 1.20-1.54 (10H, m), 1.70-2.09 (6H, m), 2.21 (2H, d, J = 11.4 Hz), 2.29 (3H, s), 2.32-2.73 (13H, m), 3.54 (2H, d, J = 11.6 Hz), 3.63-3.75 (1H, m), 3.92-4.40 (1H, m), 4.07 (2H, q, J = 6.9 Hz), 4.52 (1H, d, J = 7.3 Hz), 5.12 (1H, br-s), 6.84 (1H, d, J = 8.7 Hz), 6.93 (1H, d, J = 2.1 Hz), 7.26 (1H, s), 7.47 (2H, dd, J = 8.5, 2.2 Hz), 10.72 (1H, s). |
| 466 | 1H-NMR (CDCl3): 1.26-2.74 (38H, m), 3.12-3.15 (2H, m), 4.08 (1H, m), 4.63 (1H, d, J = 6.8 Hz), 5.14 (1H, br-s), 6.93 (1H, d, J = 8.1 Hz), 7.49-7.54 (3H, m), 10.71 (1H, br-s). |
| 490 | 1H-NMR (CDCl3): 0.96 (3H, t, J = 7.6 Hz), 1.25-2.71 (36H, m), 3.11-3.15 (2H, m), 3.95-3.97 (1H, m), 4.61 (1H, d, J = 7.3 Hz), 5.09 (1H, br-s), 6.91 (1H, d, J = 8.8 Hz), 7.40-7.56 (3H, m), 10.68 (1H, br-s). |
| 491 | 1H-NMR (CDCl3): 0.92 (3H, t, J = 7.3 Hz), 1.26-2.71 (36H, m), 3.12-3.15 (2H, m), 4.11-4.17 (1H, m), 4.64 (1H, d, J = 6.8 Hz), 5.13 (1H, br-s), 6.93 (1H, d, J = 8.1 Hz), 7.49-7.54 (3H, m), 10.71 (1H, br-s). |
| 493 | 1H-NMR (CDCl3): 0.96 (6H, d, J = 7.1 Hz), 1.26-1.30 (5H, m), 1.56-2.69 (30H, m), 3.13 (2H, d, J = 10.5 Hz), 3.94 (1H, m), 4.61 (1H, d, J = 7.8 Hz), 5.09 (1H, br-s), 6.91 (1H, d, J = 8.5 Hz), 7.40 (1H, d, J = 6.6 Hz), 7.48 (1H, br-s), 7.56 (1H, d, J = 2.7 Hz), 10.67 (1H, br-s). |
| 494 | 1H-NMR (CDCl3): 0.95 (6H, d, J = 6.8 Hz), 1.25-3.18 (37H, m), 3.64-3.67 (1H, m), 4.72 (1H, d, J = 7.1 Hz), 5.12 (1H, br-s), 6.92 (1H, d, J = 8.5 Hz), 7.48-7.54 (3H, m), 10.73 (1H, br-s). |

TABLE 179

| Ex | Data |
|---|---|
| 512 | 1H-NMR (DMSO-d6): 1.19 (3H, t, J = 7.4 Hz), 1.46-1.72 (4H, m), 1.77-1.93 (4H, m), 2.15 (3H, s), 2.20-2.40 (8H, m), 2.44-2.63 (8H, m), 2.97-3.08 (2H, m), 3.34-3.46 (2H, m), 3.88-4.00 (2H, m), 4.11 (1H, m), 6.76 (1H, d, J = 7.5 Hz), 6.94 (1H, d, J = 8.6 Hz), 7.18 (1H, br-s), 7.34 (1H, m), 7.46 (1H, m), 7.51 (1H, br-s), 11.00 (1H, s). |
| 534 | 1H-NMR (DMSO-d6): 1.18 (3H, t, J = 7.4 Hz), 1.39-1.61 (4H, m), 1.78-1.88 (4H, m), 2.14 (3H, s), 2.20-2.39 (8H, m), 2.44-2.62 (10H, m), 2.95-3.06 (4H, m), 3.95 (1H, m), 6.70 (1H, d, J = 7.6 Hz), 6.92 (1H, d, J = 8.6 Hz), 7.15 (1H, br-s), 7.36 (1H, m), 7.43-7.54 (2H, m), 11.01 (1H, s). |
| 544 | 1H-NMR (DMSO-d6): 1.18 (3H, t, J = 7.4 Hz), 1.48-1.72 (4H, m), 1.77-1.90 (4H, m), 1.90-2.01 (2H, m), 2.14 (3H, s), 2.18 (3H, s), 2.21-2.62 (16H, m), 2.77-2.87 (2H, m), 2.97-3.07 (2H, m), 3.87 (1H, m), 6.72 (1H, m), 6.92 (1H, m), 7.19 (1H, m), 7.28 (1H, m), 7.46-7.56 (2H, m), 11.02 (1H, s) |
| 545 | 1H-NMR (DMSO-d6): 1.18 (3H, t, J = 7.4 Hz), 1.55-1.69 (2H, m), 1.83-1.92 (2H, m), 2.22 (3H, s), 2.40-2.50 (4H, m), 2.57 (2H, q, J = 7.4 Hz), 2.98-3.14 (4H, m), 3.36-4.48 (2H, m), 3.88-3.98 (2H, m), 4.06 (1H, m), 6.78 (1H, m), 6.84-6.94 (2H, m), 7.18 (1H, m), 7.40-7.54 (3H, m), 10.91 (1H, s) |
| 546 | 1H-NMR (DMSO-d6): 1.18 (3H, t, J = 7.4 Hz), 1.42-1.68 (4H, m), 1.78-1.92 (4H, m), 2.13 (3H, s), 2.20-2.64 (13H, m), 3.26-3.46 (2H, m), 3.57-3.67 (2H, m), 3.89-3.97 (2H, m), 4.05 (1H, m), 6.78 (1H, m), 6.85-6.93 (2H, m), 7.17 (1H, m), 7.42-7.53 (3H, m), 10.89 (1H, s) |
| 547 | 1H-NMR (DMSO-d6): 1.19 (3H, t, J = 7.4 Hz), 1.44-1.72 (4H, m), 1.74-1.90 (4H, m), 2.14 (3H, s), 2.18-2.64 (13H, m), 3.18-3.44 (4H, m), 3.81 (3H, s), 3.86-3.96 (2H, m), 4.10 (1H, m), 6.77 (1H, m), 6.82 (1H, m), 7.03 (1H, m), 7.20 (1H, m), 7.25 (1H, m), 7.52 (1H, m), 11.01 (1H, m) |

TABLE 180

| Ex | Data |
|---|---|
| 565 | 1H-NMR (DMSO-d6): 1.17 (3H, t, J = 7.2 Hz), 1.22-1.48 (4H, m), 1.86-1.98 (4H, m), 2.26 (3H, s), 2.47-2.58 (6H, m), 3.01-3.14 (4H, m), 3.14-3.60 (1H, m), 3.82-3.87 (1H, m), 4.59 (1H, br-s), 6.60 (1H, s), 6.65 (1H, d, J = 7.6 Hz), 6.83-6.90 (2H, m), 7.12-7.19 (1H, m), 7.44-7.54 (3H, m), 10.95 (1H, s) XRD: 12.6, 17.6, 22.2, 23.5, 24.2 |
| 566 | 1H-NMR (DMSO-d6): 1.17 (3H, t, J = 7.6 Hz), 1.22-1.62 (6H, m), 1.78-2.02 (6H, m), 2.20 (3H, s), 2.24-2.76 (14H, m), 3.10-3.88 (4H, m), 6.55 (1H, s), 6.66 (1H, d, J = 6.0 Hz), 6.83-6.90 (2H, m), 7.12-7.19 (1H, m), 7.44-7.54 (3H, m), 10.93 (1H, s) XRD: 5.7, 18.0, 18.9, 20.1, 20.2 |
| 567 | 1H-NMR (DMSO-d6): 1.13 (6H, d, J = 6.8 Hz), 1.21-1.48 (4H, m), 1.84-1.98 (4H, m), 2.26 (3H, s), 2.48-2.56 (4H, m), 3.03-3.18 (5H, m), 3.37-3.47 (1H, m), 3.75-3.86 (1H, m), 4.58 (1H, br-s), 6.59 (1H, s), 6.70 (1H, d, J = 7.6 Hz), 6.84-6.90 (2H, m), 7.15-7.20 (1H, m), 7.42-7.47 (1H, m), 7.48-7.54 (2H, m), 10.92 (1H, s) XRD: 11.0, 11.2, 17.3, 17.5, 22.5 |
| 568 | 1H-NMR (DMSO-d6): 1.14-1.34 (5H, m), 1.36-1.61 (4H, m), 1.78-1.94 (6H, m), 2.22 (3H, s), 2.28-2.65 (12H, m), 2.68-2.80 (2H, m), 2.89-3.01 (2H, m), 3.36-3.47 (1H, m), 3.81-3.94 (1H, m), 6.55 (1H, s), 6.70 (1H, d, J = 7.6 Hz), 7.28-7.32 (1H, m), 7.43 (1H, d, J = 8.8 Hz), 7.54-7.64 (2H, m), 8.17 (1H, d, J = 2.4 Hz), 11.39 (1H, s) XRD: 8.4, 8.5, 20.2, 20.3, 20.4 |
| 569 | 1H-NMR (DMSO-d6): 1.17 (3H, t, J = 7.6 Hz), 1.21-1.35 (2H, m), 1.36-1.49 (2H, m), 1.50-1.63 (2H, m), 1.80-1.98 (6H, m), 2.24 (3H, s), 2.25 (3H, s), 2.30-2.70 (14H, m), 2.98-3.10 (2H, m), 3.37-3.48 (1H, m), 3.80-3.92 (1H, m), 6.57 (1H, s), 6.65 (1H, d, J = 7.6 Hz), 6.93 (1H, d, J = 8.8 Hz), 7.14-7.22 (1H, m), 7.37 (1H, dd, J = 2.4, 8.8 Hz), 7.46-7.53 (2H, m), 11.03 (1H, s) XRD: 9.5, 18.4, 19.0, 19.4, 23.9 |

TABLE 181

| Ex | Data |
|---|---|
| 570 | 1H-NMR (DMSO-d6): 1.15 (6H, d, J = 6.4 Hz), 1.18-1.32 (2H, m), 1.37-1.58 (4H, m), 1.78-1.91 (6H, m), 2.21 (3H, s), 2.28-2.80 (12H, m), 2.89-2.98 (2H, m), 3.10-3.60 (2H, m), 3.82-3.94 (1H, m), |

TABLE 181-continued

| Ex | Data |
|---|---|
| | 6.55 (1H, s), 6.75 (1H, d, J = 8.0 Hz), 7.28-7.35 (1H, m), 7.43 (1H, d, J = 8.4 Hz), 7.50-7.57 (1H, m), 7.59-7.65 (1H, m), 8.15 (1H, d, J = 2.8 Hz), 11.36 (1H, s) XRD: 17.9, 18.3, 18.4, 18.9, 19.0 |
| 571 | 1H-NMR (DMSO-d6): 1.12-1.20 (6H, m), 1.33-1.45 (2H, m), 1.59-1.89 (10H, m), 2.23 (3H, s), 2.26 (3H, s), 2.30-2.73 (13H, m), 2.97-3.07 (2H, m), 3.79-3.91 (1H, m), 4.03-4.14 (1H, m), 6.57 (1H, s), 6.72 (1H, d, J = 7.6 Hz), 6.92 (1H, d, J = 8.4 Hz), 7.14-7.19 (1H, m), 7.28 (1H, dd, J = 2.4, 8.4 Hz), 7.46-7.51 (1H, m), 7.56 (1H, d, J = 2.4 Hz), 11.01 (1H, s) XRD: 7.9, 15.1, 19.4, 19.9, 20.3 |
| 572 | 1H-NMR (DMSO-d6): 1.04 (6H, d, J = 6.8 Hz), 1.17 (3H, t, J = 7.2 Hz), 1.21-1.35 (2H, m), 1.36-1.50 (2H, m), 1.84-1.97 (4H, m), 2.27 (3H, s), 2.55 (2H, q, J = 7.2 Hz), 2.62-2.70 (4H, m), 2.72-2.86 (5H, m), 3.20-3.55 (2H, m), 3.80-3.91 (1H, m), 6.57 (1H, s), 6.66 (1H, d, J = 7.6 Hz), 6.94 (1H, d, J = 8.4 Hz), 7.15-7.21 (1H, m), 7.39 (1H, dd, J = 2.4, 8.4 Hz), 7.46-7.52 (2H, m), 11.02 (1H, s) XRD: 10.1, 14.5, 17.9, 22.1, 23.0 |
| 573 | 1H-NMR (DMSO-d6): 1.14-1.22 (6H, m), 1.43-1.65 (8H, m), 1.79-1.90 (4H, m), 2.25 (3H, s), 2.27 (3H, s), 2.30-2.70 (14H, m), 2.99-3.09 (2H, m), 3.86-3.98 (1H, m), 6.57 (2H, s), 6.62 (1H, d, J = 7.6 Hz), 6.93 (1H, d, J = 8.4 Hz), 7.15-7.21 (1H, m), 7.36 (1H, dd, J = 2.0, 8.4 Hz), 7.47-7.52 (2H, m), 11.03 (1H, s) XRD: 6.3, 13.7, 16.7, 17.7, 18.4 |

TABLE 182

| Ex | Data |
|---|---|
| 574 | 1H-NMR (DMSO-d6): 1.19 (3H, t, J = 7.6 Hz), 1.50-1.72 (4H, m), 1.80-1.93 (4H, m), 2.21 (3H, s), 2.24 (3H, s), 2.48-2.65 (13H, m), 2.99-3.08 (2H, m), 3.30-3.50 (2H, m), 3.90-4.00 (2H, m), 4.05-4.18 (1H, m), 6.56 (1H, s), 6.78 (1H, d, J = 7.6 Hz), 6.95 (1H, d, J = 8.4 Hz), 7.17-7.24 (1H, m), 7.34 (1H, dd, J = 2.4, 8.4 Hz), 7.46 (1H, d, J = 2.4 Hz), 7.49-7.55 (1H, m), 11.01 (1H, s) XRD: 11.5, 17.7, 19.1, 21.4, 22.3 |
| 575 | 1H-NMR (DMSO-d6): 1.17-1.33 (2H, m), 1.43-1.63 (4H, m), 1.79-1.94 (6H, m), 2.25 (3H, s), 2.30-2.69 (11H, m), 2.99-3.89 (5H, m), 5.75 (2H, s), 6.95 (1H, d, J = 8.4 Hz), 7.07 (1H, d, J = 8.4 Hz), 7.31-7.35 (2H, m), 7.47-7.49 (1H, m), 7.54 (1H, s), 11.19 (1H, s) XRD: 5.6, 8.0, 17.8, 18.6, 24.0 |
| 576 | 1H-NMR (DMSO-d6): 1.18 (3H, t, J = 7.2 Hz), 1.44-1.72 (4H, m), 1.80-1.97 (4H, m), 2.21 (3H, s), 2.25-2.72 (13H, m), 3.30-3.70 (4H, m), 3.90-3.98 (2H, m), 3.99-4.11 (1H, m), 6.55 (1H, s), 6.78 (1H, d, J = 7.6 Hz), 6.85-6.93 (2H, m), 7.14-7.21 (1H, m), 7.43-7.52 (3H, m), 10.89 (1H, s) XRD: 8.9, 16.6, 18.1, 20.1, 22.4 |
| 577 | 1H-NMR (DMSO-d6): 1.19 (3H, t, J = 7.6 Hz), 1.49-1.70 (4H, m), 1.77-1.91 (4H, m), 2.21 (3H, s), 2.26-2.70 (13H, m), 3.29-3.43 (4H, m), 3.81 (3H, s), 3.88-3.97 (2H, m), 4.06-4.18 (1H, m), 6.55 (1H, s), 6.77 (1H, d, J = 7.6 Hz), 6.82 (1H, d, J = 8.4 Hz), 7.03 (1H, d, J = 2.0 Hz), 7.18-7.29 (2H, m), 7.49-7.55 (1H, m), 11.01 (1H, s) XRD: 11.6, 17.7, 19.2, 21.5, 22.4 |
| 578 | 1H-NMR (DMSO-d6): 1.15 (6H, d, J = 6.8 Hz), 1.42-1.70 (4H, m), 1.78-1.92 (4H, m), 2.21 (3H, s), 2.26-2.72 (11H, m), 3.08-3.21 (1H, m), 3.34-3.48 (2H, m), 3.56-3.69 (2H, m), 3.87-3.98 (2H, m), 4.00-4.13 (1H, m), 6.55 (1H, s), 6.83 (1H, d, J = 7.6 Hz), 6.85-6.93 (2H, m), 7.15-7.22 (1H, m), 7.41-7.51 (3H, m), 10.87 (1H, s) XRD: 10.3, 16.9, 19.3, 19.9, 21.1 |

TABLE 183

| Ex | Data |
|---|---|
| 579 | 1H-NMR (DMSO-d6): 1.19 (3H, t, J = 7.6 Hz), 1.58-1.72 (2H, m), 1.84-1.94 (2H, m), 2.26 (3H, s), 2.45-2.64 (6H, m), 2.91-3.02 (4H, m), 3.33-3.49 (2H, m), 3.91-3.99 (2H, m), 4.02-4.14 (1H, m), 6.59 (1H, s), 6.86-6.92 (1H, m), 6.93-7.04 (2H, m), 7.24-7.30 (1H, m), 7.52-7.59 (1H, m), 7.88 (1H, dd, J = 2.4, 16 Hz), 11.18 (1H, s) XRD: 5.7, 11.5, 18.2, 23.6, 23.9 |

TABLE 183-continued

| Ex | Data |
|---|---|
| 580 | 1H-NMR (DMSO-d6): 1.16 (6H, d, J = 6.8 Hz), 1.57-1.70 (2H, m), 1.80-1.89 (2H, m), 2.29 (3H, s), 2.48-2.60 (4H, m), 2.89-3.00 (4H, m), 3.10-3.22 (1H, m), 3.30-3.42 (2H, m), 3.81 (3H, s), 3.87-3.96 (2H, m), 4.06-4.19 (1H, m), 6.58 (1H, s), 6.78-6.86 (2H, m), 7.04 (1H, d, J = 2.0 Hz), 7.19-7.30 (2H, m), 7.46-7.53 (1H, m), 11.00 (1H, s) XRD: 8.2, 11.8, 15.9, 18.0, 21.3 |
| 581 | 1H-NMR (DMSO-d6): 1.15 (6H, d, J = 6.4 Hz), 1.55-1.70 (2H, m), 1.81-1.91 (2H, m), 2.27 (3H, s), 2.47-2.55 (4H, m), 3.01-3.22 (5H, m), 3.34-3.50 (2H, m), 3.88-3.98 (2H, m), 4.00-4.13 (1H, m), 6.59 (1H, s), 6.83 (1H, d, J = 7.2 Hz), 6.86-6.92 (2H, m), 7.16-7.23 (1H, m), 7.43-7.51 (3H, m), 10.89 (1H, s) XRD: 11.1, 17.2, 19.5, 20.1, 20.5 |
| 582 | 1H-NMR (DMSO-d6): 1.19 (3H, t, J = 7.2 Hz), 1.43-1.57 (2H, m), 1.58-1.71 (2H, m), 1.74-1.91 (4H, m), 2.03-2.16 (2H, m), 2.20-2.30 (8H, m), 2.53-2.69 (5H, m), 2.74-2.84 (4H, m), 2.87-2.98 (2H, m), 3.34-3.45 (2H, m), 3.89-3.99 (2H, m), 4.04-4.17 (1H, m), 6.52 (1H, s), 6.79 (1H, d, J = 7.6 Hz), 6.96 (1H, d, J = 8.4 Hz), 7.18-7.23 (1H, m), 7.36 (1H, dd, J = 2.4, 8.4 Hz), 7.46 (1H, d, J = 2.4 Hz), 7.49-7.54 (1H, m), 11.01 (1H, s) XRD: 8.1, 13.1, 15.1, 17.5, 23.8 |

Tables 184 to 201 show the structures of other compounds of the present invention. These compounds were synthesized, or can be synthesized, using the above preparation processes, processes described in the Examples, processes obvious to those skilled in the art, or modified processes thereof.

The meanings of the symbols in the tables are as follows.

No: Compound No.

—$R^{11}$ and —$R^{12}$: substituents in the general formulas.

cBu: cyclobutyl, 2Py: 2-pyridyl, 3Py: 3-pyridyl, 4Py: 4-pyridyl.

TABLE 184

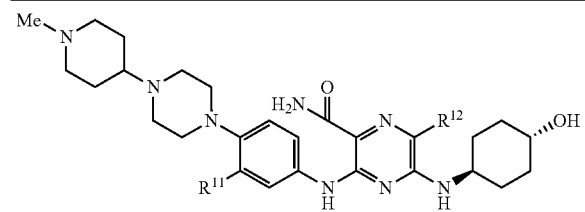

| No | —R11 | —R12 |
|---|---|---|
| A1 | —H | —H |
| A2 | —Me | —H |
| A3 | —Et | —H |
| A4 | -nPr | —H |
| A5 | -iPr | —H |
| A6 | -cPr | —H |
| A7 | -cBu | —H |
| A8 | cyclopentyl | —H |
| A9 | cyclohexyl | —H |
| A10 | tetrahydropyranyl | —H |
| A11 | —CF3 | —H |
| A12 | —CN | —H |
| A13 | —Ph | —H |
| A14 | —OMe | —H |
| A15 | —OEt | —H |
| A16 | —OnPr | —H |
| A17 | —OiPr | —H |
| A18 | —OcPr | —H |
| A19 | —OCH2cPr | —H |
| A20 | —OCHCF2 | —H |
| A21 | —OCF3 | —H |
| A22 | —OCH2CF3 | —H |
| A23 | —OCH2CH2F | —H |
| A24 | —OCH2CH2OMe | —H |
| A25 | —OCH2CH2NMe2 | —H |
| A26 | —F | —H |
| A27 | —Cl | —H |
| A28 | —Br | —H |
| A29 | —I | —H |
| A30a | —2Py | —H |
| A30b | —3Py | —H |
| A30c | —4Py | —H |
| A31 | —H | —Me |
| A32 | —Me | —Me |
| A33 | —Et | —Me |
| A34 | -nPr | —Me |
| A35 | -iPr | —Me |
| A36 | -cPr | —Me |
| A37 | -cBu | —Me |
| A38 | cyclopentyl | —Me |
| A39 | cyclohexyl | —Me |
| A40 | tetrahydropyranyl | —Me |

TABLE 184-continued

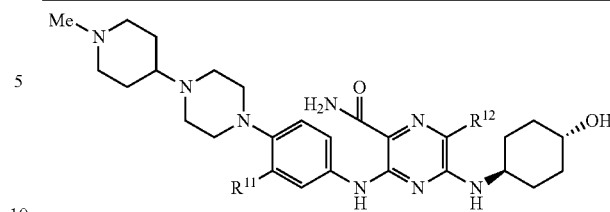

| No | —R11 | —R12 |
|---|---|---|
| A41 | —CF3 | —Me |
| A42 | —CN | —Me |
| A43 | —Ph | —Me |
| A44 | —OMe | —Me |
| A45 | —OEt | —Me |
| A46 | —OnPr | —Me |
| A47 | —OiPr | —Me |
| A48 | —OcPr | —Me |
| A49 | —OCH2cPr | —Me |
| A50 | —OCHCF2 | —Me |
| A51 | —OCF3 | —Me |
| A52 | —OCH2CF3 | —Me |
| A53 | —OCH2CH2F | —Me |
| A54 | —OCH2CH2OMe | —Me |
| A55 | —OCH2CH2NMe2 | —Me |
| A56 | —F | —Me |
| A57 | —Cl | —Me |
| A58 | —Br | —Me |
| A59 | —I | —Me |
| A60a | —2Py | —Me |
| A60b | —3Py | —Me |
| A60c | —4Py | —Me |
| A61 | —H | —Et |
| A62 | —Me | —Et |
| A63 | —Et | —Et |
| A64 | -nPr | —Et |
| A65 | -iPr | —Et |
| A66 | -cPr | —Et |
| A67 | -cBu | —Et |
| A68 | cyclopentyl | —Et |
| A69 | cyclohexyl | —Et |
| A70 | tetrahydropyranyl | —Et |
| A71 | —CF3 | —Et |
| A72 | —CN | —Et |
| A73 | —Ph | —Et |
| A74 | —OMe | —Et |
| A75 | —OEt | —Et |
| A76 | —OnPr | —Et |
| A77 | —OiPr | —Et |
| A78 | —OcPr | —Et |
| A79 | —OCH2cPr | —Et |
| A80 | —OCHCF2 | —Et |
| A81 | —OCF3 | —Et |
| A82 | —OCH2CF3 | —Et |
| A83 | —OCH2CH2F | —Et |
| A84 | —OCH2CH2OMe | —Et |
| A85 | —OCH2CH2NMe2 | —Et |
| A86 | —F | —Et |
| A87 | —Cl | —Et |
| A88 | —Br | —Et |
| A89 | —I | —Et |
| A90a | —2Py | —Et |
| A90b | —3Py | —Et |
| A90c | —4Py | —Et |

TABLE 185

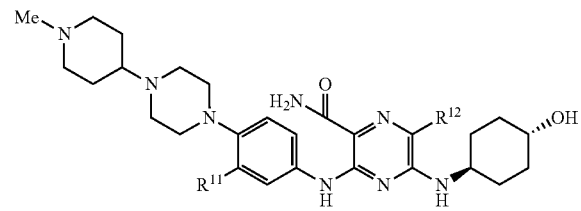

| No | —R11 | —R12 |
|---|---|---|
| B1 | —H | -nPr |
| B2 | —Me | -nPr |
| B3 | —Et | -nPr |
| B4 | -nPr | -nPr |
| B5 | -iPr | -nPr |
| B6 | -cPr | -nPr |
| B7 | -cBu | -nPr |
| B8 | cyclopentyl | -nPr |
| B9 | cyclohexyl | -nPr |
| B10 | tetrahydropyranyl | -nPr |
| B11 | —CF3 | -nPr |
| B12 | —CN | -nPr |
| B13 | —Ph | -nPr |
| B14 | —OMe | -nPr |
| B15 | —OEt | -nPr |
| B16 | —OnPr | -nPr |
| B17 | —OiPr | -nPr |
| B18 | —OcPr | -nPr |
| B19 | —OCH2cPr | -nPr |
| B20 | —OCHCF2 | -nPr |
| B21 | —OCF3 | -nPr |
| B22 | —OCH2CF3 | -nPr |
| B23 | —OCH2CH2F | -nPr |
| B24 | —OCH2CH2OMe | -nPr |
| B25 | —OCH2CH2NMe2 | -nPr |
| B26 | —F | -nPr |
| B27 | —Cl | -nPr |
| B28 | —Br | -nPr |
| B29 | —I | -nPr |
| B30a | —2Py | -nPr |
| B30b | —3Py | -nPr |
| B30c | —4Py | -nPr |
| B31 | —H | -iPr |
| B32 | —Me | -iPr |
| B33 | —Et | -iPr |
| B34 | -nPr | -iPr |
| B35 | -iPr | -iPr |
| B36 | -cPr | -iPr |
| B37 | -cBu | -iPr |
| B38 | cyclopentyl | -iPr |
| B39 | cyclohexyl | -iPr |
| B40 | tetrahydropyranyl | -iPr |

TABLE 185-continued

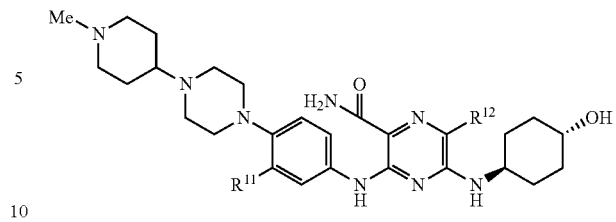

| No | —R11 | —R12 |
|---|---|---|
| B41 | —CF3 | -iPr |
| B42 | —CN | -iPr |
| B43 | —Ph | -iPr |
| B44 | —OMe | -iPr |
| B45 | —OEt | -iPr |
| B46 | —OnPr | -iPr |
| B47 | —OiPr | -iPr |
| B48 | —OcPr | -iPr |
| B49 | —OCH2cPr | -iPr |
| B50 | —OCHCF2 | -iPr |
| B51 | —OCF3 | -iPr |
| B52 | —OCH2CF3 | -iPr |
| B53 | —OCH2CH2F | -iPr |
| B54 | —OCH2CH2OMe | -iPr |
| B55 | —OCH2CH2NMe2 | -iPr |
| B56 | —F | -iPr |
| B57 | —Cl | -iPr |
| B58 | —Br | -iPr |
| B59 | —I | -iPr |
| B60a | —2Py | -iPr |
| B60b | —3Py | -iPr |
| B60c | —4Py | -iPr |
| B61 | —H | -cPr |
| B62 | —Me | -cPr |
| B63 | —Et | -cPr |
| B64 | -nPr | -cPr |
| B65 | -iPr | -cPr |
| B66 | -cPr | -cPr |
| B67 | -cBu | -cPr |
| B68 | cyclopentyl | -cPr |
| B69 | cyclohexyl | -cPr |
| B70 | tetrahydropyranyl | -cPr |
| B71 | —CF3 | -cPr |
| B72 | —CN | -cPr |
| B73 | —Ph | -cPr |
| B74 | —OMe | -cPr |
| B75 | —OEt | -cPr |
| B76 | —OnPr | -cPr |
| B77 | —OiPr | -cPr |
| B78 | —OcPr | -cPr |
| B79 | —OCH2cPr | -cPr |
| B80 | —OCHCF2 | -cPr |
| B81 | —OCF3 | -cPr |
| B82 | —OCH2CF3 | -cPr |
| B83 | —OCH2CH2F | -cPr |
| B84 | —OCH2CH2OMe | -cPr |
| B85 | —OCH2CH2NMe2 | -cPr |
| B86 | —F | -cPr |
| B87 | —Cl | -cPr |
| B88 | —Br | -cPr |
| B89 | —I | -cPr |
| B90a | —2Py | -cPr |
| B90b | —3Py | -cPr |
| B90c | —4Py | -cPr |

TABLE 186

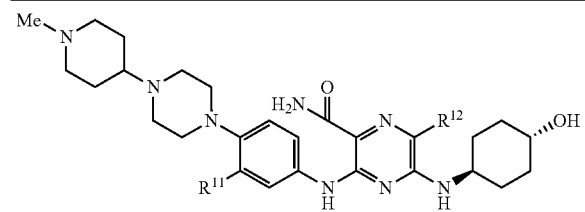

| No | —R11 | —R12 |
|---|---|---|
| C1 | —H | —Cl |
| C2 | —Me | —Cl |
| C3 | —Et | —Cl |
| C4 | -nPr | —Cl |
| C5 | -iPr | —Cl |
| C6 | -cPr | —Cl |
| C7 | -cBu | —Cl |
| C8 | cyclopentyl | —Cl |
| C9 | cyclohexyl | —Cl |
| C10 | tetrahydropyranyl | —Cl |
| C11 | —CF3 | —Cl |
| C12 | —CN | —Cl |
| C13 | —Ph | —Cl |
| C14 | —OMe | —Cl |
| C15 | —OEt | —Cl |
| C16 | —OnPr | —Cl |
| C17 | —OiPr | —Cl |
| C18 | —OcPr | —Cl |
| C19 | —OCH2cPr | —Cl |
| C20 | —OCHCF2 | —Cl |
| C21 | —OCF3 | —Cl |
| C22 | —OCH2CF3 | —Cl |
| C23 | —OCH2CH2F | —Cl |
| C24 | —OCH2CH2OMe | —Cl |
| C25 | —OCH2CH2NMe2 | —Cl |
| C26 | —F | —Cl |
| C27 | —Cl | —Cl |
| C28 | —Br | —Cl |
| C29 | —I | —Cl |
| C30a | —2Py | —Cl |
| C30b | —3Py | —Cl |
| C30c | —4Py | —Cl |
| C31 | —H | —Br |
| C32 | —Me | —Br |
| C33 | —Et | —Br |
| C34 | -nPr | —Br |
| C35 | -iPr | —Br |
| C36 | -cPr | —Br |
| C37 | -cBu | —Br |
| C38 | cyclopentyl | —Br |
| C39 | cyclohexyl | —Br |
| C40 | tetrahydropyranyl | —Br |

TABLE 186-continued

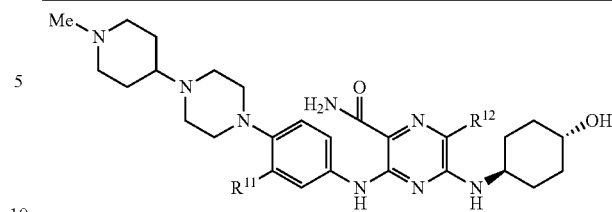

| No | —R11 | —R12 |
|---|---|---|
| C41 | —CF3 | —Br |
| C42 | —CN | —Br |
| C43 | —Ph | —Br |
| C44 | —OMe | —Br |
| C45 | —OEt | —Br |
| C46 | —OnPr | —Br |
| C47 | —OiPr | —Br |
| C48 | —OcPr | —Br |
| C49 | —OCH2cPr | —Br |
| C50 | —OCHCF2 | —Br |
| C51 | —OCF3 | —Br |
| C52 | —OCH2CF3 | —Br |
| C53 | —OCH2CH2F | —Br |
| C54 | —OCH2CH2OMe | —Br |
| C55 | —OCH2CH2NMe2 | —Br |
| C56 | —F | —Br |
| C57 | —Cl | —Br |
| C58 | —Br | —Br |
| C59 | —I | —Br |
| C60a | —2Py | —Br |
| C60b | —3Py | —Br |
| C60c | —4Py | —Br |
| C61 | —H | —I |
| C62 | —Me | —I |
| C63 | —Et | —I |
| C64 | -nPr | —I |
| C65 | -iPr | —I |
| C66 | -cPr | —I |
| C67 | -cBu | —I |
| C68 | cyclopentyl | —I |
| C69 | cyclohexyl | —I |
| C70 | tetrahydropyranyl | —I |
| C71 | —CF3 | —I |
| C72 | —CN | —I |
| C73 | —Ph | —I |
| C74 | —OMe | —I |
| C75 | —OEt | —I |
| C76 | —OnPr | —I |
| C77 | —OiPr | —I |
| C78 | —OcPr | —I |
| C79 | —OCH2cPr | —I |
| C80 | —OCHCF2 | —I |
| C81 | —OCF3 | —I |
| C82 | —OCH2CF3 | —I |
| C83 | —OCH2CH2F | —I |
| C84 | —OCH2CH2OMe | —I |
| C85 | —OCH2CH2NMe2 | —I |
| C86 | —F | —I |
| C87 | —Cl | —I |
| C88 | —Br | —I |
| C89 | —I | —I |
| C90a | —2Py | —I |
| C90b | —3Py | —I |
| C90c | —4Py | —I |

TABLE 187

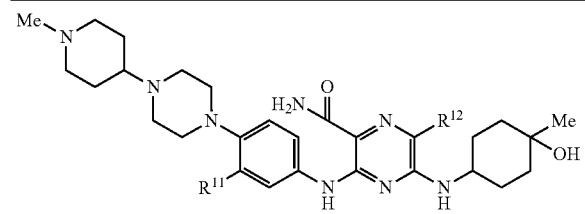

| No | —R11 | —R12 |
|---|---|---|
| D1 | —H | —H |
| D2 | —Me | —H |
| D3 | —Et | —H |
| D4 | -nPr | —H |
| D5 | -iPr | —H |
| D6 | -cPr | —H |
| D7 | -cBu | —H |
| D8 | cyclopentyl | —H |
| D9 | cyclohexyl | —H |
| D10 | tetrahydropyranyl | —H |
| D11 | —CF3 | —H |
| D12 | —CN | —H |
| D13 | —Ph | —H |
| D14 | —OMe | —H |
| D15 | —OEt | —H |
| D16 | —OnPr | —H |
| D17 | —OiPr | —H |
| D18 | —OcPr | —H |
| D19 | —OCH2cPr | —H |
| D20 | —OCHCF2 | —H |
| D21 | —OCF3 | —H |
| D22 | —OCH2CF3 | —H |
| D23 | —OCH2CH2F | —H |
| D24 | —OCH2CH2OMe | —H |
| D25 | —OCH2CH2NMe2 | —H |
| D26 | —F | —H |
| D27 | —Cl | —H |
| D28 | —Br | —H |
| D29 | —I | —H |
| D30a | —2Py | —H |
| D30b | —3Py | —H |
| D30c | —4Py | —H |
| D31 | —H | —Me |
| D32 | —Me | —Me |
| D33 | —Et | —Me |
| D34 | -nPr | —Me |
| D35 | -iPr | —Me |
| D36 | -cPr | —Me |
| D37 | -cBu | —Me |
| D38 | cyclopentyl | —Me |
| D39 | cyclohexyl | —Me |
| D40 | tetrahydropyranyl | —Me |

TABLE 187-continued

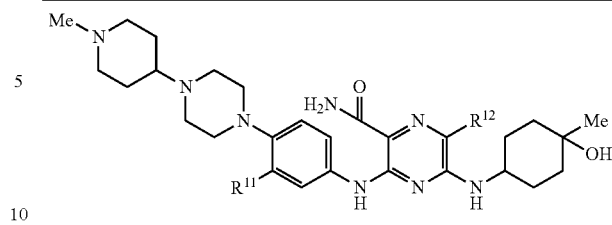

| No | —R11 | —R12 |
|---|---|---|
| D41 | —CF3 | —Me |
| D42 | —CN | —Me |
| D43 | —Ph | —Me |
| D44 | —OMe | —Me |
| D45 | —OEt | —Me |
| D46 | —OnPr | —Me |
| D47 | —OiPr | —Me |
| D48 | —OcPr | —Me |
| D49 | —OCH2cPr | —Me |
| D50 | —OCHCF2 | —Me |
| D51 | —OCF3 | —Me |
| D52 | —OCH2CF3 | —Me |
| D53 | —OCH2CH2F | —Me |
| D54 | —OCH2CH2OMe | —Me |
| D55 | —OCH2CH2NMe2 | —Me |
| D56 | —F | —Me |
| D57 | —Cl | —Me |
| D58 | —Br | —Me |
| D59 | —I | —Me |
| D60a | —2Py | —Me |
| D60b | —3Py | —Me |
| D60c | —4Py | —Me |
| D61 | —H | —Et |
| D62 | —Me | —Et |
| D63 | —Et | —Et |
| D64 | -nPr | —Et |
| D65 | -iPr | —Et |
| D66 | -cPr | —Et |
| D67 | -cBu | —Et |
| D68 | cyclopentyl | —Et |
| D69 | cyclohexyl | —Et |
| D70 | tetrahydropyranyl | —Et |
| D71 | —CF3 | —Et |
| D72 | —CN | —Et |
| D73 | —Ph | —Et |
| D74 | —OMe | —Et |
| D75 | —OEt | —Et |
| D76 | —OnPr | —Et |
| D77 | —OiPr | —Et |
| D78 | —OcPr | —Et |
| D79 | —OCH2cPr | —Et |
| D80 | —OCHCF2 | —Et |
| D81 | —OCF3 | —Et |
| D82 | —OCH2CF3 | —Et |
| D83 | —OCH2CH2F | —Et |
| D84 | —OCH2CH2OMe | —Et |
| D85 | —OCH2CH2NMe2 | —Et |
| D86 | —F | —Et |
| D87 | —Cl | —Et |
| D88 | —Br | —Et |
| D89 | —I | —Et |
| D90a | —2Py | —Et |
| D90b | —3Py | —Et |
| D90c | —4Py | —Et |

TABLE 188

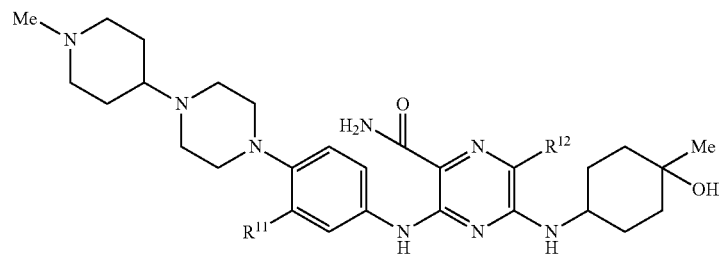

| No | —R¹¹ | —R¹² |
|---|---|---|
| E1 | —H | -nPr |
| E2 | —Me | -nPr |
| E3 | —Et | -nPr |
| E4 | -nPr | -nPr |
| E5 | -iPr | -nPr |
| E6 | -cPr | -nPr |
| E7 | -cBu | -nPr |
| E8 | cyclopentyl | -nPr |
| E9 | cyclohexyl | -nPr |
| E10 | tetrahydropyran-4-yl | -nPr |
| E11 | —CF₃ | -nPr |
| E12 | —CN | -nPr |
| E13 | —Ph | -nPr |
| E14 | —OMe | -nPr |
| E15 | —OEt | -nPr |
| E16 | —OnPr | -nPr |
| E17 | —OiPr | -nPr |
| E18 | —OcPr | -nPr |
| E19 | —OCH₂cPr | -nPr |
| E20 | —OCHCF₂ | -nPr |
| E21 | —OCF₃ | -nPr |
| E22 | —OCH₂CF₃ | -nPr |
| E23 | —OCH₂CH₂F | -nPr |
| E24 | —OCH₂CH₂OMe | -nPr |
| E25 | —OCH₂CH₂NMe₂ | -nPr |
| E26 | —F | -nPr |
| E27 | —Cl | -nPr |
| E28 | —Br | -nPr |
| E29 | —I | -nPr |
| E30a | —2Py | -nPr |
| E30b | —3Py | -nPr |
| E30c | —4Py | -nPr |
| E31 | —H | -iPr |
| E32 | —Me | -iPr |
| E33 | —Et | -iPr |
| E34 | -nPr | -iPr |
| E35 | -iPr | -iPr |
| E36 | -cPr | -iPr |
| E37 | -cBu | -iPr |
| E38 | cyclopentyl | -iPr |
| E39 | cyclohexyl | -iPr |

TABLE 188-continued

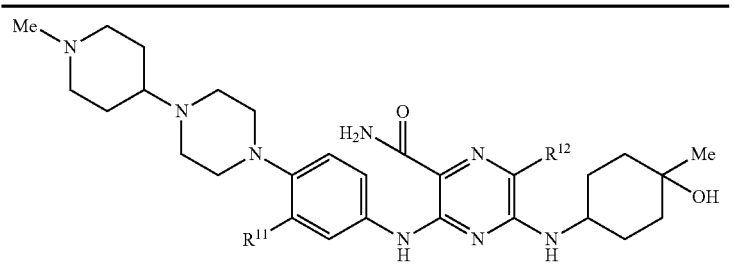

| No | —R11 | —R12 |
|---|---|---|
| E40 | (4-methyltetrahydropyran) | -iPr |
| E41 | —CF3 | -iPr |
| E42 | —CN | -iPr |
| E43 | —Ph | -iPr |
| E44 | —OMe | -iPr |
| E45 | —OEt | -iPr |
| E46 | —OnPr | -iPr |
| E47 | —OiPr | -iPr |
| E48 | —OcPr | -iPr |
| E49 | —OCH2cPr | -iPr |
| E50 | —OCHCF2 | -iPr |
| E51 | —OCF3 | -iPr |
| E52 | —OCH2CF3 | -iPr |
| E53 | —OCH2CH2F | -iPr |
| E54 | —OCH2CH2OMe | -iPr |
| E55 | —OCH2CH2NMe2 | -iPr |
| E56 | —F | -iPr |
| E57 | —Cl | -iPr |
| E58 | —Br | -iPr |
| E59 | —I | -iPr |
| E60a | —2Py | -iPr |
| E60b | —3Py | -iPr |
| E60c | —4Py | -iPr |
| E61 | —H | -cPr |
| E62 | —Me | -cPr |
| E63 | —Et | -cPr |
| E64 | -nPr | -cPr |
| E65 | -iPr | -cPr |
| E66 | -cPr | -cPr |
| E67 | -cBu | -cPr |
| E68 | (cyclopentyl) | -cPr |
| E69 | (cyclohexyl) | -cPr |
| E70 | (4-methyltetrahydropyran) | -cPr |
| E71 | —CF3 | -cPr |
| E72 | —CN | -cPr |
| E73 | —Ph | -cPr |
| E74 | —OMe | -cPr |
| E75 | —OEt | -cPr |
| E76 | —OnPr | -cPr |
| E77 | —OiPr | -cPr |
| E78 | —OcPr | -cPr |
| E79 | —OCH2cPr | -cPr |
| E80 | —OCHCF2 | -cPr |
| E81 | —OCF3 | -cPr |
| E82 | —OCH2CF3 | -cPr |
| E83 | —OCH2CH2F | -cPr |
| E84 | —OCH2CH2OMe | -cPr |
| E85 | —OCH2CH2NMe2 | -cPr |
| E86 | —F | -cPr |

TABLE 188-continued
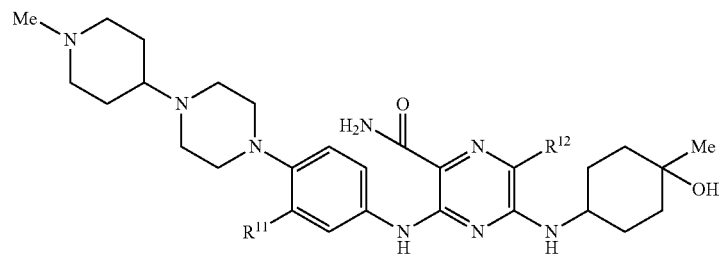
| No | —R[11] | —R[12] |
|---|---|---|
| E87 | —Cl | -cPr |
| E88 | —Br | -cPr |
| E89 | —I | -cPr |
| E90a | —2Py | -cPr |
| E90b | —3Py | -cPr |
| E90c | —4Py | -cPr |
TABLE 189
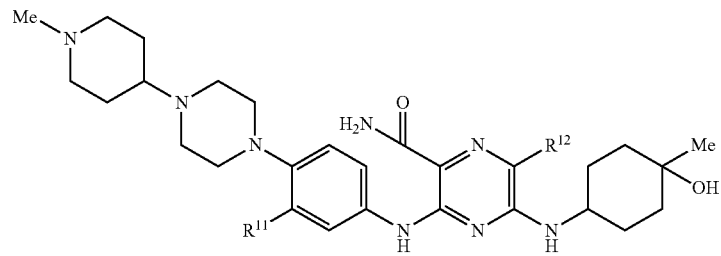
| No | —R[11] | —R[12] |
|---|---|---|
| F1 | —H | —Cl |
| F2 | —Me | —Cl |
| F3 | —Et | —Cl |
| F4 | -nPr | —Cl |
| F5 | -iPr | —Cl |
| F6 | -cPr | —Cl |
| F7 | -cBu | —Cl |
| F8 | cyclopentyl | —Cl |
| F9 | cyclohexyl | —Cl |
| F10 | tetrahydropyranyl | —Cl |
| F11 | —CF$_3$ | —Cl |
| F12 | —CN | —Cl |
| F13 | —Ph | —Cl |
| F14 | —OMe | —Cl |
| F15 | —OEt | —Cl |
| F16 | —OnPr | —Cl |
| F17 | —OiPr | —Cl |
| F18 | —OcPr | —Cl |
| F19 | —OCH$_2$cPr | —Cl |
| F20 | —OCHCF$_2$ | —Cl |
| F21 | —OCF$_3$ | —Cl |
| F22 | —OCH$_2$CF$_3$ | —Cl |
| F23 | —OCH$_2$CH$_2$F | —Cl |
| F24 | —OCH$_2$CH$_2$OMe | —Cl |
| F25 | —OCH$_2$CH$_2$NMe$_2$ | —Cl |
| F26 | —F | —Cl |

TABLE 189-continued

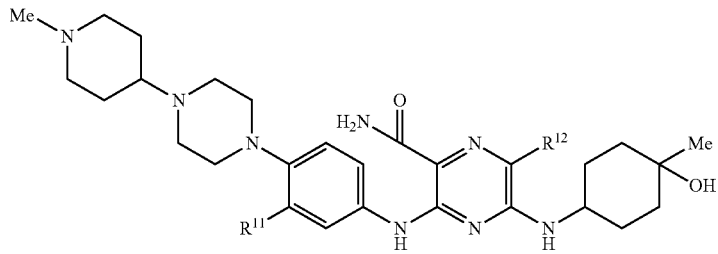

| No | —R[11] | —R[12] |
|---|---|---|
| F27 | —Cl | —Cl |
| F28 | —Br | —Cl |
| F29 | —I | —Cl |
| F30a | —2Py | —Cl |
| F30b | —3Py | —Cl |
| F30c | —4Py | —Cl |
| F31 | —H | —Br |
| F32 | —Me | —Br |
| F33 | —Et | —Br |
| F34 | -nPr | —Br |
| F35 | -iPr | —Br |
| F36 | -cPr | —Br |
| F37 | -cBu | —Br |
| F38 | 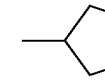 | —Br |
| F39 | 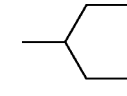 | —Br |
| F40 | 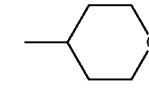 | —Br |
| F41 | —CF$_3$ | —Br |
| F42 | —CN | —Br |
| F43 | —Ph | —Br |
| F44 | —OMe | —Br |
| F45 | —OEt | —Br |
| F46 | —OnPr | —Br |
| F47 | —OiPr | —Br |
| F48 | —OcPr | —Br |
| F49 | —OCH$_2$cPr | —Br |
| F50 | —OCHCF$_2$ | —Br |
| F51 | —OCF$_3$ | —Br |
| F52 | —OCH$_2$CF$_3$ | —Br |
| F53 | —OCH$_2$CH$_2$F | —Br |
| F54 | —OCH$_2$CH$_2$OMe | —Br |
| F55 | —OCH$_2$CH$_2$NMe$_2$ | —Br |
| F56 | —F | —Br |
| F57 | —Cl | —Br |
| F58 | —Br | —Br |
| F59 | —I | —Br |
| F60a | —2Py | —Br |
| F60b | —3Py | —Br |
| F60c | —4Py | —Br |
| F61 | —H | —I |
| F62 | —Me | —I |
| F63 | —Et | —I |
| F64 | -nPr | —I |
| F65 | -iPr | —I |
| F66 | -cPr | —I |
| F67 | -cBu | —I |
| F68 | 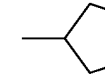 | —I |

TABLE 189-continued

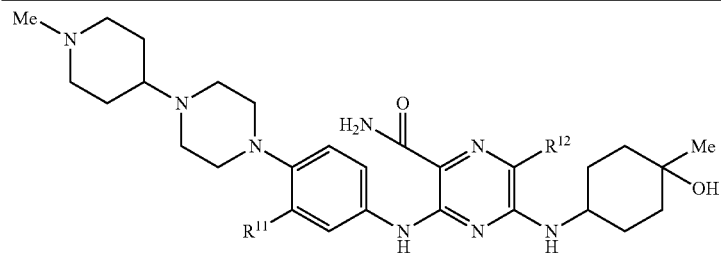

| No | —R[11] | —R[12] |
|---|---|---|
| F69 | (methylcyclohexyl) | —I |
| F70 | (methyltetrahydropyranyl) | —I |
| F71 | —CF₃ | —I |
| F72 | —CN | —I |
| F73 | —Ph | —I |
| F74 | —OMe | —I |
| F75 | —OEt | —I |
| F76 | —OnPr | —I |
| F77 | —OiPr | —I |
| F78 | —OcPr | —I |
| F79 | —OCH₂cPr | —I |
| F80 | —OCHCF₂ | —I |
| F81 | —OCF₃ | —I |
| F82 | —OCH₂CF₃ | —I |
| F83 | —OCH₂CH₂F | —I |
| F84 | —OCH₂CH₂OMe | —I |
| F85 | —OCH₂CH₂NMe₂ | —I |
| F86 | —F | —I |
| F87 | —Cl | —I |
| F88 | —Br | —I |
| F89 | —I | —I |
| F90a | —2Py | —I |
| F90b | —3Py | —I |
| F90c | —4Py | —I |

TABLE 190

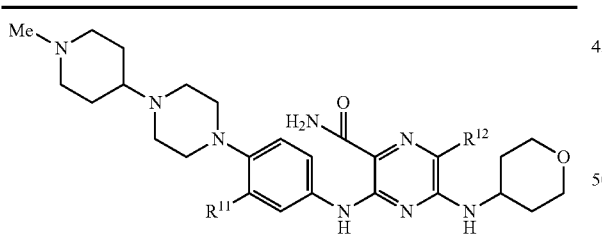

| No | —R[11] | —R[12] |
|---|---|---|
| G1 | —H | —H |
| G2 | —Me | —H |
| G3 | —Et | —H |
| G4 | -nPr | —H |
| G5 | -iPr | —H |
| G6 | -cPr | —H |
| G7 | -cBu | —H |
| G8 | (cyclopentyl) | —H |

TABLE 190-continued

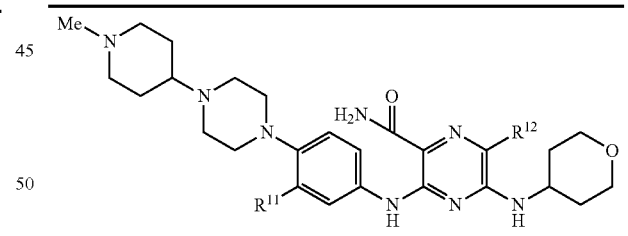

| No | —R[11] | —R[12] |
|---|---|---|
| G9 | (cyclohexyl) | —H |
| G10 | (tetrahydropyranyl) | —H |
| G11 | —CF₃ | —H |
| G12 | —CN | —H |
| G13 | —Ph | —H |
| G14 | —OMe | —H |
| G15 | —OEt | —H |

TABLE 190-continued

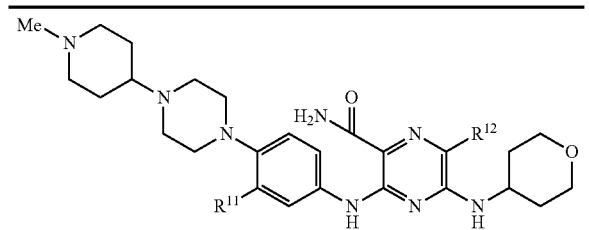

| No | —R[11] | —R[12] |
|---|---|---|
| G16 | —OnPr | —H |
| G17 | —OiPr | —H |
| G18 | —OcPr | —H |
| G19 | —OCH₂cPr | —H |
| G20 | —OCHCF₂ | —H |
| G21 | —OCF₃ | —H |
| G22 | —OCH₂CF₃ | —H |
| G23 | —OCH₂CH₂F | —H |
| G24 | —OCH₂CH₂OMe | —H |
| G25 | —OCH₂CH₂NMe₂ | —H |
| G26 | —F | —H |
| G27 | —Cl | —H |
| G28 | —Br | —H |
| G29 | —I | —H |
| G30a | —2Py | —H |
| G30b | —3Py | —H |
| G30c | —4Py | —H |
| G31 | —H | —Me |
| G32 | —Me | —Me |
| G33 | —Et | —Me |
| G34 | -nPr | —Me |
| G35 | -iPr | —Me |
| G36 | -cPr | —Me |
| G37 | -cBu | —Me |
| G38 | cyclopentyl | —Me |
| G39 | cyclohexyl | —Me |
| G40 | tetrahydropyran-4-yl | —Me |
| G41 | —CF₃ | —Me |
| G42 | —CN | —Me |
| G43 | —Ph | —Me |
| G44 | —OMe | —Me |
| G45 | —OEt | —Me |
| G46 | —OnPr | —Me |
| G47 | —OiPr | —Me |
| G48 | —OcPr | —Me |
| G49 | —OCH₂cPr | —Me |
| G50 | —OCHCF₂ | —Me |
| G51 | —OCF₃ | —Me |
| G52 | —OCH₂CF₃ | —Me |
| G53 | —OCH₂CH₂F | —Me |
| G54 | —OCH₂CH₂OMe | —Me |
| G55 | —OCH₂CH₂NMe₂ | —Me |
| G56 | —F | —Me |
| G57 | —Cl | —Me |
| G58 | —Br | —Me |
| G59 | —I | —Me |
| G60a | —2Py | —Me |
| G60b | —3Py | —Me |
| G60c | —4Py | —Me |
| G61 | —H | —Et |
| G62 | —Me | —Et |
| G63 | —Et | —Et |
| G64 | -nPr | —Et |
| G65 | -iPr | —Et |

TABLE 190-continued

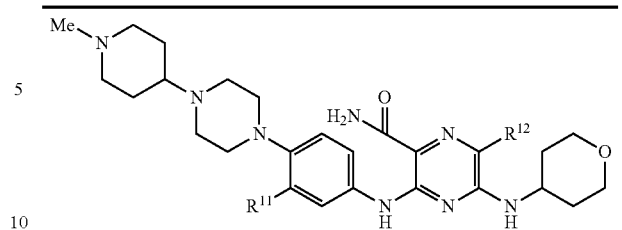

| No | —R[11] | —R[12] |
|---|---|---|
| G66 | -cPr | —Et |
| G67 | -cBu | —Et |
| G68 | cyclopentyl | —Et |
| G69 | cyclohexyl | —Et |
| G70 | tetrahydropyran-4-yl | —Et |
| G71 | —CF₃ | —Et |
| G72 | —CN | —Et |
| G73 | —Ph | —Et |
| G74 | —OMe | —Et |
| G75 | —OEt | —Et |
| G76 | —OnPr | —Et |
| G77 | —OiPr | —Et |
| G78 | —OcPr | —Et |
| G79 | —OCH₂cPr | —Et |
| G80 | —OCHCF₂ | —Et |
| G81 | —OCF₃ | —Et |
| G82 | —OCH₂CF₃ | —Et |
| G83 | —OCH₂CH₂F | —Et |
| G84 | —OCH₂CH₂OMe | —Et |
| G85 | —OCH₂CH₂NMe₂ | —Et |
| G86 | —F | —Et |
| G87 | —Cl | —Et |
| G88 | —Br | —Et |
| G89 | —I | —Et |
| G90a | —2Py | —Et |
| G90b | —3Py | —Et |
| G90c | —4Py | —Et |

TABLE 191

| No | —R[11] | —R[12] |
|---|---|---|
| H1 | —H | -nPr |
| H2 | —Me | -nPr |
| H3 | —Et | -nPr |
| H4 | -nPr | -nPr |
| H5 | -iPr | -nPr |
| H6 | -cPr | -nPr |
| H7 | -cBu | -nPr |

TABLE 191-continued

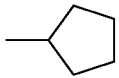

| No | —R11 | —R12 |
|---|---|---|
| H8 | 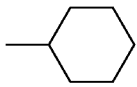 cyclopentyl | -nPr |
| H9 | 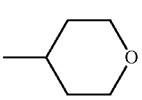 cyclohexyl | -nPr |
| H10 | 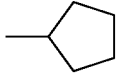 tetrahydropyran-4-yl | -nPr |
| H11 | —CF3 | -nPr |
| H12 | —CN | -nPr |
| H13 | —Ph | -nPr |
| H14 | —OMe | -nPr |
| H15 | —OEt | -nPr |
| H16 | —OnPr | -nPr |
| H17 | —OiPr | -nPr |
| H18 | —OcPr | -nPr |
| H19 | —OCH2cPr | -nPr |
| H20 | —OCHCF2 | -nPr |
| H21 | —OCF3 | -nPr |
| H22 | —OCH2CF3 | -nPr |
| H23 | —OCH2CH2F | -nPr |
| H24 | —OCH2CH2OMe | -nPr |
| H25 | —OCH2CH2NMe2 | -nPr |
| H26 | —F | -nPr |
| H27 | —Cl | -nPr |
| H28 | —Br | -nPr |
| H29 | —I | -nPr |
| H30a | —2Py | -nPr |
| H30b | —3Py | -nPr |
| H30c | —4Py | -nPr |
| H31 | —H | -iPr |
| H32 | —Me | -iPr |
| H33 | —Et | -iPr |
| H34 | -nPr | -iPr |
| H35 | -iPr | -iPr |
| H36 | -cPr | -iPr |
| H37 | -cBu | -iPr |
| H38 | 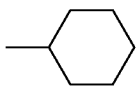 cyclopentyl | -iPr |
| H39 | 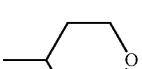 cyclohexyl | -iPr |
| H40 | 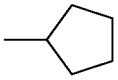 tetrahydropyran-4-yl | -iPr |
| H41 | —CF3 | -iPr |
| H42 | —CN | -iPr |
| H43 | —Ph | -iPr |
| H44 | —OMe | -iPr |
| H45 | —OEt | -iPr |
| H46 | —OnPr | -iPr |
| H47 | —OiPr | -iPr |
| H48 | —OcPr | -iPr |
| H49 | —OCH2cPr | -iPr |
| H50 | —OCHCF2 | -iPr |
| H51 | —OCF3 | -iPr |
| H52 | —OCH2CF3 | -iPr |
| H53 | —OCH2CH2F | -iPr |
| H54 | —OCH2CH2OMe | -iPr |
| H55 | —OCH2CH2NMe2 | -iPr |
| H56 | —F | -iPr |
| H57 | —Cl | -iPr |
| H58 | —Br | -iPr |
| H59 | —I | -iPr |
| H60a | —2Py | -iPr |
| H60b | —3Py | -iPr |
| H60c | —4Py | -iPr |
| H61 | —H | -cPr |
| H62 | —Me | -cPr |
| H63 | —Et | -cPr |
| H64 | -nPr | -cPr |
| H65 | -iPr | -cPr |
| H66 | -cPr | -cPr |
| H67 | -cBu | -cPr |
| H68 | 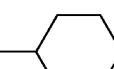 cyclopentyl | -cPr |
| H69 | 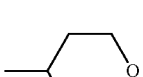 cyclohexyl | -cPr |
| H70 | tetrahydropyran-4-yl | -cPr |
| H71 | —CF3 | -cPr |
| H72 | —CN | -cPr |
| H73 | —Ph | -cPr |
| H74 | —OMe | -cPr |
| H75 | —OEt | -cPr |
| H76 | —OnPr | -cPr |
| H77 | —OiPr | -cPr |
| H78 | —OcPr | -cPr |
| H79 | —OCH2cPr | -cPr |
| H80 | —OCHCF2 | -cPr |
| H81 | —OCF3 | -cPr |
| H82 | —OCH2CF3 | -cPr |
| H83 | —OCH2CH2F | -cPr |
| H84 | —OCH2CH2OMe | -cPr |
| H85 | —OCH2CH2NMe2 | -cPr |
| H86 | —F | -cPr |
| H87 | —Cl | -cPr |
| H88 | —Br | -cPr |
| H89 | —I | -cPr |
| H90a | —2Py | -cPr |
| H90b | —3Py | -cPr |
| H90c | —4Py | -cPr |

TABLE 192

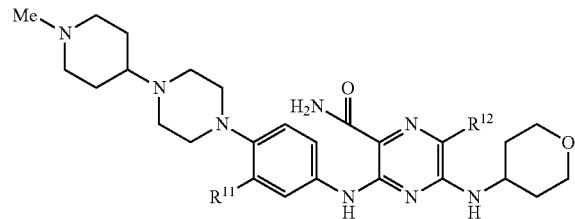

| No | —R11 | —R12 |
|---|---|---|
| I1 | —H | —Cl |
| I2 | —Me | —Cl |
| I3 | —Et | —Cl |
| I4 | -nPr | —Cl |
| I5 | -iPr | —Cl |
| I6 | -cPr | —Cl |
| I7 | -cBu | —Cl |
| I8 | cyclopentyl | —Cl |
| I9 | cyclohexyl | —Cl |
| I10 | tetrahydropyranyl | —Cl |
| I11 | —CF3 | —Cl |
| I12 | —CN | —Cl |
| I13 | —Ph | —Cl |
| I14 | —OMe | —Cl |
| I15 | —OEt | —Cl |
| I16 | —OnPr | —Cl |
| I17 | —OiPr | —Cl |
| I18 | —OcPr | —Cl |
| I19 | —OCH2cPr | —Cl |
| I20 | —OCHCF2 | —Cl |
| I21 | —OCF3 | —Cl |
| I22 | —OCH2CF3 | —Cl |
| I23 | —OCH2CH2F | —Cl |
| I24 | —OCH2CH2OMe | —Cl |
| I25 | —OCH2CH2NMe2 | —Cl |
| I26 | —F | —Cl |
| I27 | —Cl | —Cl |
| I28 | —Br | —Cl |
| I29 | —I | —Cl |
| I30a | —2Py | —Cl |
| I30b | —3Py | —Cl |
| I30c | —4Py | —Cl |
| I31 | —H | —Br |
| I32 | —Me | —Br |
| I33 | —Et | —Br |
| I34 | -nPr | —Br |
| I35 | -iPr | —Br |
| I36 | -cPr | —Br |
| I37 | -cBu | —Br |
| I38 | cyclopentyl | —Br |
| I39 | cyclohexyl | —Br |
| I40 | tetrahydropyranyl | —Br |

TABLE 192-continued

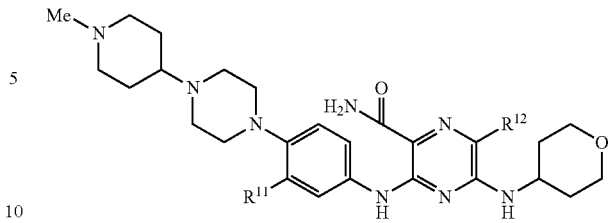

| No | —R11 | —R12 |
|---|---|---|
| I41 | —CF3 | —Br |
| I42 | —CN | —Br |
| I43 | —Ph | —Br |
| I44 | —OMe | —Br |
| I45 | —OEt | —Br |
| I46 | —OnPr | —Br |
| I47 | —OiPr | —Br |
| I48 | —OcPr | —Br |
| I49 | —OCH2cPr | —Br |
| I50 | —OCHCF2 | —Br |
| I51 | —OCF3 | —Br |
| I52 | —OCH2CF3 | —Br |
| I53 | —OCH2CH2F | —Br |
| I54 | —OCH2CH2OMe | —Br |
| I55 | —OCH2CH2NMe2 | —Br |
| I56 | —F | —Br |
| I57 | —Cl | —Br |
| I58 | —Br | —Br |
| I59 | —I | —Br |
| I60a | —2Py | —Br |
| I60b | —3Py | —Br |
| I60c | —4Py | —Br |
| I61 | —H | —I |
| I62 | —Me | —I |
| I63 | —Et | —I |
| I64 | -nPr | —I |
| I65 | -iPr | —I |
| I66 | -cPr | —I |
| I67 | -cBu | —I |
| I68 | cyclopentyl | —I |
| I69 | cyclohexyl | —I |
| I70 | tetrahydropyranyl | —I |
| I71 | —CF3 | —I |
| I72 | —CN | —I |
| I73 | —Ph | —I |
| I74 | —OMe | —I |
| I75 | —OEt | —I |
| I76 | —OnPr | —I |
| I77 | —OiPr | —I |
| I78 | —OcPr | —I |
| I79 | —OCH2cPr | —I |
| I80 | —OCHCF2 | —I |
| I81 | —OCF3 | —I |
| I82 | —OCH2CF3 | —I |
| I83 | —OCH2CH2F | —I |
| I84 | —OCH2CH2OMe | —I |
| I85 | —OCH2CH2NMe2 | —I |
| I86 | —F | —I |
| I87 | —Cl | —I |
| I88 | —Br | —I |
| I89 | —I | —I |

TABLE 192-continued

[Structure: Me-N-piperidine-piperazine-phenyl(R11)-NH-pyrazine(C(O)NH2, R12)-NH-tetrahydropyran]

| No | —R11 | —R12 |
|---|---|---|
| I90a | —2Py | —I |
| I90b | —3Py | —I |
| I90c | —4Py | —I |

TABLE 193

[Structure: Me-N-piperidine-piperazine-phenyl(R11)-NH-pyrazine(C(O)NH2, R12)-NH-piperidine-N-Me]

| No | —R11 | —R12 |
|---|---|---|
| J1 | —H | —H |
| J2 | —Me | —H |
| J3 | —Et | —H |
| J4 | -nPr | —H |
| J5 | -iPr | —H |
| J6 | -cPr | —H |
| J7 | -cBu | —H |
| J8 | cyclopentyl | —H |
| J9 | cyclohexyl | —H |
| J10 | tetrahydropyran-4-yl | —H |
| J11 | —CF3 | —H |
| J12 | —CN | —H |
| J13 | —Ph | —H |
| J14 | —OMe | —H |
| J15 | —OEt | —H |
| J16 | —OnPr | —H |
| J17 | —OiPr | —H |
| J18 | —OcPr | —H |
| J19 | —OCH2cPr | —H |
| J20 | —OCHCF2 | —H |
| J21 | —OCF3 | —H |
| J22 | —OCH2CF3 | —H |
| J23 | —OCH2CH2F | —H |
| J24 | —OCH2CH2OMe | —H |
| J25 | —OCH2CH2NMe2 | —H |
| J26 | —F | —H |
| J27 | —Cl | —H |
| J28 | —Br | —H |
| J29 | —I | —H |
| J30a | —2Py | —H |
| J30b | —3Py | —H |

TABLE 193-continued

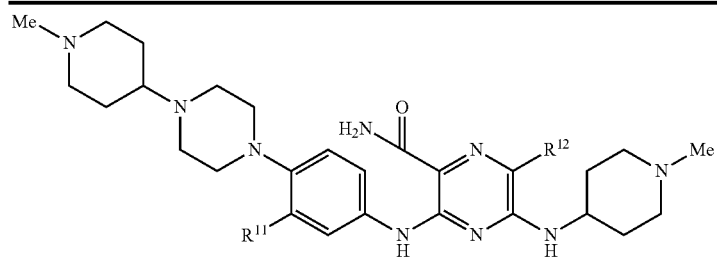

| No | —R$^{11}$ | —R$^{12}$ |
|---|---|---|
| J30c | —4Py | —H |
| J31 | —H | —Me |
| J32 | —Me | —Me |
| J33 | —Et | —Me |
| J34 | -nPr | —Me |
| J35 | -iPr | —Me |
| J36 | -cPr | —Me |
| J37 | -cBu | —Me |
| J38 | cyclopentyl | —Me |
| J39 | cyclohexyl | —Me |
| J40 | tetrahydropyranyl | —Me |
| J41 | —CF$_3$ | —Me |
| J42 | —CN | —Me |
| J43 | —Ph | —Me |
| J44 | —OMe | —Me |
| J45 | —OEt | —Me |
| J46 | —OnPr | —Me |
| J47 | —OiPr | —Me |
| J48 | —OcPr | —Me |
| J49 | —OCH$_2$cPr | —Me |
| J50 | —OCHCF$_2$ | —Me |
| J51 | —OCF$_3$ | —Me |
| J52 | —OCH$_2$CF$_3$ | —Me |
| J53 | —OCH$_2$CH$_2$F | —Me |
| J54 | —OCH$_2$CH$_2$OMe | —Me |
| J55 | —OCH$_2$CH$_2$NMe$_2$ | —Me |
| J56 | —F | —Me |
| J57 | —Cl | —Me |
| J58 | —Br | —Me |
| J59 | —I | —Me |
| J60a | —2Py | —Me |
| J60b | —3Py | —Me |
| J60c | —4Py | —Me |
| J61 | —H | —Et |
| J62 | —Me | —Et |
| J63 | —Et | —Et |
| J64 | -nPr | —Et |
| J65 | -iPr | —Et |
| J66 | -cPr | —Et |
| J67 | -cBu | —Et |
| J68 | cyclopentyl | —Et |
| J69 | cyclohexyl | —Et |

TABLE 193-continued
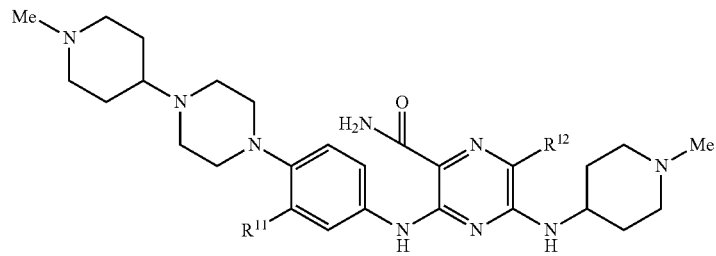
| No | —R11 | —R12 |
|---|---|---|
| J70 | 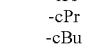 | —Et |
| J71 | —CF$_3$ | —Et |
| J72 | —CN | —Et |
| J73 | —Ph | —Et |
| J74 | —OMe | —Et |
| J75 | —OEt | —Et |
| J76 | —OnPr | —Et |
| J77 | —OiPr | —Et |
| J78 | —OcPr | —Et |
| J79 | —OCH$_2$cPr | —Et |
| J80 | —OCHCF$_2$ | —Et |
| J81 | —OCF$_3$ | —Et |
| J82 | —OCH$_2$CF$_3$ | —Et |
| J83 | —OCH$_2$CH$_2$F | —Et |
| J84 | —OCH$_2$CH$_2$OMe | —Et |
| J85 | —OCH$_2$CH$_2$NMe$_2$ | —Et |
| J86 | —F | —Et |
| J87 | —Cl | —Et |
| J88 | —Br | —Et |
| J89 | —I | —Et |
| J90a | —2Py | —Et |
| J90b | —3Py | —Et |
| J90c | —4Py | —Et |
TABLE 194
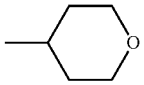
| No | —R11 | —R12 |
|---|---|---|
| K1 | —H | -nPr |
| K2 | —Me | -nPr |
| K3 | —Et | -nPr |
| K4 | -nPr | -nPr |
| K5 | -iPr | -nPr |
| K6 | -cPr | -nPr |
| K7 | -cBu | -nPr |
| K8 | 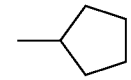 | -nPr |
| K9 | 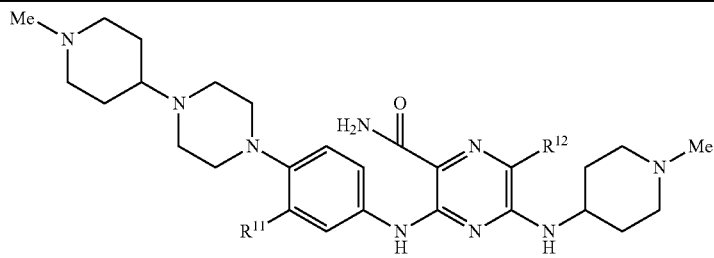 | -nPr |

TABLE 194-continued

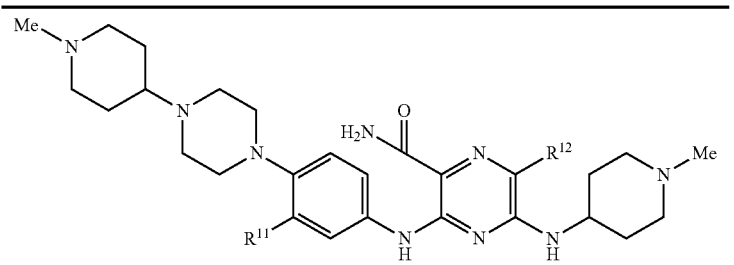

| No | —R11 | —R12 |
|---|---|---|
| K10 | (tetrahydropyran-4-yl) | -nPr |
| K11 | —CF3 | -nPr |
| K12 | —CN | -nPr |
| K13 | —Ph | -nPr |
| K14 | —OMe | -nPr |
| K15 | —OEt | -nPr |
| K16 | —OnPr | -nPr |
| K17 | —OiPr | -nPr |
| K18 | —OcPr | -nPr |
| K19 | —OCH2cPr | -nPr |
| K20 | —OCHCF2 | -nPr |
| K21 | —OCF3 | -nPr |
| K22 | —OCH2CF3 | -nPr |
| K23 | —OCH2CH2F | -nPr |
| K24 | —OCH2CH2OMe | -nPr |
| K25 | —OCH2CH2NMe2 | -nPr |
| K26 | —F | -nPr |
| K27 | —Cl | -nPr |
| K28 | —Br | -nPr |
| K29 | —I | -nPr |
| K30a | —2Py | -nPr |
| K30b | —3Py | -nPr |
| K30c | —4Py | -nPr |
| K31 | —H | -iPr |
| K32 | —Me | -iPr |
| K33 | —Et | -iPr |
| K34 | -nPr | -iPr |
| K35 | -iPr | -iPr |
| K36 | -cPr | -iPr |
| K37 | -cBu | -iPr |
| K38 | (cyclopentyl) | -iPr |
| K39 | (cyclohexyl) | -iPr |
| K40 | (tetrahydropyran-4-yl) | -iPr |
| K41 | —CF3 | -iPr |
| K42 | —CN | -iPr |
| K43 | —Ph | -iPr |
| K44 | —OMe | -iPr |
| K45 | —OEt | -iPr |
| K46 | —OnPr | -iPr |
| K47 | —OiPr | -iPr |
| K48 | —OcPr | -iPr |
| K49 | —OCH2cPr | -iPr |
| K50 | —OCHCF2 | -iPr |
| K51 | —OCF3 | -iPr |
| K52 | —OCH2CF3 | -iPr |
| K53 | —OCH2CH2F | -iPr |
| K54 | —OCH2CH2OMe | -iPr |
| K55 | —OCH2CH2NMe2 | -iPr |
| K56 | —F | -iPr |

TABLE 194-continued

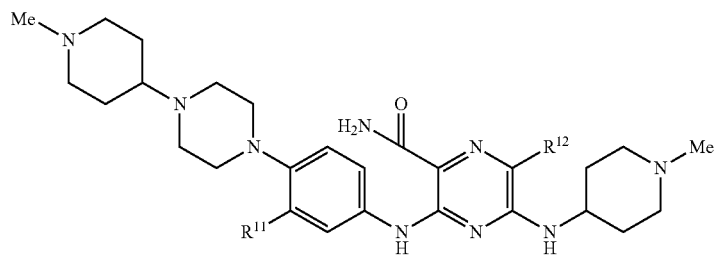

| No | —R[11] | —R[12] |
|---|---|---|
| K57 | —Cl | -iPr |
| K58 | —Br | -iPr |
| K59 | —I | -iPr |
| K60a | —2Py | -iPr |
| K60b | —3Py | -iPr |
| K60c | —4Py | -iPr |
| K61 | —H | -cPr |
| K62 | —Me | -cPr |
| K63 | —Et | -cPr |
| K64 | -nPr | -cPr |
| K65 | -iPr | -cPr |
| K66 | -cPr | -cPr |
| K67 | -cBu | -cPr |
| K68 | cyclopentyl | -cPr |
| K69 | cyclohexyl | -cPr |
| K70 | tetrahydropyranyl | -cPr |
| K71 | —CF$_3$ | -cPr |
| K72 | —CN | -cPr |
| K73 | —Ph | -cPr |
| K74 | —OMe | -cPr |
| K75 | —OEt | -cPr |
| K76 | —OnPr | -cPr |
| K77 | —OiPr | -cPr |
| K78 | —OcPr | -cPr |
| K79 | —OCH$_2$cPr | -cPr |
| K80 | —OCHCF$_2$ | -cPr |
| K81 | —OCF$_3$ | -cPr |
| K82 | —OCH$_2$CF$_3$ | -cPr |
| K83 | —OCH$_2$CH$_2$F | -cPr |
| K84 | —OCH$_2$CH$_2$OMe | -cPr |
| K85 | —OCH$_2$CH$_2$NMe$_2$ | -cPr |
| K86 | —F | -cPr |
| K87 | —Cl | -cPr |
| K88 | —Br | -cPr |
| K89 | —I | -cPr |
| K90a | —2Py | -cPr |
| K90b | —3Py | -cPr |
| K90c | —4Py | -cPr |

TABLE 195

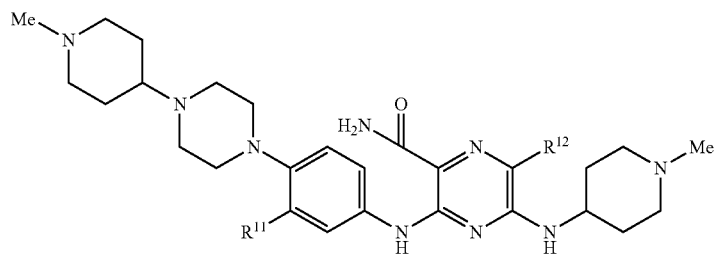

| No | —R[11] | —R[12] |
|---|---|---|
| L1 | —H | —Cl |
| L2 | —Me | —Cl |
| L3 | —Et | —Cl |
| L4 | -nPr | —Cl |
| L5 | -iPr | —Cl |
| L6 | -cPr | —Cl |
| L7 | -cBu | —Cl |
| L8 | cyclopentyl | —Cl |
| L9 | cyclohexyl | —Cl |
| L10 | tetrahydropyran-4-yl | —Cl |
| L11 | —CF$_3$ | —Cl |
| L12 | —CN | —Cl |
| L13 | —Ph | —Cl |
| L14 | —OMe | —Cl |
| L15 | —OEt | —Cl |
| L16 | —OnPr | —Cl |
| L17 | —OiPr | —Cl |
| L18 | —OcPr | —Cl |
| L19 | —OCH$_2$cPr | —Cl |
| L20 | —OCHCF$_2$ | —Cl |
| L21 | —OCF$_3$ | —Cl |
| L22 | —OCH$_2$CF$_3$ | —Cl |
| L23 | —OCH$_2$CH$_2$F | —Cl |
| L24 | —OCH$_2$CH$_2$OMe | —Cl |
| L25 | —OCH$_2$CH$_2$NMe$_2$ | —Cl |
| L26 | —F | —Cl |
| L27 | —Cl | —Cl |
| L28 | —Br | —Cl |
| L29 | —I | —Cl |
| L30a | —2Py | —Cl |
| L30b | —3Py | —Cl |
| L30c | —4Py | —Cl |
| L31 | —H | —Br |
| L32 | —Me | —Br |
| L33 | —Et | —Br |
| L34 | -nPr | —Br |
| L35 | -iPr | —Br |
| L36 | -cPr | —Br |
| L37 | -cBu | —Br |
| L38 | cyclopentyl | —Br |
| L39 | cyclohexyl | —Br |

TABLE 195-continued

| No | —R11 | —R12 |
|---|---|---|
| L40 | (4-tetrahydropyranyl) | —Br |
| L41 | —CF₃ | —Br |
| L42 | —CN | —Br |
| L43 | —Ph | —Br |
| L44 | —OMe | —Br |
| L45 | —OEt | —Br |
| L46 | —OnPr | —Br |
| L47 | —OiPr | —Br |
| L48 | —OcPr | —Br |
| L49 | —OCH₂cPr | —Br |
| L50 | —OCHCF₂ | —Br |
| L51 | —OCF₃ | —Br |
| L52 | —OCH₂CF₃ | —Br |
| L53 | —OCH₂CH₂F | —Br |
| L54 | —OCH₂CH₂OMe | —Br |
| L55 | —OCH₂CH₂NMe₂ | —Br |
| L56 | —F | —Br |
| L57 | —Cl | —Br |
| L58 | —Br | —Br |
| L59 | —I | —Br |
| L60a | —2Py | —Br |
| L60b | —3Py | —Br |
| L60c | —4Py | —Br |
| L61 | —H | —I |
| L62 | —Me | —I |
| L63 | —Et | —I |
| L64 | -nPr | —I |
| L65 | -iPr | —I |
| L66 | -cPr | —I |
| L67 | -cBu | —I |
| L68 | (cyclopentyl) | —I |
| L69 | (cyclohexyl) | —I |
| L70 | (4-tetrahydropyranyl) | —I |
| L71 | —CF₃ | —I |
| L72 | —CN | —I |
| L73 | —Ph | —I |
| L74 | —OMe | —I |
| L75 | —OEt | —I |
| L76 | —OnPr | —I |
| L77 | —OiPr | —I |
| L78 | —OcPr | —I |
| L79 | —OCH₂cPr | —I |
| L80 | —OCHCF₂ | —I |
| L81 | —OCF₃ | —I |
| L82 | —OCH₂CF₃ | —I |
| L83 | —OCH₂CH₂F | —I |
| L84 | —OCH₂CH₂OMe | —I |
| L85 | —OCH₂CH₂NMe₂ | —I |
| L86 | —F | —I |

TABLE 195-continued

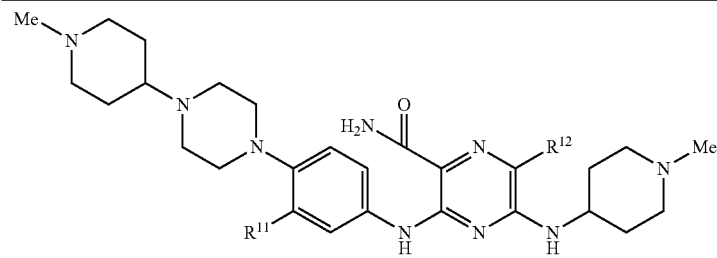

| No | —R11 | —R12 |
|---|---|---|
| L87 | —Cl | —I |
| L88 | —Br | —I |
| L89 | —I | —I |
| L90a | —2Py | —I |
| L90b | —3Py | —I |
| L90c | —4Py | —I |

TABLE 196

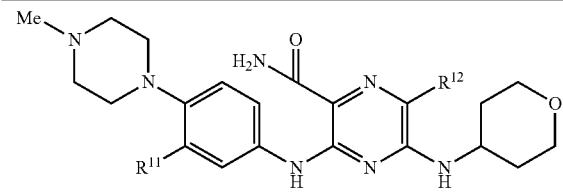

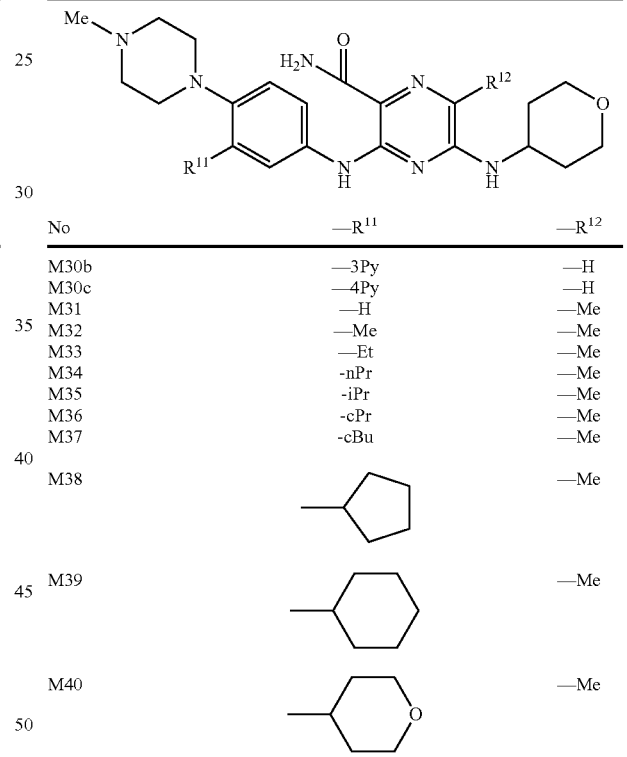

| No | —R11 | —R12 |
|---|---|---|
| M1 | —H | —H |
| M2 | —Me | —H |
| M3 | —Et | —H |
| M4 | -nPr | —H |
| M5 | -iPr | —H |
| M5 | -cPr | —H |
| M7 | -cBu | —H |
| M8 | cyclopentyl | —H |
| M9 | cyclohexyl | —H |
| M10 | tetrahydropyranyl | —H |
| M11 | —CF3 | —H |
| M12 | —CN | —H |
| M13 | —Ph | —H |
| M14 | —OMe | —H |
| M15 | —OEt | —H |
| M16 | —OnPr | —H |
| M17 | —OiPr | —H |
| M18 | —OcPr | —H |
| M19 | —OCH2cPr | —H |
| M20 | —OCHCF2 | —H |
| M21 | —OCF3 | —H |
| M22 | —OCH2CF3 | —H |
| M23 | —OCH2CH2F | —H |
| M24 | —OCH2CH2OMe | —H |
| M25 | —OCH2CH2NMe2 | —H |
| M26 | —F | —H |
| M27 | —Cl | —H |
| M28 | —Br | —H |
| M29 | —I | —H |
| M30a | —2Py | —H |

TABLE 196-continued

| No | —R11 | —R12 |
|---|---|---|
| M30b | —3Py | —H |
| M30c | —4Py | —H |
| M31 | —H | —Me |
| M32 | —Me | —Me |
| M33 | —Et | —Me |
| M34 | -nPr | —Me |
| M35 | -iPr | —Me |
| M36 | -cPr | —Me |
| M37 | -cBu | —Me |
| M38 | cyclopentyl | —Me |
| M39 | cyclohexyl | —Me |
| M40 | tetrahydropyranyl | —Me |
| M41 | —CF3 | —Me |
| M42 | —CN | —Me |
| M43 | —Ph | —Me |
| M44 | —OMe | —Me |
| M45 | —OEt | —Me |
| M46 | —OnPr | —Me |
| M47 | —OiPr | —Me |
| M48 | —OcPr | —Me |
| M49 | —OCH2cPr | —Me |
| M50 | —OCHCF2 | —Me |
| M51 | —OCF3 | —Me |
| M52 | —OCH2CF3 | —Me |
| M53 | —OCH2CH2F | —Me |
| M54 | —OCH2CH2OMe | —Me |
| M55 | —OCH2CH2NMe2 | —Me |
| M56 | —F | —Me |
| M57 | —Cl | —Me |
| M58 | —Br | —Me |

TABLE 196-continued

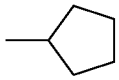

| No | —R11 | —R12 |
|---|---|---|
| M59 | —I | —Me |
| M60a | —2Py | —Me |
| M60b | —3Py | —Me |
| M60c | —4Py | —Me |
| M61 | —H | —Et |
| M62 | —Me | —Et |
| M63 | —Et | —Et |
| M64 | -nPr | —Et |
| M65 | -iPr | —Et |
| M66 | -cPr | —Et |
| M67 | -cBu | —Et |
| M68 | 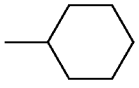 | —Et |
| M69 | 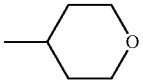 | —Et |
| M70 | 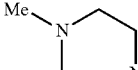 | —Et |
| M71 | —CF3 | —Et |
| M72 | —CN | —Et |
| M73 | —Ph | —Et |
| M74 | —OMe | —Et |
| M75 | —OEt | —Et |
| M76 | —OnPr | —Et |
| M77 | —OiPr | —Et |
| M78 | —OcPr | —Et |
| M79 | —OCH2cPr | —Et |
| M80 | —OCHCF2 | —Et |
| M81 | —OCF3 | —Et |
| M82 | —OCH2CF3 | —Et |
| M83 | —OCH2CH2F | —Et |
| M84 | —OCH2CH2OMe | —Et |
| M85 | —OCH2CH2NMe2 | —Et |
| M86 | —F | —Et |
| M87 | —Cl | —Et |
| M88 | —Br | —Et |
| M89 | —I | —Et |
| M90a | —2Py | —Et |
| M90b | —3Py | —Et |
| M90c | —4Py | —Et |

TABLE 197

| No | —R11 | —R12 |
|---|---|---|
| N1 | —H | -nPr |
| N2 | —Me | -nPr |
| N3 | —Et | -nPr |

TABLE 197-continued

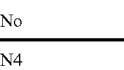

| No | —R11 | —R12 |
|---|---|---|
| N4 | -nPr | -nPr |
| N5 | -iPr | -nPr |
| N6 | -cPr | -nPr |
| N7 | -cBu | -nPr |
| N8 |  | -nPr |
| N9 |  | -nPr |
| N10 |  | -nPr |
| N11 | —CF3 | -nPr |
| N12 | —CN | -nPr |
| N13 | —Ph | -nPr |
| N14 | —OMe | -nPr |
| N15 | —OEt | -nPr |
| N16 | —OnPr | -nPr |
| N17 | —OiPr | -nPr |
| N18 | —OcPr | -nPr |
| N19 | —OCH2cPr | -nPr |
| N20 | —OCHCF2 | -nPr |
| N21 | —OCF3 | -nPr |
| N22 | —OCH2CF3 | -nPr |
| N23 | —OCH2CH2F | -nPr |
| N24 | —OCH2CH2OMe | -nPr |
| N25 | —OCH2CH2NMe2 | -nPr |
| N26 | —F | -nPr |
| N27 | —Cl | -nPr |
| N28 | —Br | -nPr |
| N29 | —I | -nPr |
| N30a | —2Py | -nPr |
| N30b | —3Py | -nPr |
| N30c | —4Py | -nPr |
| N31 | —H | -iPr |
| N32 | —Me | -iPr |
| N33 | —Et | -iPr |
| N34 | -nPr | -iPr |
| N35 | -iPr | -iPr |
| N36 | -cPr | -iPr |
| N37 | -cBu | -iPr |
| N38 |  | -iPr |
| N39 |  | -iPr |
| N40 | 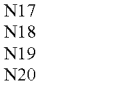 | —iPr |
| N41 | —CF3 | -iPr |
| N42 | —CN | -iPr |
| N43 | —Ph | -iPr |
| N44 | —OMe | -iPr |

TABLE 197-continued

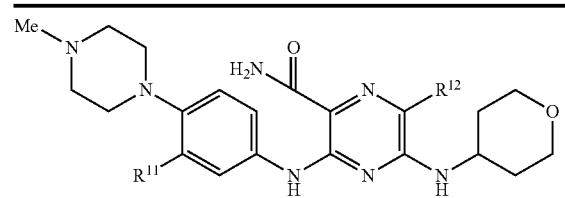

| No | —R11 | —R12 |
|---|---|---|
| N45 | —OEt | -iPr |
| N46 | —OnPr | -iPr |
| N47 | —OiPr | -iPr |
| N48 | —OcPr | -iPr |
| N49 | —OCH$_2$cPr | -iPr |
| N50 | —OCHCF$_2$ | -iPr |
| N51 | —OCF$_3$ | -iPr |
| N52 | —OCH$_2$CF$_3$ | -iPr |
| N53 | —OCH$_2$CH$_2$F | -iPr |
| N54 | —OCH$_2$CH$_2$OMe | -iPr |
| N55 | —OCH$_2$CH$_2$NMe$_2$ | -iPr |
| N56 | —F | -iPr |
| N57 | —Cl | -iPr |
| N58 | —Br | -iPr |
| N59 | —I | -iPr |
| N60a | —2Py | -iPr |
| N60b | —3Py | -iPr |
| N60c | —4Py | -iPr |
| N61 | —H | -cPr |
| N62 | —Me | -cPr |
| N63 | —Et | -cPr |
| N64 | -nPr | -cPr |
| N65 | -iPr | -cPr |
| N66 | -cPr | -cPr |
| N67 | -cBu | -cPr |
| N68 | cyclopentyl | -cPr |
| N69 | cyclohexyl | -cPr |
| N70 | tetrahydropyranyl | -cPr |
| N71 | —CF$_3$ | -cPr |
| N72 | —CN | -cPr |
| N73 | —Ph | -cPr |
| N74 | —OMe | -cPr |
| N75 | —OEt | -cPr |
| N76 | —OnPr | -cPr |
| N77 | —OiPr | -cPr |
| N78 | —OcPr | -cPr |
| N79 | —OCH$_2$cPr | -cPr |
| N80 | —OCHCF$_2$ | -cPr |
| N81 | —OCF$_3$ | -cPr |
| N82 | —OCH$_2$CF$_3$ | -cPr |
| N83 | —OCH$_2$CH$_2$F | -cPr |
| N84 | —OCH$_2$CH$_2$OMe | -cPr |
| N85 | —OCH$_2$CH$_2$NMe$_2$ | -cPr |
| N86 | —F | -cPr |
| N87 | —Cl | -cPr |
| N88 | —Br | -cPr |
| N89 | —I | -cPr |
| N90a | —2Py | -cPr |
| N90b | —3Py | -cPr |
| N90c | —4Py | -cPr |

TABLE 198

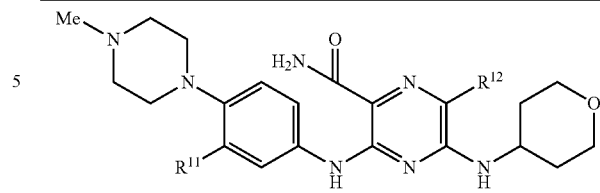

| No | —R11 | —R12 |
|---|---|---|
| O1 | —H | —Cl |
| O2 | —Me | —Cl |
| O3 | —Et | —Cl |
| O4 | -nPr | —Cl |
| O5 | -iPr | —Cl |
| O6 | -cPr | —Cl |
| O7 | -cBu | —Cl |
| O8 | cyclopentyl | —Cl |
| O9 | cyclohexyl | —Cl |
| O10 | tetrahydropyranyl | —Cl |
| O11 | —CF$_3$ | —Cl |
| O12 | —CN | —Cl |
| O13 | —Ph | —Cl |
| O14 | —OMe | —Cl |
| O15 | —OEt | —Cl |
| O16 | —OnPr | —Cl |
| O17 | —OiPr | —Cl |
| O18 | —OcPr | —Cl |
| O19 | —OCH$_2$cPr | —Cl |
| O20 | —OCHCF$_2$ | —Cl |
| O21 | —OCF$_3$ | —Cl |
| O22 | —OCH$_2$CF$_3$ | —Cl |
| O23 | —OCH$_2$CH$_2$F | —Cl |
| O24 | —OCH$_2$CH$_2$OMe | —Cl |
| O25 | —OCH$_2$CH$_2$NMe$_2$ | —Cl |
| O26 | —F | —Cl |
| O27 | —Cl | —Cl |
| O28 | —Br | —Cl |
| O29 | —I | —Cl |
| O30a | —2Py | —Cl |
| O30b | —3Py | —Cl |
| O30c | —4Py | —Cl |
| O31 | —H | —Br |
| O32 | —Me | —Br |
| O33 | —Et | —Br |
| O34 | -nPr | —Br |
| O35 | -iPr | —Br |
| O36 | -cPr | —Br |
| O37 | -cBu | —Br |
| O38 | cyclopentyl | —Br |
| O39 | cyclohexyl | —Br |
| O40 | tetrahydropyranyl | —Br |

TABLE 198-continued

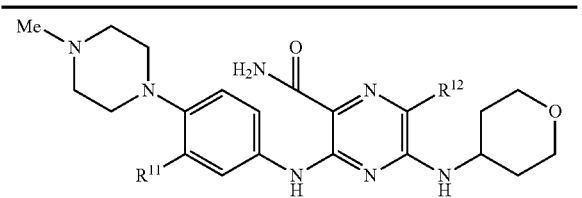

| No | —R11 | —R12 |
|---|---|---|
| O41 | —CF3 | —Br |
| O42 | —CN | —Br |
| O43 | —Ph | —Br |
| O44 | —OMe | —Br |
| O45 | —OEt | —Br |
| O46 | —OnPr | —Br |
| O47 | —OiPr | —Br |
| O48 | —OcPr | —Br |
| O49 | —OCH2cPr | —Br |
| O50 | —OCHCF2 | —Br |
| O51 | —OCF3 | —Br |
| O52 | —OCH2CF3 | —Br |
| O53 | —OCH2CH2F | —Br |
| O54 | —OCH2CH2OMe | —Br |
| O55 | —OCH2CH2NMe2 | —Br |
| O56 | —F | —Br |
| O57 | —Cl | —Br |
| O58 | —Br | —Br |
| O59 | —I | —Br |
| O60a | —2Py | —Br |
| O60b | —3Py | —Br |
| O60c | —4Py | —Br |
| O61 | —H | —I |
| O62 | —Me | —I |
| O63 | —Et | —I |
| O64 | -nPr | —I |
| O65 | -iPr | —I |
| O66 | -cPr | —I |
| O67 | -cBu | —I |
| O68 | cyclopentyl | —I |
| O69 | cyclohexyl | —I |
| O70 | tetrahydropyranyl | —I |
| O71 | —CF3 | —I |
| O72 | —CN | —I |
| O73 | —Ph | —I |
| O74 | —OMe | —I |
| O75 | —OEt | —I |
| O76 | —OnPr | —I |
| O77 | —OiPr | —I |
| O78 | —OcPr | —I |
| O79 | —OCH2cPr | —I |
| O80 | —OCHCF2 | —I |
| O81 | —OCF3 | —I |
| O82 | —OCH2CF3 | —I |
| O83 | —OCH2CH2F | —I |
| O84 | —OCH2CH2OMe | —I |
| O85 | —OCH2CH2NMe2 | —I |
| O86 | —F | —I |
| O87 | —Cl | —I |
| O88 | —Br | —I |
| O89 | —I | —I |
| O90a | —2Py | —I |
| O90b | —3Py | —I |
| O90c | —4Py | —I |

TABLE 199

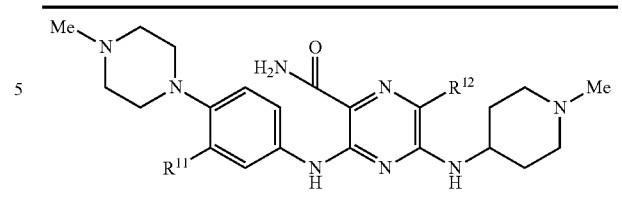

| No | —R11 | —R12 |
|---|---|---|
| P1 | —H | —H |
| P2 | —Me | —H |
| P3 | —Et | —H |
| P4 | -nPr | —H |
| P5 | -iPr | —H |
| P6 | -cPr | —H |
| P7 | -cBu | —H |
| P8 | cyclopentyl | —H |
| P9 | cyclohexyl | —H |
| P10 | tetrahydropyranyl | —H |
| P11 | —CF3 | —H |
| P12 | —CN | —H |
| P13 | —Ph | —H |
| P14 | —OMe | —H |
| P15 | —OEt | —H |
| P16 | —OnPr | —H |
| P17 | —OiPr | —H |
| P18 | —OcPr | —H |
| P19 | —OCH2cPr | —H |
| P20 | —OCHCF2 | —H |
| P21 | —OCF3 | —H |
| P22 | —OCH2CF3 | —H |
| P23 | —OCH2CH2F | —H |
| P24 | —OCH2CH2OMe | —H |
| P25 | —OCH2CH2NMe2 | —H |
| P26 | —F | —H |
| P27 | —Cl | —H |
| P28 | —Br | —H |
| P29 | —I | —H |
| P30a | —2Py | —H |
| P30b | —3Py | —H |
| P30c | —4Py | —H |
| P31 | —H | —Me |
| P32 | —Me | —Me |
| P33 | —Et | —Me |
| P34 | -nPr | —Me |
| P35 | -iPr | —Me |
| P36 | -cPr | —Me |
| P37 | -cBu | —Me |
| P38 | cyclopentyl | —Me |
| P39 | cyclohexyl | —Me |
| P40 | tetrahydropyranyl | —Me |
| P41 | —CF3 | —Me |
| P42 | —CN | —Me |

TABLE 199-continued

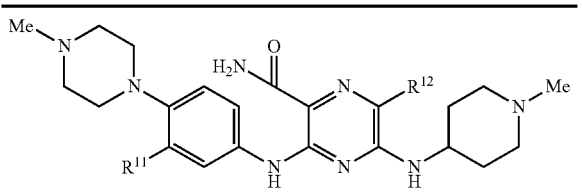

| No | —R[11] | —R[12] |
|---|---|---|
| P43 | —Ph | —Me |
| P44 | —OMe | —Me |
| P45 | —OEt | —Me |
| P46 | —OnPr | —Me |
| P47 | —OiPr | —Me |
| P48 | —OcPr | —Me |
| P49 | —OCH$_2$cPr | —Me |
| P50 | —OCHCF$_2$ | —Me |
| P51 | —OCF$_3$ | —Me |
| P52 | —OCH$_2$CF$_3$ | —Me |
| P53 | —OCH$_2$CH$_2$F | —Me |
| P54 | —OCH$_2$CH$_2$OMe | —Me |
| P55 | —OCH$_2$CH$_2$NMe$_2$ | —Me |
| P56 | —F | —Me |
| P57 | —Cl | —Me |
| P58 | —Br | —Me |
| P59 | —I | —Me |
| P60a | —2Py | —Me |
| P60b | —3Py | —Me |
| P60c | —4Py | —Me |
| P61 | —H | —Et |
| P62 | —Me | —Et |
| P63 | —Et | —Et |
| P64 | -nPr | —Et |
| P65 | -iPr | —Et |
| P66 | -cPr | —Et |
| P67 | -cBu | —Et |
| P68 | 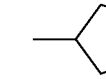 | —Et |
| P69 | 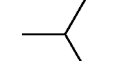 | —Et |
| P70 | 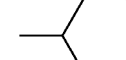 | —Et |
| P71 | —CF$_3$ | —Et |
| P72 | —CN | —Et |
| P73 | —Ph | —Et |
| P74 | —OMe | —Et |
| P75 | —OEt | —Et |
| P76 | —OnPr | —Et |
| P77 | —OiPr | —Et |
| P78 | —OcPr | —Et |
| P79 | —OCH$_2$cPr | —Et |
| P80 | —OCHCF$_2$ | —Et |
| P81 | —OCF$_3$ | —Et |
| P82 | —OCH$_2$CF$_3$ | —Et |
| P83 | —OCH$_2$CH$_2$F | —Et |
| P84 | —OCH$_2$CH$_2$OMe | —Et |
| P85 | —OCH$_2$CH$_2$NMe$_2$ | —Et |
| P86 | —F | —Et |
| P87 | —Cl | —Et |
| P88 | —Br | —Et |
| P89 | —I | —Et |
| P90a | —2Py | —Et |
| P90b | —3Py | —Et |
| P90c | —4Py | —Et |

TABLE 200

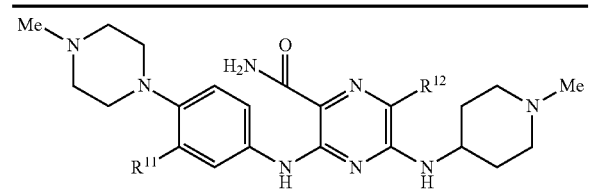

| No | —R[11] | —R[12] |
|---|---|---|
| Q1 | —H | -nPr |
| Q2 | —Me | -nPr |
| Q3 | —Et | -nPr |
| Q4 | -nPr | -nPr |
| Q5 | -iPr | -nPr |
| Q6 | -cPr | -nPr |
| Q7 | -cBu | -nPr |
| Q8 |  | -nPr |
| Q9 | 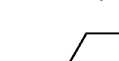 | -nPr |
| Q10 | 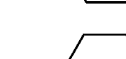 | -nPr |
| Q11 | —CF$_3$ | -nPr |
| Q12 | —CN | -nPr |
| Q13 | —Ph | -nPr |
| Q14 | —OMe | -nPr |
| Q15 | —OEt | -nPr |
| Q16 | —OnPr | -nPr |
| Q17 | —OiPr | -nPr |
| Q18 | —OcPr | -nPr |
| Q19 | —OCH$_2$cPr | -nPr |
| Q20 | —OCHCF$_2$ | -nPr |
| Q21 | —OCF$_3$ | -nPr |
| Q22 | —OCH$_2$CF$_3$ | -nPr |
| Q23 | —OCH$_2$CH$_2$F | -nPr |
| Q24 | —OCH$_2$CH$_2$OMe | -nPr |
| Q25 | —OCH$_2$CH$_2$NMe$_2$ | -nPr |
| Q26 | —F | -nPr |
| Q27 | —Cl | -nPr |
| Q28 | —Br | -nPr |
| Q29 | —I | -nPr |
| Q30a | —2Py | -nPr |
| Q30b | —3Py | -nPr |
| Q30c | —4Py | -nPr |
| Q31 | —H | -iPr |
| Q32 | —Me | -iPr |
| Q33 | —Et | -iPr |
| Q34 | -nPr | -iPr |
| Q35 | -iPr | -iPr |
| Q36 | -cPr | -iPr |
| Q37 | -cBu | -iPr |
| Q38 | 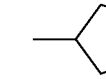 | -iPr |
| Q39 | 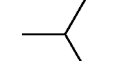 | -iPr |
| Q40 | 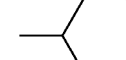 | -iPr |

TABLE 200-continued

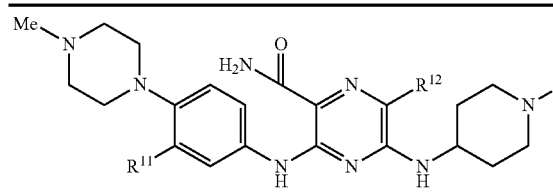

| No | —R11 | —R12 |
|---|---|---|
| Q41 | —CF3 | -iPr |
| Q42 | —CN | -iPr |
| Q43 | —Ph | -iPr |
| Q44 | —OMe | -iPr |
| Q45 | —OEt | -iPr |
| Q46 | —OnPr | -iPr |
| Q47 | —OiPr | -iPr |
| Q48 | —OcPr | -iPr |
| Q49 | —OCH2cPr | -iPr |
| Q50 | —OCHCF2 | -iPr |
| Q51 | —OCF3 | -iPr |
| Q52 | —OCH2CF3 | -iPr |
| Q53 | —OCH2CH2F | -iPr |
| Q54 | —OCH2CH2OMe | -iPr |
| Q55 | —OCH2CH2NMe2 | -iPr |
| Q56 | —F | -iPr |
| Q57 | —Cl | -iPr |
| Q58 | —Br | -iPr |
| Q59 | —I | -iPr |
| Q60a | —2Py | -iPr |
| Q60b | —3Py | -iPr |
| Q60c | —4Py | -iPr |
| Q61 | —H | -cPr |
| Q62 | —Me | -cPr |
| Q63 | —Et | -cPr |
| Q64 | -nPr | -cPr |
| Q65 | -iPr | -cPr |
| Q66 | -cPr | -cPr |
| Q67 | -cBu | -cPr |
| Q68 | cyclopentyl | -cPr |
| Q69 | cyclohexyl | -cPr |
| Q70 | tetrahydropyranyl | -cPr |
| Q71 | —CF3 | -cPr |
| Q72 | —CN | -cPr |
| Q73 | —Ph | -cPr |
| Q74 | —OMe | -cPr |
| Q75 | —OEt | -cPr |
| Q76 | —OnPr | -cPr |
| Q77 | —OiPr | -cPr |
| Q78 | —OcPr | -cPr |
| Q79 | —OCH2cPr | -cPr |
| Q80 | —OCHCF2 | -cPr |
| Q81 | —OCF3 | -cPr |
| Q82 | —OCH2CF3 | -cPr |
| Q83 | —OCH2CH2F | -cPr |
| Q84 | —OCH2CH2OMe | -cPr |
| Q85 | —OCH2CH2NMe2 | -cPr |
| Q86 | —F | -cPr |
| Q87 | —Cl | -cPr |
| Q88 | —Br | -cPr |
| Q89 | —I | -cPr |
| Q90a | —2Py | -cPr |
| Q90b | —3Py | -cPr |
| Q90c | —4Py | -cPr |

TABLE 201

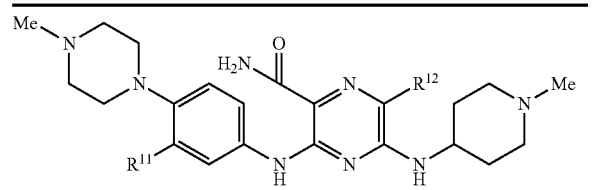

| No | —R11 | —R12 |
|---|---|---|
| R1 | —H | —Cl |
| R2 | —Me | —Cl |
| R3 | —Et | —Cl |
| R4 | -nPr | —Cl |
| R5 | -iPr | —Cl |
| R6 | -cPr | —Cl |
| R7 | -cBu | —Cl |
| R8 | cyclopentyl | —Cl |
| R9 | cyclohexyl | —Cl |
| R10 | tetrahydropyranyl | —Cl |
| R11 | —CF3 | —Cl |
| R12 | —CN | —Cl |
| R13 | —Ph | —Cl |
| R14 | —OMe | —Cl |
| R15 | —OEt | —Cl |
| R16 | —OnPr | —Cl |
| R17 | —OiPr | —Cl |
| R18 | —OcPr | —Cl |
| R19 | —OCH2cPr | —Cl |
| R20 | —OCHCF2 | —Cl |
| R21 | —OCF3 | —Cl |
| R22 | —OCH2CF3 | —Cl |
| R23 | —OCH2CH2F | —Cl |
| R24 | —OCH2CH2OMe | —Cl |
| R25 | —OCH2CH2NMe2 | —Cl |
| R26 | —F | —Cl |
| R27 | —Cl | —Cl |
| R28 | —Br | —Cl |
| R29 | —I | —Cl |
| R30a | —2Py | —Cl |
| R30b | —3Py | —Cl |
| R30c | —4Py | —Cl |
| R31 | —H | —Br |
| R32 | —Me | —Br |
| R33 | —Et | —Br |
| R34 | -nPr | —Br |
| R35 | -iPr | —Br |
| R36 | -cPr | —Br |
| R37 | -cBu | —Br |
| R38 | cyclopentyl | —Br |
| R39 | cyclohexyl | —Br |
| R40 | tetrahydropyranyl | —Br |
| R41 | —CF3 | —Br |
| R42 | —CN | —Br |

TABLE 201-continued

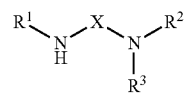

| No | —R¹¹ | —R¹² |
|---|---|---|
| R43 | —Ph | —Br |
| R44 | —OMe | —Br |
| R45 | —OEt | —Br |
| R46 | —OnPr | —Br |
| R47 | —OiPr | —Br |
| R48 | —OcPr | —Br |
| R49 | —OCH₂cPr | —Br |
| R50 | —OCHCF₂ | —Br |
| R51 | —OCF₃ | —Br |
| R52 | —OCH₂CF₃ | —Br |
| R53 | —OCH₂CH₂F | —Br |
| R54 | —OCH₂CH₂OMe | —Br |
| R55 | —OCH₂CH₂NMe₂ | —Br |
| R56 | —F | —Br |
| R57 | —Cl | —Br |
| R58 | —Br | —Br |
| R59 | —I | —Br |
| R60a | —2Py | —Br |
| R60b | —3Py | —Br |
| R60c | —4Py | —Br |
| R61 | —H | —I |
| R62 | —Me | —I |
| R63 | —Et | —I |
| R64 | -nPr | —I |
| R65 | -iPr | —I |
| R66 | -cPr | —I |
| R67 | -cBu | —I |
| R68 | cyclopentyl | —I |
| R69 | cyclohexyl | —I |
| R70 | tetrahydropyran-4-yl | —I |
| R71 | —CF₃ | —I |
| R72 | —CN | —I |
| R73 | —Ph | —I |
| R74 | —OMe | —I |
| R75 | —OEt | —I |
| R76 | —OnPr | —I |
| R77 | —OiPr | —I |
| R78 | —OcPr | —I |
| R79 | —OCH₂cPr | —I |
| R80 | —OCHCF₂ | —I |
| R81 | —OCF₃ | —I |
| R82 | —OCH₂CF₃ | —I |
| R83 | —OCH₂CH₂F | —I |
| R84 | —OCH₂CH₂OMe | —I |
| R85 | —OCH₂CH₂NMe₂ | —I |
| R86 | —F | —I |
| R87 | —Cl | —I |
| R88 | —Br | —I |
| R89 | —I | —I |
| R90a | —2Py | —I |
| R90b | —3Py | —I |
| R90c | —4Py | —I |

INDUSTRIAL APPLICABILITY

The compound of formula (I) or a salt thereof has inhibitory activity against the kinase activity of EML4-ALK fusion protein, as well as growth inhibitory activity against EML4-ALK fusion protein-dependent cells, and can be used as an active ingredient in pharmaceutical compositions for preventing and/or treating cancer, such as lung cancer in one embodiment, non-small cell lung cancer or small cell lung cancer in another embodiment, ALK fusion polynucleotide-positive cancer in yet another embodiment, ALK fusion polynucleotide-positive lung cancer in yet another embodiment, ALK fusion polynucleotide-positive non-small cell lung cancer in yet another embodiment, ALK fusion protein-positive cancer in yet another embodiment, ALK fusion protein-positive lung cancer in yet another embodiment, ALK fusion protein-positive non-small cell lung cancer in yet another embodiment, EML4-ALK fusion polynucleotide-positive cancer in yet another embodiment, EML4-ALK fusion polynucleotide-positive lung cancer in yet another embodiment, EML4-ALK fusion polynucleotide-positive non-small cell lung cancer in yet another embodiment, EML4-ALK fusion protein-positive cancer in yet another embodiment, EML4-ALK fusion protein-positive lung cancer in yet another embodiment, or EML4-ALK fusion protein-positive non-small cell lung cancer in yet another embodiment.

The invention claimed is:
1. A compound of formula (I) or a salt thereof:

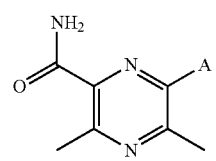

(I)

wherein the symbols are as defined below:
—X— is a group of formula (II):

(II)

A is chloro, ethyl, or isopropyl;
R¹ is phenyl in which the carbon at the 4-position is substituted with —W—Y—Z and the carbon at the 3-position may be substituted with a group selected from the group consisting of halogen, R⁰⁰, and —O—R⁰⁰;
R⁰⁰ is lower alkyl which may be substituted with one or more halogens;
—W— is a bond, piperidine-1,4-diyl, or piperazine-1,4-diyl;
—Y— is a bond;
Z is
a non-aromatic heterocyclic ring which may be substituted with one or more R⁰⁰;
R² is (i) cycloalkyl which may be substituted with one or more groups selected from the group consisting of —N(lower alkyl)₂, lower alkyl, —COO-lower alkyl, —OH, —COOH, —CONH—R^{ZB}, and morpholinyl, or (ii) a non-aromatic heterocyclic ring which may be substituted with one or more groups selected from the group consisting of lower alkyl, —CO-lower alkyl, oxo, —CO—$R^{ZB}$, and benzyl;

$R^{ZB}$ is phenyl which may be substituted with a group selected from the group consisting of halogen and —O-lower alkyl; and $R^3$ is —H.

2. The compound according to claim 1 or a salt thereof, wherein $R^1$ is phenyl in which the carbon at the 4-position is substituted with a group selected from the group consisting of 4-(4-methylpiperazin-1-yl)piperidin-1-yl, 4-(1-methylpiperidin-4-yl)piperazin-1-yl, 4-methylpiperazin-1-yl, and 4-isopropylpiperazin-1-yl, and the carbon at the 3-position may be substituted with a group selected from the group consisting of fluoro, methyl, trifluoromethyl, and methoxy.

3. The compound according to claim 1 or a salt thereof, wherein $R^2$ is 4-hydroxycyclohexyl, 4-hydroxy-4-methylcyclohexyl, or tetrahydropyran-4-yl.

4. The compound according to claim 1 or a salt thereof, wherein said compound is:
   6-ethyl-5-[(trans-4-hydroxycyclohexyl)amino]-3-{[4-(4-methylpiperazin-1-yl)phenyl]amino}pyrazine-2-carboxamide,
   6-ethyl-5-[(trans-4-hydroxycyclohexyl)amino]-3-({4-[4-(4-methylpiperazin-1-yl)piperidin-1-yl]phenyl}amino)pyrazine-2-carboxamide,
   5-[(trans-4-hydroxycyclohexyl)amino]-6-isopropyl-3-{[4-(4-methylpiperazin-1-yl)phenyl]amino}pyrazine-2-carboxamide,
   6-ethyl-5-[(trans-4-hydroxycyclohexyl)amino]-3-({4-[4-(4-methylpiperazin-1-yl)piperidin-1-yl]-3-(trifluoromethyl)phenyl}amino)pyrazine-2-carboxamide,
   6-ethyl-5-[(trans-4-hydroxycyclohexyl)amino]-3-({3-methyl-4-[4-(4-methylpiperazin-1-yl)piperidin-1-yl]phenyl}amino)pyrazine-2-carboxamide,
   5-[(trans-4-hydroxycyclohexyl)amino]-6-isopropyl-3-({4-[4-(4-methylpiperazin-1-yl)piperidin-1-yl]-3-(trifluoromethyl)phenyl}amino)pyrazine-2-carboxamide,
   6-ethyl-5-[(cis-4-hydroxy-4-methylcyclohexyl)amino]-3-({3-methyl-4-[4-(4-methylpiperazin-1-yl)piperidin-1-yl]phenyl}amino)pyrazine-2-carboxamide,
   6-ethyl-5-[(trans-4-hydroxycyclohexyl)amino]-3-{[4-(4-isopropylpiperazin-1-yl)-3-methylphenyl]amino}pyrazine-2-carboxamide,
   6-ethyl-5-[(trans-4-hydroxy-4-methylcyclohexyl)amino]-3-({3-methyl-4-[4-(4-methylpiperazin-1-yl)piperidin-1-yl]phenyl}amino)pyrazine-2-carboxamide,
   6-ethyl-3-({3-methyl-4-[4-(4-methylpiperazin-1-yl)piperidin-1-yl]phenyl}amino)-5-(tetrahydro-2H-pyran-4-ylamino)pyrazine-2-carboxamide,
   6-chloro-5-[(trans-4-hydroxycyclohexyl)amino]-3-({3-methyl-4-[4-(4-methylpiperazin-1-yl)piperidin-1-yl]phenyl}amino)pyrazine-2-carboxamide,
   6-ethyl-3-({4-[4-(4-methylpiperazin-1-yl)piperidin-1-yl]phenyl}amino)-5-(tetrahydro-2H-pyran-4-ylamino)pyrazine-2-carboxamide,
   6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide,
   6-isopropyl-3-({4-[4-(4-methylpiperazin-1-yl)piperidin-1-yl]phenyl}amino)-5-(tetrahydro-2H-pyran-4-ylamino)pyrazine-2-carboxamide,
   6-ethyl-3-{[3-fluoro-4-(4-methylpiperazin-1-yl)phenyl]amino}-5-(tetrahydro-2H-pyran-4-ylamino)pyrazine-2-carboxamide,
   6-isopropyl-3-{[3-methoxy-4-(4-methylpiperazin-1-yl)phenyl]amino}-5-(tetrahydro-2H-pyran-4-ylamino)pyrazine-2-carboxamide,
   6-isopropyl-3-{[4-(4-methylpiperazin-1-yl)phenyl]amino}-5-(tetrahydro-2H-pyran-4-ylamino)pyrazine-2-carboxamide, or
   6-ethyl-3-({3-methyl-4-[4-(1-methylpiperidin-4-yl)piperazin-1-yl]phenyl}amino)-5-(tetrahydro-2H-pyran-4-ylamino)pyrazine-2-carboxamide.

5. A pharmaceutical composition, which comprises the compound according to claim 1 or a salt thereof and a pharmaceutically acceptable excipient.

6. An inhibitor against the kinase activity of EML4-ALK fusion protein, which comprises the compound according to claim 1 or a salt thereof.

7. A pharmaceutical composition for preventing or treating cancer, lung cancer, non-small cell lung cancer, small cell lung cancer, EML4-ALK fusion polynucleotide-positive cancer, EML4-ALK fusion polynucleotide-positive lung cancer, or EML4-ALK fusion polynucleotide-positive non-small cell lung cancer, which comprises the compound according to claim 1 or a salt thereof.

8. The compound according to claim 1 or a salt thereof, wherein said compound is:
   5-[(trans-4-hydroxycyclohexyl)amino]-6-isopropyl-3-({4-[4-(4-methylpiperazin-1-yl)piperidin-1-yl]-3-(trifluoromethyl)phenyl}amino)pyrazine-2-carboxamide.

9. The compound according to claim 1 or a salt thereof, wherein said compound is:
   6-ethyl-5-[(trans-4-hydroxy-4-methylcyclohexyl)amino]-3-({3-methyl-4-[4-(4-methylpiperazin-1-yl)piperidin-1-yl]phenyl}amino)pyrazine-2-carboxamide.

10. The compound according to claim 1 or a salt thereof, wherein said compound is:
    6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide.

11. The compound according to claim 1 or a salt thereof, wherein said compound is:
    6-isopropyl-3-({4-[4-(4-methylpiperazin-1-yl)piperidin-1-yl]phenyl}amino)-5-(tetrahydro-2H-pyran-4-ylamino)pyrazine-2-carboxamide.

12. The compound according to claim 1 or a salt thereof, wherein said compound is:
    6-ethyl-3-({3-methyl-4-[4-(1-methylpiperidin-4-yl)piperazin-1-yl]phenyl}amino)-5-(tetrahydro-2H-pyran-4-ylamino)pyrazine-2-carboxamide.

* * * * *